(12) United States Patent
Boehm et al.

(10) Patent No.: US 8,501,982 B2
(45) Date of Patent: Aug. 6, 2013

(54) GLP-1 RECEPTOR STABILIZERS AND MODULATORS

(75) Inventors: Marcus F. Boehm, San Diego, CA (US); Esther Martinborough, San Diego, CA (US); Manisha Moorjani, San Diego, CA (US); Liming Huang, San Diego, CA (US); Junko Tamiya, Oceanside, CA (US); Mark T. Griffith, San Diego, CA (US); Thomas Fowler, Melton Mowbray (GB); Andrew Novak, Nottingham (GB); Michael Knaggs, Burton-on-Trent (GB); Premji Meghani, Leicestershire (GB)

(73) Assignee: Receptos, Inc., San Diego, CA (US)

( * ) Notice: Subject to any disclaimer, the term of this patent is extended or adjusted under 35 U.S.C. 154(b) by 188 days.

(21) Appl. No.: 13/157,264

(22) Filed: Jun. 9, 2011

(65) Prior Publication Data

US 2011/0306542 A1 Dec. 15, 2011

Related U.S. Application Data

(60) Provisional application No. 61/353,174, filed on Jun. 9, 2010.

(51) Int. Cl.
*C07C 69/76* (2006.01)
*A61K 31/235* (2006.01)

(52) U.S. Cl.
USPC .................. 560/86; 560/84; 560/85; 514/533

(58) Field of Classification Search
USPC ................................. 560/84, 85, 86; 514/533
See application file for complete search history.

(56) References Cited

U.S. PATENT DOCUMENTS 4,004,008 A * 1/1977 Makovec et al. ............ 514/235.5
6,191,171 B1 2/2001 DeLaszlo et al.

FOREIGN PATENT DOCUMENTS

WO WO 2011/094890 A1 8/2011
WO WO 2011/097300 A1 8/2011

OTHER PUBLICATIONS

Wolff, M.E. "Burger's Medicinal Chemistry 4th Ed. Part I", Wiley: New York, 1979, 336-337.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Knudsen et al., "Small-molecule agonists for the glucagon-like peptide 1 receptor", PNAS USA 2007, 104(3):937-942, p. 937-939, 941-942.
Underwood et al., "Crystal Structure of Glucagon-like Peptide-1 in Complex with the Extracellular Domain of the Clucagon-like Peptide-1 Receptor", The Journal of Biological Chemistry, Jan. 1, 2010, 285(1):723-730; p. 723, 725-730.
Patent Cooperation Treaty, PCT/ISA/220, International Search Report for PCT/US2011/039873, Dec. 1, 2011, p. 1-3.

* cited by examiner

*Primary Examiner* — Shailendra Kumar
(74) *Attorney, Agent, or Firm* — Seed IP Law Group PLLC

(57) ABSTRACT

Compounds that bind the glucagon-like peptide 1 receptor (GLP-1) receptor are provided including compounds which are modulators of the GLP-1 receptors and compounds which are capable of inducing a stabilizing effect on the receptor for use in structural analyses of the GLP-1 receptor. Methods of synthesis, methods of therapeutic and/or prophylactic use, and methods of use in stabilizing GLP-1 receptor in vitro for crystallization of the GLP-1 receptor of such compounds are provided.

48 Claims, No Drawings

SEQUENCE LISTING

```
<160> NUMBER OF SEQ ID NOS: 3

<210> SEQ ID NO 1
<211> LENGTH: 30
<212> TYPE: PRT
<213> ORGANISM: Artificial Sequence
<220> FEATURE:
<223> OTHER INFORMATION: GLP-1 Modulators

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: GLP-1 Modulators

<400> SEQUENCE: 2

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg
            20                  25

<210> SEQ ID NO 3
<211> LENGTH: 29
<212> TYPE: PRT
<213> ORGANISM: Artificial Sequence
<220> FEATURE:
<223> OTHER INFORMATION: GLP-1 Modulators
<220> FEATURE:
<221> NAME/KEY: MOD_RES
<222> LOCATION: (8)..(8)
<223> OTHER INFORMATION: Xaa is Norleucine
```

```
<400> SEQUENCE: 3

Gly Glu Gly Thr Phe Thr Ser Xaa Leu Ser Lys Gln Met Glu Glu Glu
1               5                   10                  15

Ala Val Arg Leu Phe Ile Glu Trp Leu Lys Asn Gly Arg
            20                  25
```

GLP-1 RECEPTOR STABILIZERS AND MODULATORS

This application claims the priority of U.S. Ser. No. 61/353,174, filed Jun. 9, 2010, the disclosure of which is incorporated herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 800059_405_SEQUENCE_LISTING.txt. The text file is about 2 KB, was created on May 10, 2013, and is being submitted electronically via EFS-Web.

FIELD OF THE INVENTION

The invention relates to compounds that bind the glucagon-like peptide 1 (GLP-1) receptor, methods of their synthesis, methods of their therapeutic and/or prophylactic use, and methods of their use in stabilizing GLP-1 receptor in vitro for crystallization of the GLP-1 receptor. Particularly, the invention relates to compounds that are modulators of the GLP-1 receptors and also compounds capable of inducing a stabilizing effect on the receptor for use in structural analyses of the GLP-1 receptor.

BACKGROUND

Glucagon-like peptide 1 receptor (GLP-1R) belongs to Family B1 of the seven-transmembrane G protein-coupled receptors, and its natural agonist ligand is the peptide hormone glucagon-like peptide-1 (GLP-1). GLP-1 is a peptide hormone arising by its alternative enzymatic cleavage from proglucagon, the prohormone precursor for GLP-1, which is highly expressed in enteroendocrine cells of the intestine, the alpha cells of the endocrine pancreas (islets of Langerhans), and the brain (Kieffer T. J. and Habener, J. F. Endocrin. Rev. 20:876-913 (1999); Drucker, D. J., Endocrinology 142:521-7 (2001); Hoist, J. J., Diabetes Metab. Res. Rev. 18:430-41 (2002)). The initial actions of GLP-1 observed were on the insulin-producing cells of the islets, where it stimulates glucose-dependent insulin secretion. Subsequently, multiple additional antidiabetogenic actions of GLP-1 were discovered including the stimulation of the growth and inhibition of the apoptosis of pancreatic beta cells (Drucker, D. J., Endocrinology 144:5145-8 (2003); Holz, G. G. and Chepurny O. G., Curr. Med. Chem. 10:2471-83 (2003); List, J. F. and Habener, J. F., Am. J. Physiol. Endocrinol. Metab. 286:E875-81 (2004)).

On activation, GLP-1 receptors couple to the α subunit of G protein, with subsequent activation of adenylate cyclase and increase of cAMP levels, thereby potentiating glucose-stimulated insulin secretion. Therefore, GLP-1 is an attractive therapeutic to lower blood glucose and preserve the β-cells of the pancreas of diabetic patients. Glucagon has been used for decades in medical practice within diabetes and several glucagon-like peptides are being developed for various therapeutic indications. GLP-1 analogs and derivatives are being developed for the treatment for patients suffering from diabetes.

As it has been well established in the field of protein crystallography that the monodispersity of protein samples is a major determinant of success in crystallization, development of compounds that are capable of maintaining the GLP-1 receptor in a monodisperse, functional state throughout purification, concentration and crystallization trials is a crucial preliminary step in the structural determination effort of the GLP-1 receptor. Disclosed herein are compounds that are capable of inducing such stabilizing effects on the GLP-1 receptor. The compounds of the disclosure are screened for their ability to support structural determination of the GLP-1 receptor to high resolution, thus allowing an additional dimension of diversity in crystallization. The compounds of the disclosure enable drug development through the structural solution of clinically relevant GPCR targets. Structural coordinates can be leveraged as a discovery platform for generating novel chemical leads through virtual ligand screening followed by in vitro screening and chemical optimization of hits for standard drug-like properties and efficacy. In addition, it is well known in the field of structural biology that the initial structural solution of a given target enables subsequent structures with less favorable ligands due to the growth in knowledge and restriction of crystallization space that must be screened.

SUMMARY OF THE INVENTION

The present invention is directed to compounds adapted to act as stabilizers or modulators of GLP-1 receptor; methods of preparation and methods of use, such as in treatment of a malcondition mediated by GLP-1 receptor activation, or when modulation of GLP-1 receptor is medically indicated.

Certain embodiments of the present invention comprise a compound having the structure of Formula I or a pharmaceutically acceptable isomer, enantiomer, racemate, salt, ester, prodrug, hydrate or solvate thereof:

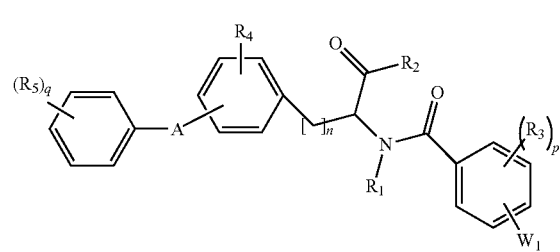

wherein
each $R_1$ can be independently H or $C_{1-4}$ alkyl;
$R_2$ can be —OH, —O—$R_8$, —N($R_1$)—$SO_2$—$R_8$, —N($R_1$)—$(CR_aR_b)_m$—COOH, or —N($R_1$)-tetrazolyl;
each $R_3$ and $R_4$ can be independently H, alkyl, alkoxy, halo, —$NO_2$, —CN, perhaloalkyl, perhaloalkoxy, haloalkyl, alkyl substituted with $R_{31}$, —$OR_{40}$, —$NR_{41}R_{42}$;
each $R_{40}$ can be independently H or alkyl;
each $R_{41}$ and $R_{42}$ can be independently H or alkyl, —$(CH_2)_n$—COO—$R_{40}$, —C(O)—$R_{40}$, aryl, heteroaryl, or two taken together with the N atom to which they are attached can form a 3- to 7-membered heterocyclic ring;
each $R_{31}$ can be independently H, halo, hydroxyl, —$NR_{41}R_{42}$, or alkoxy;
each A can be independently, from the proximal to distal end of the structure of Formula I, —O—, —OC(O)—, —$NR_1$—, —$NR_1$—$CH_2$—, —C(O)$NR_1$—, —N($R_1$)—C(O)—, or —N($R_1$)—S($O_2$)—;
$W_1$ can be null or -$L_1$-$(CR_aR_b)_m$-$L_1$-$R_6$;

each $L_1$ can be independently, from the proximal to distal end of the structure of Formula I, null, A, —C(O)O—, —S(O$_2$)—, —S—, —N(R$_1$)—C(O)—N(R$_1$)—, —N(R$_1$)—C(O)—O—, —C(O)— or —S(O$_2$)—NR$_1$—;

each $R_a$ and $R_b$ can be independently H, alkyl, alkoxy, aralkyl, or two taken together with the carbon to which they are attached form a cycloalkyl;

$R_6$ can be H, alkyl, cycloalkyl, aryl, heteroaryl, heterocyclyl, heterocycloalkyl, any of which may be optionally singly or multiply substituted with $R_7$ or —(CH$_2$)$_m$-L$_2$-(CH$_2$)$_m$—R$_7$;

$R_7$ is H, halo, alkyl, alkoxy, —OH, —CN, —S(O)—R$_8$, —S(O)$_2$—R$_8$, —S(O)$_2$—NR$_1$R$_8$, —NR$_1$—S(O)$_2$—R$_8$, or a ring moiety selected from cycloalkyl, phenyl, aryl, heteroaryl, heterocyclyl, or heterocycloalkyl, where such ring moiety may be optionally singly or multiply substituted with halo, alkyl, alkoxy, perhaloalkyl, perhaloalkoxy, haloalkyl, hydroxy, cyano, —S(O)—R$_8$, —S(O)$_2$—R$_8$, —S(O)$_2$—NR$_1$R$_8$, or —NR$_1$—S(O)$_2$—R$_8$;

$L_2$ can be independently, from the proximal to distal end of the structure of Formula I, null, —O—, —OC(O)—, —NR$_1$—, —C(O)NR$_1$—, —N(R$_1$)—C(O)—, —S(O$_2$)—, —C(O)— or —S(O$_2$)—N(R$_1$)—;

$R_5$ can be $R_7$, —(CH$_2$)$_m$-L$_2$-(CH$_2$)$_m$—R$_7$, or -(-L$_3$-(CR$_a$R$_b$)$_r$)$_s$-L$_3$-R$_7$;

each $L_3$ can be independently null, —O—, or —N(R$_1$)— each $R_8$ can be independently H, C$_{1-7}$ alkyl, cycloalkyl or aryl; each m can be independently 0, 1, 2, 3, 4, 5, or 6;

each n can be independently 0 or 1;

p can be 0, 1, 2, or 3;

q can be 0, 1, 2, or 3;

each r can be independently 2, 3, or 4; and each s can be independently 1, 2, 3, or 4.

In certain embodiments, a pharmaceutical composition comprising a compound of the invention together with at least one pharmaceutically acceptable carrier, diluent or excipient is provided.

In certain embodiments, a method of use of a compound of the invention comprising preparation of a medicament is provided.

In certain embodiments, the invention provides a pharmaceutical combination comprising a compound of the invention and a second medicament is provided. In various embodiments, the second medicament is medically indicated for the treatment of type II diabetes.

In certain embodiments, a method of activation or agonism of a GLP-1 receptor comprising contacting the receptor with a compound of the invention is provided.

In certain embodiments, a method of treatment of a malcondition in a subject for which activation or agonism of a GLP-1 receptor is medically indicated, is provided. In various embodiments, selective activation or agonism of a GLP-1 receptor, is medically indicated. In various embodiments, the malcondition comprises type I diabetes, type II diabetes, gestational diabetes, obesity, excessive appetite, insufficient satiety, or metabolic disorder.

In certain embodiments, the invention provides methods for synthesis of certain compounds including compounds of the invention. In certain other embodiments, the invention provides certain intermediate compounds associated with such methods of synthesis.

In certain embodiments, compounds for enhancing the stabilization of a GLP-1 receptor are provided. In certain embodiments, methods for enhancing the stabilizing of a GLP-1 receptor in structural biology studies are provided through the use of compounds of the invention.

DETAILED DESCRIPTION OF THE INVENTION

Certain embodiments comprise a compound having the chiral structure of Formula I-R or I-S (with the chirality as indicated) or a pharmaceutically acceptable isomer, enantiomer, racemate, salt, ester, prodrug, hydrate or solvate thereof:

I-R

I-S wherein each $R_1$ can be independently H or C$_{1-4}$ alkyl;

$R_2$ can be —OH, —O—R$_8$, —N(R$_1$)—SO$_2$—R$_8$, —N(R$_1$)—(CR$_a$R$_b$)$_m$—COOH, or —N(R$_1$)—tetrazolyl;

each $R_3$ and $R_4$ can be independently H, alkyl, alkoxy, halo, —NO$_2$, —CN, perhaloalkyl, perhaloalkoxy, haloalkyl, alkyl substituted with R$_{31}$, —OR$_{40}$, —NR$_{41}$R$_{42}$;

each $R_{40}$ can be independently H or alkyl;

each $R_{41}$ and $R_{42}$ can be independently H or alkyl, —(CH$_2$)$_n$—COO—R$_{40}$, —C(O)—R$_{40}$, aryl, heteroaryl, or two taken together with the N atom to which they are attached can form a 3- to 7-membered heterocyclic ring;

each $R_{31}$ can be independently H, halo, hydroxyl, —NR$_{41}$R$_{42}$, or alkoxy;

each A can be independently, from the proximal to distal end of the structure of Formula I-R or I-S, —O—, —OC(O)—, —NR$_1$—, —NR$_1$—CH$_2$—, —C(O)NR$_1$—, —N(R$_1$)—C(O)—, or —N(R$_1$)—S(O$_2$)—;

$W_1$ can be null or -L$_1$-(CR$_a$R$_b$)$_m$-L$_1$-R$_6$;

each $L_1$ can be independently, from the proximal to distal end of the structure of Formula I-R or I-S, null, A, —C(O)O—, —S(O$_2$)—, —S—, —N(R$_1$)—C(O)—N(R$_1$)—, —N(R$_1$)—C(O)—O—, —C(O)— or —S(O$_2$)—NR$_1$—;

each $R_a$ and $R_b$ can be independently H, alkyl, alkoxy, aralkyl, or two taken together with the carbon to which they are attached form a cycloalkyl;

$R_6$ can be H, alkyl, cycloalkyl, aryl, heteroaryl, heterocyclyl, heterocycloalkyl, any of which may be optionally singly or multiply substituted with $R_7$ or —(CH$_2$)$_m$-L$_2$-(CH$_2$)$_m$—R$_7$;

$R_7$ is H, halo, alkyl, alkoxy, —OH, —CN, —S(O)—R$_8$, —S(O)$_2$—R$_8$, —S(O)$_2$—NR$_1$R$_8$, —NR$_1$—S(O)$_2$—R$_8$, or a ring moiety selected from cycloalkyl, phenyl, aryl, heteroaryl, heterocyclyl, or heterocycloalkyl, where such ring moiety may be optionally singly or multiply substituted with halo, alkyl, alkoxy, perhaloalkyl, perhaloalkoxy, haloalkyl, hydroxy, cyano, —S(O)—$R_8$, —S(O)$_2$—$R_8$, —S(O)$_2$—$NR_1R_8$, or —$NR_1$—S(O)$_2$—$R_8$;

$L_2$ can be independently, from the proximal to distal end of the structure of Formula I-R or I-S, null, —O—, —OC(O)—, —$NR_1$—, —C(O)$NR_1$—, —N($R_1$)—C(O)—, —S(O$_2$)—, —C(O)— or —S(O$_2$)—N($R_1$)—;

$R_5$ can be $R_7$, —(CH$_2$)$_m$-$L_2$-(CH$_2$)$_m$—$R_7$, or -(-$L_3$-(C$R_aR_b$)$_r$—)$_s$-$L_3$-$R_7$;

each $L_3$ can be independently null, —O—, or —N($R_1$)— each $R_8$ can be independently H, $C_{1-7}$ alkyl, cycloalkyl or aryl;

each m can be independently 0, 1, 2, 3, 4, 5, or 6;

each n can be independently 0 or 1;

p can be 0, 1, 2, or 3;

q can be 0, 1, 2, or 3;

each r can be independently 2, 3, or 4; and each s can be independently 1, 2, 3, or 4.

In certain embodiments, the compounds have the structure of Formula I-R or a pharmaceutically acceptable isomer, enantiomer, salt, ester, prodrug, hydrate or solvate thereof. In other embodiments, the compounds have the structure of Formula I-S or a pharmaceutically acceptable isomer, enantiomer, salt, ester, prodrug, hydrate or solvate thereof.

In certain embodiments, the compounds are substantially enantiomerically pure.

In certain embodiments, the invention provides compounds where $W_1$ can be -$L_1$-(C$R_aR_b$)$_m$-$L_1$-$R_6$. In further embodiments, $W_1$ can be -$L_1$-(C$R_aR_b$)$_m$—$R_6$.

In certain embodiments, the invention provides compounds where $L_1$ can be —O—.

In certain embodiments, $L_1$ can be —C(O)O—. In certain embodiments, $L_1$ can be —S(O$_2$)—. In certain embodiments, $L_1$ can be —S—. $L_1$ is —N($R_1$). In certain embodiments, $L_1$ can be —N($R_1$)—C(O)—N($R_1$)—. In certain embodiments, $L_1$ can be —N($R_1$)—C(O)—. In certain embodiments, $L_1$ can be —S(O$_2$)—N($R_1$)—. In certain embodiments, one of $L_1$ can be —C(O)—, and in certain such embodiments $W_1$ can be —C(O)—$R_6$.

In certain embodiments, the invention provides compounds where $R_1$ can be H.

In certain embodiments, one of $L_1$ can be —O—.

In certain embodiments, the invention provides compounds where both $R_a$ and $R_b$ can be H. In certain embodiments, one of $R_a$ and $R_b$ can be methyl. In certain embodiments, one of $R_a$ and $R_b$ can be methoxy. In certain embodiments, in at least one instance $R_a$ and $R_b$ taken together with the carbon to which they are attached form a cycloalkyl.

In certain embodiments, the invention provides compounds where $R_6$ can be alkyl substituted with $R_7$ and $R_7$ is phenyl or heterocyclyl.

In certain embodiments, the invention provides compounds where $W_1$ can be —NHC(O)—(CH$_2$)$_m$—$L_1$-$R_6$.

In certain embodiments, the invention provides compounds where $R_6$ can be H or alkyl.

In other embodiments, the invention provides compounds where $R_6$ can be cycloalkyl, heterocyclyl, aryl, heteroaryl, or heterocycloalkyl, and any of which may be optionally singly or multiply substituted with alkyl, alkoxy or halo. In certain of such embodiments, $R_6$ is cyclopentyl, cyclohexyl, phenyl, pyridinyl, naphthyl, furanyl, thiophenyl, benzo[b]furanyl, isobenzofuranyl, oxazolyl, isoxazolyl, benzothiazolyl, tetrahydro-2H-pyranyl, pyrazolyl, benzo[b]thiophenyl, benzo[d][1,2,3]thiadiazolyl, quinoxalinyl, quinolinyl, thiazolyl, pyrrolidinyl, pyrrolyl, pyrazolo[1,5-a]pyridinyl, imidazolyl, benzo[d]isoxazolyl, and $R_6$ may be optionally singly or multiply substituted with methyl, methoxy, chloro or fluoro.

In certain embodiments, the invention provides compounds where m can be 0, 1 or 2.

In certain embodiments, the invention provides compounds where $W_1$ can be attached in the para position.

In certain embodiments, the invention provides compounds where $W_1$ can be null.

In certain embodiments, the invention provides compounds where each $R_3$ can be independently H, methyl, ethyl, t-butyl, methoxy, isopropoxy, ethoxy, chloro, fluoro, —CF$_3$, —OCF$_3$, —OCF$_2$H, —CN, or —NO$_2$. In further embodiments, each $R_3$ can be independently H, t-butyl, or methoxy.

In certain embodiments, the invention provides compounds where p can be 1.

In certain embodiments, the invention provides compounds where $R_1$ can be H.

In certain embodiments, the invention provides compounds where $R_2$ can be —OH.

In certain embodiments, the invention provides compounds where $R_4$ can be H.

In other embodiments, the invention provides compounds where $R_4$ can be alkoxy. In certain of such embodiments, $R_4$ can be methoxy.

In certain embodiments, the invention provides compounds where A can be —OC(O)—, —N($R_1$)—S(O$_2$)—, —O—, or —N($R_1$)—C(O)—. In further embodiments, A can be —OC(O)—. In certain embodiments, the invention provides compounds where A can be in the para position.

In certain embodiments, the invention provides compounds where p can be 1.

In certain embodiments, the invention provides compounds where $R_5$ can be alkoxy. In further embodiments, $R_5$ can be heptoxy. In certain embodiments, $R_5$ can be -(-$L_3$-(C$R_aR_b$)$_r$—)$_s$-$L_3$-$R_7$. In certain embodiments, $R_5$ can be -(-$L_3$-(CH$_2$)$_r$—)$_s$-$L_3$-$R_7$. In certain embodiments, each $L_3$ can be the same (e.g., —O—), for example $R_5$ can be —O—(CH$_2$)$_2$—O—(CH$_2$)$_2$—O—CH$_3$; in certain embodiments all $L_3$ are not the same.

In certain embodiments $R_7$ can be a ring moiety selected from cycloalkyl, phenyl, aryl, heteroaryl, heterocyclyl, or heterocycloalkyl, where such ring moiety may be optionally singly or multiply substituted with halo, alkyl, alkoxy, perhaloalkyl, perhaloalkoxy, haloalkyl, hydroxy, or cyano, —S(O)—$R_8$, —S(O)$_2$—$R_8$, —S(O)$_2$—$NR_1R_8$, —$NR_1$—S(O)$_2$—$R_8$.

In certain embodiments $R_8$ can be H, $C_{1-7}$ alkyl, cycloalkyl or aryl; in certain embodiments where $R_8$ is attached to a sulfur atom or an oxygen atom, $R_8$ can be $C_{1-7}$ alkyl, cycloalkyl or aryl.

In certain embodiments, the invention provides compounds where n is 1.

In certain embodiments, the invention provides one or more of compounds 1-334 or a pharmaceutically acceptable isomer, enantiomer, racemate, salt, ester, prodrug, hydrate or solvate thereof. In certain of such embodiments, the invention provides a compound selected from compounds 2, 57, 63, 103, 120, 178, 179, 263 and 273, or a pharmaceutically acceptable isomer, enantiomer, racemate, salt, ester, prodrug, hydrate or solvate thereof.

Certain embodiments comprise a compound having the chiral structure of Formula II-R or II-S (with the chirality as indicated) or a pharmaceutically acceptable isomer, enantiomer, salt, ester, prodrug, hydrate or solvate thereof:

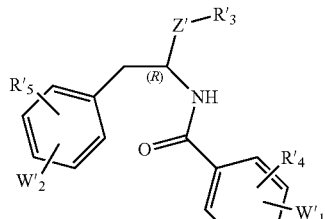

II-R

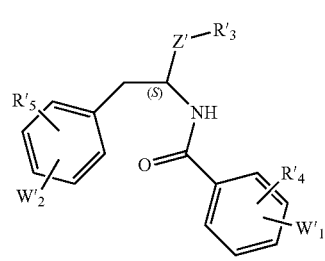

II-S wherein

W'$_1$ can be H, optionally substituted alkyl, —OR'$_{10}$, —(CH$_2$)$_{m'}$—NHCO—R'$_1$, or —(CH$_2$)$_{m'}$—OCO—R'$_1$;

W'$_2$ can be H, optionally substituted alkyl, —OR'$_{20}$, —(CH$_2$)$_{n'}$—NR'$_{21}$R'$_{22}$, —(CH$_2$)$_{n'}$—NHCO—R'$_2$ or —(CH$_2$)$_{n'}$—OCO—R'$_2$;

R'$_1$ can be H, alkyl, alkoxy, alkenyl, alkylamino, cycloalkyl, aryl, heteroaryl, or —(CH$_2$)$_{m'}$—NR'$_{11}$R'$_{12}$, any of which may be optionally substituted;

R'$_2$ can be H, alkyl, alkoxy, alkenyl, alkylamino, cycloalkyl, aryl, heteroaryl, or —(CH$_2$)$_{n'}$—NR'$_{21}$R'$_{22}$, any of which may be optionally substituted;

R'$_3$ can be H, optionally substituted alkyl, —OR'$_{30}$, or —NR'$_{31}$R'$_{32}$;

each R'$_4$ and R'$_5$ can be independently H, optionally substituted alkyl, halogen, perhaloalkyl, —CN, —OR'$_{40}$, —NR'$_{41}$R'$_{42}$;

each R'$_{11}$, R'$_{12}$, R'$_{21}$, R'$_{22}$, R'$_{31}$, R'$_{32}$, R'$_{41}$ and R'$_{42}$ can be independently H or alkyl, aryl, heteroaryl, or together form a 3- to 7-membered ring;

each R'$_{10}$, R'$_{20}$, R'$_{30}$ and R'$_{40}$ can be independently H or alkyl;

Z' can be —C(O) or CH$_2$;

each m' can be independently 0 or 1; and each n' can be independently 0 or 1.

In certain other such embodiments, the invention provides one or more of the following compounds having a structure of Formula II:

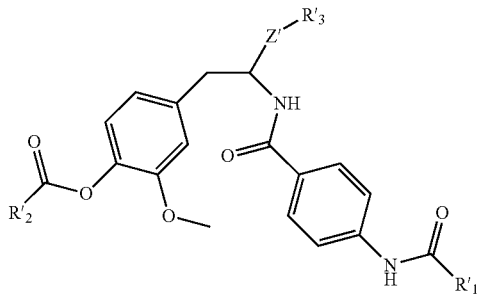

II

TABLE A

| ID | R'$_1$ | R'$_2$ | R'$_3$ | Z' |
|---|---|---|---|---|
| 1-1 | cyclopentyl | 2-thienyl | OH | carbonyl |
| 5-1 | cyclopentyl | 2-thienyl | O-t-butyl | carbonyl |
| 9-1 | cyclopentyl | 2-thienyl | OCH$_3$ | carbonyl |
| 1-2 | tert-butoxyl | 2-thienyl | OH | carbonyl |
| 1-7 | 2-1H-imidazolyl | 2-thienyl | OH | carbonyl |
| 1-3 | cyclopropyl | 2-thienyl | OH | carbonyl |
| 1-4 | cyclobutyl | 2-thienyl | OH | carbonyl |
| 1-5 | CH$_3$ | 2-thienyl | OH | carbonyl |
| 1-6 | 5-1H-imidazol | 2-thienyl | OH | carbonyl |
| 1-8 | 2-thienyl | 2-thienyl | OH | carbonyl |
| 1-9 | phenyl | 2-thienyl | OH | carbonyl |
| 1-10 | 2-methylbut-2-enyl | 2-thienyl | OH | carbonyl |
| 1-11 | cyclopentyl | 2-pyridinyl | OH | carbonyl |
| 1-12 | cyclopentyl | 3-pyridinyl | OH | carbonyl |
| 1-13 | cyclopentyl | 4-pyridinyl | OH | carbonyl |
| 1-14 | cyclopentyl | 5-1H-imidazol | OH | carbonyl |
| 1-15 | cyclopentyl | 3-1H-indole | OH | carbonyl |
| 1-16 | cyclopentyl | phenyl | OH | carbonyl |
| 1-17 | cyclopentyl | 2-hydroxyphenyl | OH | carbonyl |
| 1-18 | cyclopentyl | 3-hydroxyphenyl | OH | carbonyl |
| 1-19 | cyclopentyl | 4-hydroxyphenyl | OH | carbonyl |
| 1-20 | cyclopentyl | 3-thienyl | OH | carbonyl |
| 1-21 | cyclopentyl | methyl-2-thiophene | OH | carbonyl |
| 1-22 | cyclopentyl | 2-1H-imidazol | OH | carbonyl |
| 1-23 | cyclopentyl | cyclopentyl | OH | carbonyl |
| 1-24 | cyclopentyl | CH$_3$ | OH | carbonyl |
| 1-25 | cyclopentyl | methylamine | OH | carbonyl |
| 1-26 | cyclopentyl | methyl-dimethylamino | OH | carbonyl |
| 1-27 | cyclopentyl | 2-thienyl | OH | H |
| 10-1 | cyclohexyl | 2-thienyl | OH | carbonyl |
| 11-1 | cyclohexyl | 2-thienyl | O-t-butyl | carbonyl |
| 12-1 | cyclohexyl | 2-thienyl | OCH$_3$ | carbonyl |
| 10-2 | cyclohexyl | 2-pyridinyl | OH | carbonyl |
| 10-3 | cyclohexyl | 3-pyridinyl | OH | carbonyl |
| 10-4 | cyclohexyl | 4-pyridinyl | OH | carbonyl |
| 10-5 | cyclohexyl | 5-1H-imidazolyl | OH | carbonyl |
| 10-6 | cyclohexyl | 3-1H-indolyl | OH | carbonyl |
| 10-7 | cyclohexyl | phenyl | OH | carbonyl |
| 10-8 | cyclohexyl | 2-hydroxyphenyl | OH | carbonyl |
| 10-9 | cyclohexyl | 3-hydroxyphenyl | OH | carbonyl |
| 10-10 | cyclohexyl | 4-hydroxyphenyl | OH | carbonyl |
| 10-11 | cyclohexyl | 3-thienyl | OH | carbonyl |
| 13-1 | isopropyl | 2-thienyl | OH | carbonyl |
| 14-1 | isopropyl | 2-thienyl | O-t-butyl | carbonyl |
| 15-1 | isopropyl | 2-thienyl | OCH$_3$ | carbonyl |
| 13-2 | isopropyl | 2-pyridinyl | OH | carbonyl |
| 13-3 | isopropyl | 3-pyridinyl | OH | carbonyl |
| 13-4 | isopropyl | 4-pyridinyl | OH | carbonyl |
| 13-5 | isopropyl | 5-1H-imidazolyl | OH | carbonyl |
| 13-6 | isopropyl | 3-1H-indolyl | OH | carbonyl |
| 13-7 | isopropyl | phenyl | OH | carbonyl |
| 13-8 | isopropyl | 2-hydroxyphenyl | OH | carbonyl |
| 13-9 | isopropyl | 3-hydroxyphenyl | OH | carbonyl |
| 13-10 | isopropyl | 4-hydroxyphenyl | OH | carbonyl |
| 13-11 | isopropyl | 3-thienyl | OH | carbonyl |
| 16-1 | 2-thienyl | cyclopentyl | OH | carbonyl |
| 17-1 | 2-thienyl | cyclopentyl | O-t-butyl | carbonyl |
| 18-1 | 2-thienyl | cyclopentyl | OCH$_3$ | carbonyl |
| 16-2 | 2-pyridinyl | cyclopentyl | OH | carbonyl |
| 16-3 | 3-pyridinyl | cyclopentyl | OH | carbonyl |
| 16-4 | 4-pyridinyl | cyclopentyl | OH | carbonyl |
| 16-5 | 5-1H-imidazolyl | cyclopentyl | OH | carbonyl |
| 16-6 | 3-1H-indolyl | cyclopentyl | OH | carbonyl |
| 16-7 | phenyl | cyclopentyl | OH | carbonyl |
| 16-8 | 2-hydroxyphenyl | cyclopentyl | OH | carbonyl |
| 16-9 | 3-hydroxyphenyl | cyclopentyl | OH | carbonyl |
| 16-10 | 4-hydroxyphenyl | cyclopentyl | OH | carbonyl |
| 16-11 | 3-thienyl | cyclopentyl | OH | carbonyl |
| 19-1 | 2-thienyl | cyclohexyl | OH | carbonyl |
| 20-1 | 2-thienyl | cyclohexyl | O-t-butyl | carbonyl |
| 21-1 | 2-thienyl | cyclohexyl | OCH$_3$ | carbonyl |
| 19-2 | 2-pyridinyl | cyclohexyl | OH | carbonyl |
| 19-3 | 3-pyridinyl | cyclohexyl | OH | carbonyl |
| 19-4 | 4-pyridinyl | cyclohexyl | OH | carbonyl |
| 19-5 | 5-1H-imidazolyl | cyclohexyl | OH | carbonyl |
| 19-6 | 3-1H-indolyl | cyclohexyl | OH | carbonyl |
| 19-7 | phenyl | cyclohexyl | OH | carbonyl |

TABLE A-continued

| ID | R'₁ | R'₂ | R'₃ | Z' |
|---|---|---|---|---|
| 19-8 | 2-hydroxyphenyl | cyclohexyl | OH | carbonyl |
| 19-9 | 3-hydroxyphenyl | cyclohexyl | OH | carbonyl |
| 19-10 | 4-hydroxyphenyl | cyclohexyl | OH | carbonyl |
| 19-11 | 3-thienyl | cyclohexyl | OH | carbonyl |
| 22-1 | 2-thienyl | isopropyl | OH | carbonyl |
| 23-1 | 2-thienyl | isopropyl | O-t-butyl | carbonyl |
| 24-1 | 2-thienyl | isopropyl | OCH₃ | carbonyl |
| 22-2 | 2-pyridinyl | isopropyl | OH | carbonyl |
| 22-3 | 3-pyridinyl | isopropyl | OH | carbonyl |
| 22-4 | 4-pyridinyl | isopropyl | OH | carbonyl |
| 22-5 | 5-1H-imidazolyl | isopropyl | OH | carbonyl |
| 22-6 | 3-1H-indolyl | isopropyl | OH | carbonyl |
| 22-7 | phenyl | isopropyl | OH | carbonyl |
| 22-8 | 2-hydroxyphenyl | isopropyl | OH | carbonyl |
| 22-9 | 3-hydroxyphenyl | isopropyl | OH | carbonyl |
| 22-10 | 4-hydroxyphenyl | isopropyl | OH | carbonyl |
| 22-11 | 3-thienyl | isopropyl | OH | carbonyl |

In certain embodiments, the invention provides a pharmaceutical composition comprising a compound of the invention together with at least one pharmaceutically acceptable carrier, diluent or excipient.

In certain embodiments, the invention provides a pharmaceutical composition comprising a compound of the invention and a second medicament. In certain of such embodiments, the second medicament is a peptidic GLP-1 agonist or a DPP-4 inhibitor.

In certain embodiments, the invention provides a method of use of compounds of the invention for preparation of a medicament.

In certain embodiments a method of activation or agonism of a GLP-1 receptor by contacting the receptor with an effective amount of an invention compound. In further embodiments, a method of activation or agonism of a GLP-1 receptor by contacting the receptor with an effective amount of an invention compound is provided, wherein the compound activates or agonizes the GLP-1 receptor to a greater extent than the compound activates or agonizes a GLP-1 receptor. In further embodiments, a method of activation or agonism of a GLP-1 receptor by contacting the receptor with an effective amount of an invention compound is provided, wherein the GLP-1 receptor is disposed within a living mammal.

In certain embodiments, a method is provided for treatment of a malcondition in a subject for which activation or agonism of a GLP-1 receptor is medically indicated, by administering an effective amount of an invention compound to the subject at a frequency and for a duration of time sufficient to provide a beneficial effect to the patient. In yet further embodiments, a method is provided for treatment of a malcondition in a patient for which activation or agonism of a GLP-1 receptor is medically indicated, by administering an effective amount of an invention compound to the patient at a frequency and for a duration of time sufficient to provide a beneficial effect to the patient, wherein the malcondition comprises type I diabetes, type II diabetes, gestational diabetes, obesity, excessive appetite, insufficient satiety, or metabolic disorder.

In certain embodiment, the subject is a patient or a human being. In certain embodiment, the human being is afflicted with, or at risk of developing, a disease or condition selected from the group consisting of type I diabetes, type II diabetes, gestational diabetes, obesity, excessive appetite, insufficient satiety, and metabolic disorder. Preferably said disease is type I diabetes or type II diabetes.

In certain embodiments, methods are provided for use of an invention compound for preparation of a medicament adapted for treatment of a disorder or a malcondition wherein activation or inhibition of a GLP-1 receptor is medically indicated. In certain embodiments, the malcondition comprises type I diabetes, type II diabetes, gestational diabetes, obesity, excessive appetite, insufficient satiety, and metabolic disorder. Preferably said disease is type I diabetes or type II diabetes.

In certain embodiments, the method additionally comprises administering to the subject a second medicament selected from the group of peptidic GLP-1 agonists and DPP-4 inhibitors, wherein such second medicament is either a component of the pharmaceutical composition or a second pharmaceutical composition. In certain of such embodiments, the second medicament can be exenatide or sitagliptin.

In certain embodiments, compounds of the invention may stabilize a GLP-1 receptor, such as, by binding with such receptor and enhancing its thermal stability in connection with the preparation of crystals of such GLP-1 receptor complexed with such stabilizing compound preferably for the preparation of crystals of sufficient quality for use in X-ray diffraction crystallography structure determination for the GLP-1 receptor. The ability of a compound of the invention to enhance the thermal stability of a GLP-1 receptor may be evaluated by a thermal stability assay such as that described herein.

As used in the specification and the appended claims, the singular forms "a," "an" and "the" include plural referents unless the context clearly dictates otherwise.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist."

An "GLP-1 compound" or "GLP-1 agonist" or "GLP-1 activator" or "GLP-1 inhibitor" or "GLP-1 antagonist" as the terms are used herein refer to compounds that interact in some way with the GLP-1 receptor. They can be agonist or activators, or they can be antagonists or inhibitors. An "GLP-1 compound" of the invention can be selective for action of the GLP-1 receptor family.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Substantially enantiomerically pure means a level of enantiomeric enrichment of one enantiomer with respect to the other enantiomer of at least 90%, 95%, 98%, 99%, 99.5% or 99.9%.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the invention in providing therapy to a patient suffering from a disorder or malcondition mediated by GLP-1 refers to the amount of a compound of the invention that is effective to bind to as an agonist or as an antagonist a GLP-1 receptor in the individual's tissues, wherein the GLP-1 is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of GLP-1 activity. A therapeutically effective amount is also one in which any toxic or detrimental effects of compounds of the invention are outweighed by the therapeutically beneficial effects. For example, in the context of treating a malcondition mediated by activation of a GLP-1 receptor, a therapeutically effective amount of a GLP-1 receptor agonist of the invention is an amount sufficient to control the malcondition, to mitigate the progress of the malcondition, or to relieve the symptoms of the malcondition. Examples of malconditions that can be so treated include, but not limited to, type II diabetes.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

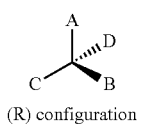

(R) configuration

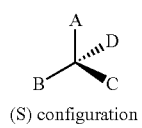

(S) configuration

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Enantiomers are sometimes called optical isomers because a pure enantiomer rotates plane-polarized light in a particular direction. If the light rotates clockwise, then that enantiomer is labeled "(+)" or "d" for dextrorotatory, its counterpart will rotate the light counterclockwise and is labeled "(−)" or "l" for levorotatory.

The terms "racemate" and "racemic mixture" are frequently used interchangeably. A racemate is an equal mixture of two enantiomers. A racemate is labeled "(±)" because it is not optically active (i.e., will not rotate plane-polarized light in either direction since its constituent enantiomers cancel each other out).

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species, example shown below. It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of compounds of the invention which are biologically active in the treatment of cancer or other proliferative disease states.

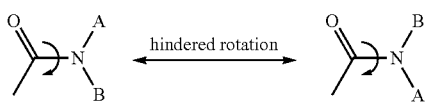

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

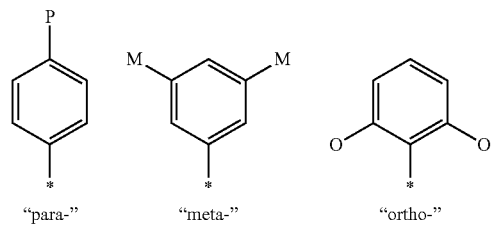

All structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups includes substituted aryl, heterocyclyl and heteroaryl groups. Substituted ring groups can be substituted by one or more substituents at any available ring position. In some embodiments, two substituents on a substituted ring group may taken together with the ring to which they are attached to form a ring, such that the two rings are fused together. For example, benzodioxolyl is a fused ring system formed by two substituents taken together on a phenyl group.

Such substituted ring groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The linking groups (e.g., A, L$_1$ and L$_2$) of Formula I-R or I-S are partial structures which may be represented by a formula, say, for example, —N(R$_1$)—C(O)—, which is read from left-to-right. Accordingly, the nitrogen atom of the —N(R$_1$)—C(O)— linker will be attached to the proximal end of the structure of Formula I-R or I-S, and the carbonyl carbon atom of the —N(R$_1$)—C(O)— linker will be attached to the distal end of the structure of Formula I-R or I-S. In one specific example, where A is —N(R$_1$)—C(O)—, the embodiment of the compound of Formula I-R or I-S will have the following terminus:

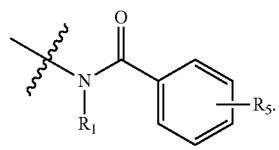

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms, and typically from 1 to 12 carbons (C$_1$-C$_{12}$ alkyl), or, in some embodiments, from 1 to 8 carbon atoms (C$_1$-C$_8$ alkyl), or, in some embodiments, from 1 to 4 carbon atoms (C$_1$-C$_4$ alkyl). Examples of straight chain alkyl groups include, but are not limited to, methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Alkyl groups as used herein may optionally include one or more further substituent groups. Representative substituted alkyl groups can be substituted one or more times with any of the groups listed above, for example, amino, hydroxy, cyano, carboxy, nitro, thio, alkoxy, and halogen groups.

Cycloalkyl groups are alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted one or more times with any of the groups listed above, for example, but not limited to, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_9$, vinyl, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen atom of an alkyl group is replaced with an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms.

The phrase "heterocyclyl group" includes fused ring species including those having fused aromatic and non-aromatic groups. The phrase also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, tetrahydro-2H-pyranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring compounds containing 5 or more ring members, of which, one or more is a heteroatom such as, but not limited to, N, O, and S. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), pyrazolo[1,5-α]pyridinyl, quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), isobenzofuranyl, 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), benzo[d]isoxazolyl, carbazolyl (1-carbazolyl, 2-carbazolyl, 3-carbazolyl, 4-carbazolyl), 5H-dibenz [b,f]azepine (5H-dibenz[b,f]azepin-1-yl, 5H-dibenz[b,f] azepine-2-yl, 5H-dibenz[b,f]azepine-3-yl, 5H-dibenz[b,f] azepine-4-yl, 5H-dibenz[b,f]azepine-5-yl), 10,11-dihydro-5H-dibenz[b,f]azepine (10,11-dihydro-5H-dibenz[b,f] azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f] azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above. Heteroarylalkyl groups can be substituted on the heteroaryl moiety, the alkyl moiety, or both.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or Spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

When two R groups are said to be joined together to form a ring, it is meant that together with the carbon atom or a non-carbon atom (e.g. nitrogen atom), to which they are bonded, they may furthermore form a ring system. In general, they are bonded to one another to form a 3- to 7-membered ring, or a 5- to 7-membered ring. Non-limiting specific examples are the cyclopentyl, cyclohexyl, cycloheptyl, piperidinyl, piperazinyl, pyrrolidinyl, pyrrolyl, pyridinyl.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —$NHR$, —$NR_2$, —$NR_3^+$, wherein each R is independently selected, and protonated forms of each. Accordingly, any compound substituted with an amino group can be viewed as an amine.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —$C(O)NR_2$, and —$NRC(O)R$ groups, respectively. Amide groups therefore include but are not limited to carbamoyl groups (—$C(O)NH_2$) and formamide groups (—$NHC(O)H$). A "carboxamido" group is a group of the formula $C(O)NR_2$, wherein R can be H, alkyl, aryl, etc.

The term "carbonyl," refers to a —$C(O)$— group.

"Halo," "halogen," and "halide" include fluorine, chlorine, bromine and iodine.

The term "perhaloalkyl" refers to an alkyl group where all of the hydrogen atoms are replaced by halogen atoms. Perhaloalkyl groups include, but are not limited to, —$CF_3$ and —$C(CF_3)_3$. The term "haloalkyl" refers to an alkyl group where some but not necessarily all of the hydrogen atoms are replaced by halogen atoms. Haloalkyl groups include but are not limited to —$CHF_2$ and —$CH_2F$.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula I compounds, for example in their purification by recrystallization. All of these salts may be prepared by conventional means from the corresponding compound according to Formula I by reacting, for example, the appropriate acid or base with the compound according to Formula I. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

Compositions and Combination Treatments

The GLP-1 compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g. intravenous, oral, topical, suppository, or parenteral).

In preparing the compositions in oral liquid dosage forms (e.g. suspensions, elixirs and solutions), typical pharmaceutical media, such as water, glycols, oils, alcohols, flavoring agents, preservatives, coloring agents and the like can be employed. Similarly, when preparing oral solid dosage forms (e.g. powders, tablets and capsules), carriers such as starches, sugars, diluents, granulating agents, lubricants, binders, disintegrating agents and the like can be employed.

Another aspect of an embodiment of the invention provides compositions of the compounds of the invention, alone or in combination with another GLP-1 agonist or another type of therapeutic agent, or both. For example, in certain embodiments, such combination includes a peptidic GLP-1 agonist, such as exenatide which is marketed as Byetta® for the treatment of diabetes mellitus type II, or a DPP-4 (dipeptidyl peptidase-4) inhibitor, such as sitagliptin or sitagliptin phosphate which is marketed as Januvia® or an oral antihyperglycemic.

As set forth herein, compounds of the invention include stereoisomers, tautomers, solvates, hydrates, salts including pharmaceutically acceptable salts, and mixtures thereof. Compositions containing a compound of the invention can be prepared by conventional techniques, e.g. as described in Remington: *The Science and Practice of Pharmacy*, 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g., specific enzymatically catalyzed) and non-enzymatic (e.g., general or specific acid or base induced) chemical transfotination of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other GLP-1 modulators and/or ii) one or more other types of therapeutic agents which can be administered orally in the same dosage form, in a separate oral dosage form (e.g., sequentially or non-sequentially) or by injection together or separately (e.g., sequentially or non-sequentially). Examples of combination therapeutic agents include Sitagliptin (MK-0431, Januvia) an oral anti-hyperglycemic (antidiabetic drug) of the dipeptidyl peptidase-4 (DPP-4) inhibitor class and Exenatide (Byetta) an incretin mimetic.

Combinations of the invention include mixtures of compounds from (a) and (b) in a single formulation and compounds from (a) and (b) as separate formulations. Some combinations of the invention can be packaged as separate formulations in a kit. In some embodiments, two or more compounds from (b) are formulated together while a compound of the invention is formulated separately.

The dosages and formulations for the other agents to be employed, where applicable, will be as set out in the latest edition of the *Physicians' Desk Reference*, incorporated herein by reference.

Methods of Treatment

In certain embodiments, the present invention encompasses compounds that bind with high affinity and specificity to the GLP-1 receptor in an agonist manner.

In certain embodiments, the present invention provides a method for activating or agonizing (i.e., to have an agonist effect, to act as an agonist) a GLP-1 receptor, with a compound of the invention. The method involves contacting the receptor with a suitable concentration of an inventive compound to bring about activation of the receptor. The contacting can take place in vitro, for example in carrying out an assay to determine the GLP-1 receptor activation activity of an inventive compound undergoing experimentation related to a submission for regulatory approval.

In certain embodiments, the method for activating an GLP-1 receptor, can also be carried out in vivo, that is, within the living body of a mammal, such as a human patient or a test animal. The inventive compound can be supplied to the living organism via one of the routes as described above, e.g., orally, or can be provided locally within the body tissues. In the presence of the inventive compound, activation of the receptor takes place, and the effect thereof can be studied.

An embodiment of the present invention provides a method of treatment of a malcondition in a patient for which activation of an GLP-1 receptor is medically indicated, wherein the patient is administered the inventive compound in a dosage, at a frequency, and for a duration to produce a beneficial effect on the patient. The inventive compound can be administered by any suitable means, examples of which are described above.

Preparation of Certain Embodiments

General Synthetic Methods for Preparing Compounds

Molecular embodiments of the present invention can be synthesized using standard synthetic techniques known to those of skill in the art. Compounds of the present invention can be synthesized using the general synthetic procedures set forth in Schemes 1-8.

Scheme 1:

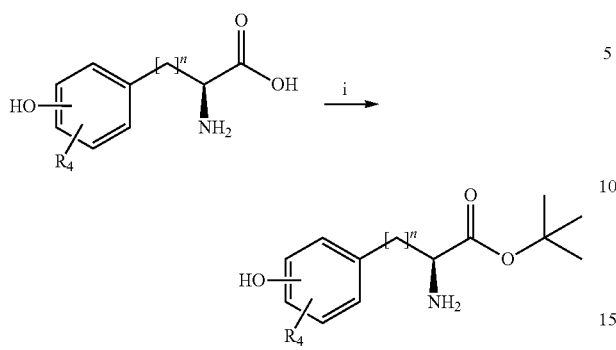

Reagents: (i) tBuOAc, TfOH.

Intermediates containing the (R)-enantiomer of the tert-butyl protected acid were prepared in the same manner as outlined in Scheme 1 using the (R)-enantiomer of the acid in Step (i).

Racemic intermediates were prepared in the same manner as outlined in Scheme 1 using the racemic acid in Step (i).

Scheme 2:

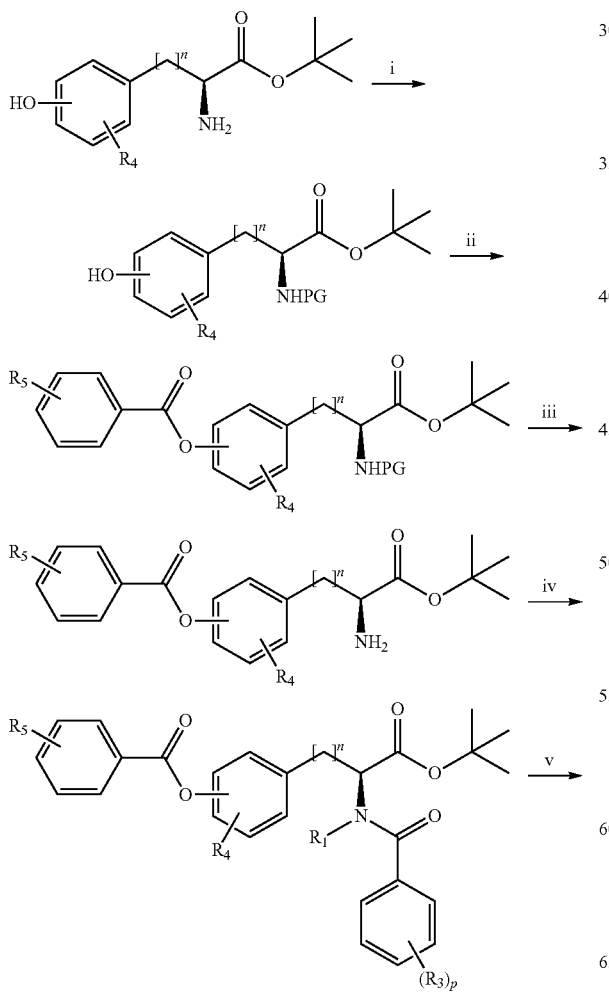

-continued

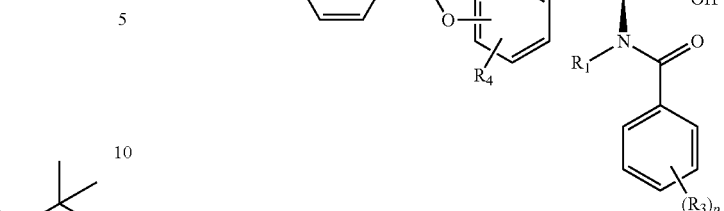

Reagents: (i) PG—Cl, where PG is protecting group e.g., Cbz: Cbz—Cl, NaOH, DCM (ii) $R_5$—Ph—COCl, TEA, DCM (iii) Deprotection e.g., Cbz deprotection: Pd/C, $H_2$, EtOH (iv) (a) where $R_1$ is H: $(R_3)_p$—Ph—COCl, TEA, DCM or $(R_3)_p$—Ph—COOH, EDC, HOBt, DMF or $(R_3)_p$—Ph—COOH, HATU, DMF (b) where $R_1$ is alkyl: $(R_3)_p$—Ph—COCl, TEA, DCM or $(R_3)_p$—Ph—COOH, or $(R_3)_p$—Ph—COOH, HATU, DMF then $R_1$—I or $R_1$—Br, KHMDS, 18-crown-6 (v) TFA, DCM.

Compounds containing the (R)-enantiomer of the acid were prepared in the same manner as outlined in Scheme 2 using the (R)-enantiomer of the tert-butyl protected acid in Step (i).

Racemic compounds were prepared in the same manner as outlined in Scheme 2 using the racemic tert-butyl protected acid in Step (i).

Scheme 3:

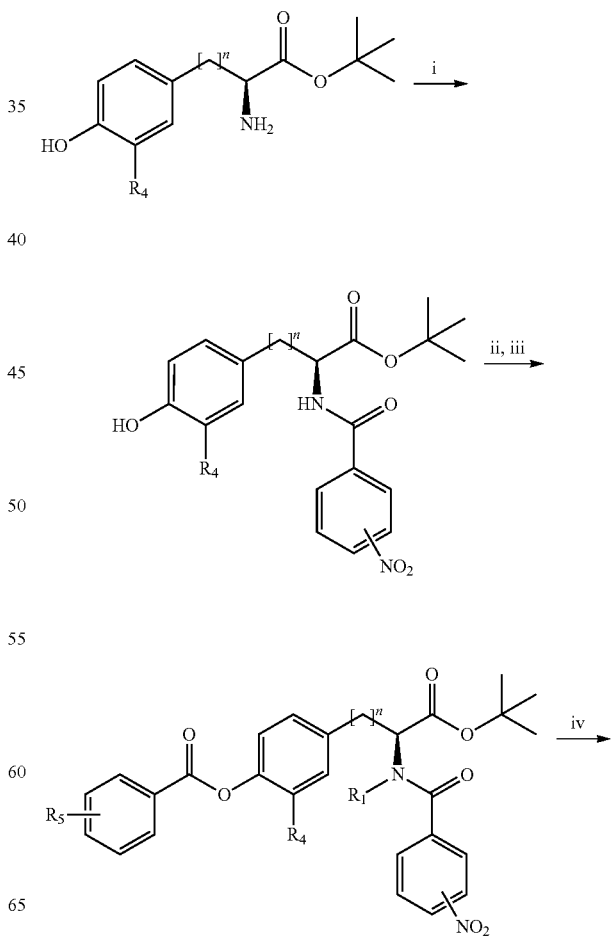

27
-continued

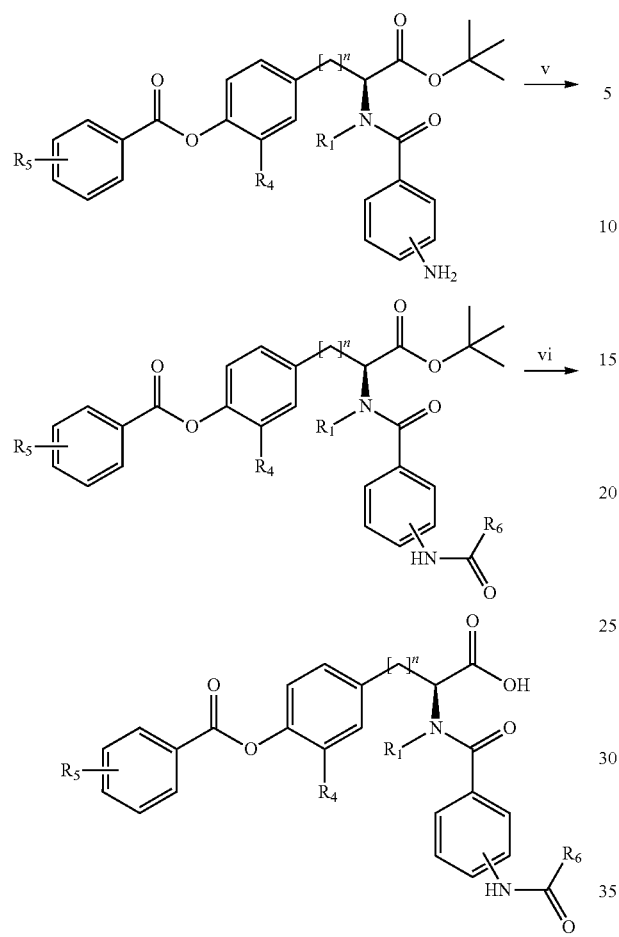

Reagents: (i) nitrobenzoyl chloride, TEA, DCM or nitrobenzoic acid, HATU, DMF (ii) $R_5$—Ph—COCl, TEA, DCM (iii) where $R_1$ is alkyl: NaH, $R_1$—I or $R_1$—Br, DMF (iv) Pd/C, $H_2$, THF (v) $R_6$COCl, TEA, DCM or $R_6$COOH, EDC, HOBt, DMF or $R_6$COOH, HATU, DMF (vi) TFA, DCM.

Compounds containing the (R)-enantiomer of the acid were prepared in the same manner as outlined in Scheme 3 using the (R)-enantiomer of the t-butyl protected acid in Step (i).

Racemic compounds were prepared in the same manner as outlined in Scheme 3 using the racemic tert-butyl protected acid in Step (i).

Scheme 4:

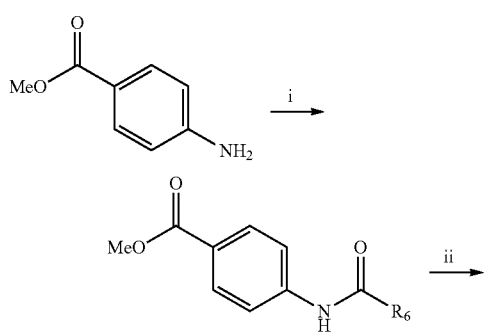

28
-continued

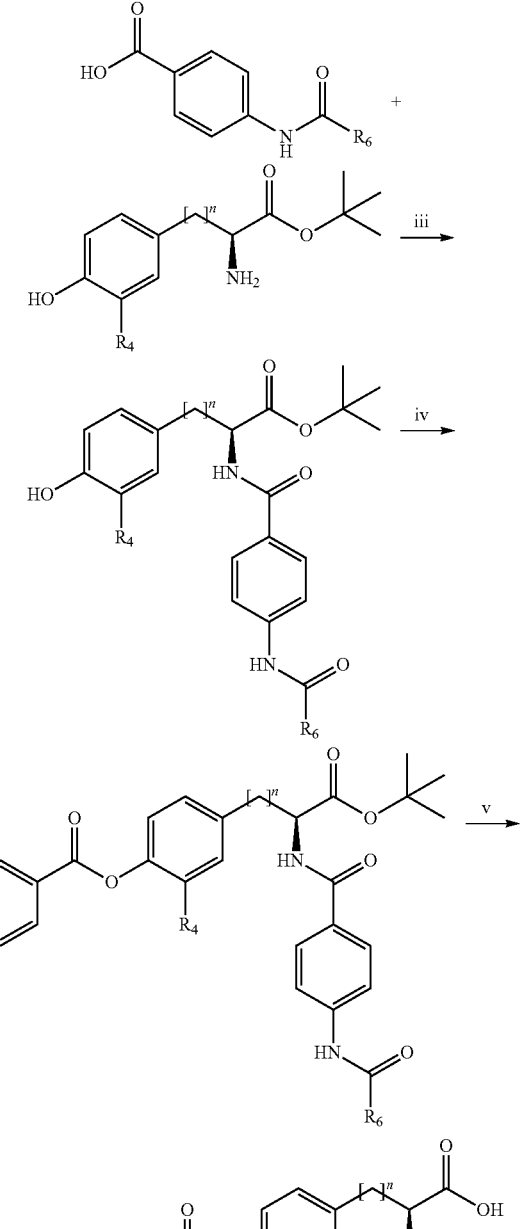

Reagents: (i) $R_6$COCl, DCM, TEA (ii) KOH, MeOH, $H_2O$, 60° C., rt then HCl (iii) EDC, HOBt, DIEA, DMF (iv) $R_5$—Ph—COCl, TEA, DCM or $R_5$—Ph—COOH, DCC, DMAP, DCM (v) TFA, DCM.

Compounds containing the (R)-enantiomer of the acid were prepared in the same manner as outlined in Scheme 4 using the (R)-enantiomer of the tert-butyl protected acid in Step (iii).

Racemic compounds were prepared in the same manner as outlined in Scheme 4 using the racemic tert-butyl protected acid in Step (iii).

Scheme 5:

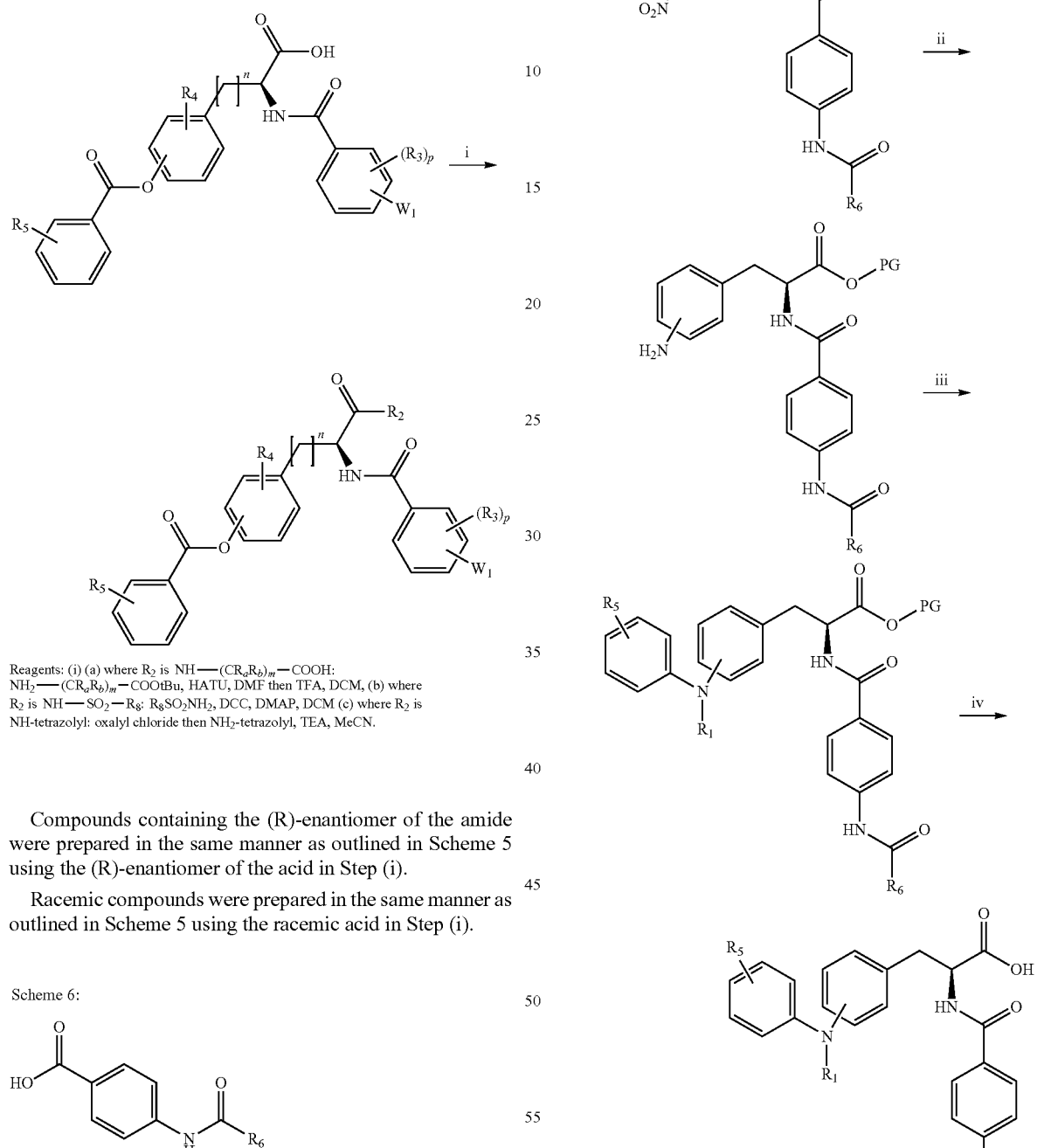

Reagents: (i) (a) where R$_2$ is NH—(CR$_a$R$_b$)$_m$—COOH: NH$_2$—(CR$_a$R$_b$)$_m$—COOtBu, HATU, DMF then TFA, DCM, (b) where R$_2$ is NH—SO$_2$—R$_8$: R$_8$SO$_2$NH$_2$, DCC, DMAP, DCM (c) where R$_2$ is NH-tetrazolyl: oxalyl chloride then NH$_2$-tetrazolyl, TEA, MeCN.

Compounds containing the (R)-enantiomer of the amide were prepared in the same manner as outlined in Scheme 5 using the (R)-enantiomer of the acid in Step (i).

Racemic compounds were prepared in the same manner as outlined in Scheme 5 using the racemic acid in Step (i).

Scheme 6:

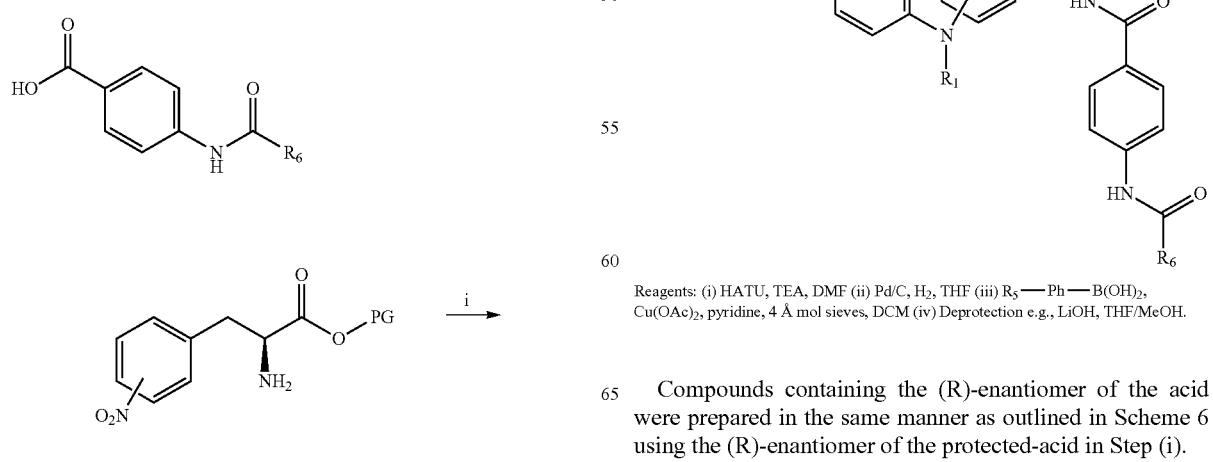

Reagents: (i) HATU, TEA, DMF (ii) Pd/C, H$_2$, THF (iii) R$_5$—Ph—B(OH)$_2$, Cu(OAc)$_2$, pyridine, 4 Å mol sieves, DCM (iv) Deprotection e.g., LiOH, THF/MeOH.

Compounds containing the (R)-enantiomer of the acid were prepared in the same manner as outlined in Scheme 6 using the (R)-enantiomer of the protected-acid in Step (i).

Racemic compounds were prepared in the same manner as outlined in Scheme 6 using the racemic protected-acid in Step (i).

Scheme 7:

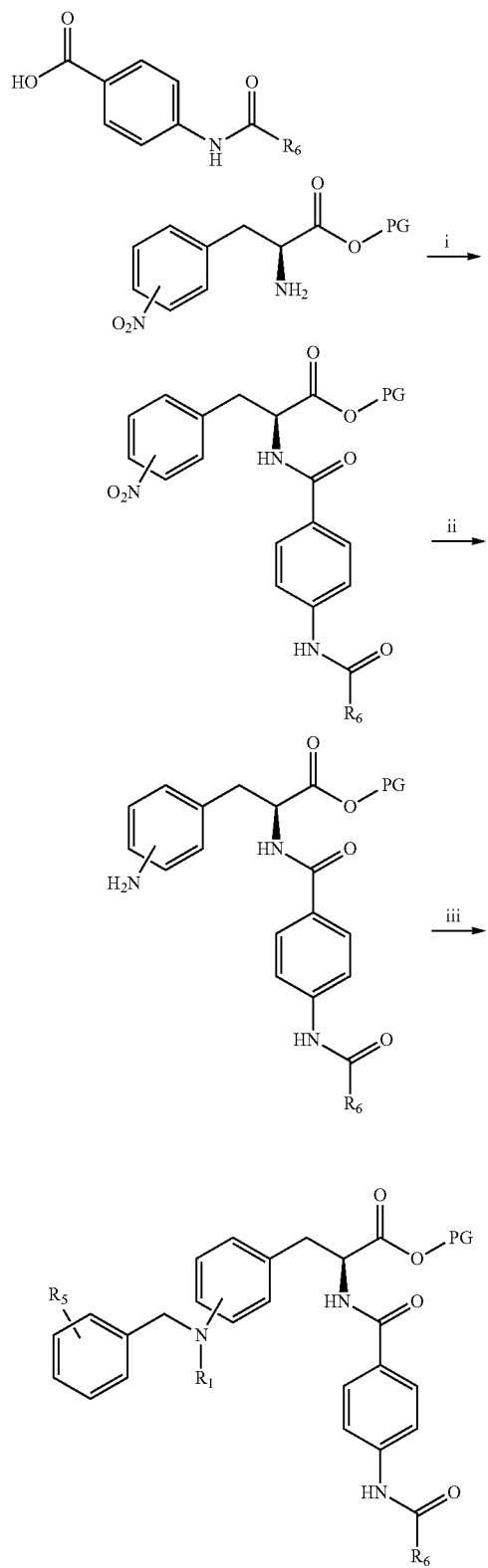

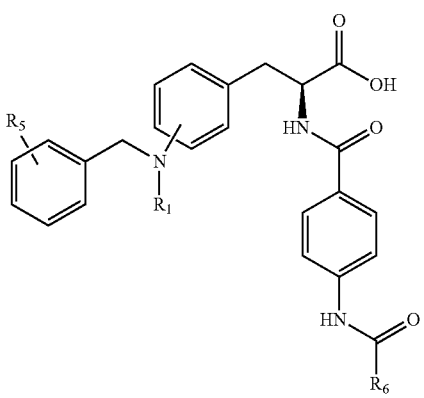

Reagents: (i) HATU, TEA, DMF (ii) Pd/C, H₂, THF (iii) (a) where R₁ is H:
R₅—Ph—CHO, Na(OAc)₃BH, DCM (b) where R₁ is alkyl:
R₅—Ph—CHO, Na(OAc)₃BH, DCM then R₁—I, NaHCO₃, DMF (iv) Deprotection e.g., LiOH, THF/MeOH.

Compounds containing the (R)-enantiomer of the acid were prepared in the same manner as outlined in Scheme 7 using the (R)-enantiomer of the protected-acid in Step (i).

Racemic compounds were prepared in the same manner as outlined in Scheme 7 using the racemic protected-acid in Step (i).

Scheme 8:

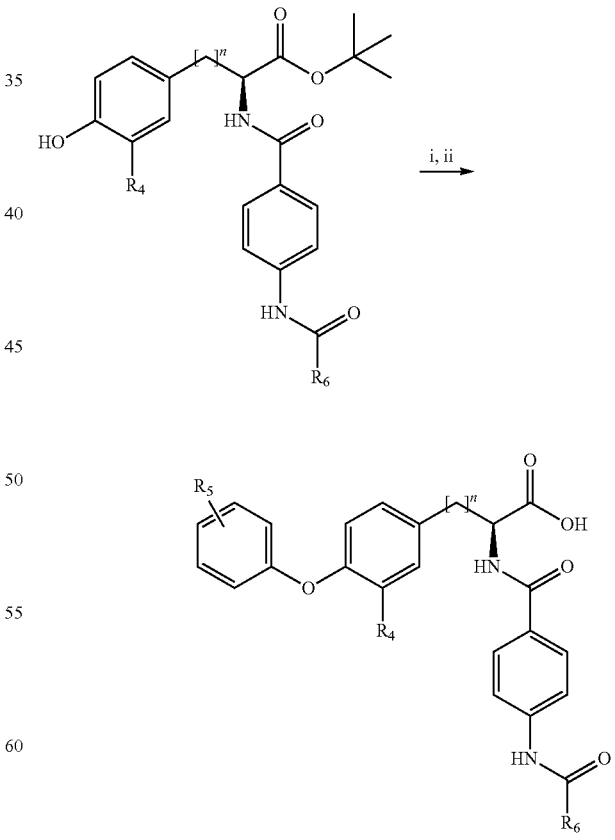

Reagents: (i) R₅—Ph—B(OH)₂, Cu(OAc)₂, pyridine, 4 Å mol sieves, DCM (ii) TFA, DCM.

Compounds containing the (S)-enantiomer of the acid were prepared according to Scheme 8.

Compounds containing the (R)-enantiomer of the acid were prepared in the same manner as outlined in Scheme 8 except instead of using the (R)-enantiomer of the protected-acid in Step (i).

Racemic compounds were prepared in the same manner as outlined in Scheme 8 using the racemic protected-acid in Step (i).

EXAMPLES

The invention is further illustrated by the following examples.

The examples below are non-limiting and are merely representative of various aspects of the invention.

General Methods $^1$H NMR (400 MHz) and $^{13}$C NMR (100 MHz) were obtained in solution of deuterochloroform (CDCl$_3$) or dimethyl sulfoxide-D$_6$ (DMSO). NMR spectra were processed using Mestrec 5.3.0, MestReNova 6.0.3-5604 or MestreNovaLITE 5.2.5-5780. Mass spectra (LCMS) were obtained using one of 4 systems. System 1: Agilent 1100/6110 HPLC system equipped with a Thompson ODS-A, 100 A, 5µ (50× 4.6 mm) column using water with 0.1% formic acid as the mobile phase A, and acetonitrile with 0.1% formic acid as the mobile phase B. Method 1: 20-100% mobile phase B over 2.5 min then held at 100% for 2.5 mins with a flow rate of 1 mL/min. Method 2: 5% mobile phase B for 1 min, 5-95% over 9 min, then held at 95% for 5 min, with a flow rate of 1 mL/min. Method 3: 20-100% mobile phase B over 2.5 min then held at 100% for 4.5 mins with a flow rate of 1 mL/min. System 2: Agilent 1200 LCMS equipped with an Agilent Zorbax Extend RRHT 1.8 µm (4.6×30 mm) column using water with 0.1% formic acid as mobile phase A and acetonitrile with 0.1% formic acid as mobile phase B. Method 4: 5-95% mobile phase B over 3.0 min with a flow rate of 2.5 ml/min, then held at 95% for 0.5 min with an flow rate of 4.5 mL/min. Method 5: 5-95% mobile phase B over 14 min with a flow rate of 2.5 mL/min, then held at 95% for 0.5 min with an flow rate of 4.5 mL/min. System 3: Waters Fractionlynx LCMS system equipped with an Agilent Zorbax Extend RRHT 1.8 µm, (4.6×30 mm) column using water with 0.1% formic acid as mobile phase A and acetonitrile with 0.1% formic acid as mobile phase B. Method 6: 5-95% mobile phase B over 3.0 min with a flow rate of 2.5 ml/min, then held at 95% for 0.5 min with an flow rate of 4.5 mL/min. Method 7: 5-95% mobile phase B over 14 min with a flow rate of 2.5 ml/min, then held at 95% for 0.5 min with an flow rate of 4.5 mL/min. System 4: Agilent 1260 LCMS equipped with an Agilent Zorbax Extend RRHT 1.8 µm (4.6×30 mm) column using water with 0.1% formic acid as mobile phase A and acetonitrile with 0.1% formic acid as mobile phase B. Method 8: 5-95% mobile phase B over 14 min with a flow rate of 2.5 mL/min, then held at 95% for 0.5 min with an flow rate of 4.5 mL/min. Pyridine, dichloromethane (DCM), tetrahydrofuran (THF), and toluene used in the procedures were from Aldrich Sure-Seal bottles or Acros AcroSeal dry solvent and kept under nitrogen (N$_2$). All reactions were stirred magnetically and temperatures are external reaction temperatures. Chromatographies were carried out using either a Combiflash Rf or Combiflash Companion flash purification system (Teledyne Isco) equipped with either Redisep (Teledyne Isco), Telos (Kinesis) or GraceResolv (Grace Davison Discovery Sciences) silica gel (SiO$_2$) columns. Preparative HPLC purifications were done on one of two systems. System 1: Varian ProStar/PrepStar system equipped with a Waters SunFire Prep C18 OBD, 5 µM, 19×150 mm column using water containing 0.05% trifluoroacetic acid as mobile phase A, and acetonitrile with 0.05% trifluoroacetic acid as mobile phase B. The gradient was 40-95% mobile phase B over 10 min, held at 95% for 5-10 min, and then return to 40% over 2 min with flow rate of 18 mL/min. Fractions were collected using a Varian Prostar fraction collector by UV detection at 254 nm and were evaporated using a Savant SpeedVac Plus vacuum pump or a Genevac EZ-2. System 2: Waters Fractionlynx system equipped with an Agilent Prep-C18, 5 µm, 21.2×50 mm column using water containing 0.1% formic acid as mobile phase A, and acetonitrile with 0.1% formic acid as mobile phase B. The gradient was 45-95% mobile phase B over 7.5 min, held at 95% for 1 min, and then returned to 45% over 1.5 min with flow rate of 28 mL/min. Fractions were collected by UV detection at 254 nm or by mass and evaporated using a Genevac EZ-2. Compounds with salt-able centers were presumed to be the trifluoroacetic acid (TFA) or formic acid salts. Hydrogenation reactions were performed using a Thales Nanotechnology H-Cube reactor equipped with the specified CatCart or using standard laboratory techniques. The following abbreviations are used: ethyl acetate (EA), triethylamine (TEA), N-hydroxybenzotriazole (HOBt), 1-ethyl-3-(3-dimethylaminopropyl) carbodiimide hydrochloride (EDC), isopropanol (IPA), N,N-dimethylformamide (DMF), dimethyl acetamide (DMA), Di-tert-butyl dicarbonate (Boc$_2$O), 1,2-dimethoxyethane (DME), N,N-Diisopropylethylamine (DIEA) acetic acid (AcOH), O-(7-azabenzotriazol-1-yl)-N,N,N',N'-tetramethyluronium hexafluorophosphate (HATU), N-methyl morpholine (NMM), 4-dimethylaminopyridine (DMAP), tetrabutylammonium fluoride (TBAF).

Experimental Procedures

General Procedure 1: Preparation of t-Butyl Protected Acids

Finely ground carboxylic acid (1 eq) was added to tert-butyl acetate (0.033 M). The mixture was sonicated to give a suspension. Trifluoromethanesulfonic acid (1.3 eq) was added with stirring and the mixture was stirred overnight. The crude reaction was poured into a mixture of 2N NaOH, brine, ice, and EA and basified to pH 9 with solid K$_2$CO$_3$. The mixture was filtered through celite and extracted with EA. The organics were dried over MgSO$_4$ and concentrated. The product was purified by chromatography.

tert-butyl 2-amino-3-(4-hydroxy-3-methoxyphenyl) propanoate (INT-1)

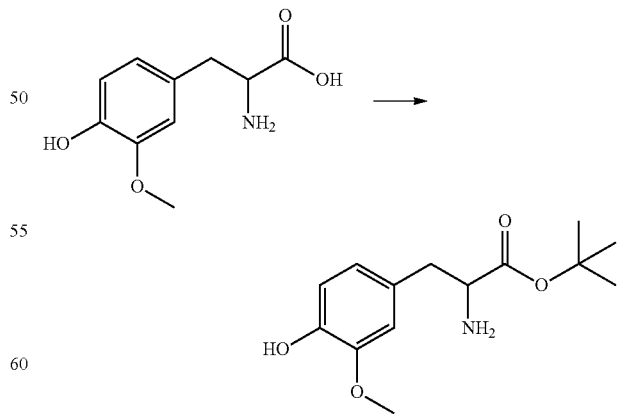

Prepared using General Procedure 1: To tert-butyl acetate (192 ml, 1435 mmol) was added finely ground 2-amino-3-(4-hydroxy-3-methoxyphenyl)propanoic acid (10.1 g, 47.8 mmol). The mixture was sonicated for 10 min to give a suspension. Trifluoromethanesulfonic acid (5.50 ml, 62.2 mmol) was added with stirring and the mixture was stirred overnight. The crude reaction was poured into a mixture of 2N NaOH (150 mL), brine (100 mL), ice (200 mL), and EA (100 mL) and basified to pH 9 with solid $K_2CO_3$. The mixture was filtered through celite and extracted with EA (2×100 mL). The organics were dried over $MgSO_4$ and concentrated. The product residue was purified by chromatography (MeOH/DCM) to afford 4.75 g (37%) of tert-butyl 2-amino-3-(4-hydroxy-3-methoxyphenyl)propanoate INT-1. LCMS-ESI (m/z) calculated for $C_{14}H_{21}NO_4$: 267; found 268 $[M+H]^+$, $t_R$=0.9 min (Method 4). $^1$H NMR (400 MHz, DMSO) δ 8.71 (s, 1H), 6.76-6.71 (d, J=1.9 Hz, 1H), 6.70-6.61 (m, 1H), 6.60-6.53 (m, 1H), 3.75-3.68 (s, 3H), 3.32 (s, 1H), 2.68 (m, 2H), 1.75 (s, 2H), 1.33 (s, 9H).

General Procedure 2: Preparation of Cbz Protected Amines

To a stirred solution of the appropriate amine (1 eq) and a base (either TEA or $NaHCO_3$) (1.5-2.5 eq) in an appropriate solvent (either DCM or THF) (0.35-1.00 M) at 0° C. was treated with benzyl carbonochloridate (1.05-1.20 eq) dropwise over 5 min. The reaction mixture was stirred at room temperature until the reaction was complete. The crude mixture was washed with 1M HCl, dried over $MgSO_4$, and concentrated. The product was purified by chromatography.

Tert-butyl 2-(((benzyloxy)carbonyl)amino)-3-(4-hydroxy-3-methoxyphenyl)propanoate (INT-2)

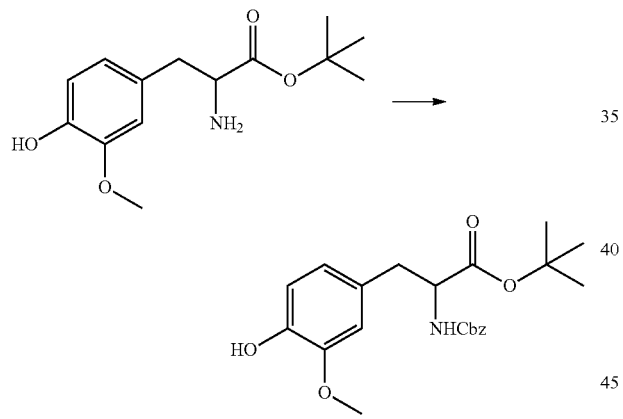

Prepared using General Procedure 2: To a stirred solution of tert-butyl 2-amino-3-(4-hydroxy-3-methoxyphenyl)propanoate INT-1 (5.29 g, 19.8 mmol) and TEA (4.29 mL, 29.7 mmol) in DCM (50 mL) at 0° C. was treated with benzyl carbonochloridate (3.00 mL, 21.1 mmol) dropwise over 5 min. After stirring for 10 min, the mixture was washed with 1M HCl (150 mL), dried over $MgSO_4$, and concentrated. The residue was taken up in MeOH (20 mL) and treated with 2 N NaOH (5 mL). After 10 min, the mixture was acidified and the product was purified by chromatography (EA/hexanes) to afford 4.7 g (59%) of tert-butyl 2-(((benzyloxy)carbonyl) amino)-3-(4-hydroxy-3-methoxyphenyl)propanoate INT-2. LCMS-ESI (m/z) calculated for $C_{22}H_{27}NO_6$: 401; found 424 $[M+Na]^+$, $t_R$=2.47 min (Method 6).

General Procedure 3: Preparation of Aryl Esters via Acid Chlorides

To a stirred solution of the phenol (1 eq) and TEA (1.8-3.0 eq) in DCM (0.23-1.00 M) at 0° C. was added the appropriate acid chloride (1.05 eq) dropwise. Alternatively, acetonitrile (0.5 M) can be used as a co-solvent. The reaction mixture was stirred at room temperature until the reaction was complete. The crude mixture was quenched with saturated aqueous $NaHCO_3$ and water. The organic layer was dried over $MgSO_4$ and concentrated. The product was purified by chromatography.

4-(2-(((benzyloxy)carbonyl)amino)-3-(tert-butoxy)-3-oxopropyl)-2-methoxyphenyl 4-(heptyloxy)benzoate (INT-3)

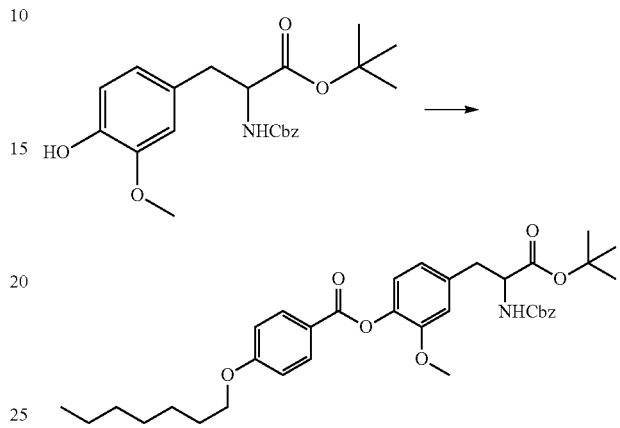

Prepared using General Procedure 3: To a stirred solution of tert-butyl 2-(((benzyloxy)carbonyl)amino)-3-(4-hydroxy-3-methoxyphenyl)propanoate INT-2 (4.7 g, 11.71 mmol) and TEA (3.05 mL, 21.07 mmol) in DCM (50 mL) at 0° C. was added 4-(heptyloxy)benzoyl chloride (2.95 mL, 12.29 mmol) dropwise. After warming to room temperature and stirring for 10 min, the mixture was quenched with saturated aqueous $NaHCO_3$ (50 mL) and water (50 mL). The organic layer was dried over $MgSO_4$ and concentrated. The product was purified by chromatography (EA/hexanes) to afford 5.46 g (75%) of 4-(2-(((benzyloxy)carbonyl)amino)-3-(tert-butoxy)-3-oxopropyl)-2-methoxyphenyl 4-(heptyloxy)benzoate INT-3. LCMS-ESI (m/z) calculated for $C_{36}H_{45}NO_8$: 619; found 564 $[M+H-tBu]^+$, $t_R$=3.22 min (Method 4).

(S)-4-(2-(((benzyloxy)carbonyl)amino)-3-(tert-butoxy)-3-oxopropyl)phenyl 4-(heptyloxy)benzoate (INT-4)

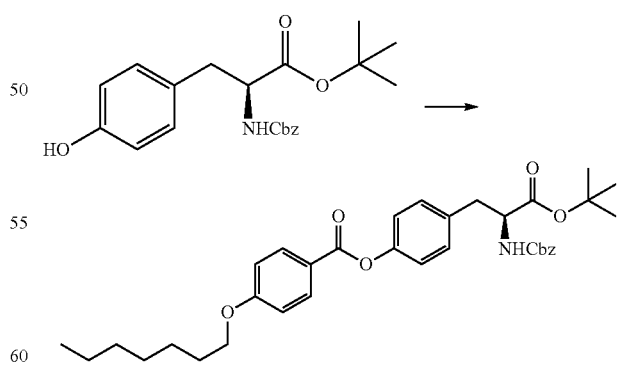

Prepared using General Procedure 3: To a stirred solution of (S)-tert-butyl 2-(((benzyloxy)carbonyl)amino)-3-(4-hydroxyphenyl)propanoate (5.57 g, 15.0 mmol) and TEA (6.27 mL, 45.0 mmol) in DCM (15 mL) and acetonitrile (30 mL) was added 4-(heptyloxy)benzoyl chloride (3.78 mL, 15.75 mmol) dropwise. After stirring overnight, the mixture was quenched with saturated aqueous NaHCO₃ (50 mL). The organic layer was dried over MgSO₄, and concentrated. The product was purified by chromatography (EA/hexanes) to afford 8.19 g (93%) of (S)-4-(2-(((benzyloxy)carbonyl)amino)-3-(tert-butoxy)-3-oxopropyl)phenyl 4-(heptyloxy)benzoate INT-4. LCMS-ESI (m/z) calculated for $C_{35}H_{43}NO_7$: 589; no mass ion observed, $t_R$=5.26 min (Method 3). $^1$H NMR (400 MHz, CDCl₃) δ 8.17-8.08 (m, 2H), 7.41-7.28 (m, 5H), 7.19 (d, J=8.4 Hz, 2H), 7.15-7.07 (m, 2H), 7.01-6.91 (m, 2H), 5.35-5.23 (m, 1H), 5.17-5.04 (m, 2H), 4.54 (dd, J=13.9, 6.1 Hz, 1H), 4.04 (t, J=6.6 Hz, 2H), 3.10 (d, J=5.9 Hz, 2H), 1.91-1.76 (m, 2H), 1.47 (ddd, J=15.2, 8.9, 6.7 Hz, 2H), 1.43-1.36 (m, 10H), 1.36-1.30 (m, 5H), 0.90 (t, J=6.9 Hz, 3H).

General Procedure 4: Deprotection of Cbz and Benzyl Groups

A solution of the Cbz- or benzyl protected amine or alcohol (1 eq) in alcoholic solvent (0.059-0.250 M) and AcOH (2-10 eq) was hydrogenated over Pd/C (5 mol %) using either conventional hydrogenation conditions or an H-cube system. After complete conversion, the catalyst and solvent were removed to give product which was used without purification in subsequent steps.

4-(2-amino-3-(tert-butoxy)-3-oxopropyl)-2-methoxyphenyl 4-(heptyloxy)benzoate (INT-5)

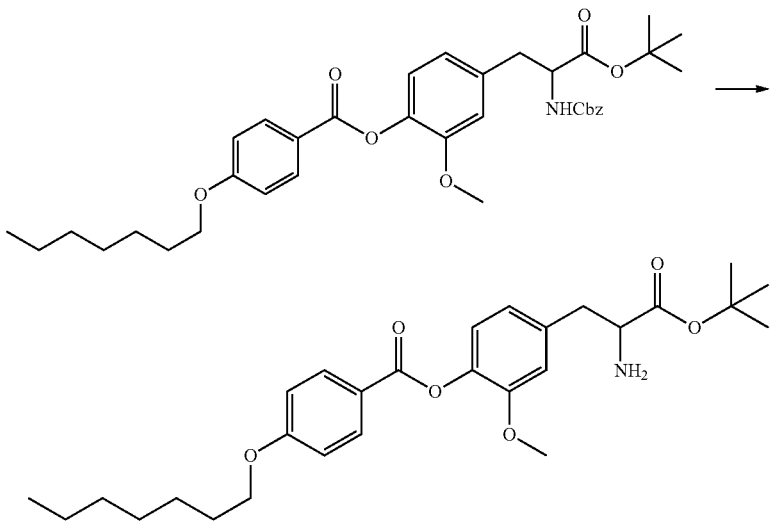

Prepared using General Procedure 4: A solution of 4-(2-(((benzyloxy)carbonyl)amino)-3-(tert-butoxy)-3-oxopropyl)-2-methoxyphenyl 4-(heptyloxy)benzoate INT-3 (5.46 g, 8.81 mmol) and AcOH (5 mL) in MeOH (150 mL) was passed through the H-cube system with 10% Pd/C as a catalyst at 1 mL/min and 45° C. The reaction mixture was evaporated, dissolved in DCM (50 mL), and washed with saturated aqueous NaHCO₃ (200 mL). The organic layer was dried over MgSO₄ and concentrated to afford 3.93 g (92%) of 4-(2-amino-3-(tert-butoxy)-3-oxopropyl)-2-methoxyphenyl 4-(heptyloxy)benzoate INT-5. LCMS-ESI (m/z) calculated for $C_{28}H_{39}NO_6$: 485; found 430 [M+H-tBu]⁺, $t_R$=2.15 min (Method 4). $^1$H NMR (400 MHz, DMSO) δ 8.06-7.99 (m, 2H), 7.12-7.05 (m, 3H), 7.02-6.98 (d, J=1.9 Hz, 1H), 6.85-6.78 (dd, J=8.1, 1.8 Hz, 1H), 4.11-4.03 (t, J=6.5 Hz, 2H), 3.71 (s, 3H), 3.51-3.45 (t, J=6.9 Hz, 1H), 2.87-2.73 (dt, J=16.9, 6.5 Hz, 2H), 1.91 (s, 2H), 1.79-1.69 (p, J=6.8 Hz, 2H), 1.47-1.23 (m, 17H), 0.90-0.83 (m, 3H).

(S)-4-(2-amino-3-(tert-butoxy)-3-oxopropyl)phenyl 4-(heptyloxy)benzoate (INT-6)

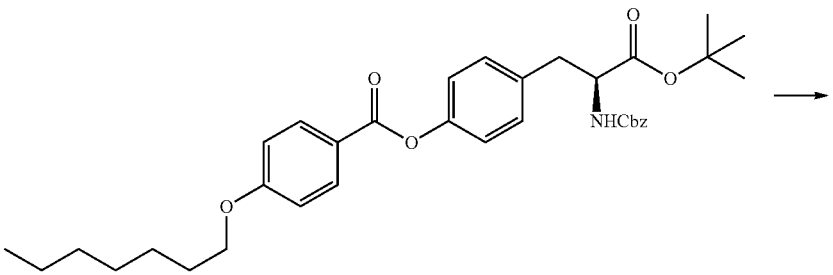

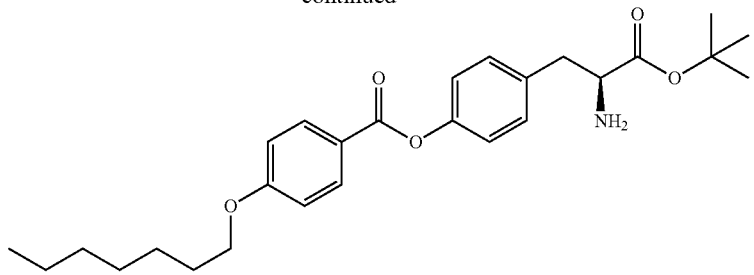

Prepared using General Procedure 4: A solution of 4-(2-(((benzyloxy)carbonyl)amino)-3-(tert-butoxy)-3-oxopropyl)-2-methoxyphenyl 4-(heptyloxy)benzoate INT-4 (4.94 g, 8.38 mmol) and AcOH (0.96 mL) in EtOH (33.5 mL) was degassed under $N_2$ flow. Pd/C (10 wt % 0.45 g, 0.42 mmol) was added and the suspension was degassed under $N_2$ flow. The reaction vessel was flushed with hydrogen gas and the reaction was stirred under an atmosphere of hydrogen for 3 hr. The reaction was diluted with DCM (50 mL) and filtered over celite. The product was concentrated under reduced pressure to give 3.37 g (88%) of (S)-4-(2-amino-3-(tert-butoxy)-3-oxopropyl)phenyl 4-(heptyloxy)benzoate INT-6. LCMS-ESI (m/z) calculated for $C_{27}H_{37}NO_5$: 455; found 478 [M+Na]$^+$, $t_R$=3.11 min (Method 3). $^1$H NMR (400 MHz, CDCl$_3$) δ 8.12 (d, J=8.9 Hz, 2H), 7.28 (d, J=8.5 Hz, 2H), 7.17-7.09 (m, 2H), 7.02-6.91 (m, 2H), 4.04 (t, J=6.6 Hz, 2H), 3.72-3.64 (m, 1H), 3.08 (dd, J=13.7, 5.8 Hz, 1H), 2.92 (dd, J=13.7, 7.6 Hz, 1H), 2.09 (s, 3H), 1.87-1.76 (m, 2H), 1.55-1.46 (m, 1H), 1.44 (s, 9H), 1.41-1.23 (m, 6H), 0.90 (t, J=6.9 Hz, 3H).

General Procedure 5: Preparation of Amides via Acid Chlorides

To a solution of amine (1 eq) and base (either DIEA or TEA) (2 eq) in DCM (0.06-0.30 M) was treated with the appropriate acid chloride (1.0-1.5 eq). The reaction mixture was stirred until the reaction was complete. The reaction was diluted with DCM and washed with saturated aqueous NaHCO$_3$. The organic layer was dried over MgSO$_4$ and concentrated. The product was purified by chromatography. Alternatively, the crude reaction mixture can be carried on to the next step without further purification.

General Procedure 6: Preparation of Amides via Peptide Coupling

A solution of amine (1 eq) and base (either DIEA, TEA or NMM) (2-3 eq) in DMF (0.08-0.10 M) was treated with the appropriate carboxylic acid (1.0-1.5 eq). To this mixture was added HATU (1.05-2.5 eq) or EDC (1.5 eq) and HOBt (1.5 eq). The reaction mixture was stirred until the reaction was complete. The reaction was diluted with EA and washed with saturated aqueous NaHCO$_3$. The organic layer was dried over MgSO$_4$ and concentrated. The product was purified by chromatography. Alternatively, the crude reaction mixture can be carried on to the next step without further purification.

General Procedure 7: Deprotection of t-Butyl Esters to Acids

A solution of the tert-butyl ester (1 eq) in DCM (0.06 M) was treated with TFA (0.16-0.33 M). The reaction mixture was stirred at either room temperature or 30° C. until complete. The solvent was removed and the product was purified by chromatography or preparative HPLC.

Compounds 1-10 were prepared from INT-5 using General Procedures 5 or 6, then 7 sequentially.

3-(4-((4-(heptyloxy)benzoyl)oxy)-3-methoxyphenyl)-2-(4-methoxybenzamido)propanoic acid (Compound 2)

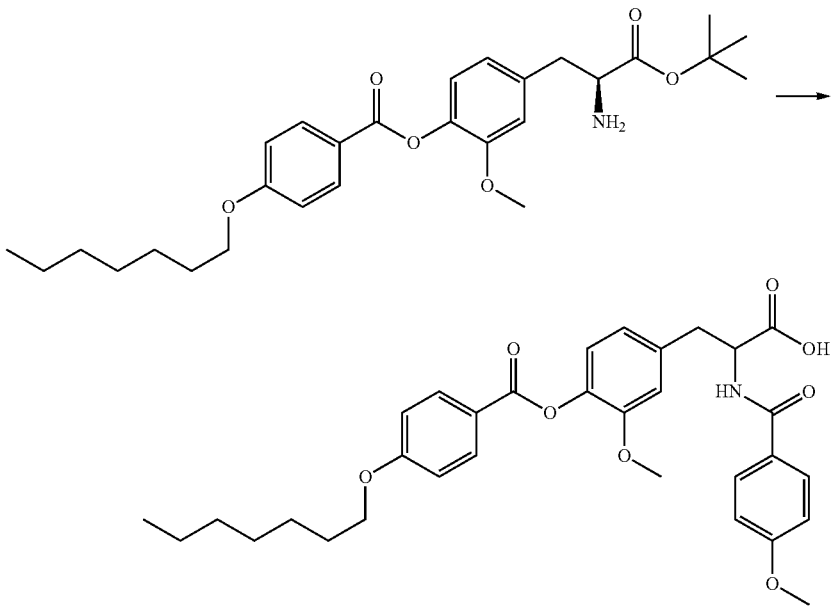

Prepared using General Procedures 5 and 7: To a solution of 4-(2-amino-3-(tert-butoxy)-3-oxopropyl)-2-methoxyphenyl 4-(heptyloxy)benzoate INT-5 (30.0 mg, 0.062 mmol) and TEA (17.2 μL, 0.124 mmol) in DCM (1 mL) was added 4-methoxybenzoyl chloride (15.9 mg, 0.093 mmol). After stirring for 2 h, the solvent was evaporated to give the intermediate tert-butyl ester.

A crude solution of 4-(3-(tert-butoxy)-2-(4-methoxybenzamido)-3-oxopropyl)-2-methoxyphenyl 4-(heptyloxy)benzoate in DCM (1 mL) was treated with TFA (0.1 mL) and stirred overnight at 30° C. The solvent was evaporated and the residue was purified by preparative HPLC to give 16.9 mg (48%) of 3-(4-((4-(heptyloxy)benzoyl)oxy)-3-methoxyphenyl)-2-(4-methoxybenzamido)propanoic acid 2. LCMS-ESI (m/z) calculated for $C_{32}H_{37}NO_8$: 563; found 564 [M+H]$^+$, $t_R$=11.01 min (Method 2). $^1$H NMR (400 MHz, DMSO) δ 12.79 (s, 1H), 8.57 (d, J=8.1 Hz, 1H), 8.00 (d, J=9.0 Hz, 2H), 7.82 (d, J=8.9 Hz, 2H), 7.13 (d, J=1.7 Hz, 1H), 7.11-7.03 (m, 3H), 6.99 (d, J=8.9 Hz, 2H), 6.92 (dd, J=8.1, 1.7 Hz, 1H), 4.61 (ddd, J=10.8, 8.1, 4.4 Hz, 1H), 4.07 (t, J=6.5 Hz, 2H), 3.80 (s, 3H), 3.69 (s, 3H), 3.20 (dd, J=13.8, 4.2 Hz, 1H), 3.08 (dd, J=13.7, 10.7 Hz, 1H), 1.84-1.66 (m, 2H), 1.51-1.17 (m, 8H), 0.87 (t, J=6.9 Hz, 3H).

Compounds 11-61 were prepared from INT-6 using General Procedures 5 or 6, then 7 sequentially.

(S)-2-(4-(tert-butyl)benzamido)-3-(4-((4-(heptyloxy)benzoyl)oxy)phenyl)propanoic acid (Compound 57)

stirring for 3 h, the solvent was evaporated to give the intermediate tert-butyl ester.

A crude solution of (S)-4-(3-(tert-butoxy)-2-(4-(tert-butyl)benzamido)-3-oxopropyl)phenyl 4-(heptyloxy)benzoate in DCM (1 mL) was treated with TFA (0.15 mL) and stirred overnight at 30° C. The solvent was evaporated and the residue was purified by preparative HPLC to give 12.3 mg (33%) of (S)-2-(4-(tert-butyl)benzamido)-3-(4-((4-(heptyloxy)benzoyl)oxy)phenyl)propanoic acid 57. LCMS-ESI (m/z) calculated for $C_{34}H_{41}NO_6$: 559; found 560 [M+H]$^+$, $t_R$=12.14 min (Method 2). $^1$H NMR (400 MHz, DMSO) δ 12.76 (s, 1H), 8.65 (d, J=8.2 Hz, 1H), 8.03 (d, J=8.9 Hz, 2H), 7.75 (d, J=8.6 Hz, 2H), 7.47 (d, J=8.6 Hz, 2H), 7.38 (d, J=8.6 Hz, 2H), 7.15 (d, J=8.5 Hz, 2H), 7.09 (d, J=9.0 Hz, 2H), 4.63 (ddd, J=10.8, 8.2, 4.4 Hz, 1H), 4.07 (t, J=6.5 Hz, 2H), 3.22 (dd, J=13.9, 4.3 Hz, 1H), 3.10 (dd, J=13.8, 10.8 Hz, 1H), 1.81-1.66 (m, 2H), 1.50-1.20 (m, 8H), 1.29 (s, 9H), 0.87 (t, J=6.9 Hz, 3H).

General Procedure 8: Preparation of Secondary Amines via Reductive Amination

A solution of the amine (1 eq) and aldehyde (1.1 eq) in DCM (0.03-0.16 M) was stirred in the presence or absence of AcOH (1 eq). To this mixture was added sodium triacetoxyborohydride (2 eq) or sodium borohydride (2 eq). The reaction mixture was stirred at room temperature until complete. The reaction was diluted with DCM and washed with saturated aqueous NaHCO$_3$. The organic layer was dried over

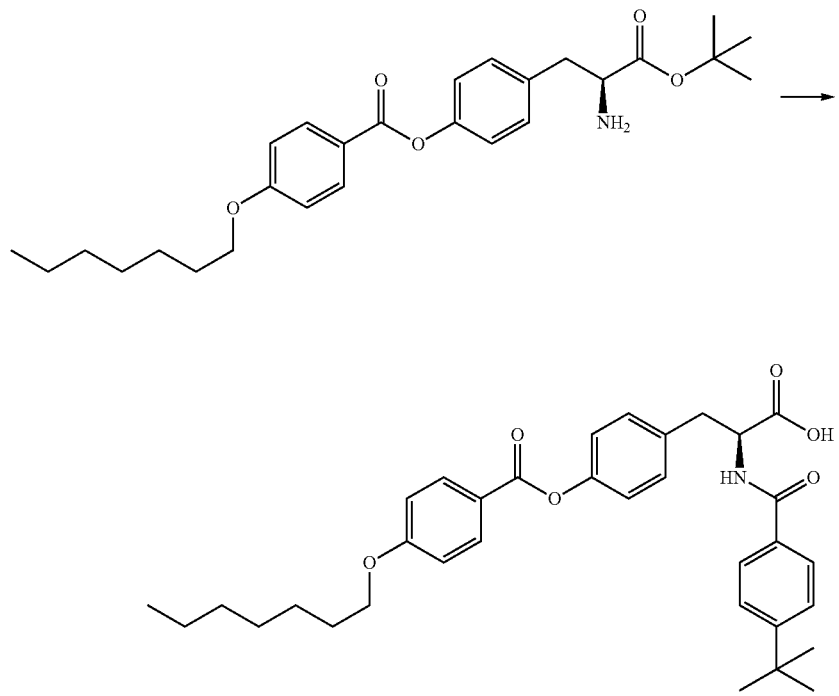

Prepared using General Procedures 5 and 7: To a solution of (S)-4-(2-amino-3-(tert-butoxy)-3-oxopropyl)phenyl 4-(heptyloxy)benzoate INT-6 (30.0 mg, 0.066 mmol) and DIEA (22 μL, 0.132 mmol) in DCM (1 mL) was added 4-(tert-butyl)benzoyl chloride (15.9 mg, 0.093 mmol). After MgSO$_4$ and concentrated. The product was purified by chromatography. Alternatively, the crude reaction mixture can be carried on to the next step without further purification.

Compounds 62 was prepared from (R)-tert-butyl 2-amino-3-(4-hydroxyphenyl)propanoate using General Procedures 6, 3, and 7 sequentially.

(S)-2-(4-(tert-butyl)benzamido)-3-(4-((4-(heptyloxy)benzoyl)oxy)phenyl)propanoic acid (Compound 63)

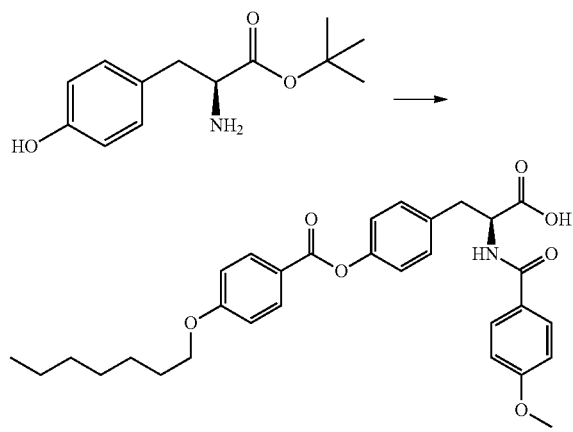

Prepared using General Procedures 6, 3, and 7: LCMS-ESI (m/z) calculated for $C_{31}H_{35}NO_7$: 533; found 534 $[M+H]^+$, $t_R$=11.20 min (Method 2). $^1$H NMR (400 MHz, DMSO) δ 12.76 (s, 1H), 8.59 (d, J=8.2 Hz, 1H), 8.02 (d, J=8.9 Hz, 2H), 7.80 (d, J=8.9 Hz, 2H), 7.38 (d, J=8.6 Hz, 2H), 7.14 (d, J=8.5 Hz, 2H), 7.09 (d, J=9.0 Hz, 2H), 6.99 (d, J=8.9 Hz, 2H), 4.61 (ddd, J=10.7, 8.2, 4.5 Hz, 1H), 4.07 (t, J=6.5 Hz, 2H), 3.80 (s, 3H), 3.20 (dd, J=13.9, 4.3 Hz, 1H), 3.09 (dd, J=13.8, 10.8 Hz, 1H), 1.80-1.65 (m, 2H), 1.51-1.18 (m, 8H), 0.87 (t, J=6.9 Hz, 3H).

Tert-butyl 3-(4-hydroxy-3-methoxyphenyl)-2-(4-nitrobenzamido)propanoate (INT-7)

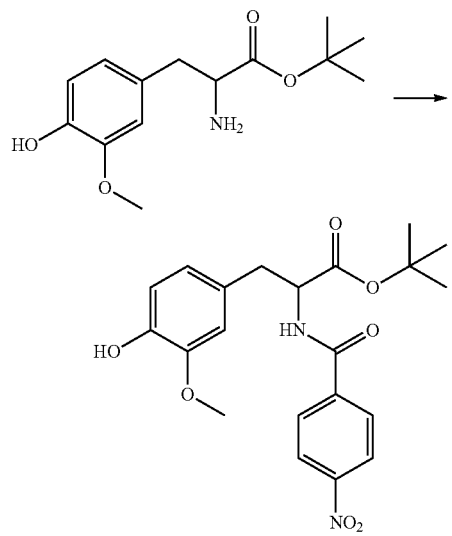

Prepared using General Procedure 5: To a stirred solution of tert-butyl 2-amino-3-(4-hydroxy-3-methoxyphenyl)propanoate INT-1 (1.85 g, 6.93 mmol) and TEA (1.93 mL, 13.9 mmol) in DCM (15 mL) at 0° C. was added 4-nitrobenzoyl chloride (1.29 g, 6.93 mmol) in DCM (10 mL) dropwise. The reaction mixture was stirred for 1 h, diluted with DCM (100 mL) and washed with saturated aqueous NaHCO$_3$ (100 mL). The organic layer was dried over MgSO$_4$, and concentrated. The product was purified by chromatography (EA/hexanes) to afford 1.38 g (44%) of tert-butyl 3-(4-hydroxy-3-methoxyphenyl)-2-(4-nitrobenzamido)propanoate INT-7. LCMS-ESI (m/z) calculated for $C_{21}H_{24}N_2O_7$: 416; found 415 $[M-H]^-$, $t_R$=2.18 min (Method 4).

4-(3-(tert-butoxy)-2-(4-nitrobenzamido)-3-oxopropyl)-2-methoxyphenyl 4-(heptyloxy)benzoate (INT-8)

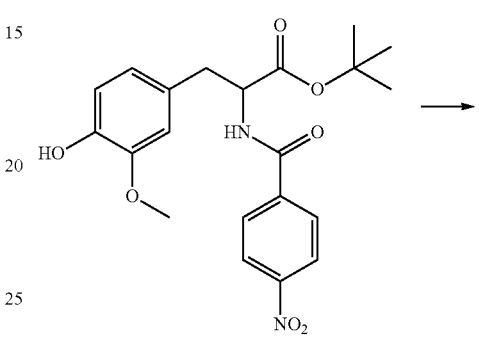

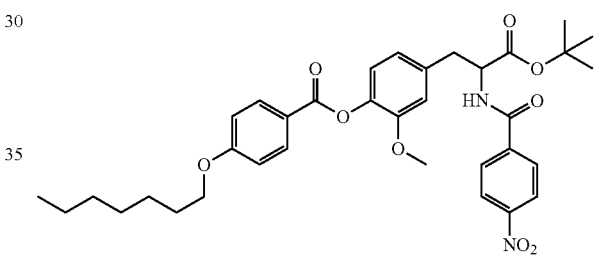

Prepared using General Procedure 3: To a stirred solution of tert-butyl 3-(4-hydroxy-3-methoxyphenyl)-2-(4-nitrobenzamido)propanoate INT-7 (1.34 g, 3.05 mmol) and TEA (1.28 mL, 9.15 mmol) in DCM (8 mL) at 0° C. was added 4-(heptyloxy)benzoyl chloride (0.81 mL, 3.36 mmol) dropwise. After warming to room temperature and stirring for 1 h, the mixture was quenched with saturated aqueous NaHCO$_3$ (100 mL) and diluted with DCM (100 mL). The organic layer was dried over MgSO$_4$ and concentrated. The product was purified by chromatography (EA/hexanes) to afford 1.70 g (86%) of 4-(3-(tert-butoxy)-2-(4-nitrobenzamido)-3-oxopropyl)-2-methoxyphenyl 4-(heptyloxy)benzoate INT-8. LCMS-ESI (m/z) calculated for $C_{35}H_{42}N_2O_9$: 634; no mass ion observed, $t_R$=3.26 min (Method 4).

General Procedure 9: Reduction of Aryl Nitro to an Aryl Amine

A solution of an aromatic nitro (1 eq) in THF (0.9 M) was reacted over Pd/C (5-6 mol %) under hydrogen atmosphere until the reaction was complete. The catalyst was removed by filtration and the material was purified by chromatography.

4-(2-(4-aminobenzamido)-3-(tert-butoxy)-3-oxopropyl)-2-methoxyphenyl 4-(heptyloxy)benzoate (INT-9)

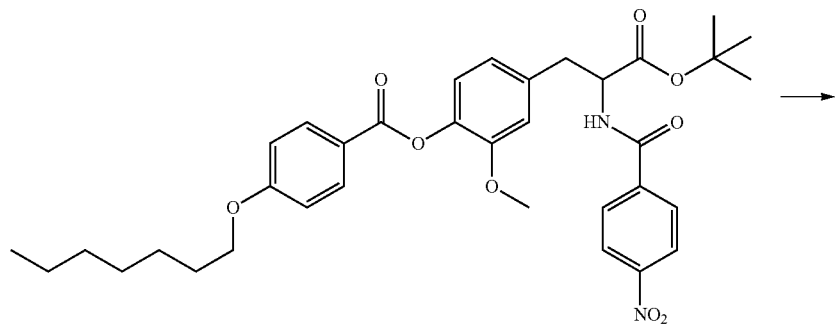

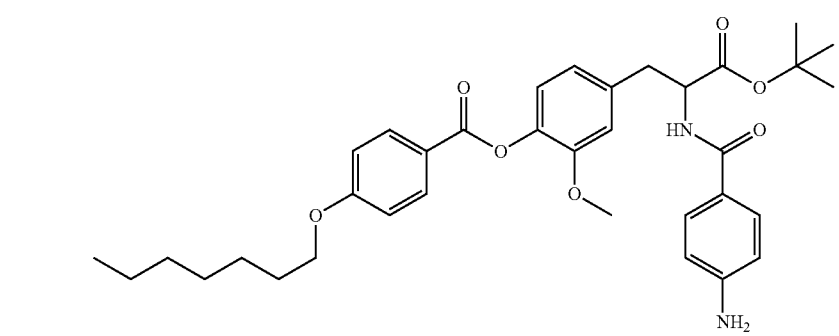

Prepared using General Procedure 9: A stirred solution of 4-(3-(tert-butoxy)-2-(4-nitrobenzamido)-3-oxopropyl)-2-methoxyphenyl 4-(heptyloxy)benzoate INT-8 (1.70 g, 2.68 mmol) in THF (30 mL) was degassed under $N_2$ flow. Pd/C (10 wt % 0.17 g, 0.16 mmol) was added and the suspension was degassed under $N_2$ flow. The reaction vessel was flushed with hydrogen gas and the reaction was stirred under an atmosphere of hydrogen overnight. The reaction was diluted with THF (10 mL) and filtered over celite. The material was concentrated and purified by chromatography (EA/hexanes) to afford 1.20 g (73%) of 4-(2-(4-aminobenzamido)-3-(tert-butoxy)-3-oxopropyl)-2-methoxyphenyl 4-(heptyloxy)benzoate INT-9. LCMS-ESI (m/z) calculated for $C_{35}H_{44}N_2O_7$: 604; found 605 [M+H]$^+$, $t_R$=3.15 min (Method 4). $^1$H NMR (400 MHz, DMSO) δ 8.24-8.18 (d, J=7.8 Hz, 1H), 8.05-7.94 (m, 2H), 7.61-7.52 (m, 2H), 7.13-7.04 (m, 4H), 6.93-6.85 (m, 1H), 6.57-6.48 (m, 2H), 5.65 (s, 2H), 4.58-4.50 (m, 1H), 4.12-4.03 (t, J=6.5 Hz, 2H), 3.71 (s, 3H), 3.16-3.03 (m, 2H), 1.79-1.69 (m, 2H), 1.47-1.23 (m, 17H), 0.90-0.82 (m, 3H).

Compounds 64-130 were prepared from INT-9 using General Procedures 5 or 6, then 7 sequentially.

2-(4-(2-(benzyloxy)acetamido)benzamido)-3-(4-((4-(heptyloxy)benzoyl)oxy)-3-methoxyphenyl)propanoic acid (Compound 103)

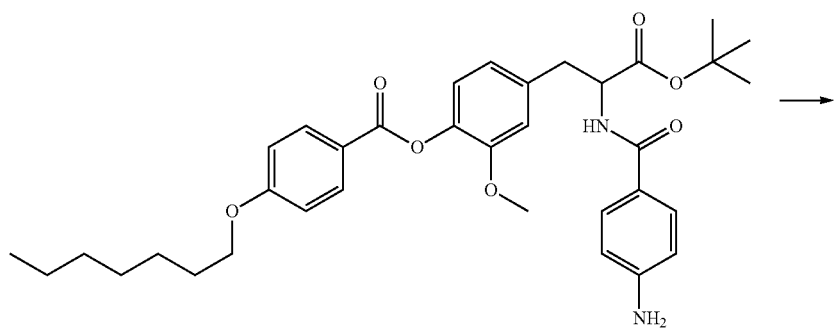

-continued

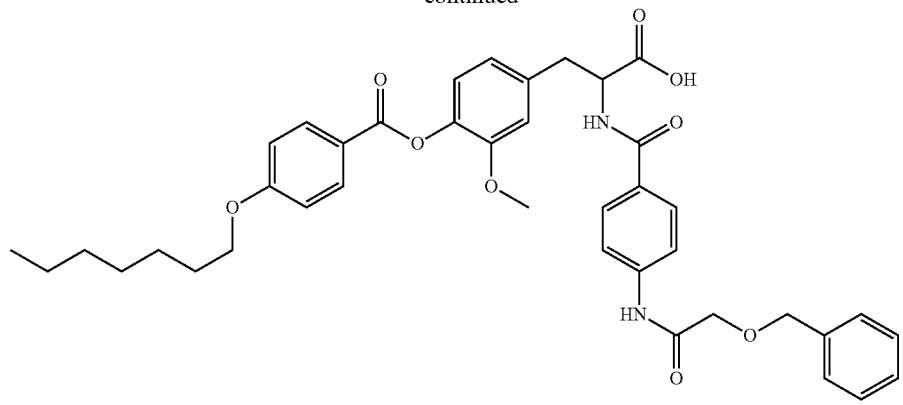

Prepared using General Procedures 6 and 7: To a solution of 4-(2-(4-aminobenzamido)-3-(tert-butoxy)-3-oxopropyl)-2-methoxyphenyl 4-(heptyloxy)benzoate INT-9 (100 mg, 0.165 mmol) and DMA (92 μL, 0.50 mmol) in DMF (2 mL) was added HATU (157 mg, 0.413 mmol). After stirring for 2 h, the mixture was quenched with saturated aqueous NaHCO$_3$ (20 mL) and diluted with EA (20 mL). The organic layer was dried over MgSO$_4$ and concentrated. The intermediate tert-butyl ester was purified by chromatography (EA/hexanes).

The tert-butyl ester was dissolved in DCM (2 mL) and treated with TFA (2 mL). The reaction was stirred at room temperature for 3 h. The solvent was evaporated to provide 103 mg (85%) of 2-(4-(2-(benzyloxy)acetamido)benzamido)-3-(4-((4-(heptyloxy)benzoyl)oxy)-3-methoxyphenyl)propanoic acid 103. LCMS-ESI (m/z) calculated for C$_{40}$H$_{44}$N$_2$O$_9$: 696; no mass ion observed, t$_R$=9.86 min (Method 5). $^1$H NMR (400 MHz, DMSO) δ 12.77 (s, 1H), 10.04 (s, 1H), 8.67-8.59 (d, J=8.1 Hz, 1H), 8.04-7.96 (m, 2H), 7.84-7.77 (m, 2H), 7.76-7.67 (m, 2H), 7.44-7.27 (m, 5H), 7.17-7.11 (d, J=1.9 Hz, 1H), 7.11-7.04 (m, 3H), 6.96-6.89 (dd, J=8.2, 1.8 Hz, 1H), 4.68-4.59 (m, 3H), 4.12 (s, 2H), 4.10-4.04 (t, J=6.5 Hz, 2H), 3.70 (s, 3H), 3.25-3.17 (dd, J=14.1, 4.3 Hz, 1H), 3.13-3.04 (dd, J=13.8, 10.7 Hz, 1H), 1.78-1.70 (m, 2H), 1.46-1.22 (m, 8H), 0.90-0.83 (t, J=6.6 Hz, 3H).

3-(4-((4-(heptyloxy)benzoyl)oxy)-3-methoxyphenyl)-2-(4-(2-(4-methoxyphenyl)acetamido)benzamido)propanoic acid (Compound 120)

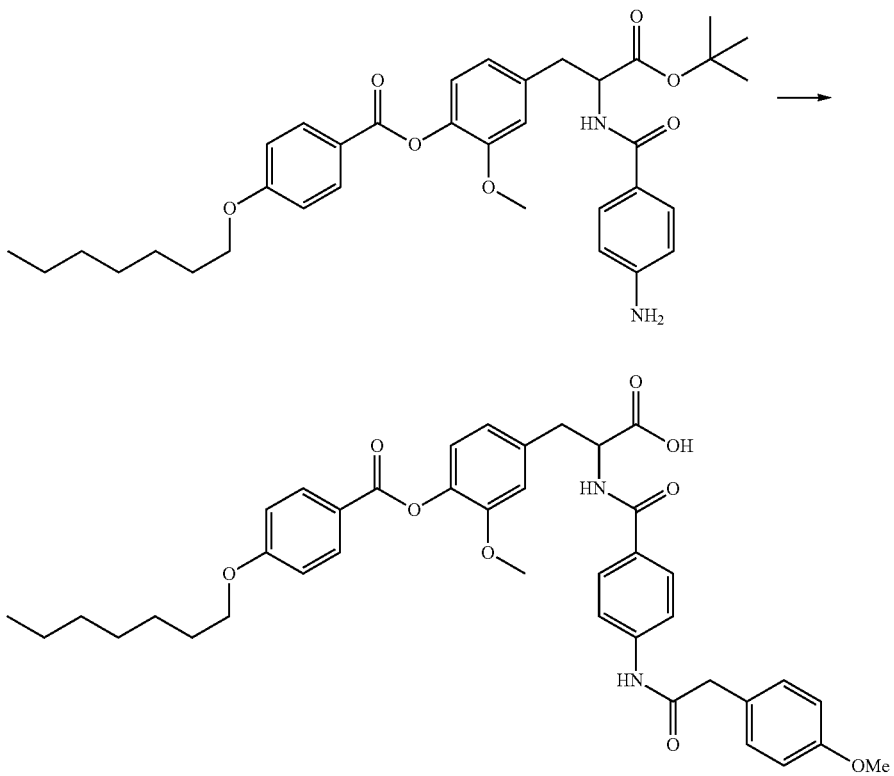

Prepared using General Procedures 6 and 7: LCMS-ESI (m/z) calculated for $C_{40}H_{44}N_2O_9$: 696; no mass ion observed, $t_R$=9.49 min (Method 5). $^1$H NMR (400 MHz, DMSO) δ 12.72 (s, 1H), 10.32 (s, 1H), 8.64-8.54 (d, J=8.2 Hz, 1H), 8.06-7.95 (m, 2H), 7.85-7.75 (m, 2H), 7.69-7.62 (m, 2H), 7.29-7.22 (m, 2H), 7.16-7.03 (m, 4H), 6.95-6.85 (m, 3H), 4.67-4.59 (m, 1H), 4.10-4.02 (t, J=6.5 Hz, 2H), 3.72 (s, 3H), 3.69 (s, 3H), 3.58 (s, 2H), 3.24-3.17 (m, 1H), 3.13-3.02 (dd, J=13.9, 10.6 Hz, 1H), 1.78-1.70 (p, J=6.7 Hz, 2H), 1.46-1.25 (m, 8H), 0.92-0.83 (t, J=6.7 Hz, 3H).

General Procedure 10: Preparation of Ureas

A solution of the aryl amine (1 eq) in DCM (0.06-0.20 M) was treated with isocyanate (1.1 eq). The reaction mixture was stirred at room temperature until complete. The reaction was diluted with DCM and washed with saturated aqueous NaHCO$_3$. The organic layer was dried over MgSO$_4$ and concentrated. The product was purified by chromatography. Alternatively, the crude reaction mixture can be carried on to the next step without further purification.

Compounds 131-132 were prepared from INT-9 using General Procedures 10 and 7 sequentially.

3-(4-((4-(heptyloxy)benzoyl)oxy)-3-methoxyphenyl)-2-(4-(3-phenylureido)benzamido)propanoic acid (Compound 131)

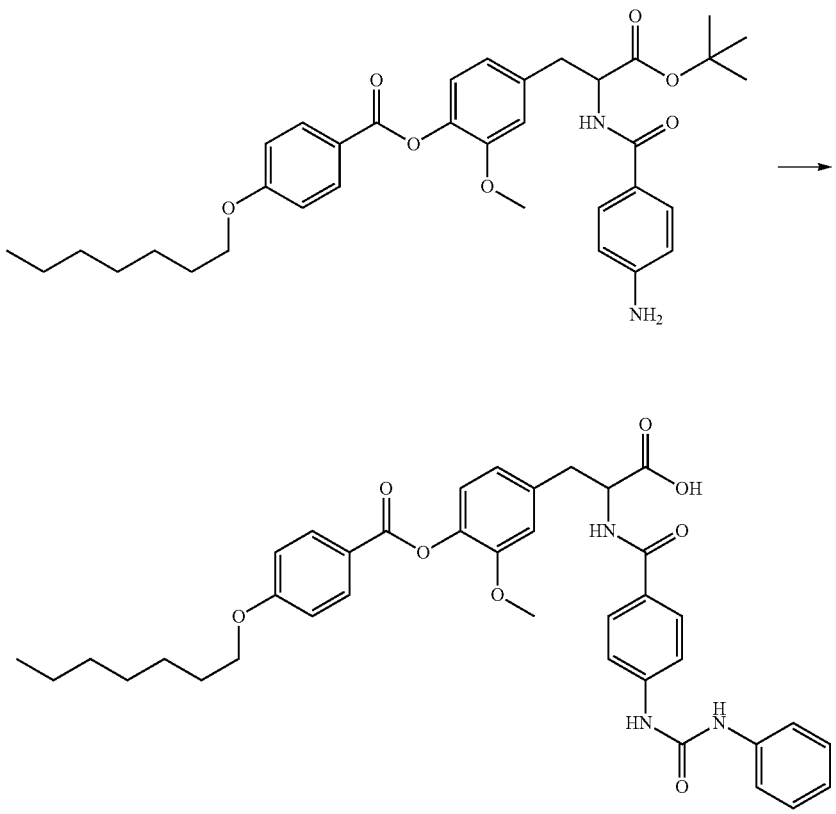

Prepared using General Procedures 10 and 7: LCMS-ESI (m/z) calculated for $C_{38}H_{41}N_3O_8$: 667; found 666, [M–H]$^-$, $t_R$=9.42 min (Method 5).

General Procedure 11: Preparation of Sulfonamides via Sulfonyl Chlorides

A solution of the amine (1 eq) and TEA (2 eq) in DCM (0.06 M) was treated with sulfonyl chloride (1.1 eq). The reaction mixture was stirred at room temperature until complete. The reaction was diluted with DCM and washed with saturated aqueous NaHCO$_3$. The organic layer was dried over MgSO$_4$ and concentrated. The product was purified by chromatography. Alternatively, the crude reaction mixture can be carried on to the next step without further purification.

3-(4-((4-(heptyloxy)benzoyl)oxy)-3-methoxyphenyl)-2-(4-(phenylsulfonamido) benzamido) propanoic acid (Compound 133)

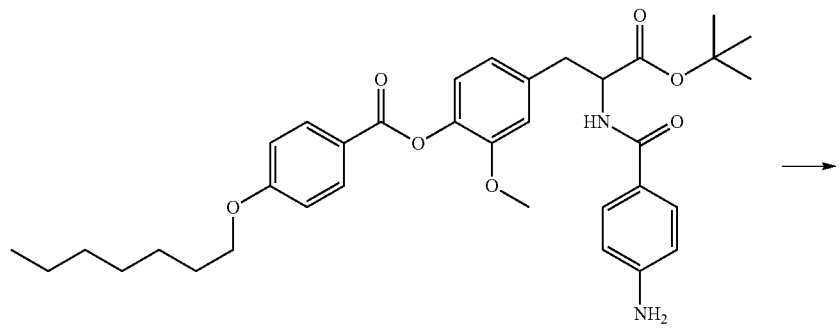

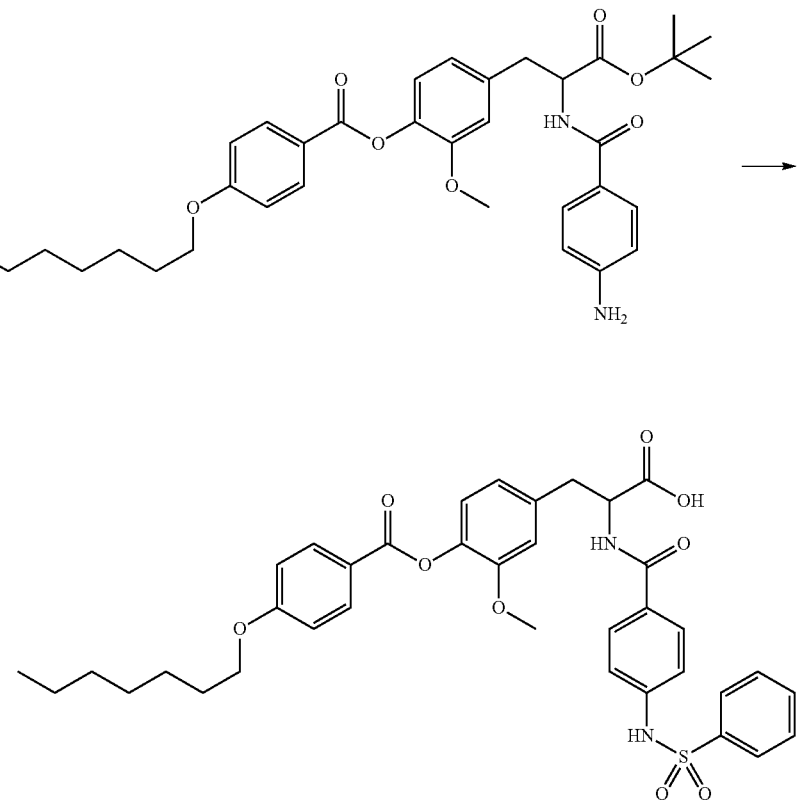

Prepared using General Procedure 11 and 7: LCMS-ESI (m/z) calculated for $C_{37}H_{40}N_2O_9S$: 688; no mass observed, $t_R$=10.56 min (Method 5).

Compound 134 was prepared from INT-9 using General Procedures 8 and 7 sequentially.

2-(4-((cyclopentylmethyl)amino)benzamido)-3-(4-((4-(heptyloxy)benzoyl)oxy)-3-methoxyphenyl)propanoic acid (Compound 134)

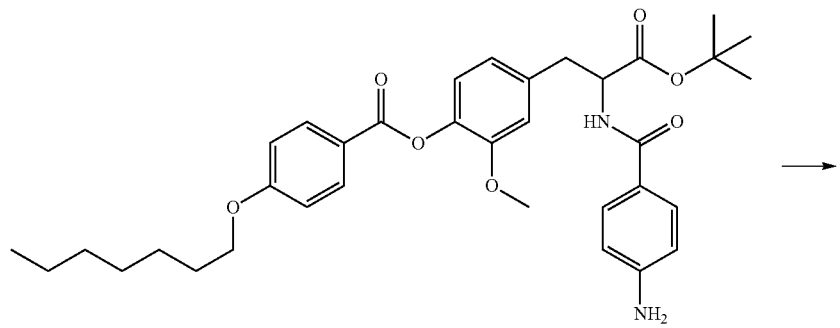

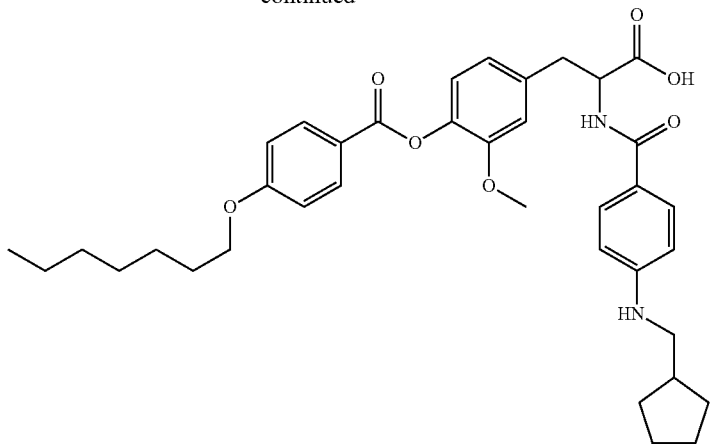

Prepared using General Procedures 8 and 7: LCMS-ESI (m/z) calculated for $C_{37}H_{46}N_2O_7$: 630; no mass observed, $t_R$=10.66 min (Method 5).

4-(2-(3-aminobenzamido)-3-(tert-butoxy)-3-oxopropyl)-2-methoxyphenyl 4-(heptyloxy)benzoate (INT-10)

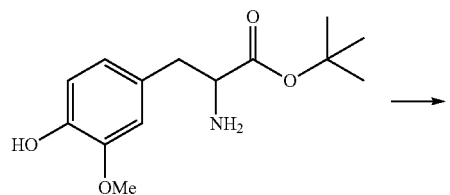

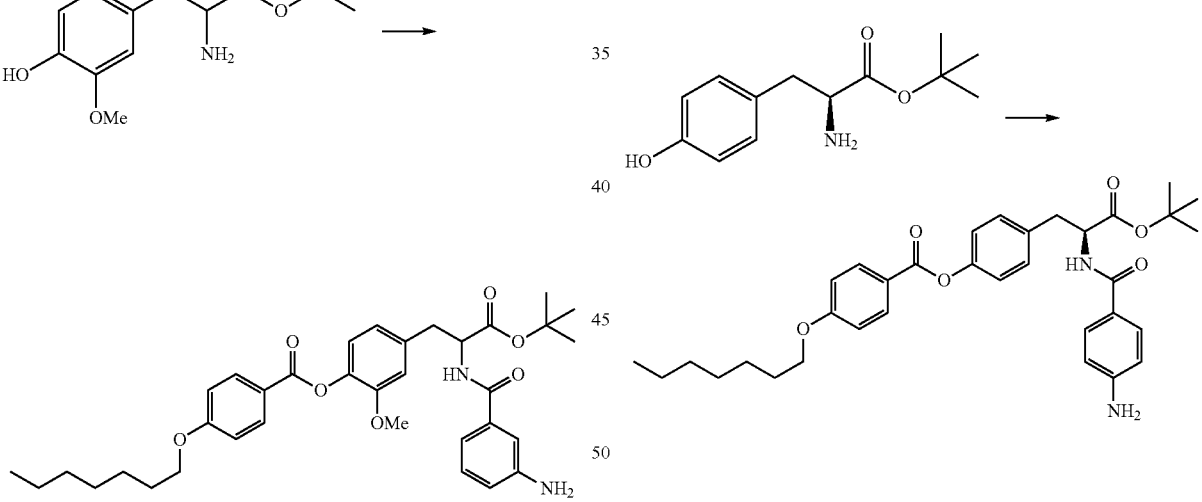

Prepared using General Procedures 6, 3, and 9 using 3-nitrobenzoic acid and 4-(heptyloxy)benzoyl chloride. LCMS-ESI (m/z) calculated for $C_{35}H_{44}N_2O_6$: 604; found 605, [M+H]$^+$, $t_R$=3.42 min (Method 4).

Compounds 135-166 were prepared from INT-10 using General Procedures 5 or 6, then 7 sequentially.

2-(3-(benzo[b]thiophene-2-carboxamido)benzamido)-3-(4-((4-(heptyloxy)benzoyl)oxy)-3-methoxyphenyl)propanoic acid (Compound 156)

Prepared using General Procedures 6 and 7 starting from 4-(2-(3-aminobenzamido)-3-(tert-butoxy)-3-oxopropyl)-2-methoxyphenyl 4-(heptyloxy)benzoate INT-10.

(S)-4-(2-(4-aminobenzamido)-3-(tert-butoxy)-3-oxopropyl)phenyl 4-(heptyloxy)benzoate (INT-11)

Prepared using General Procedures 5, 3, and 9 sequentially using 4-nitrobenzoyl chloride and 4-(heptyloxy)benzoyl chloride. LCMS-ESI (m/z) calculated for $C_{34}H_{42}N_2O_6$: 574; found 575, [M+H]$^+$, $t_R$=3.20 min (Method 4). $^1$H NMR (400 MHz, DMSO) δ 8.11-8.01 (m, 3H), 7.62-7.54 (m, 2H), 7.38-7.32 (m, 2H), 7.18-7.13 (m, 2H), 7.11-7.06 (m, 2H), 6.57-6.50 (m, 2H), 5.55 (s, 2H), 4.59-4.48 (m, 1H), 4.14-4.02 (t, J=6.5 Hz, 2H), 3.14-3.06 (m, 2H), 1.81-1.71 (m, 2H), 1.48-1.25 (m, 17H), 0.93-0.80 (m, 3H).

Compounds 167, 180, and 181 can be prepared from the enantiomer of INT-11 using General Procedures 5 or 6, then 7 sequentially.

Compounds 168-179 and 184-262 can be prepared from INT-11 using General Procedures 5 or 6, then 7 sequentially.

(S)-3-(4-((4-(heptyloxy)benzoyl)oxy)phenyl)-2-(4-(2-(4-methoxyphenyl)acetamido) benzamido)propanoic acid (Compound 178)

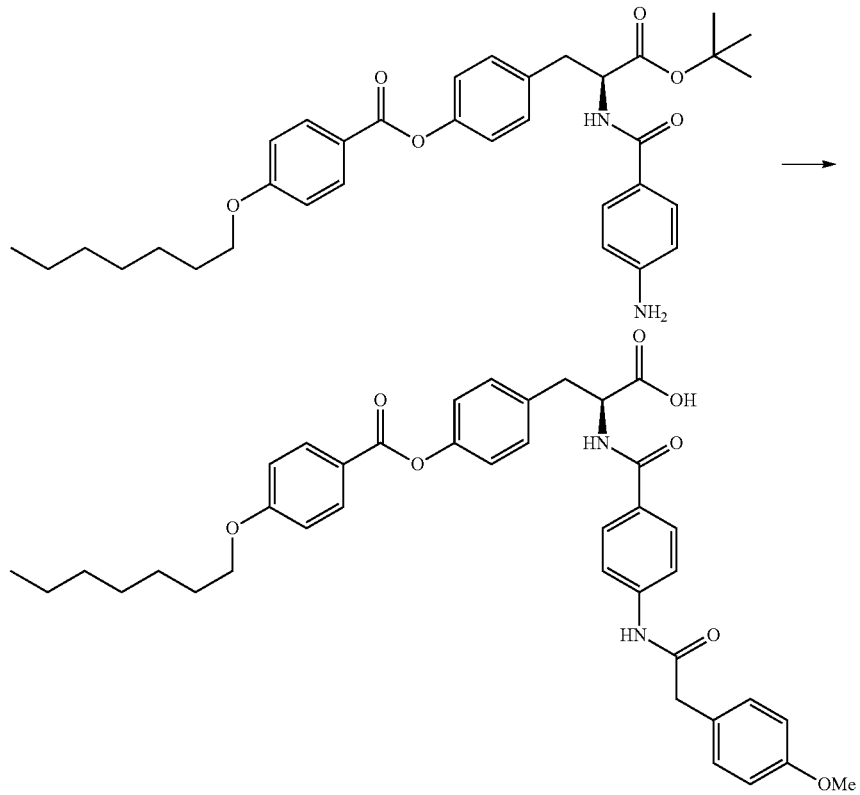

Prepared using General Procedures 6 and 7: To a solution of (S)-4-(2-(4-aminobenzamido)-3-(tert-butoxy)-3-oxopropyl)phenyl 4-(heptyloxy)benzoate INT-11 (600 mg, 1.04 mmol) and TEA (437 μL, 3.13 mmol) in DMF (3 mL) was added 2-(4-methoxyphenyl)acetic acid (182 mg, 1.10 mmol) and HATU (476 mg, 1.25 mmol). After stirring for 2 h, the reaction mixture was diluted with EA (50 mL) and washed with brine (2×50 mL). The organic layer was dried over $MgSO_4$ and concentrated. The intermediate tert-butyl ester was purified by chromatography (EA/hexanes).

The intermediate tert-butyl ester was dissolved in DCM (10 mL) and treated with TFA (5 mL). The reaction was stirred at room temperature for 2 h. The solvent was evaporated to provide 376 mg (54%) of (S)-3-(4-((4-(heptyloxy)benzoyl)oxy)phenyl)-2-(4-(2-(4-methoxyphenyl)acetamido)benzamido)propanoic acid 178. LCMS-ESI (m/z) calculated for $C_{39}H_{42}N_2O_8$: 666; found 665 [M−H]$^-$, $t_R$=9.53 min (Method 5). $^1$H NMR (400 MHz, DMSO) δ 12.76 (s, 1H), 10.33 (s, 1H), 8.60 (d, J=8.2 Hz, 1H), 8.05-8.00 (m, 2H), 7.82-7.76 (m, 2H), 7.69-7.62 (m, 2H), 7.37 (dd, J=6.8, 1.9 Hz, 2H), 7.27-7.21 (m, 2H), 7.17-7.12 (m, 2H), 7.11-7.06 (m, 2H), 6.92-6.85 (m, 2H), 4.65-4.57 (m, 1H), 4.06 (t, J=6.5 Hz, 2H), 3.72 (s, 3H), 3.58 (s, 2H), 3.25-3.17 (m, 1H), 3.14-3.04 (m, 1H), 1.78-1.69 (m, 2H), 1.45-1.25 (m, 8H), 0.87 (t, J=6.6 Hz, 3H).

(S)-2-(4-(2-(benzyloxy)acetamido)benzamido)-3-(4-((4-(heptyloxy)benzoyl)oxy)phenyl)propanoic acid (Compound 179)

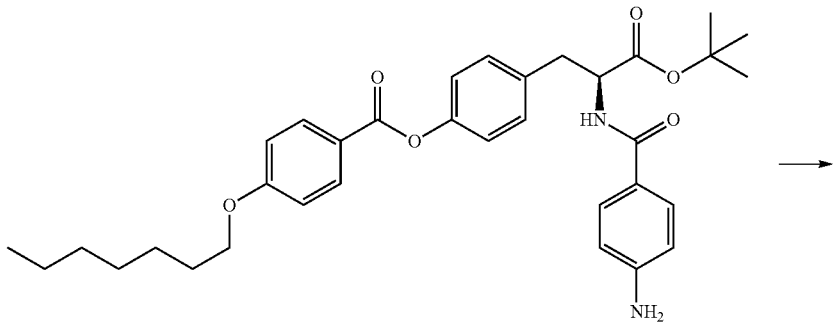

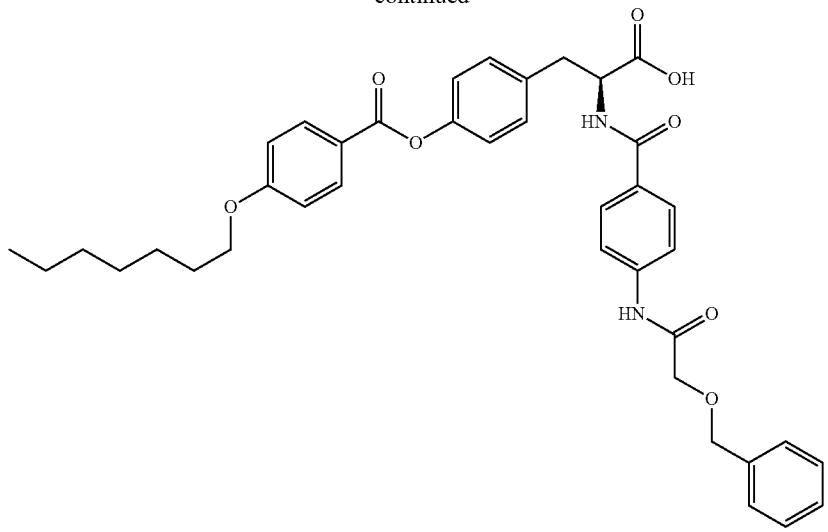

Prepared using General Procedures 6 and 7: To a solution of (S)-4-(2-(4-aminobenzamido)-3-(tert-butoxy)-3-oxopropyl)phenyl 4-(heptyloxy)benzoate INT-11 (197 mg, 0.343 mmol) and DIEA (190 μL, 1.03 mmol) in DMF (3 mL) was added HATU (326 mg, 0.857 mmol). After stirring for 1 h, the mixture was quenched with saturated aqueous NaHCO$_3$ (50 mL) and extracted with EA (3×20 mL). The organic layer was dried over MgSO$_4$ and concentrated. The intermediate tert-butyl ester was purified by chromatography (EA/hexanes).

The intermediate tert-butyl ester (47 mg) was dissolved in DCM (1 mL) and treated with TFA (1 mL). The reaction was stirred at room temperature for 3 h. The solvent was evaporated to give 40 mg (88%) of (S)-2-(4-(2-(benzyloxy)acetamido)benzamido)-3-(4-((4-(heptyloxy)benzoyl)oxy)phenyl) propanoic acid 179. LCMS-ESI (m/z) calculated for C$_{39}$H$_{42}$N$_2$O$_8$: 666; found 665, [M–H]$^-$, $t_R$=9.91 min (Method 5). $^1$H NMR (400 MHz, DMSO) δ 12.77 (s, 1H), 10.04 (s, 1H), 8.62 (d, J=8.1 Hz, 1H), 8.06-8.00 (m, 2H), 7.82-7.76 (m, 2H), 7.75-7.69 (m, 2H), 7.44-7.35 (m, 6H), 7.34-7.28 (m, 1H), 7.18-7.12 (m, 2H), 7.12-7.05 (m, 2H), 4.67-4.57 (m, 3H), 4.12 (s, 2H), 4.05 (t, J=6.5 Hz, 2H), 3.25-3.17 (m, 1H), 3.09 (dd, J=13.8, 10.6 Hz, 1H), 1.79-1.68 (m, 2H), 1.46-1.24 (m, 8H), 0.91-0.82 (m, 3H).

Compounds 182-183 were prepared from INT-11 using General Procedures 8 and 7 sequentially.

General Procedure 12: Hydrolysis of Aryl Esters to Acids

A solution of an aryl ester (1 eq) in THF and/or MeOH (0.4-1.8 M) was treated with 1 M lithium hydroxide (1.2 eq) or 2 M sodium hydroxide (1.2 eq). The reaction was stirred until complete and 1 M HCl (5.8 eq) was added. The product was extracted into EA, dried over MgSO$_4$ and concentrated.

4-(2-(4-methoxyphenyl)acetamido)benzoic acid (INT-12)

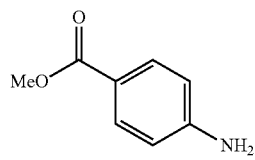

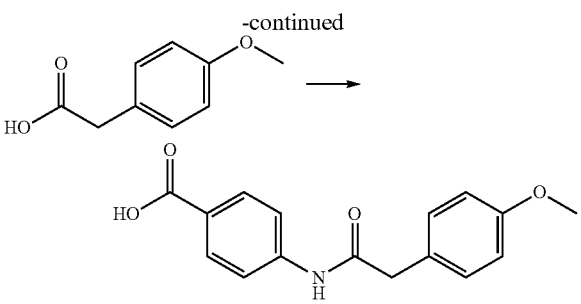

Prepared using General Procedures 6 and 12: To a stirred solution of methyl 4-aminobenzoate (1.3 g, 8.60 mmol) and 2-(4-methoxyphenyl)acetic acid (1.429 g, 8.60 mmol) in DMF (10 mL) was added TEA (3.00 ml, 21.50 mmol) and HATU (3.43 g, 9.03 mmol). After stirring for 2 h the reaction was diluted with EA (150 mL) and washed with brine (2×100 mL). The crude material was purified by chromatography (EA/hexanes).

To the intermediate amide dissolved in THF (20 mL) was added 1M LiOH solution (10.32 ml, 10.32 mmol) and MeOH (5 mL). The reaction stirred overnight. The reaction mixture was acidified by the addition of 1M HCl (50 mL) and the desired compound was extracted into EA (150 mL). The organic layer was dried over MgSO$_4$, washed with brine, and concentrated to give 1.82 g (73%) of 4-(2-(4-methoxyphenyl)acetamido)benzoic acid. LCMS-ESI (m/z) calculated for C$_{16}$H$_{15}$NO$_4$: 285; found 284, [M–H]$^-$, $t_R$=1.66 min (Method 4).

(S)-tert-butyl 2-(4-hydroxyphenyl)-2-(4-(2-(4-methoxyphenyl)acetamido)benzamido)acetate (INT-13)

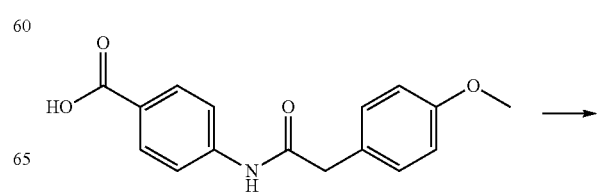

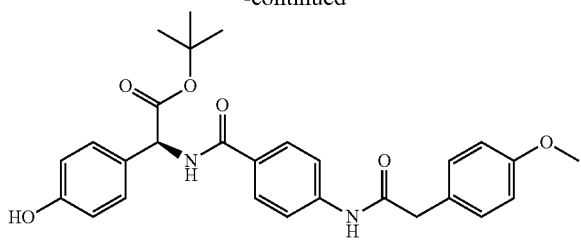

Prepared using General Procedure 6: To a stirred solution of 4-(2-(4-methoxyphenyl)acetamido)benzoic acid INT-12 (500 mg, 1.75 mmol) and (S)-tert-butyl 2-amino-2-(4-hydroxyphenyl)acetate (391 mg, 1.75 mmol) in DMF (10 mL) was added TEA (611 μL, 4.38 mmol) and HATU (700 mg, 1.84 mmol). After stirring for 2 h the reaction was diluted with EA (10 mL) and washed with brine (2×100 mL). The crude material was purified by chromatography (EA/hexanes) to give 860 mg (100%) of (S)-tert-butyl 2-(4-hydroxyphenyl)-2-(4-(2-(4-methoxyphenyl)acetamido)benzamido)acetate INT-13. LCMS-ESI (m/z) calculated for $C_{28}H_{30}N_2O_6$: 490; found 489, [M–H]⁻, $t_R$=2.14 min (Method 4).

Compounds 263-265 were prepared from methyl 4-aminobenzoate using General Procedures 5 or 6, 12, 6, 3, and 7 sequentially.

(S)-2-(4-((4-(heptyloxy)benzoyl)oxy)phenyl)-2-(4-(2-(4-methoxyphenyl)acetamido)benzamido)acetic acid (Compound 263)

(EA/hexanes with 1% AcOH) to give 190 mg (16%) of (S)-2-(4-((4-(heptyloxy)benzoyl)oxy)phenyl)-2-(4-(2-(4-methoxyphenyl)acetamido)benzamido)acetic acid 263. LCMS-ESI (m/z) calculated for $C_{38}H_{40}N_2O_8$: 652; found 651, [M–H], $t_R$=9.5 min (Method 5). ¹H NMR (400 MHz, DMSO) δ 12.96 (s, 1H), 10.34 (s, 1H), 8.95 (d, J=7.5 Hz, 1H), 8.10-8.02 (m, 2H), 7.93-7.87 (m, 2H), 7.69-7.63 (m, 2H), 7.60-7.55 (m, 2H), 7.30-7.22 (m, 4H), 7.14-7.08 (m, 2H), 6.91-6.86 (m, 2H), 5.57 (d, J=7.4 Hz, 1H), 4.08 (t, J=6.5 Hz, 2H), 3.72 (s, 3H), 3.58 (s, 2H), 1.81-1.68 (m, 2H), 1.48-1.18 (m, 8H), 0.91-0.83 (m, 3H).

Tert-butyl 2-(4-(cyclopentanecarboxamido)benzamido)-3-(4-hydroxy-3-methoxyphenyl)propanoate (INT-14)

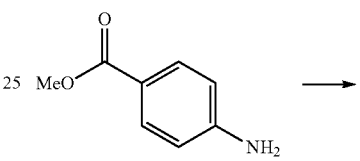

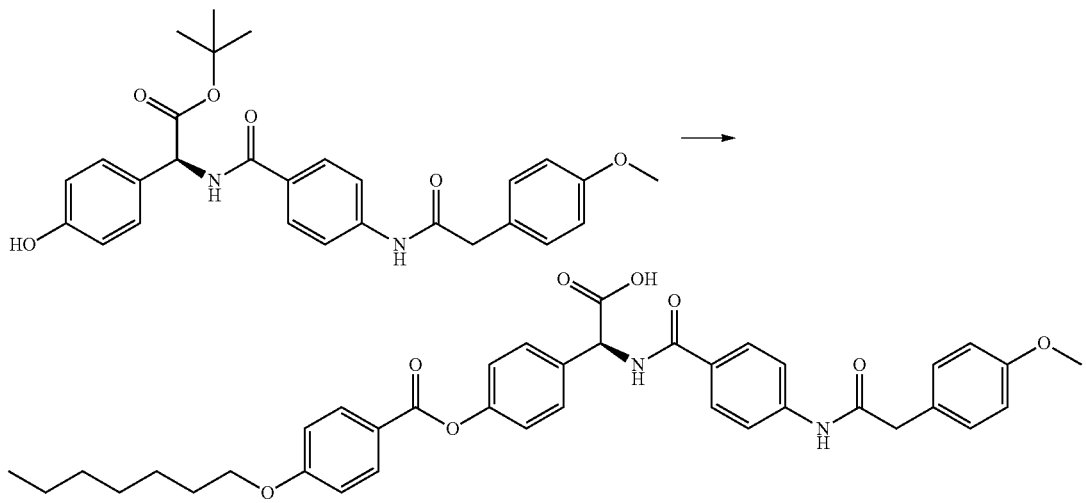

Prepared using General Procedures 3 and 7: To a stirred solution of 4-(heptyloxy)benzoic acid (456 mg, 1.928 mmol) in DCM (10 mL) and DMF (50 μL) was added oxalyl dichloride (181 μl, 2.10 mmol) and stirred for 1 h. This solution was added to (S)-tert-butyl 2-(4-hydroxyphenyl)-2-(4-(2-(4-methoxyphenyl)acetamido) benzamido) acetate INT-13 (860 mg, 1.75 mmol) in DCM (10 mL) and TEA (489 μl, 3.51 mmol). The reaction mixture was diluted with DCM (30 mL) and washed with saturated aqueous NaHCO₃ (50 mL). The organic layer was dried over MgSO₄ and concentrated. The product was purified by chromatography (EA/hexanes) to afford the intermediate tert-butyl ester.

The tert-butyl ester was dissolved in DCM (5 mL) and treated with TFA (5 mL) and stirred for 2 h. The solvent was removed and the product was purified by chromatography -continued

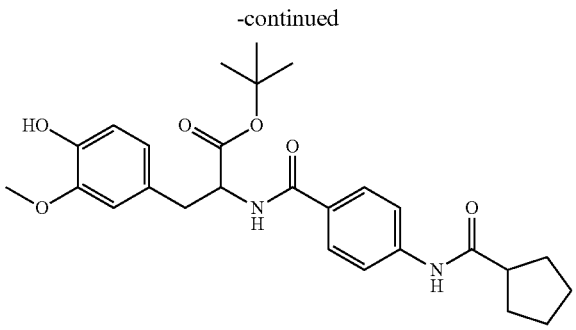

Prepared using General Procedures 5, 12 and 6 starting from methyl 4-aminobenzoate and using cyclopentane carbonyl chloride and tert-butyl 2-amino-3-(4-hydroxy-3-methoxyphenyl)propanoate. LCMS-ESI (m/z) calculated for $C_{27}H_{34}N_2O_6$: 482; found 505, [M+Na]$^+$, $t_R$=3.21 min (Method 1). NMR (400 MHz, CDCl$_3$) δ 7.79-7.67 (m, 2H), 7.60 (d, J=8.7 Hz, 2H), 6.88-6.75 (m, 1H), 6.73-6.60 (m, 2H), 6.56 (d, J=7.4 Hz, 1H), 5.52 (s, 1H), 4.89 (ddd, J=7.3, 6.1, 5.0 Hz, 1H), 3.76 (s, 3H), 3.16 (m, 2H), 2.69 (m, 1H), 2.01-1.85 (m, 4H), 1.80 (m, 2H), 1.69-1.58 (m, 2H), 1.46 (s, 9H).

General Procedure 13: Preparation of Aryl Amides and Esters via DCC Mediated Peptide Coupling To a stirred solution of the phenol or amine (1 eq) and DIEA (3 eq) in DCM (0.04 M) was added the appropriate acid (2.5 eq), DCC (2.5 eq), and DMAP (2.5 eq). The reaction mixture was stirred until the reaction was complete. The crude reaction mixture was carried on to the next step without further purification.

Compounds 266-275 were prepared from INT-14 using General Procedures 3 or 13, then 7 sequentially.

2-(4-(cyclopentanecarboxamido)benzamido)-3-(4-((4-(heptyloxy)benzoyl)oxy)-3-methoxyphenyl)propanoic acid (Compound 273)

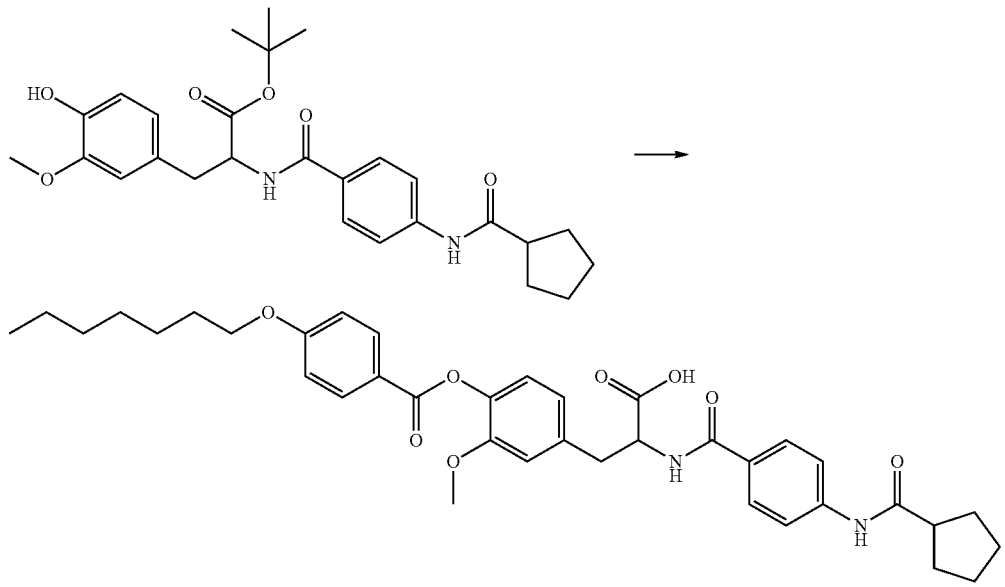

Prepared using General Procedures 3 and 7: To a stirred solution of tert-butyl 2-(4-(cyclopentanecarboxamido)benzamido)-3-(4-hydroxy-3-methoxyphenyl)propanoate INT-14 (250 mg, 0.518 mmol) at 0° C. in DCM (10 mL) was added TEA (217 μL, 1.55 mmol) and 4-(heptyloxy)benzoyl chloride (311 μL, 1.30 mmol). The reaction was stirred at room temperature for 1 h. The reaction mixture was diluted with DCM (5 mL) and washed with saturated aqueous NaHCO$_3$ (10 mL). The organic layer was dried over MgSO$_4$ and concentrated. The intermediate tert-butyl ester was purified by chromatography (EA/hexanes) to yield 336 mg of the tert-butyl ester.

The tert-butyl ester (300 mg, 0.428 mmol) was dissolved in DCM (4 mL) and treated with TFA (2 mL) and stirred for 1.5 hr. The solvent was removed to give 170 mg (55%) of 2-(4-(cyclopentanecarboxamido)benzamido)-3-(4-((4-(heptyloxy)benzoyl)oxy)-3-methoxyphenyl)propanoic acid 273. LCMS-ESI (m/z) calculated for $C_{37}H_{44}N_2O_8$: 644; found 643, [M–H]$^-$, $t_R$=3.09 min (Method 4). $^1$H NMR (400 MHz, DMSO) δ 12.74 (s, 1H), 10.08 (s, 1H), 8.58 (d, J=8.1 Hz, 1H), 8.05-7.96 (m, 2H), 7.85-7.73 (m, 2H), 7.70-7.60 (m, 2H), 7.14 (d, J=1.9 Hz, 1H), 7.12-7.03 (m, 3H), 6.93 (dd, J=8.1, 1.8 Hz, 1H), 4.70-4.58 (m, 1H), 4.07 (t, J=6.5 Hz, 2H), 3.69 (s, 3H), 3.25-3.18 (m, 1H), 3.13-3.06 (m, 1H), 2.84-2.74 (m, 1H), 1.91-1.79 (m, 2H), 1.79-1.60 (m, 6H), 1.59-1.48 (m, 2H), 1.46-1.22 (m, 8H), 0.90-0.82 (m, 3H).

3-(4-((4-acetamidobenzoyl)oxy)-3-methoxyphenyl)-2-(4-(cyclopentanecarboxamido)benzamido)propanoic acid (Compound 274)

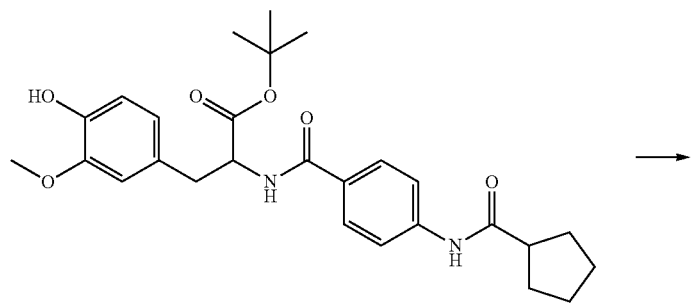

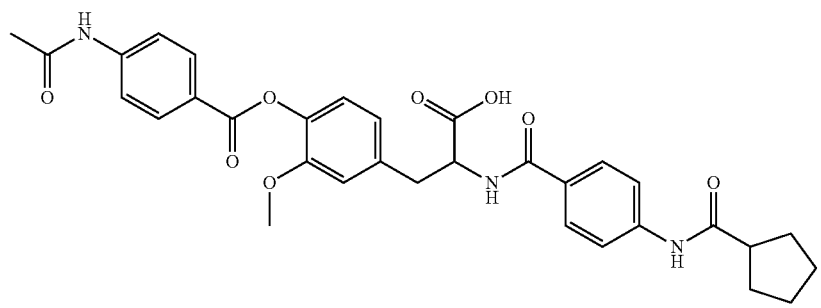

Prepared using General Procedures 13 and 7: LCMS-ESI (m/z) calculated for $C_{32}H_{33}N_3O_8$: 587; found 588, $[M+H]^+$, $t_R$=7.19 min (Method 2).

Compounds 305-307 were prepared from Compound 168 using General Procedures 6 and 7 sequentially.

Compounds 308-310 were prepared from Compound 179 using General Procedures 6 and 7 sequentially.

Compounds 311-313 were prepared from Compound 178 using General Procedures 6 and 7 sequentially.

2-(3-(4-β4-(heptyloxy)benzoyl)oxy)phenyl)-2-(4-(2-(4-methoxyphenyl)acetamido)benzamido)propanamido)acetic acid (Compound 313)

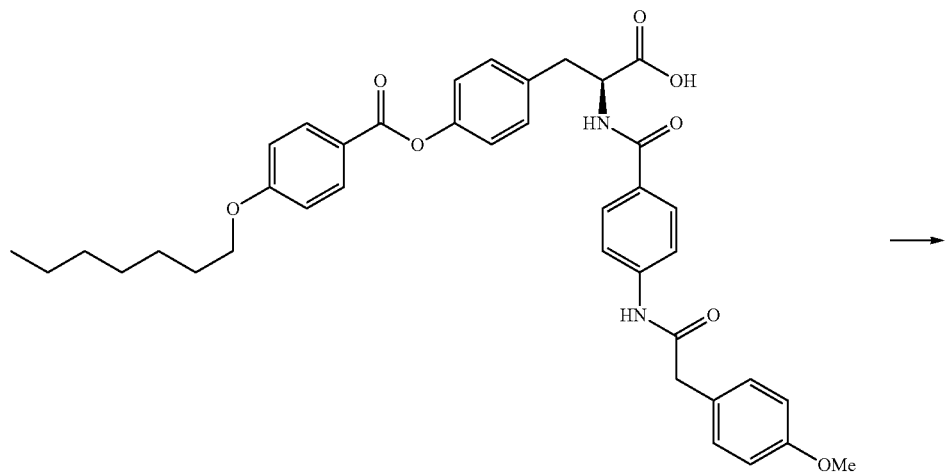

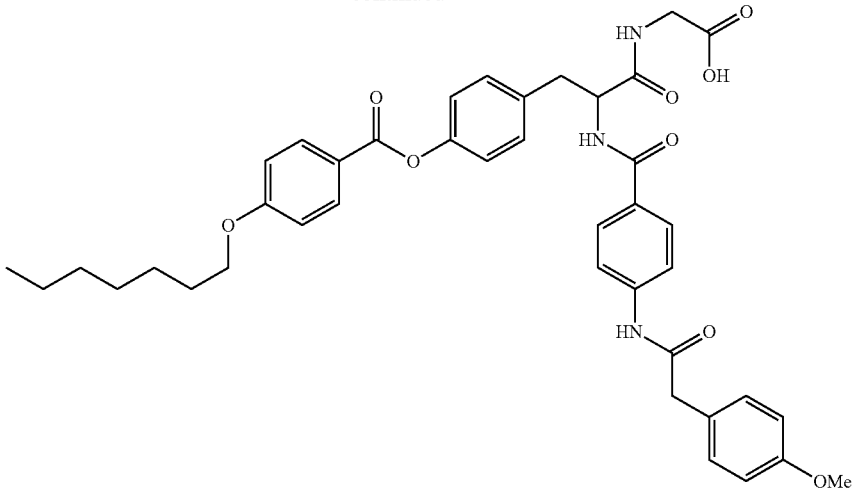

Prepared using General Procedures 6 and 7: LCMS-ESI (m/z) calculated for $C_{41}H_{45}N_3O_9$: 723; found 724, $[M+H]^+$, $t_R$=9.05 min (Method 5).

Compound 314 was prepared from Compound 63 using General Procedures 6 and 7 sequentially.

Compound 315 was prepared from Compound 178 using General Procedure 13.

General Procedure 14A-C: Preparation of Secondary and Tertiary Amines via Alkylation General Procedure 14A: To a stirred solution of amide (1 eq) in DMF (0.1 M) at −10 to 0° C. was added iodomethane (2 eq) and sodium hydride (1.1 eq). The reaction mixture was allowed to warm to room temperature and stirred until the reaction was complete. The reaction was quenched with 1 M HCl and extracted with DCM. The organic layer was dried and concentrated. The product was purified by chromatography.

General Procedure 14B: To a stirred solution of the amide (1 eq) in THF (0.1 M) at −10 to 0° C. was added 18-crown-6 (1.05 eq) and KHMDS (1.0 eq). To this mixture was added iodomethane (2 eq). The reaction mixture was allowed to warm to room temperature and stirred until the reaction was complete. The reaction was quenched with AcOH and extracted with DCM. The organic layer was dried over $MgSO_4$ and concentrated. The product was purified by chromatography.

General Procedure 14C: To a stirred solution of the amine (1 eq) in DMF (0.15 M) was added iodomethane (2 eq) and sodium bicarbonate (3 eq). The reaction mixture was stirred until the reaction was complete. The reaction was diluted with EA and washed with brine. The organic layer was dried over $MgSO_4$ and concentrated. The product was purified by chromatography.

Compounds 276-277 were prepared from (S)-tert-butyl 2-amino-3-(4-hydroxyphenyl)propanoate using General Procedures 5, 3, 14, 9, 6, and 7 sequentially.

Compounds 278-280 were prepared from 4-(methylamino)benzoic acid using General Procedures 2, 6, 3, 4, 6, 7 sequentially.

General Procedure 15: Deprotection of Silyl Ethers

To a stirred solution of the silyl-protected alcohol (1 eq) in THF (0.1 M) was added TBAF (2 eq). The reaction mixture was stirred until the reaction was complete. The reaction was quenched with 0.1 M citric acid and extracted with DCM. The organic layer was dried and concentrated. The product was purified by chromatography.

Compounds 281-282 were prepared from (S)-tert-butyl 2-amino-3-(4-hydroxyphenyl)propanoate using General Procedures 6, 12, 6, 13, and 15 sequentially.

Compound 283 was prepared from (S)-tert-butyl 2-amino-3-(4-hydroxyphenyl)propanoate and 4-(heptyloxy)benzoic acid using General Procedures 6, 3, and 7 sequentially.

Compound 284 was prepared from (S)-2-amino-2-(4-hydroxyphenyl)acetic acid using General Procedures 1, 6, 3, and 7 sequentially.

Compound 285 was prepared from (S)-tert-butyl 2-amino-3-(4-hydroxyphenyl)propanoate using General Procedures 6, 3, 14, and 7 sequentially.

Compound 316 can be from Compound 63 using General Procedure 5.

Compounds 286-288 can be prepared from methyl 4-aminobenzoate using General Procedures 5, 12, 6, 9, 5, and 12 sequentially.

Compounds 289-291 can be prepared from methyl 4-aminobenzoate using General Procedures 5, 12, 6, 9, 11, and 12 sequentially.

General Procedure 16: Preparation of aryl ether and aryl amines via copper-mediated couplings To a stirred solution of the aniline or phenol (1 eq) in DCM (0.07 M) was added boronic acid (2 eq), copper (II) acetate (1 eq), pyridine (5 eq), and 4 Å molecular sieves. The reaction mixture was stirred under an atmosphere of air until the reaction was complete. The reaction was quenched with saturated aqueous $NaHCO_3$ and extracted with DCM. The organic layer was dried and concentrated. The product was purified by chromatography.

Compounds 292-294 can be prepared from methyl 4-aminobenzoate using General Procedures 5, 12, 6, 16, and 7 sequentially.

Compounds 295-297 can be prepared from methyl 4-aminobenzoate using General Procedures 5, 12, 6, 9, 16, and 12 sequentially.

Compounds 298-299 can be prepared using from methyl 4-aminobenzoate General Procedures 5, 12, 6, 7, 6, and 12 sequentially.

Compounds 300-301 can be prepared from methyl 4-aminobenzoate using General Procedures 5, 12, 6, 9, 8, and 12 sequentially.

Compound 302 was prepared from methyl 4-aminobenzoate and (S)-methyl 2-amino-3-(4-nitrophenyl)propanoate hydrochloride using General Procedures 5, 12, 6, 9, 8, 14, and 12 sequentially.

Compound 303 was prepared from 4-(2-(4-aminobenzamido)-3-(tert-butoxy)-3-oxopropyl)-2-methoxyphenyl 4-(heptyloxy)benzoate INT-9 using General Procedures 5, 7, and 4 sequentially.

General Procedure 17: Preparation of Succinate Derivatives from Aryl amines

To a stirred solution of the amine (1 eq) in DCM (0.4 M) was added succinic anhydride (1.5 eq), TEA (3 eq), and DMAP (0.1 eq). The reaction mixture was stirred until the reaction was complete. The reaction was diluted with DCM and washed with saturated aqueous $NaHCO_3$. The organic layer was dried and concentrated. The product was purified by chromatography.

Compound 304 was prepared from 4-(2-(4-aminobenzamido)-3-(tert-butoxy)-3-oxopropyl)-2-methoxyphenyl 4-(heptyloxy)benzoate INT-9 using General Procedures 17 and 7 sequentially.

Compounds 317-318 can be prepared from methyl 4-aminobenzoate using General Procedures 6, 12, 5, and 3 sequentially.

Selected compounds and their corresponding analytical data are shown in Table 1.

TABLE 1

| STRUCTURE | COMPOUND NUMBER | LCMS RETENTION TIME (min) | LCMS method |
|---|---|---|---|
| 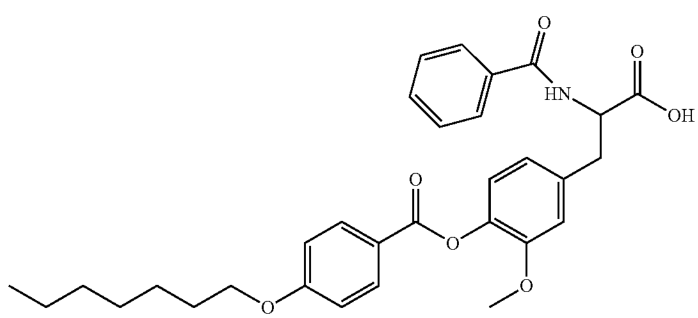 [SMILES: CCCCCCCOc1ccc(C(=O)Oc2ccc(CC(NC(=O)c3ccccc3)C(=O)O)cc2OC)cc1] | 1 | 10.90 | 2 |
| 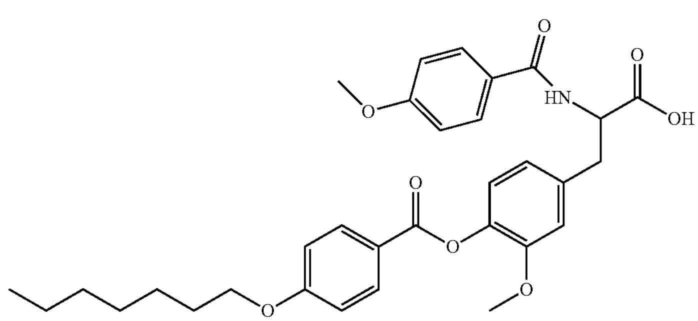 [SMILES: CCCCCCCOc1ccc(C(=O)Oc2ccc(CC(NC(=O)c3ccc(OC)cc3)C(=O)O)cc2OC)cc1] | 2 | 11.01 | 2 |
| 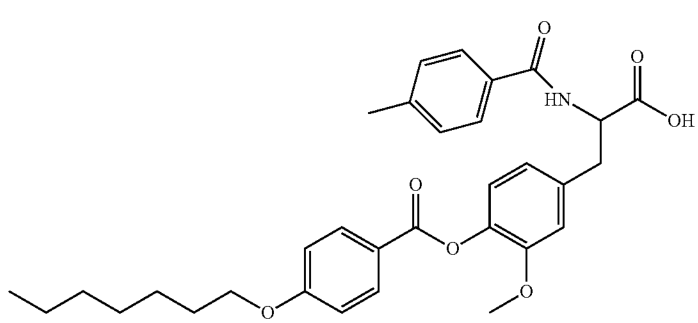 [SMILES: CCCCCCCOc1ccc(C(=O)Oc2ccc(CC(NC(=O)c3ccc(C)cc3)C(=O)O)cc2OC)cc1] | 3 | 11.27 | 2 |

TABLE 1-continued

| STRUCTURE | COMPOUND NUMBER | LCMS RETENTION TIME (min) | LCMS method |
|---|---|---|---|
| 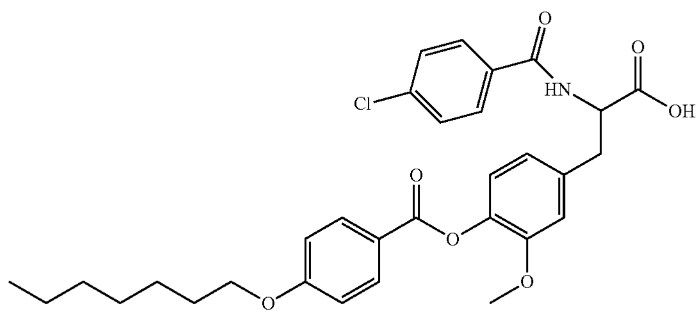 [SMILES: CCCCCCCOc1ccc(C(=O)Oc2ccc(CC(NC(=O)c3ccc(Cl)cc3)C(=O)O)cc2OC)cc1] | 4 | 11.49 | 2 |
| 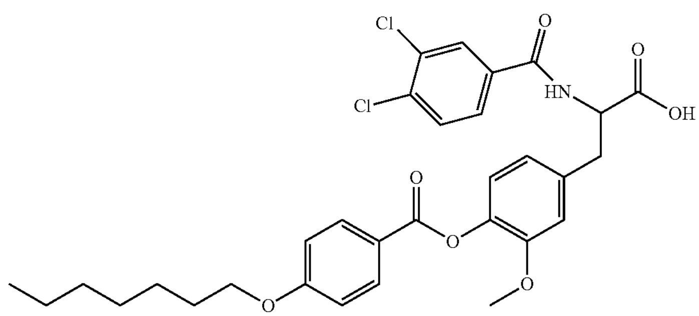 [SMILES: CCCCCCCOc1ccc(C(=O)Oc2ccc(CC(NC(=O)c3ccc(Cl)c(Cl)c3)C(=O)O)cc2OC)cc1] | 5 | 11.84 | 2 |
| 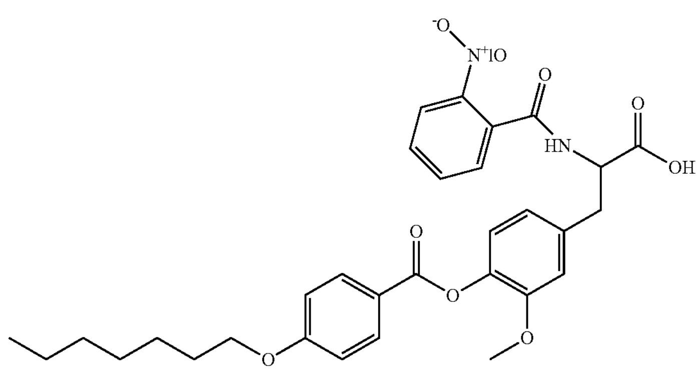 | 6 | 11.03 | 2 |
| 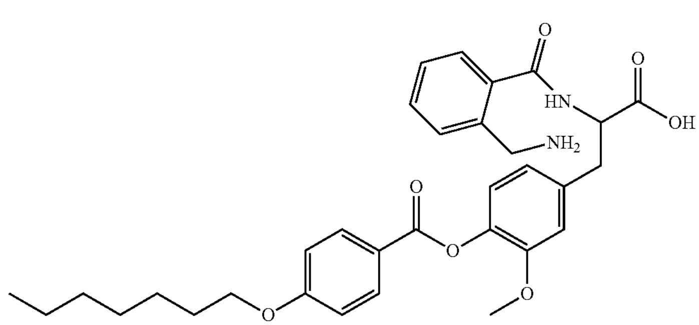 [SMILES: CCCCCCCOc1ccc(C(=O)Oc2ccc(CC(NC(=O)c3ccccc3CN)C(=O)O)cc2OC)cc1] | 7 | 8.12 | 2 |

TABLE 1-continued
| STRUCTURE | COMPOUND NUMBER | LCMS RETENTION TIME (min) | LCMS method |
|---|---|---|---|
| 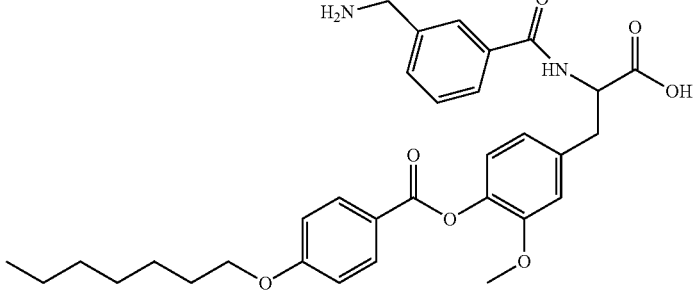 | 8 | 7.72 | 2 |
| 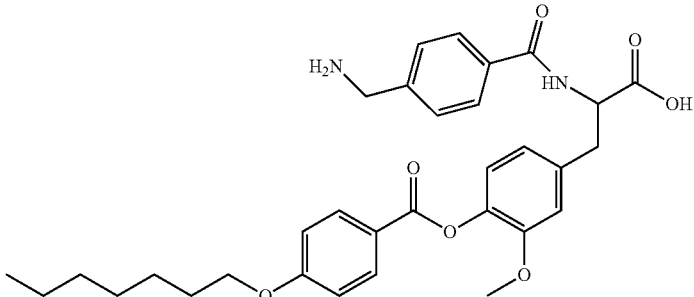 | 9 | 7.60 | 2 |
| 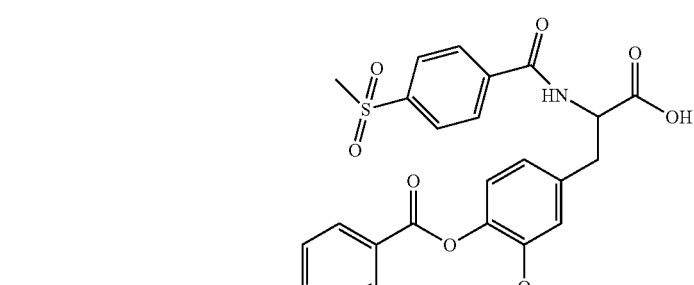 | 10 | 10.50 | 2 |
| 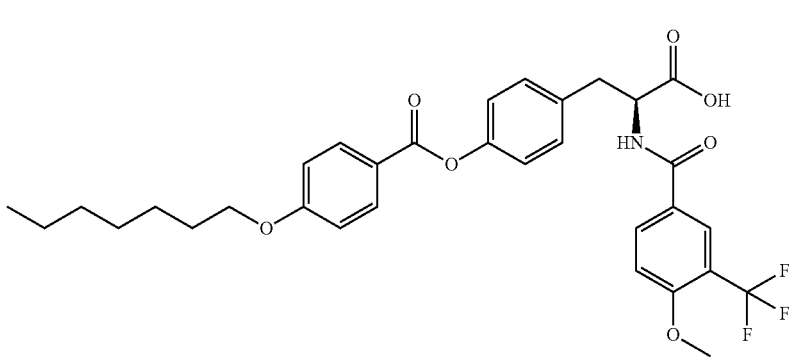 [SMILES: CCCCCCCOc1ccc(C(=O)Oc2ccc(C[C@H](NC(=O)c3ccc(OC)c(C(F)(F)F)c3)C(=O)O)cc2)cc1] | 11 | 11.48 | 2 |
| 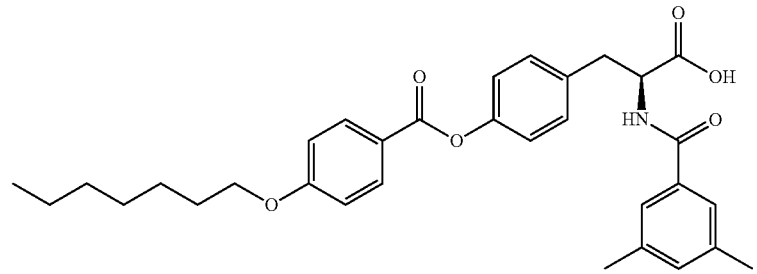 [SMILES: CCCCCCCOc1ccc(C(=O)Oc2ccc(C[C@H](NC(=O)c3cc(C)cc(C)c3)C(=O)O)cc2)cc1] | 12 | 11.71 | 2 |

TABLE 1-continued
| STRUCTURE | COMPOUND NUMBER | LCMS RETENTION TIME (min) | LCMS method |
|---|---|---|---|
| 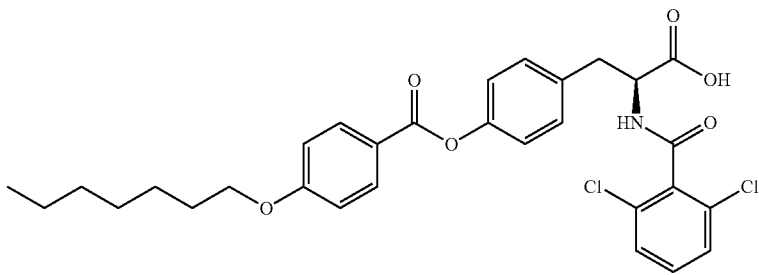 [SMILES: CCCCCCCOc1ccc(C(=O)Oc2ccc(C[C@H](NC(=O)c3c(Cl)cccc3Cl)C(=O)O)cc2)cc1] | 13 | 11.26 | 2 |
| 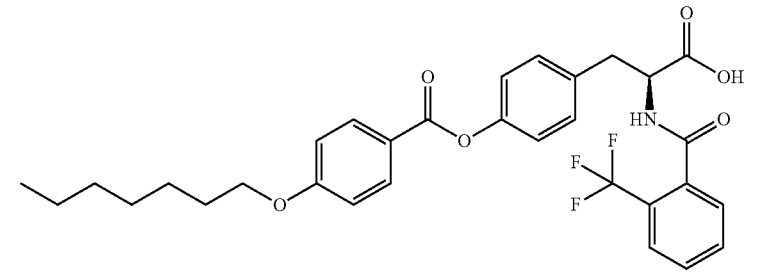 [SMILES: CCCCCCCOc1ccc(C(=O)Oc2ccc(C[C@H](NC(=O)c3ccccc3C(F)(F)F)C(=O)O)cc2)cc1] | 14 | 11.32 | 2 |
| 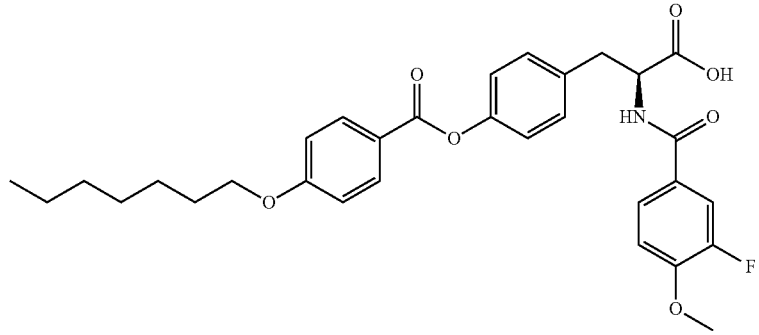 [SMILES: CCCCCCCOc1ccc(C(=O)Oc2ccc(C[C@H](NC(=O)c3ccc(OC)c(F)c3)C(=O)O)cc2)cc1] | 15 | 11.15 | 2 |
| 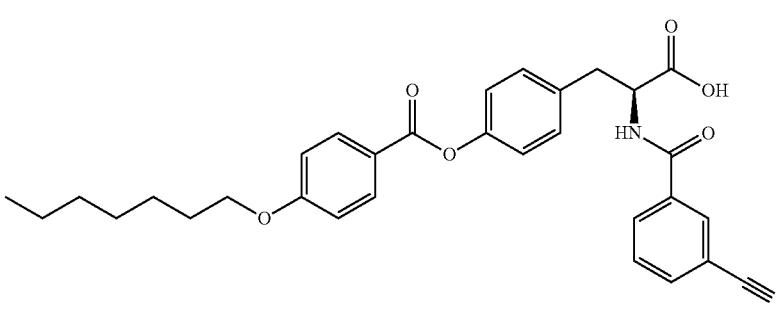 | 16 | 11.05 | 2 |
| 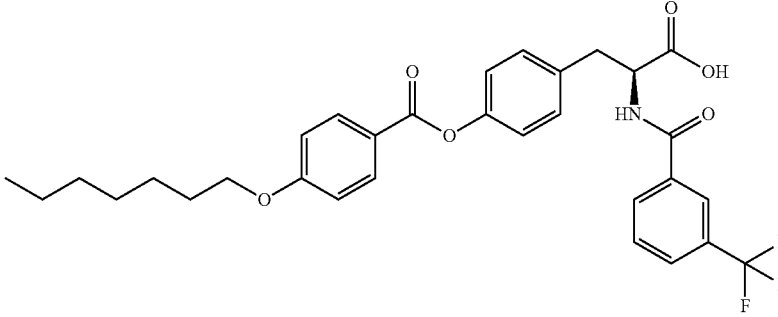 | 17 | 11.55 | 2 |

TABLE 1-continued

| STRUCTURE | COMPOUND NUMBER | LCMS RETENTION TIME (min) | LCMS method |
|---|---|---|---|
| 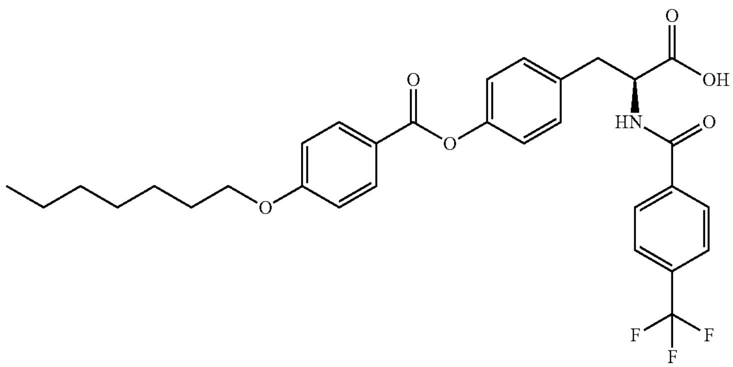 [SMILES: CCCCCCCOc1ccc(C(=O)Oc2ccc(C[C@H](NC(=O)c3ccc(C(F)(F)F)cc3)C(=O)O)cc2)cc1] | 18 | 11.62 | 2 |
| 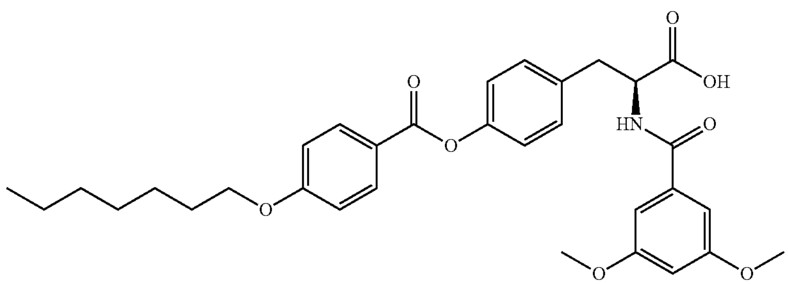 [SMILES: CCCCCCCOc1ccc(C(=O)Oc2ccc(C[C@H](NC(=O)c3cc(OC)cc(OC)c3)C(=O)O)cc2)cc1] | 19 | 11.23 | 2 |
| 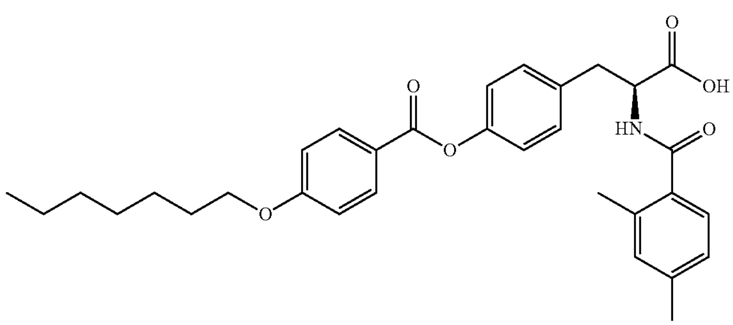 [SMILES: CCCCCCCOc1ccc(C(=O)Oc2ccc(C[C@H](NC(=O)c3ccc(C)cc3C)C(=O)O)cc2)cc1] | 20 | 11.57 | 2 |
| 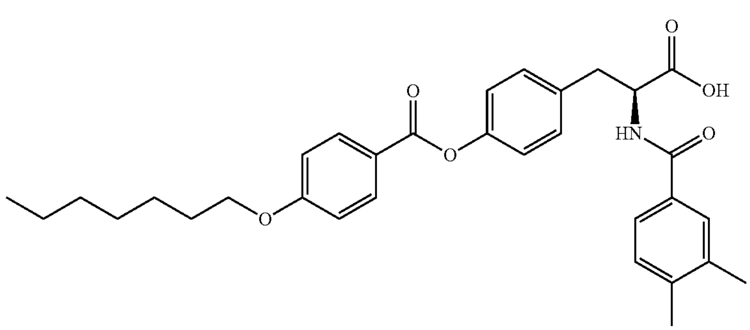 [SMILES: CCCCCCCOc1ccc(C(=O)Oc2ccc(C[C@H](NC(=O)c3ccc(C)c(C)c3)C(=O)O)cc2)cc1] | 21 | 11.59 | 2 |

TABLE 1-continued

| STRUCTURE | COMPOUND NUMBER | LCMS RETENTION TIME (min) | LCMS method |
|---|---|---|---|
| (structure) | 22 | 11.30 | 2 |
| (structure) | 23 | 10.88 | 2 |
| (structure) | 24 | 11.75 | 2 |
| (structure) | 25 | 11.23 | 2 |

TABLE 1-continued
| STRUCTURE | COMPOUND NUMBER | LCMS RETENTION TIME (min) | LCMS method |
|---|---|---|---|
| 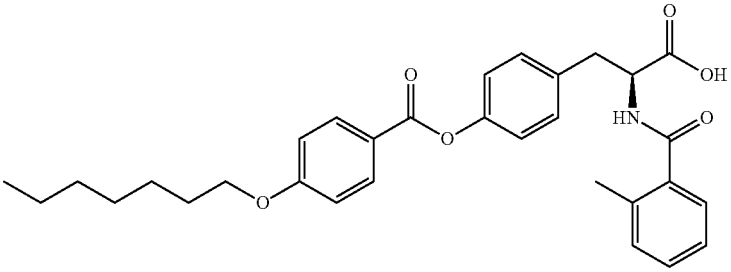 [SMILES: CCCCCCCOc1ccc(C(=O)Oc2ccc(C[C@H](NC(=O)c3ccccc3C)C(=O)O)cc2)cc1] | 26 | 11.34 | 2 |
| 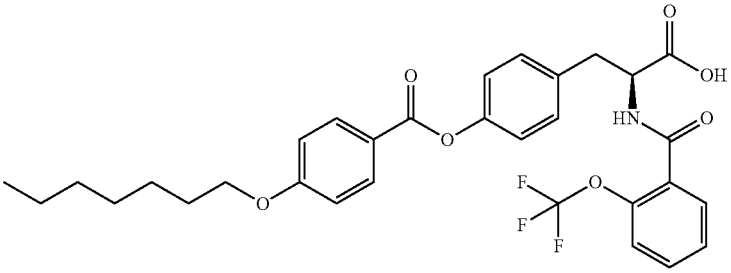 [SMILES: CCCCCCCOc1ccc(C(=O)Oc2ccc(C[C@H](NC(=O)c3ccccc3OC(F)(F)F)C(=O)O)cc2)cc1] | 27 | 11.52 | 2 |
| 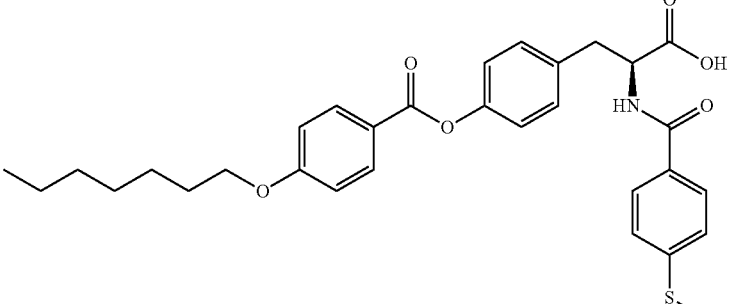 | 28 | 11.44 | 2 |
| 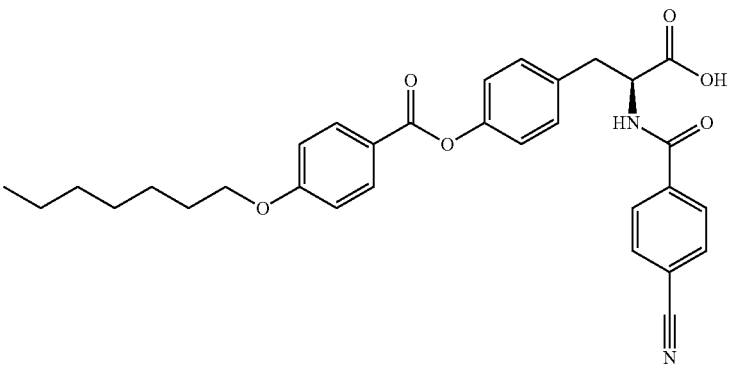 [SMILES: CCCCCCCOc1ccc(C(=O)Oc2ccc(C[C@H](NC(=O)c3ccc(C#N)cc3)C(=O)O)cc2)cc1] | 29 | 11.05 | 2 |
| 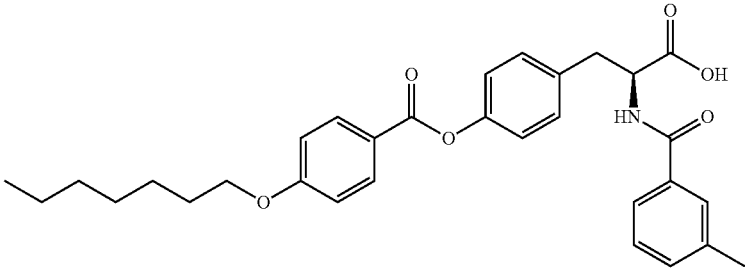 [SMILES: CCCCCCCOc1ccc(C(=O)Oc2ccc(C[C@H](NC(=O)c3cccc(C)c3)C(=O)O)cc2)cc1] | 30 | 11.41 | 2 |

TABLE 1-continued

| STRUCTURE | COMPOUND NUMBER | LCMS RETENTION TIME (min) | LCMS method |
|---|---|---|---|
| 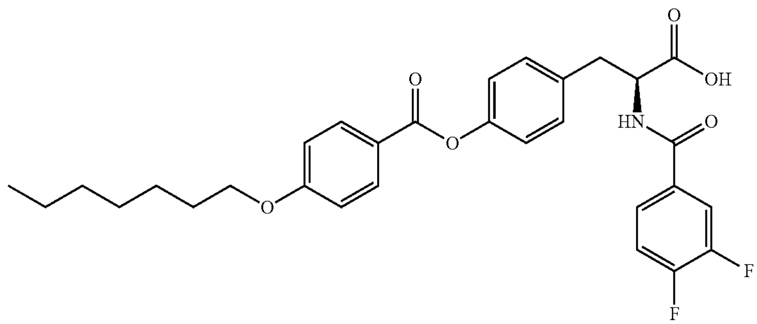 [SMILES: CCCCCCCOc1ccc(C(=O)Oc2ccc(C[C@H](NC(=O)c3ccc(F)c(F)c3)C(=O)O)cc2)cc1] | 31 | 11.40 | 2 |
| 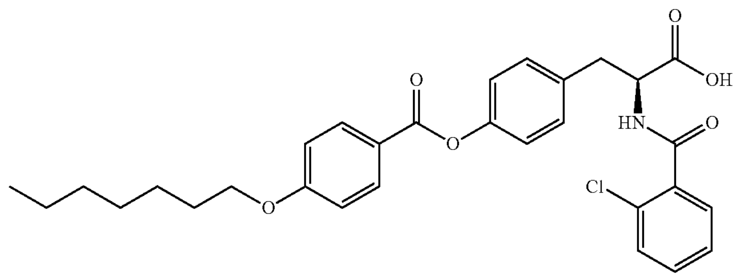 [SMILES: CCCCCCCOc1ccc(C(=O)Oc2ccc(C[C@H](NC(=O)c3ccccc3Cl)C(=O)O)cc2)cc1] | 32 | 11.27 | 2 |
| 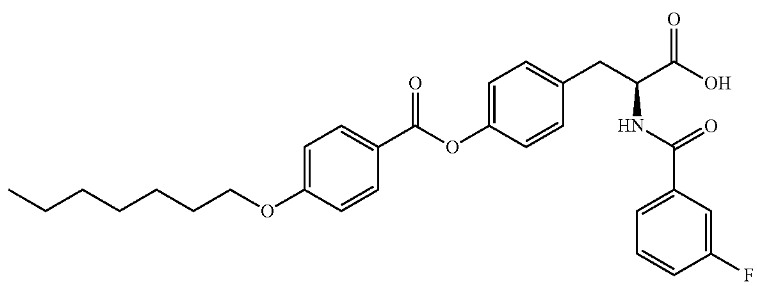 [SMILES: CCCCCCCOc1ccc(C(=O)Oc2ccc(C[C@H](NC(=O)c3cccc(F)c3)C(=O)O)cc2)cc1] | 33 | 11.30 | 2 |
| 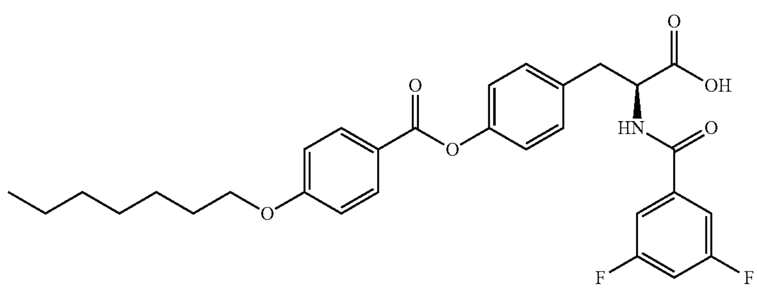 [SMILES: CCCCCCCOc1ccc(C(=O)Oc2ccc(C[C@H](NC(=O)c3cc(F)cc(F)c3)C(=O)O)cc2)cc1] | 34 | 11.44 | 2 |
| 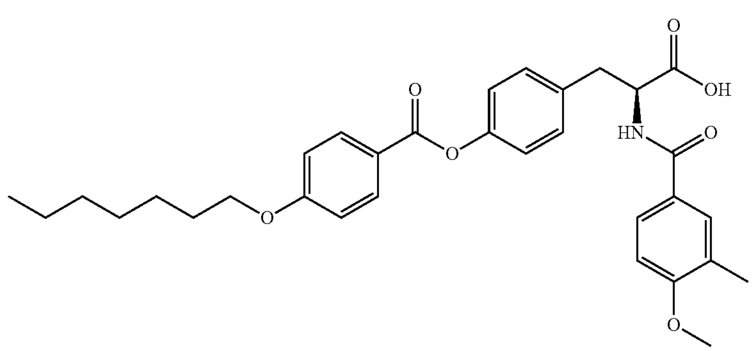 [SMILES: CCCCCCCOc1ccc(C(=O)Oc2ccc(C[C@H](NC(=O)c3ccc(OC)c(C)c3)C(=O)O)cc2)cc1] | 35 | 11.45 | 2 |

TABLE 1-continued

| STRUCTURE | COMPOUND NUMBER | LCMS RETENTION TIME (min) | LCMS method |
|---|---|---|---|
| 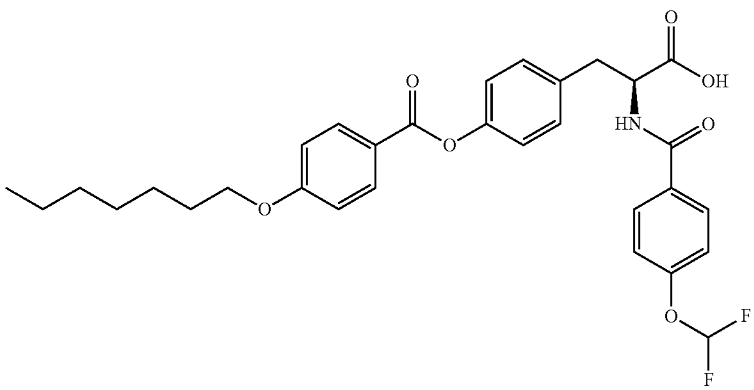 [SMILES: CCCCCCCOc1ccc(C(=O)Oc2ccc(C[C@H](NC(=O)c3ccc(OC(F)F)cc3)C(=O)O)cc2)cc1] | 36 | 11.23 | 2 |
| 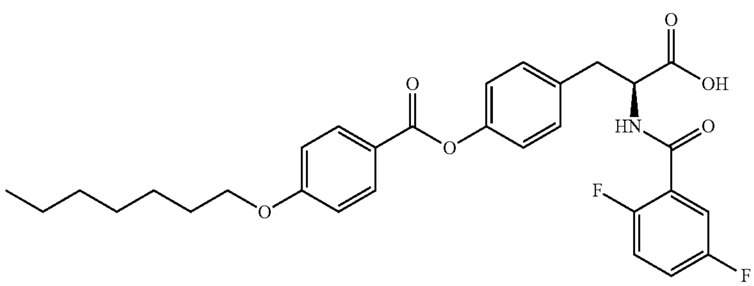 [SMILES: CCCCCCCOc1ccc(C(=O)Oc2ccc(C[C@H](NC(=O)c3cc(F)ccc3F)C(=O)O)cc2)cc1] | 37 | 11.44 | 2 |
| 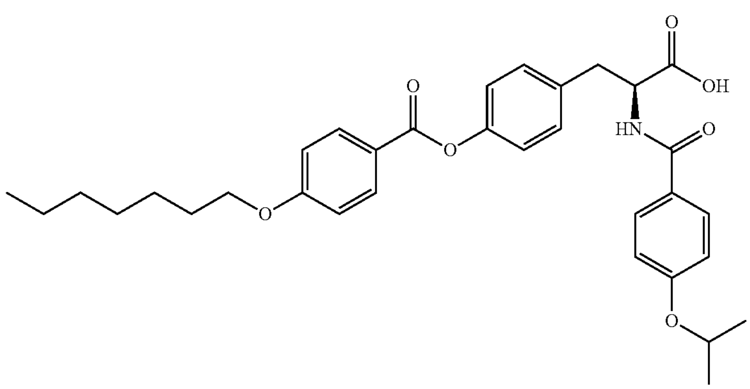 [SMILES: CCCCCCCOc1ccc(C(=O)Oc2ccc(C[C@H](NC(=O)c3ccc(OC(C)C)cc3)C(=O)O)cc2)cc1] | 38 | 11.64 | 2 |
| 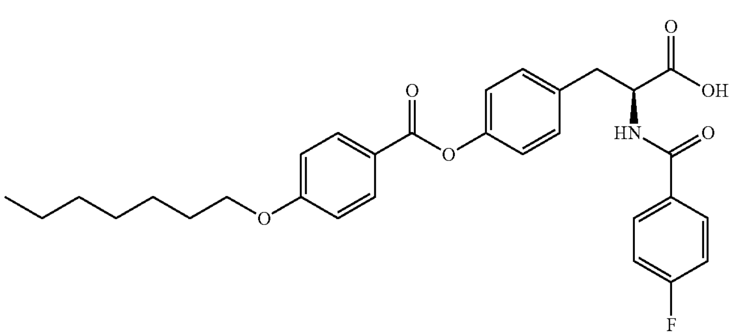 [SMILES: CCCCCCCOc1ccc(C(=O)Oc2ccc(C[C@H](NC(=O)c3ccc(F)cc3)C(=O)O)cc2)cc1] | 39 | 11.26 | 2 |

TABLE 1-continued

| STRUCTURE | COMPOUND NUMBER | LCMS RETENTION TIME (min) | LCMS method |
|---|---|---|---|
| [structure] | 40 | 11.31 | 2 |
| [structure] | 41 | 11.35 | 2 |
| [structure] | 42 | 11.39 | 2 |
| [structure] | 43 | 11.60 | 2 |

TABLE 1-continued

| STRUCTURE | COMPOUND NUMBER | LCMS RETENTION TIME (min) | LCMS method |
|---|---|---|---|
| 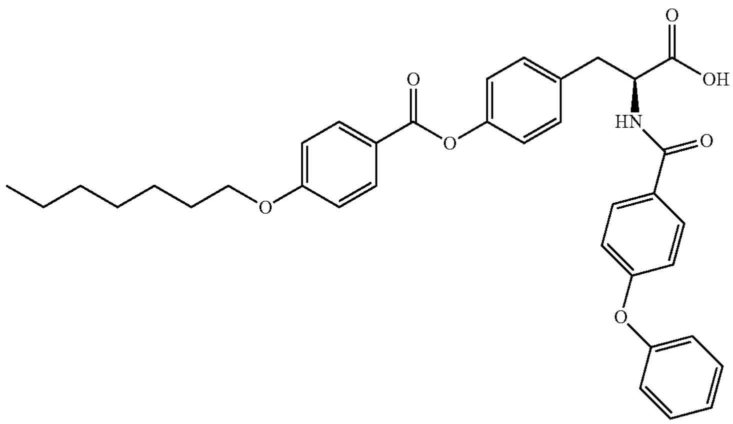 [SMILES: CCCCCCCOc1ccc(C(=O)Oc2ccc(C[C@H](NC(=O)c3ccc(Oc4ccccc4)cc3)C(=O)O)cc2)cc1] | 44 | 11.83 | 2 |
| 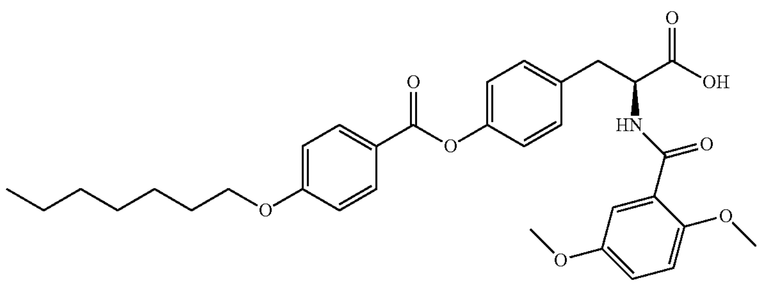 [SMILES: CCCCCCCOc1ccc(C(=O)Oc2ccc(C[C@H](NC(=O)c3cc(OC)ccc3OC)C(=O)O)cc2)cc1] | 45 | 11.39 | 2 |
| 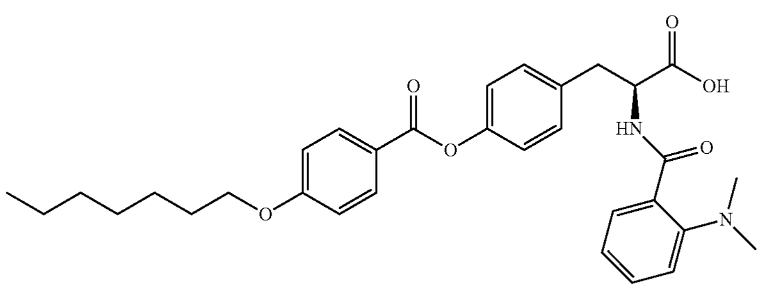 [SMILES: CCCCCCCOc1ccc(C(=O)Oc2ccc(C[C@H](NC(=O)c3ccccc3N(C)C)C(=O)O)cc2)cc1] | 46 | 11.19 | 2 |
| 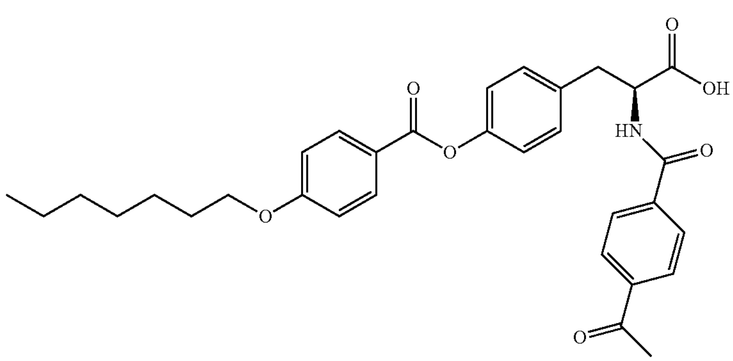 [SMILES: CCCCCCCOc1ccc(C(=O)Oc2ccc(C[C@H](NC(=O)c3ccc(C(C)=O)cc3)C(=O)O)cc2)cc1] | 47 | 10.95 | 2 |

TABLE 1-continued

| STRUCTURE | COMPOUND NUMBER | LCMS RETENTION TIME (min) | LCMS method |
|---|---|---|---|
| 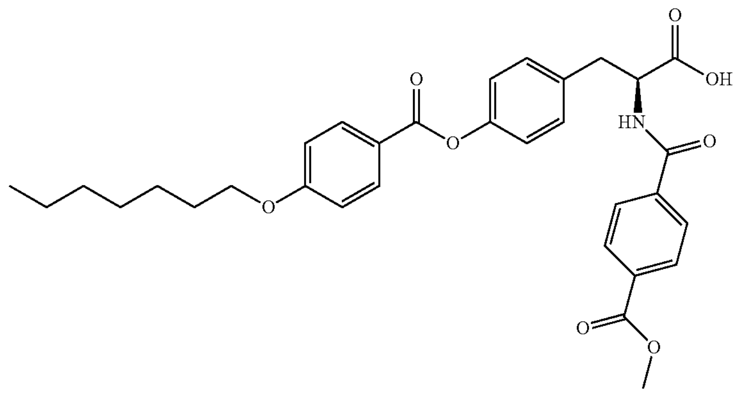 [SMILES: CCCCCCCOc1ccc(C(=O)Oc2ccc(C[C@H](NC(=O)c3ccc(C(=O)OC)cc3)C(=O)O)cc2)cc1] | 48 | 11.19 | 2 |
| 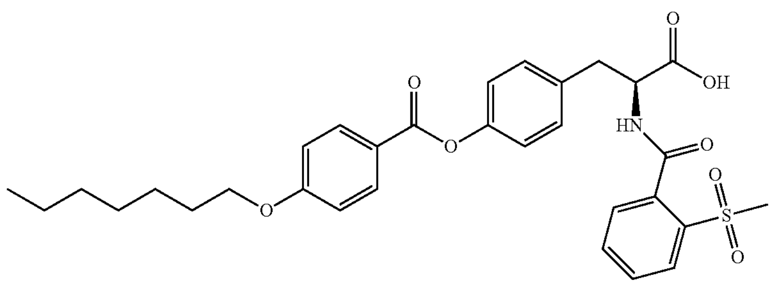 [SMILES: CCCCCCCOc1ccc(C(=O)Oc2ccc(C[C@H](NC(=O)c3ccccc3S(C)(=O)=O)C(=O)O)cc2)cc1] | 49 | 10.76 | 2 |
| 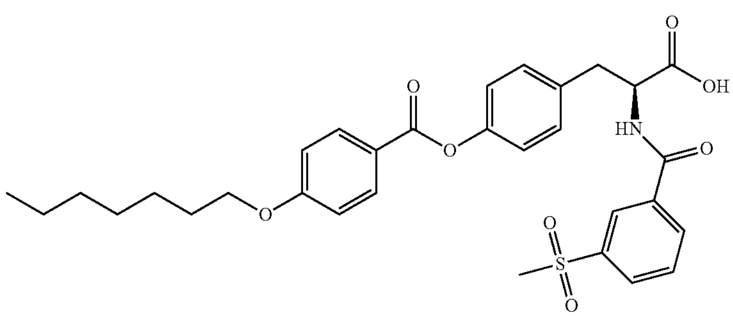 [SMILES: CCCCCCCOc1ccc(C(=O)Oc2ccc(C[C@H](NC(=O)c3cccc(S(C)(=O)=O)c3)C(=O)O)cc2)cc1] | 50 | 10.63 | 2 |
| 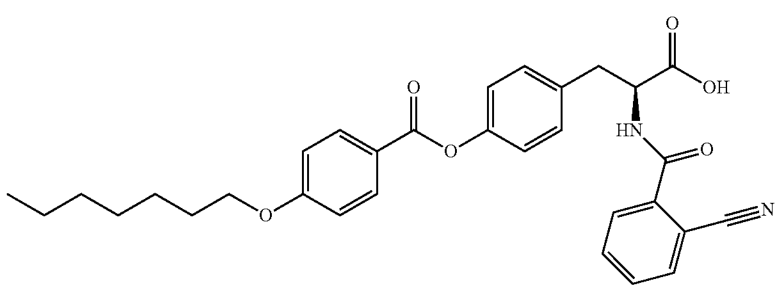 [SMILES: CCCCCCCOc1ccc(C(=O)Oc2ccc(C[C@H](NC(=O)c3ccccc3C#N)C(=O)O)cc2)cc1] | 51 | 11.02 | 2 |
| 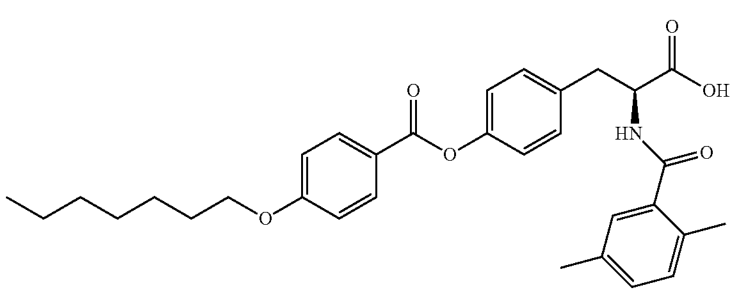 [SMILES: CCCCCCCOc1ccc(C(=O)Oc2ccc(C[C@H](NC(=O)c3cc(C)ccc3C)C(=O)O)cc2)cc1] | 52 | 11.58 | 2 |

TABLE 1-continued
| STRUCTURE | COMPOUND NUMBER | LCMS RETENTION TIME (min) | LCMS method |
|---|---|---|---|
| 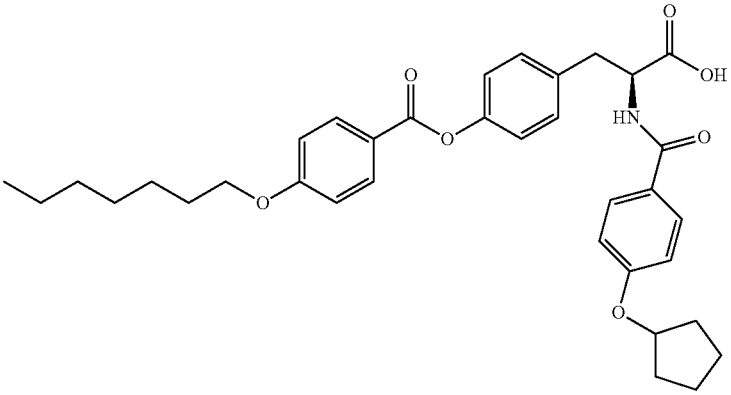 [SMILES: CCCCCCCOc1ccc(C(=O)Oc2ccc(C[C@H](NC(=O)c3ccc(OC4CCCC4)cc3)C(=O)O)cc2)cc1] | 53 | 12.16 | 2 |
| 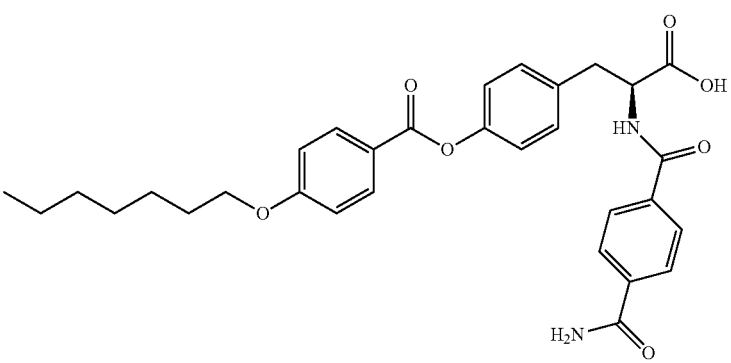 [SMILES: CCCCCCCOc1ccc(C(=O)Oc2ccc(C[C@H](NC(=O)c3ccc(C(N)=O)cc3)C(=O)O)cc2)cc1] | 54 | 9.87 | 2 |
| 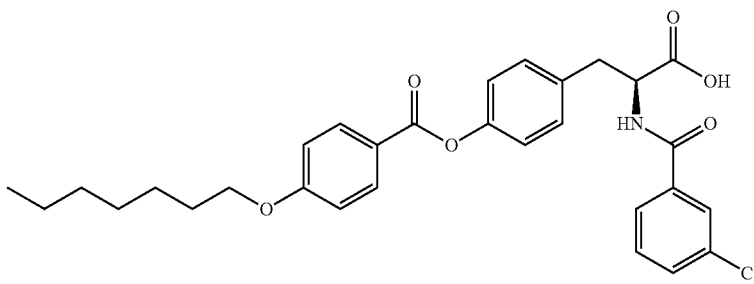 | 55 | 11.57 | 2 |
| 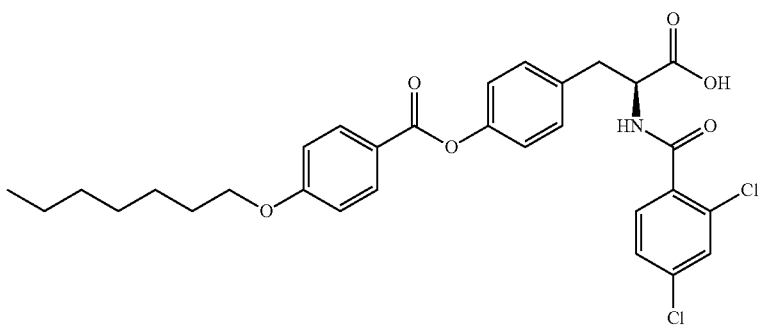 [SMILES: CCCCCCCOc1ccc(C(=O)Oc2ccc(C[C@H](NC(=O)c3ccc(Cl)cc3Cl)C(=O)O)cc2)cc1] | 56 | 11.70 | 2 |

TABLE 1-continued
| STRUCTURE | COMPOUND NUMBER | LCMS RETENTION TIME (min) | LCMS method |
|---|---|---|---|
| 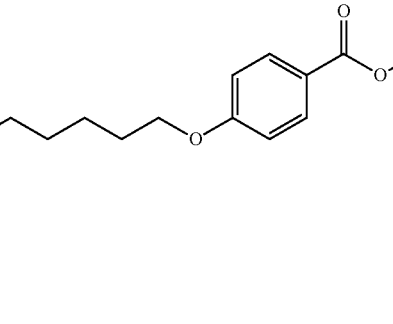 | 57 | 12.14 | 2 |
| 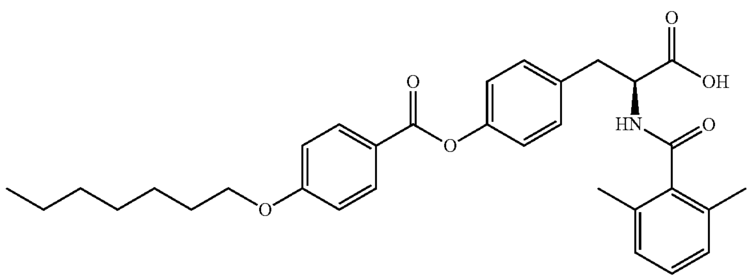 [SMILES: CCCCCCCOc1ccc(C(=O)Oc2ccc(C[C@H](NC(=O)c3c(C)cccc3C)C(=O)O)cc2)cc1] | 58 | 11.40 | 2 |
| 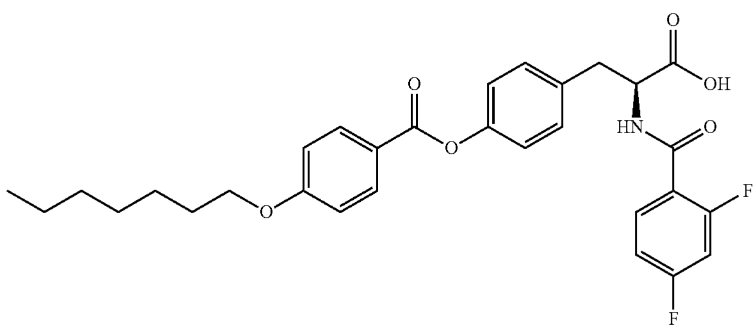 [SMILES: CCCCCCCOc1ccc(C(=O)Oc2ccc(C[C@H](NC(=O)c3ccc(F)cc3F)C(=O)O)cc2)cc1] | 59 | 11.44 | 2 |
| 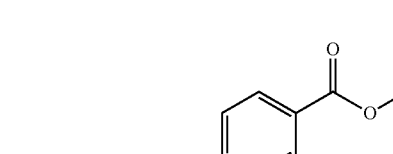 | 60 | 11.21 | 2 |
| 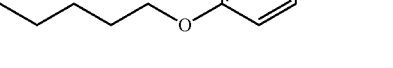 | 61 | 11.13 | 2 |

TABLE 1-continued

| STRUCTURE | COMPOUND NUMBER | LCMS RETENTION TIME (min) | LCMS method |
|---|---|---|---|
| 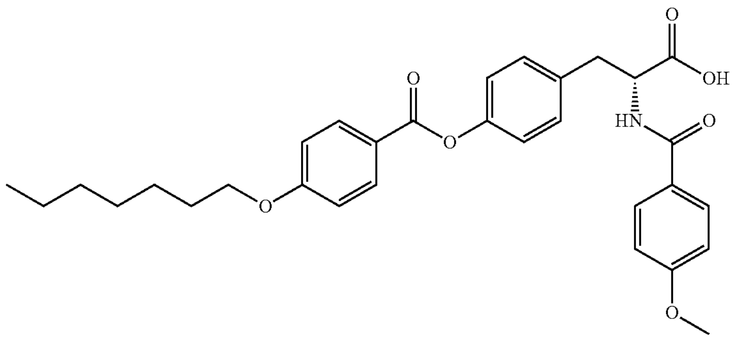 [SMILES: CCCCCCCOc1ccc(C(=O)Oc2ccc(C[C@@H](NC(=O)c3ccc(OC)cc3)C(=O)O)cc2)cc1] | 62 | 11.11 | 2 |
| 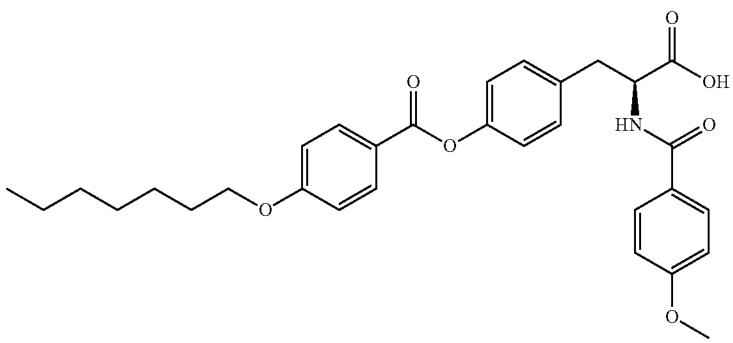 | 63 | 11.12 | 2 |
| 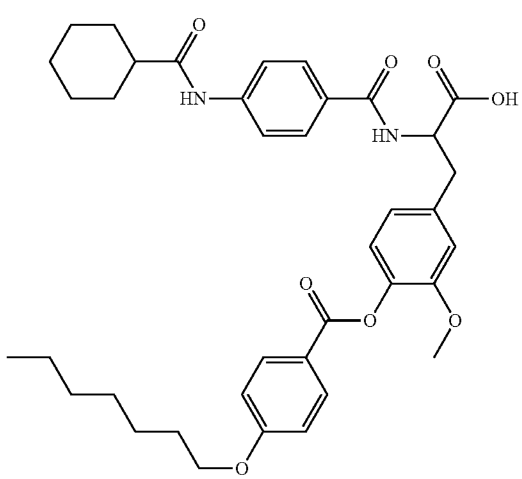 [SMILES: CCCCCCCOc1ccc(C(=O)Oc2ccc(CC(NC(=O)c3ccc(NC(=O)C4CCCCC4)cc3)C(=O)O)cc2OC)cc1] | 64 | 3.15 | 4 |

TABLE 1-continued
| STRUCTURE | COMPOUND NUMBER | LCMS RETENTION TIME (min) | LCMS method |
|---|---|---|---|
| 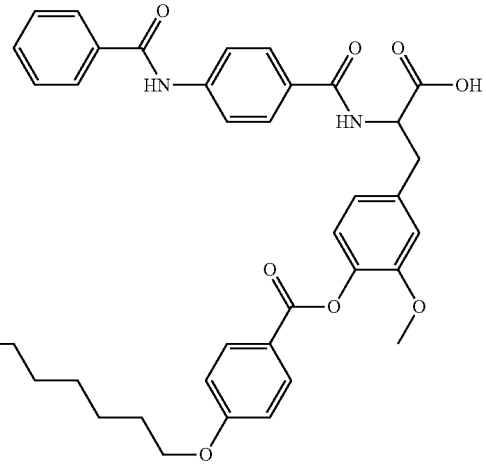 | 65 | 3.28 | 4 |
| 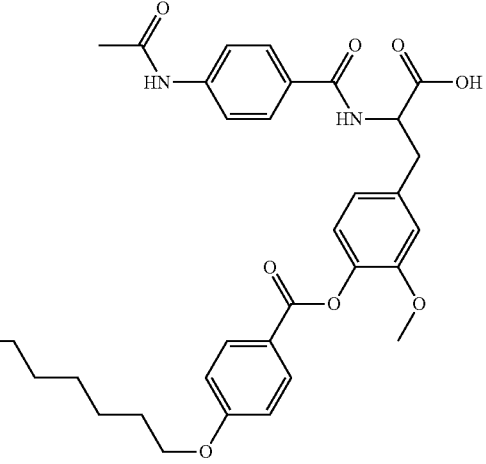 | 66 | 10.14 | 2 |
| 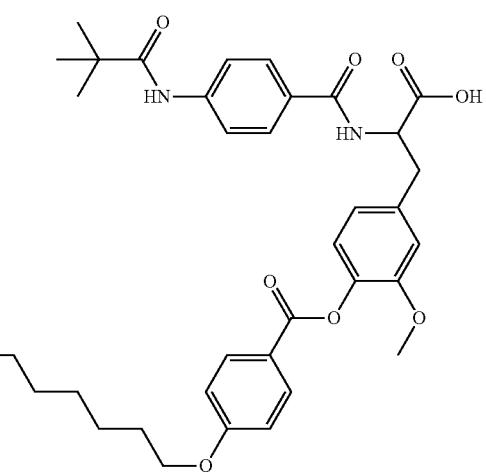 | 67 | 9.92 | 5 |

TABLE 1-continued

| STRUCTURE | COMPOUND NUMBER | LCMS RETENTION TIME (min) | LCMS method |
|---|---|---|---|
| 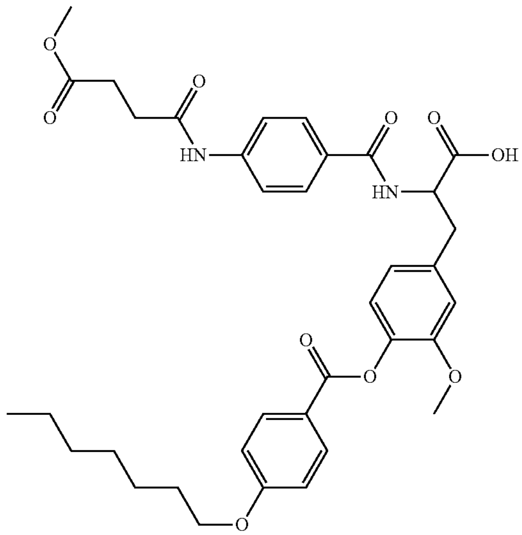 [SMILES: CCCCCCCOc1ccc(C(=O)Oc2ccc(CC(NC(=O)c3ccc(NC(=O)CCC(=O)OC)cc3)C(=O)O)cc2OC)cc1] | 68 | 8.66 | 5 |
| 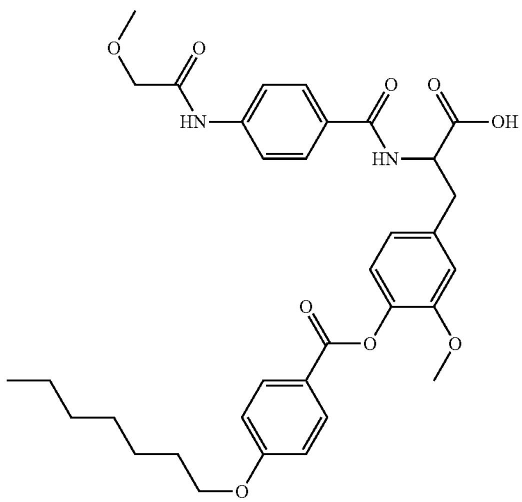 [SMILES: CCCCCCCOc1ccc(C(=O)Oc2ccc(CC(NC(=O)c3ccc(NC(=O)COC)cc3)C(=O)O)cc2OC)cc1] | 69 | 8.58 | 5 |
| 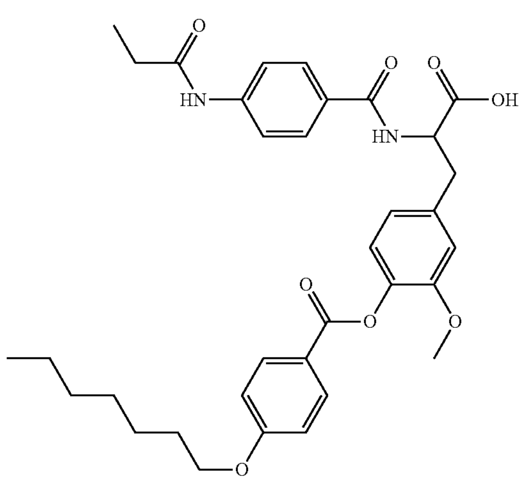 [SMILES: CCCCCCCOc1ccc(C(=O)Oc2ccc(CC(NC(=O)c3ccc(NC(=O)CC)cc3)C(=O)O)cc2OC)cc1] | 70 | 8.73 | 5 |

TABLE 1-continued
| STRUCTURE | COMPOUND NUMBER | LCMS RETENTION TIME (min) | LCMS method |
|---|---|---|---|
| 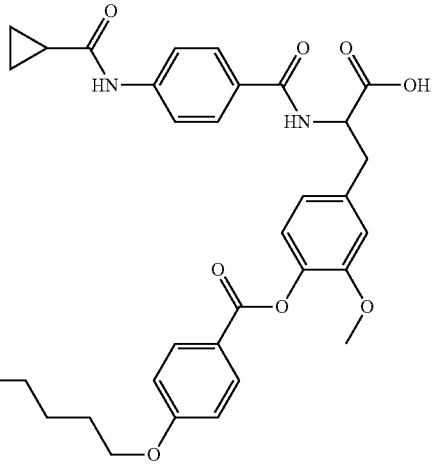 | 71 | 8.89 | 5 |
| 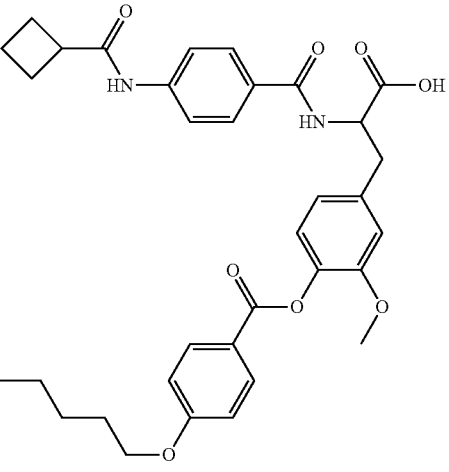 | 72 | 9.28 | 5 |
| 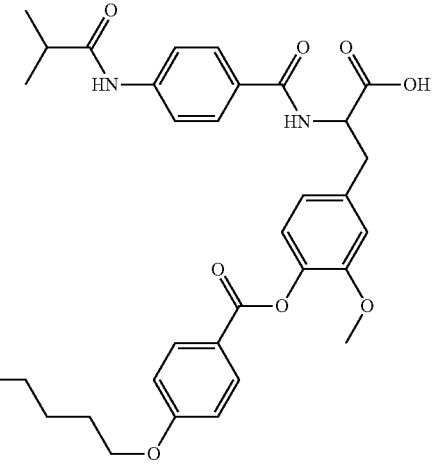 | 73 | 9.09 | 5 |

TABLE 1-continued

| STRUCTURE | COMPOUND NUMBER | LCMS RETENTION TIME (min) | LCMS method |
|---|---|---|---|
| [structure] | 74 | 9.75 | 5 |
| [structure] | 75 | 9.92 | 5 |
| [structure] | 76 | 8.31 | 5 |

TABLE 1-continued
| STRUCTURE | COMPOUND NUMBER | LCMS RETENTION TIME (min) | LCMS method |
|---|---|---|---|
| 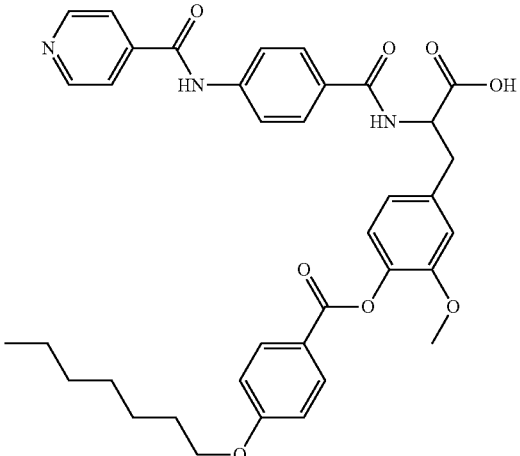 | 77 | 8.24 | 5 |
| 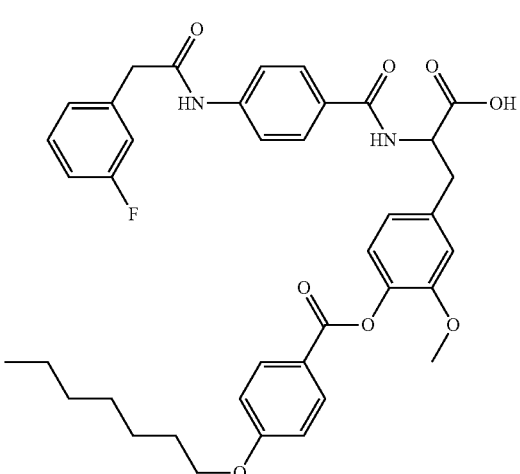 | 78 | 9.58 | 5 |
| 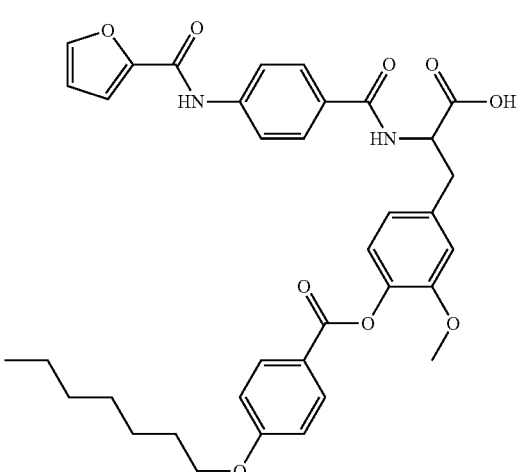 | 79 | 8.94 | 5 |

TABLE 1-continued
| STRUCTURE | COMPOUND NUMBER | LCMS RETENTION TIME (min) | LCMS method |
|---|---|---|---|
| 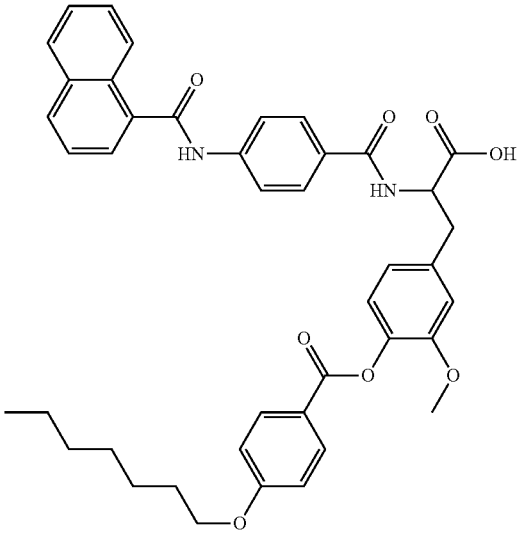 [SMILES: CCCCCCCOc1ccc(C(=O)Oc2ccc(CC(NC(=O)c3ccc(NC(=O)c4cccc5ccccc45)cc3)C(=O)O)cc2OC)cc1] | 80 | 9.97 | 5 |
| 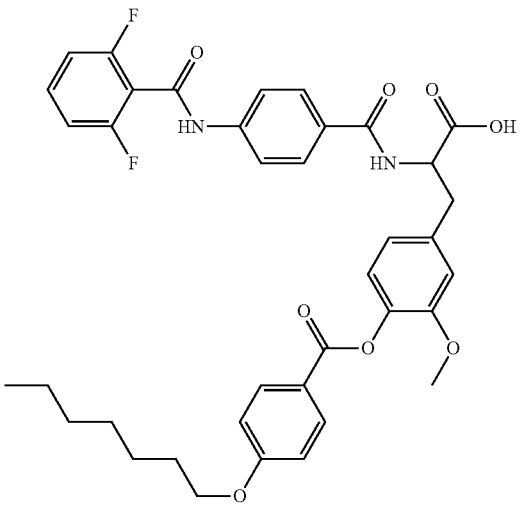 [SMILES: CCCCCCCOc1ccc(C(=O)Oc2ccc(CC(NC(=O)c3ccc(NC(=O)c4c(F)cccc4F)cc3)C(=O)O)cc2OC)cc1] | 81 | 9.35 | 5 |
| 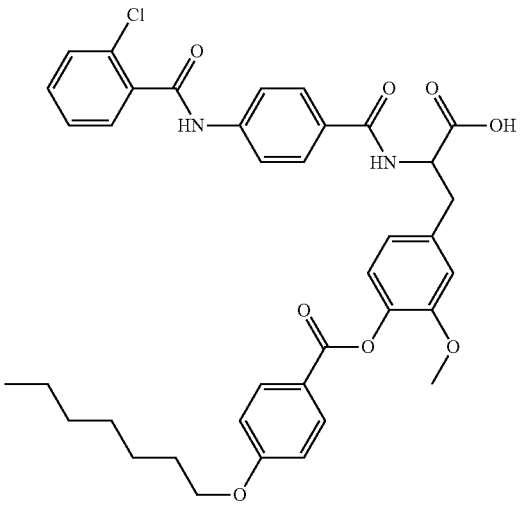 [SMILES: CCCCCCCOc1ccc(C(=O)Oc2ccc(CC(NC(=O)c3ccc(NC(=O)c4ccccc4Cl)cc3)C(=O)O)cc2OC)cc1] | 82 | 9.51 | 5 |

TABLE 1-continued
| STRUCTURE | COMPOUND NUMBER | LCMS RETENTION TIME (min) | LCMS method |
|---|---|---|---|
| 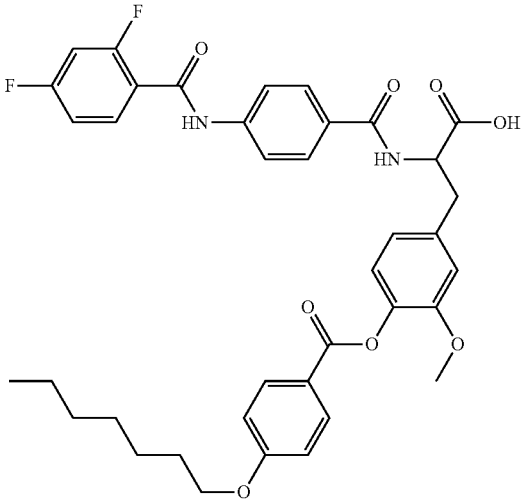 [SMILES: CCCCCCCOc1ccc(C(=O)Oc2ccc(CC(NC(=O)c3ccc(NC(=O)c4ccc(F)cc4F)cc3)C(=O)O)cc2OC)cc1] | 83 | 9.64 | 5 |
| 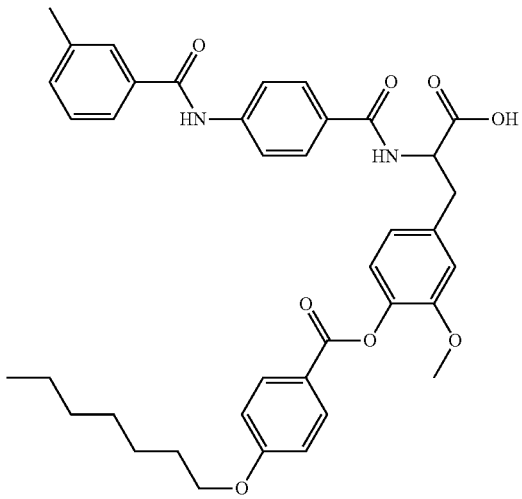 [SMILES: CCCCCCCOc1ccc(C(=O)Oc2ccc(CC(NC(=O)c3ccc(NC(=O)c4cccc(C)c4)cc3)C(=O)O)cc2OC)cc1] | 84 | 9.91 | 5 |
| 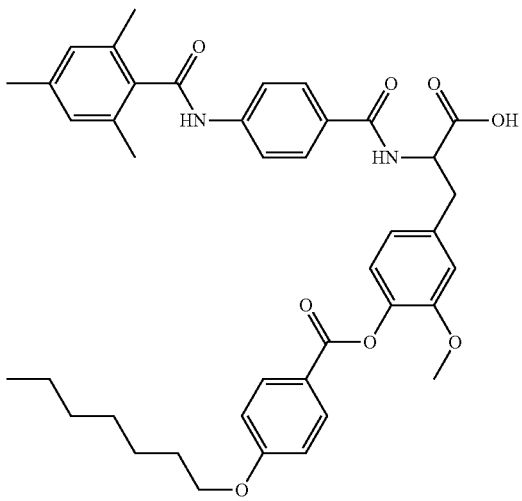 [SMILES: CCCCCCCOc1ccc(C(=O)Oc2ccc(CC(NC(=O)c3ccc(NC(=O)c4c(C)cc(C)cc4C)cc3)C(=O)O)cc2OC)cc1] | 85 | 10.18 | 5 |

TABLE 1-continued

| STRUCTURE | COMPOUND NUMBER | LCMS RETENTION TIME (min) | LCMS method |
|---|---|---|---|
| 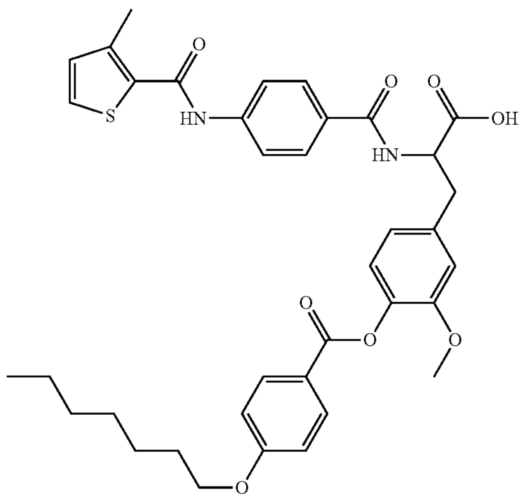 [SMILES: CCCCCCCOc1ccc(C(=O)Oc2ccc(CC(NC(=O)c3ccc(NC(=O)c4sccc4C)cc3)C(=O)O)cc2OC)cc1] | 86 | 9.71 | 5 |
| 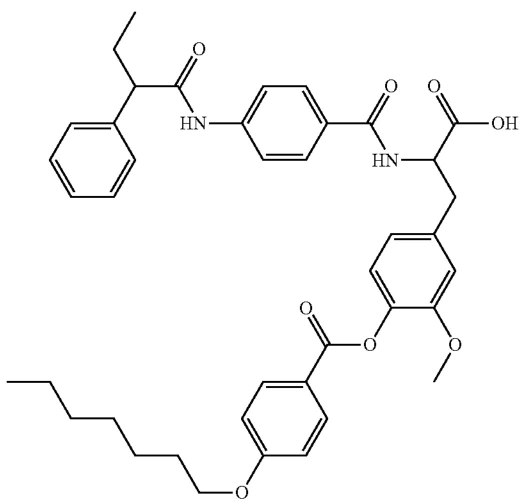 [SMILES: CCCCCCCOc1ccc(C(=O)Oc2ccc(CC(NC(=O)c3ccc(NC(=O)C(CC)c4ccccc4)cc3)C(=O)O)cc2OC)cc1] | 87 | 10.28 | 5 |
| 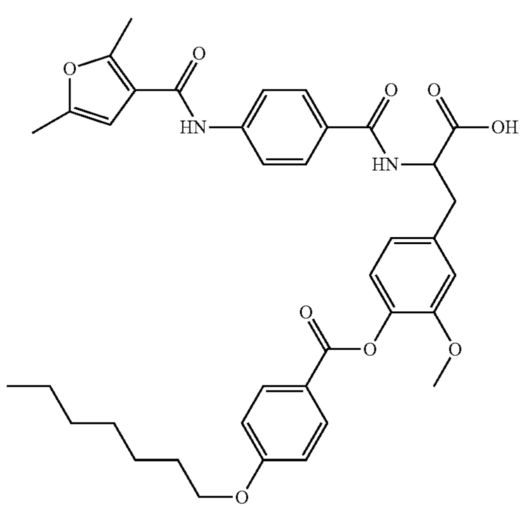 [SMILES: CCCCCCCOc1ccc(C(=O)Oc2ccc(CC(NC(=O)c3ccc(NC(=O)c4cc(C)oc4C)cc3)C(=O)O)cc2OC)cc1] | 88 | 9.91 | 5 |

TABLE 1-continued
| STRUCTURE | COMPOUND NUMBER | LCMS RETENTION TIME (min) | LCMS method |
|---|---|---|---|
| 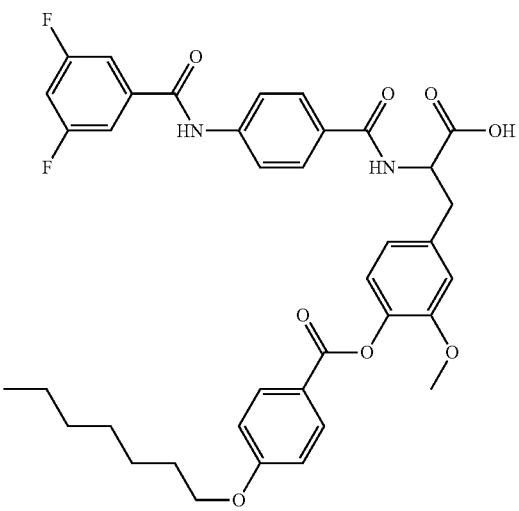 [SMILES: CCCCCCCOc1ccc(C(=O)Oc2ccc(CC(NC(=O)c3ccc(NC(=O)c4cc(F)cc(F)c4)cc3)C(=O)O)cc2OC)cc1] | 89 | 9.96 | 5 |
| 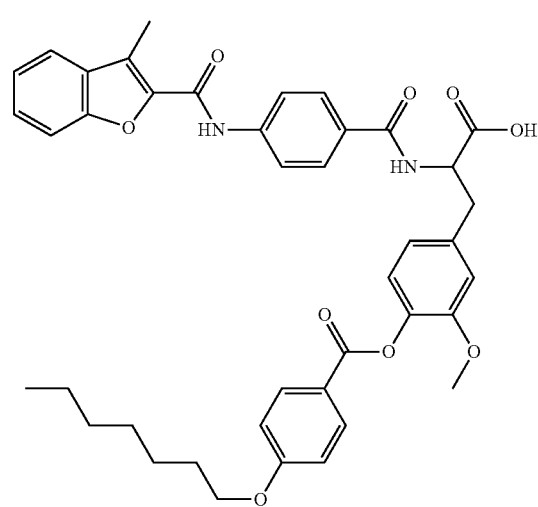 [SMILES: CCCCCCCOc1ccc(C(=O)Oc2ccc(CC(NC(=O)c3ccc(NC(=O)c4oc5ccccc5c4C)cc3)C(=O)O)cc2OC)cc1] | 90 | 10.64 | 5 |
| 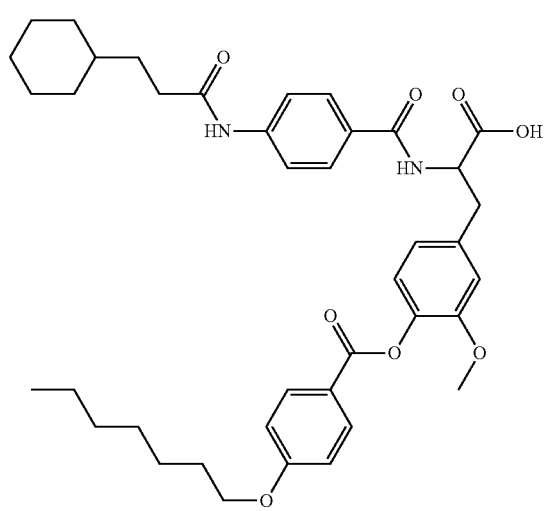 [SMILES: CCCCCCCOc1ccc(C(=O)Oc2ccc(CC(NC(=O)c3ccc(NC(=O)CCC4CCCCC4)cc3)C(=O)O)cc2OC)cc1] | 91 | 10.84 | 5 |

TABLE 1-continued
| STRUCTURE | COMPOUND NUMBER | LCMS RETENTION TIME (min) | LCMS method |
|---|---|---|---|
| 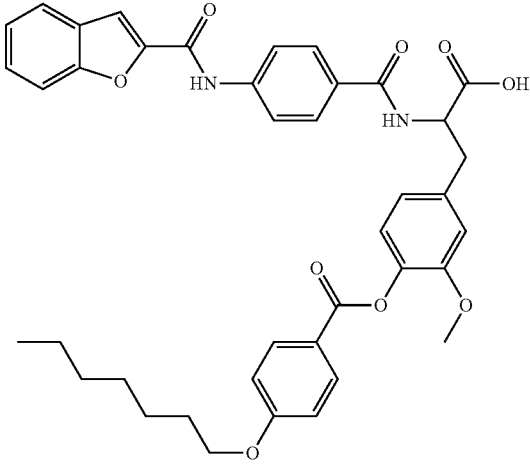 [SMILES: CCCCCCCOc1ccc(C(=O)Oc2ccc(CC(NC(=O)c3ccc(NC(=O)c4cc5ccccc5o4)cc3)C(=O)O)cc2OC)cc1] | 92 | 10.00 | 5 |
| 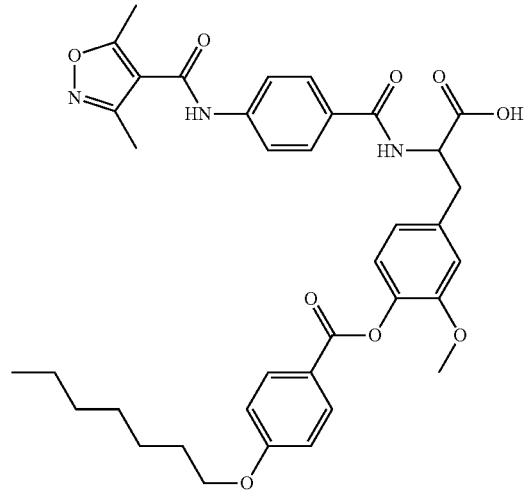 [SMILES: CCCCCCCOc1ccc(C(=O)Oc2ccc(CC(NC(=O)c3ccc(NC(=O)c4c(C)noc4C)cc3)C(=O)O)cc2OC)cc1] | 93 | 9.10 | 5 |
| 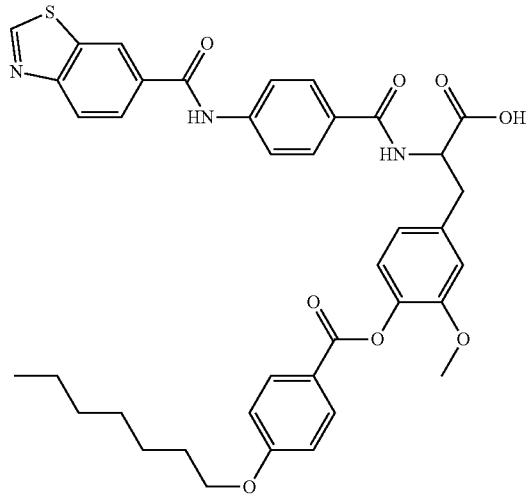 [SMILES: CCCCCCCOc1ccc(C(=O)Oc2ccc(CC(NC(=O)c3ccc(NC(=O)c4ccc5ncsc5c4)cc3)C(=O)O)cc2OC)cc1] | 94 | 9.02 | 5 |

TABLE 1-continued

| STRUCTURE | COMPOUND NUMBER | LCMS RETENTION TIME (min) | LCMS method |
|---|---|---|---|
| 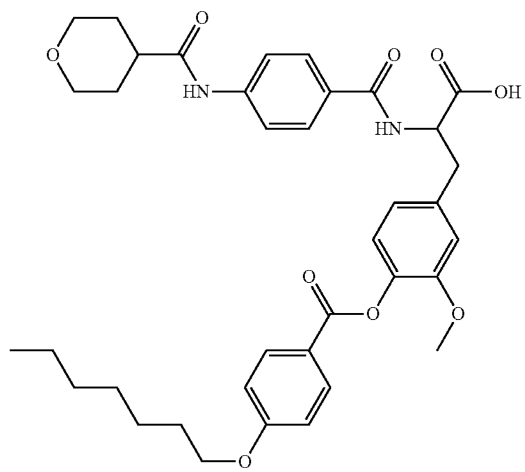 [SMILES: CCCCCCCOc1ccc(C(=O)Oc2ccc(CC(NC(=O)c3ccc(NC(=O)C4CCOCC4)cc3)C(=O)O)cc2OC)cc1] | 95 | 8.51 | 5 |
| 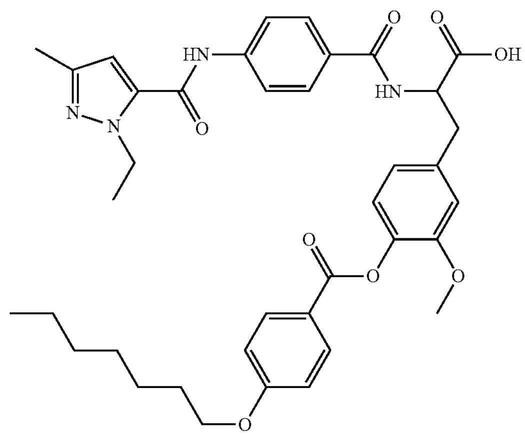 [SMILES: CCCCCCCOc1ccc(C(=O)Oc2ccc(CC(NC(=O)c3ccc(NC(=O)c4cc(C)nn4CC)cc3)C(=O)O)cc2OC)cc1] | 96 | 9.37 | 5 |
| 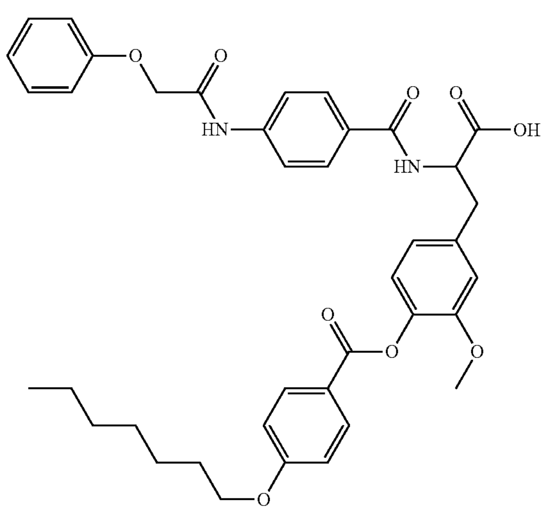 | 97 | 9.67 | 5 |

TABLE 1-continued
| STRUCTURE | COMPOUND NUMBER | LCMS RETENTION TIME (min) | LCMS method |
|---|---|---|---|
| 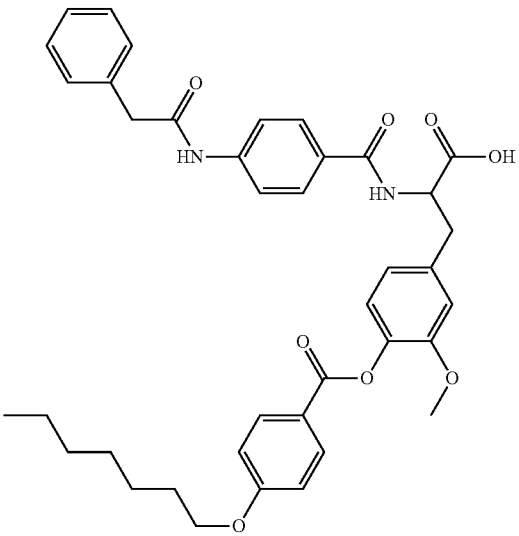 [SMILES: CCCCCCCOc1ccc(C(=O)Oc2ccc(CC(NC(=O)c3ccc(NC(=O)Cc4ccccc4)cc3)C(=O)O)cc2OC)cc1] | 98 | 9.58 | 5 |
| 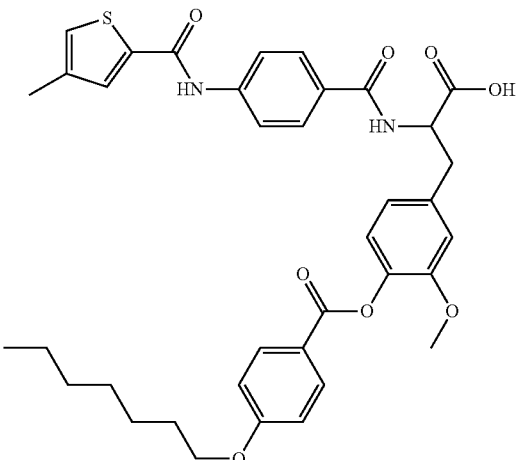 | 99 | 9.79 | 5 |
| 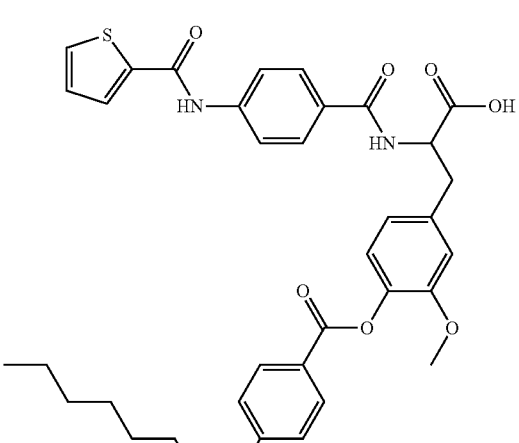 | 100 | 9.41 | 5 |

TABLE 1-continued

| STRUCTURE | COMPOUND NUMBER | LCMS RETENTION TIME (min) | LCMS method |
|---|---|---|---|
| (structure) | 101 | 9.77 | 5 |
| (structure) | 102 | 10.29 | 5 |
| (structure) | 103 | 9.86 | 5 |

TABLE 1-continued

| STRUCTURE | COMPOUND NUMBER | LCMS RETENTION TIME (min) | LCMS method |
|---|---|---|---|
| 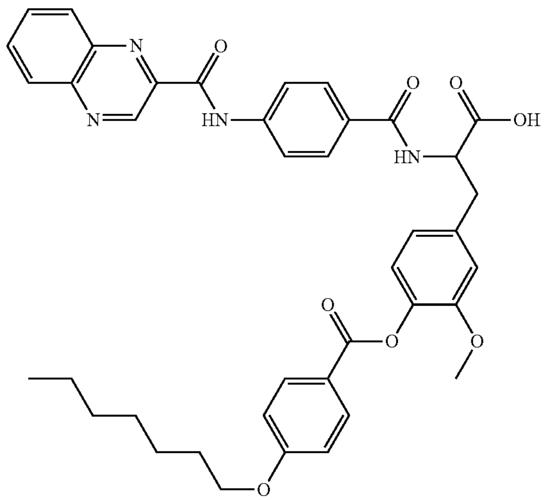 [SMILES: CCCCCCCOc1ccc(C(=O)Oc2ccc(CC(NC(=O)c3ccc(NC(=O)c4cnc5ccccc5n4)cc3)C(=O)O)cc2OC)cc1] | 104 | 9.88 | 5 |
| 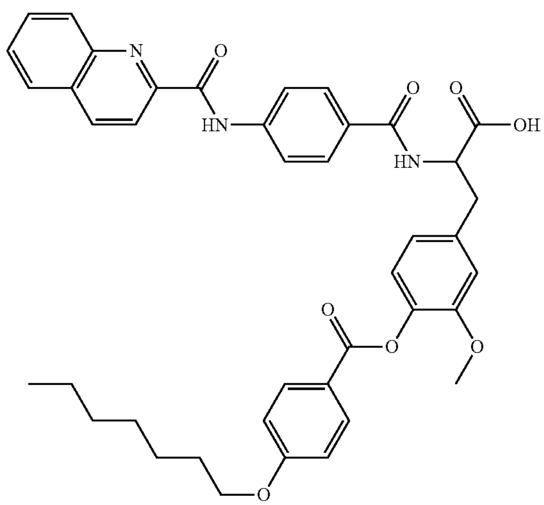 [SMILES: CCCCCCCOc1ccc(C(=O)Oc2ccc(CC(NC(=O)c3ccc(NC(=O)c4ccc5ccccc5n4)cc3)C(=O)O)cc2OC)cc1] | 105 | 10.45 | 5 |
| 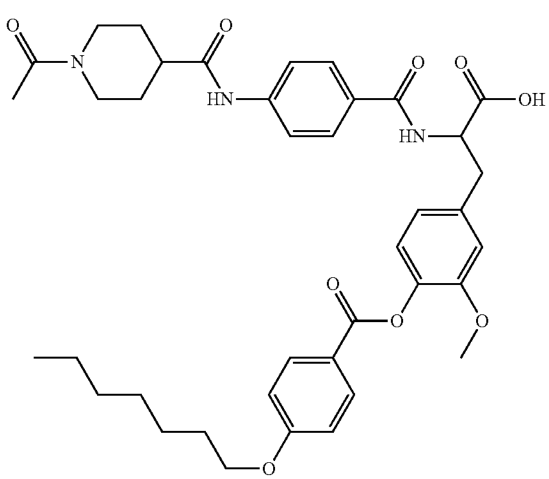 [SMILES: CCCCCCCOc1ccc(C(=O)Oc2ccc(CC(NC(=O)c3ccc(NC(=O)C4CCN(C(C)=O)CC4)cc3)C(=O)O)cc2OC)cc1] | 106 | 8.06 | 5 |

TABLE 1-continued
| STRUCTURE | COMPOUND NUMBER | LCMS RETENTION TIME (min) | LCMS method |
|---|---|---|---|
| 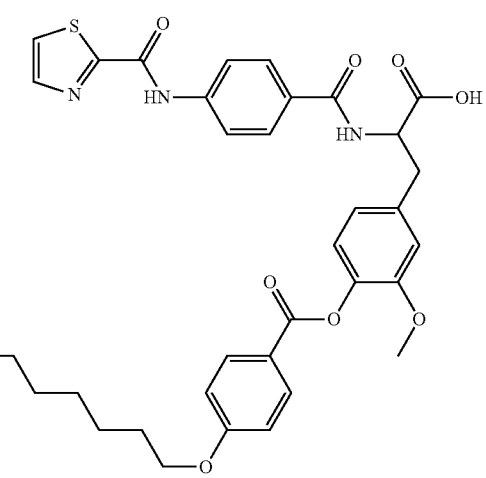 | 107 | 9.31 | 5 |
| 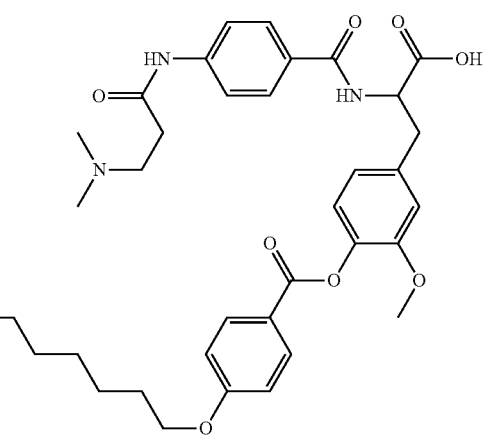 | 108 | 5.91 | 5 |
| 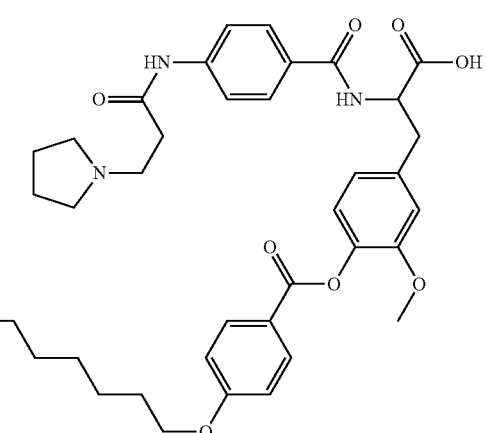 | 109 | 6.00 | 5 |

TABLE 1-continued
| STRUCTURE | COMPOUND NUMBER | LCMS RETENTION TIME (min) | LCMS method |
|---|---|---|---|
| 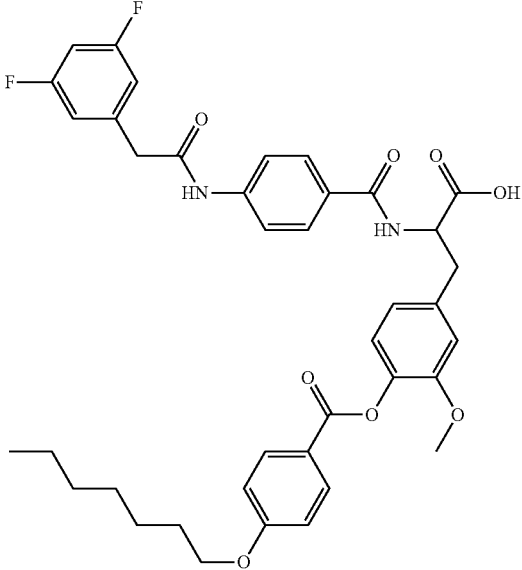 [SMILES: CCCCCCCOc1ccc(C(=O)Oc2ccc(CC(NC(=O)c3ccc(NC(=O)Cc4cc(F)cc(F)c4)cc3)C(=O)O)cc2OC)cc1] | 110 | 9.77 | 5 |
| 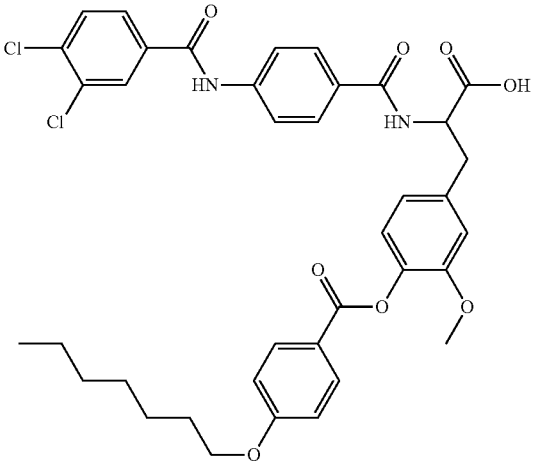 [SMILES: CCCCCCCOc1ccc(C(=O)Oc2ccc(CC(NC(=O)c3ccc(NC(=O)c4ccc(Cl)c(Cl)c4)cc3)C(=O)O)cc2OC)cc1] | 111 | 10.60 | 5 |
| 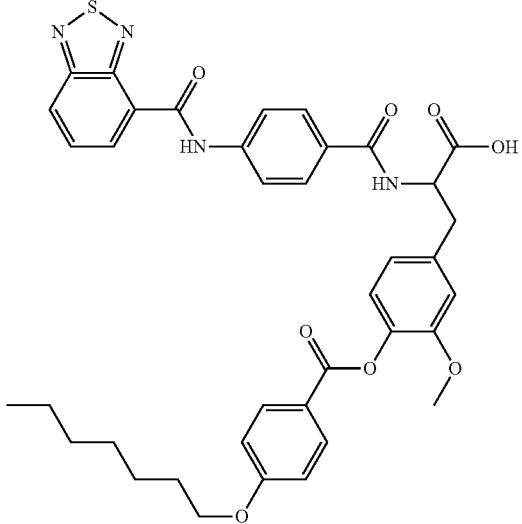 | 112 | 10.12 | 5 |

TABLE 1-continued
| STRUCTURE | COMPOUND NUMBER | LCMS RETENTION TIME (min) | LCMS method |
|---|---|---|---|
| 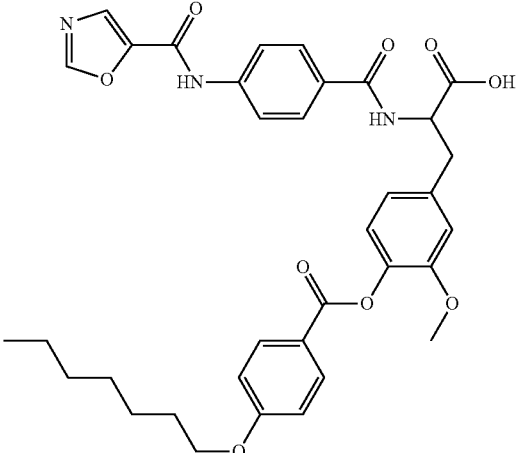 | 113 | 8.40 | 5 |
| 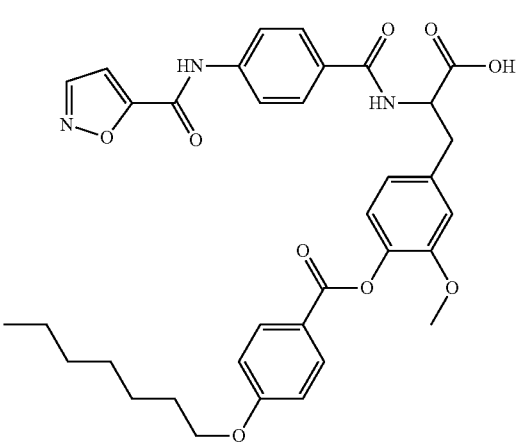 [SMILES: CCCCCCCOc1ccc(C(=O)Oc2ccc(CC(NC(=O)c3ccc(NC(=O)c4ccno4)cc3)C(=O)O)cc2OC)cc1] | 114 | 8.83 | 5 |
| 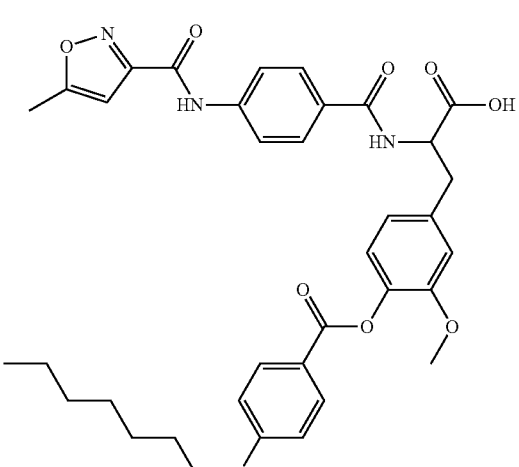 | 115 | 9.31 | 5 |

TABLE 1-continued

| STRUCTURE | COMPOUND NUMBER | LCMS RETENTION TIME (min) | LCMS method |
|---|---|---|---|
| 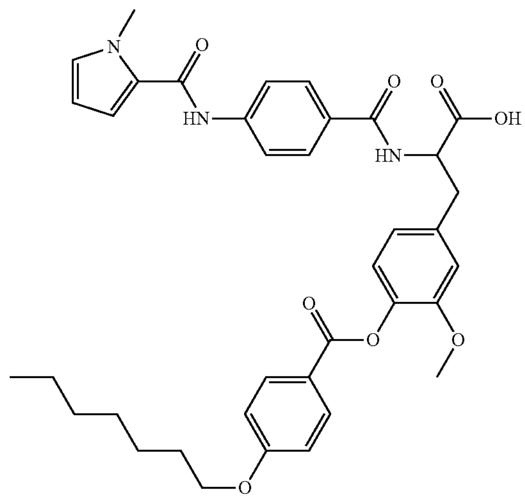 [SMILES: CCCCCCCOc1ccc(C(=O)Oc2ccc(CC(NC(=O)c3ccc(NC(=O)c4cccn4C)cc3)C(=O)O)cc2OC)cc1] | 116 | 9.38 | 5 |
| 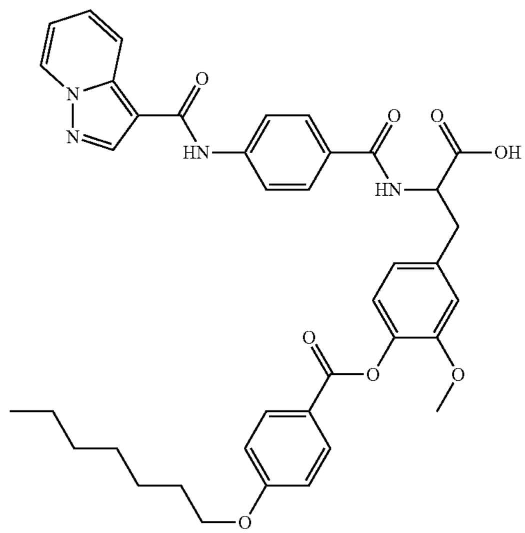 [SMILES: CCCCCCCOc1ccc(C(=O)Oc2ccc(CC(NC(=O)c3ccc(NC(=O)c4cnn5ccccc45)cc3)C(=O)O)cc2OC)cc1] | 117 | 8.93 | 5 |
| 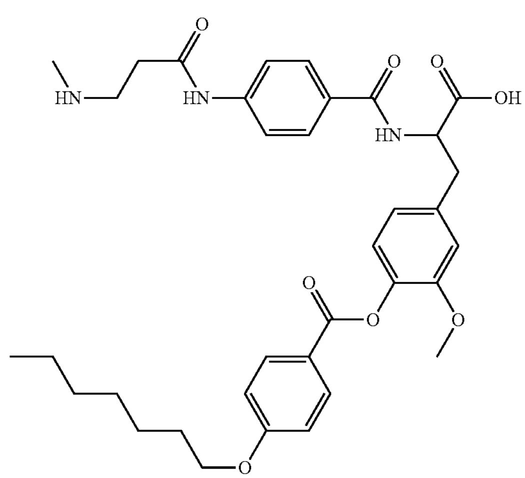 [SMILES: CCCCCCCOc1ccc(C(=O)Oc2ccc(CC(NC(=O)c3ccc(NC(=O)CCNC)cc3)C(=O)O)cc2OC)cc1] | 118 | 5.78 | 5 |

TABLE 1-continued
| STRUCTURE | COMPOUND NUMBER | LCMS RETENTION TIME (min) | LCMS method |
|---|---|---|---|
| 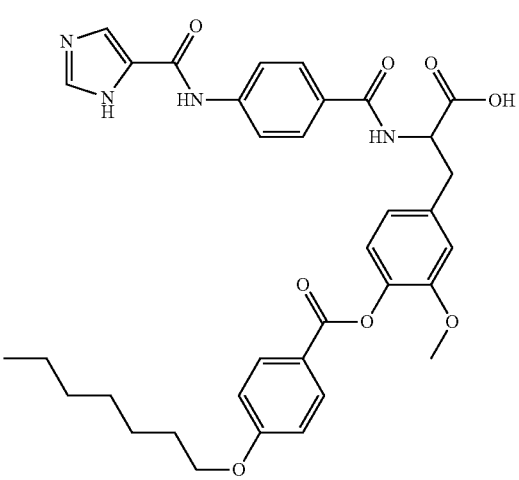 [SMILES: CCCCCCCOc1ccc(C(=O)Oc2ccc(CC(NC(=O)c3ccc(NC(=O)c4cnc[nH]4)cc3)C(=O)O)cc2OC)cc1] | 119 | 2.60 | 4 |
| 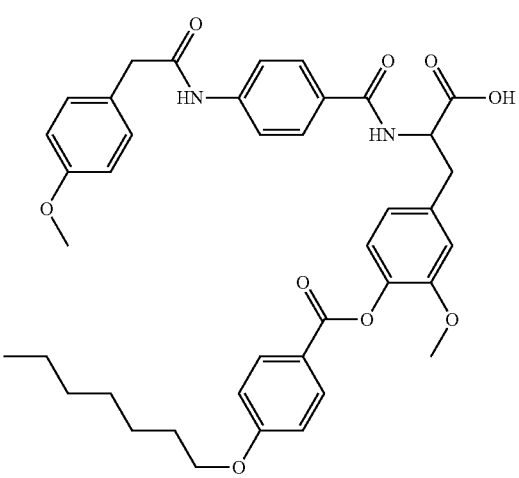 [SMILES: CCCCCCCOc1ccc(C(=O)Oc2ccc(CC(NC(=O)c3ccc(NC(=O)Cc4ccc(OC)cc4)cc3)C(=O)O)cc2OC)cc1] | 120 | 9.49 | 5 |
| 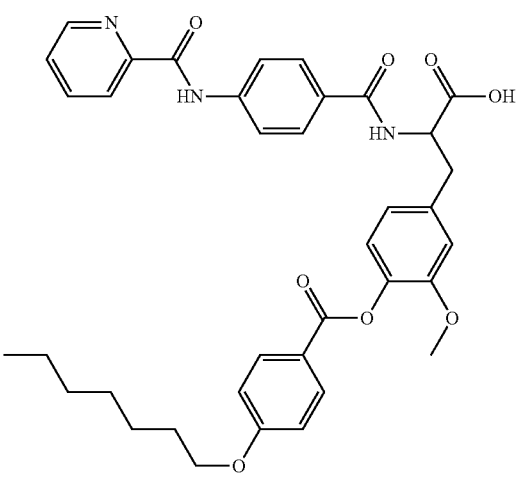 | 121 | 9.42 | 5 |

TABLE 1-continued
| STRUCTURE | COMPOUND NUMBER | LCMS RETENTION TIME (min) | LCMS method |
|---|---|---|---|
| 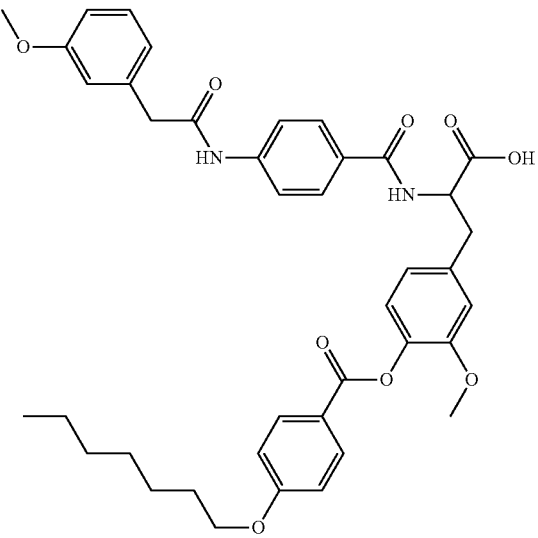 [SMILES: CCCCCCCOc1ccc(C(=O)Oc2ccc(CC(NC(=O)c3ccc(NC(=O)Cc4cccc(OC)c4)cc3)C(=O)O)cc2OC)cc1] | 122 | 3.06 | 4 |
| 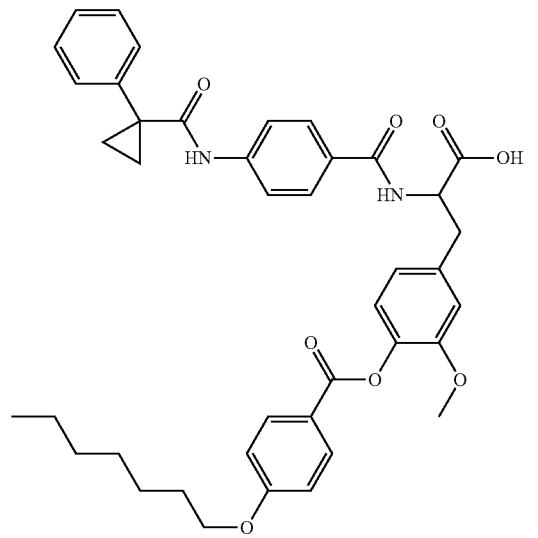 [SMILES: CCCCCCCOc1ccc(C(=O)Oc2ccc(CC(NC(=O)c3ccc(NC(=O)C4(c5ccccc5)CC4)cc3)C(=O)O)cc2OC)cc1] | 123 | 3.18 | 4 |

TABLE 1-continued
| STRUCTURE | COMPOUND NUMBER | LCMS RETENTION TIME (min) | LCMS method |
|---|---|---|---|
| 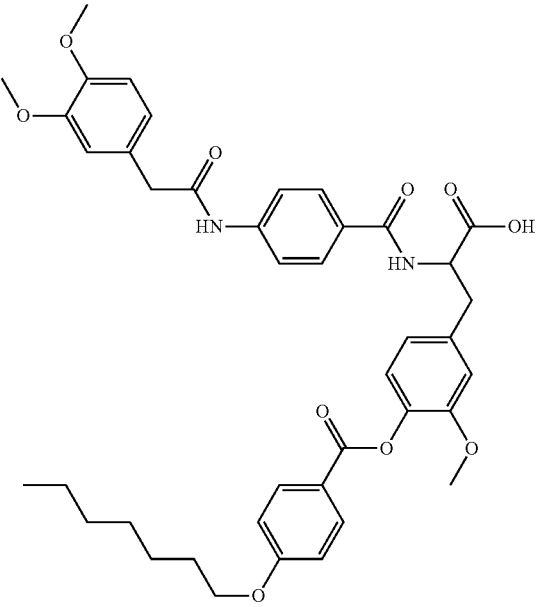 [SMILES: CCCCCCCOc1ccc(C(=O)Oc2ccc(CC(NC(=O)c3ccc(NC(=O)Cc4ccc(OC)c(OC)c4)cc3)C(=O)O)cc2OC)cc1] | 124 | 2.97 | 4 |
| 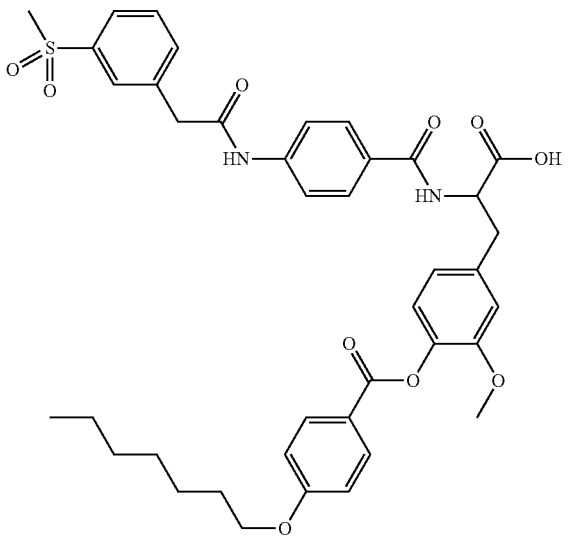 [SMILES: CCCCCCCOc1ccc(C(=O)Oc2ccc(CC(NC(=O)c3ccc(NC(=O)Cc4cccc(S(C)(=O)=O)c4)cc3)C(=O)O)cc2OC)cc1] | 125 | 2.84 | 4 |

TABLE 1-continued
| STRUCTURE | COMPOUND NUMBER | LCMS RETENTION TIME (min) | LCMS method |
|---|---|---|---|
| 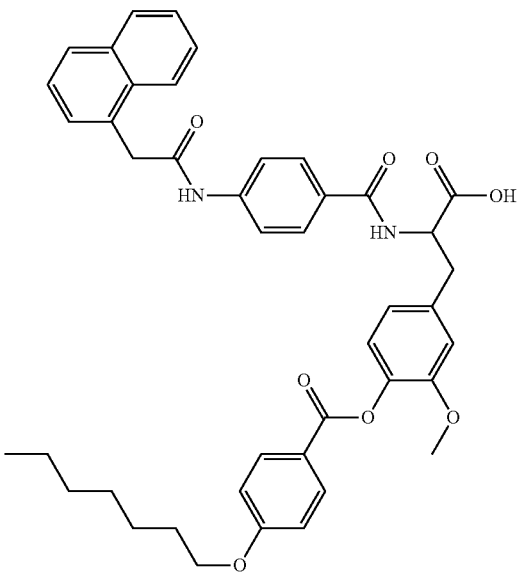 [SMILES: CCCCCCCOc1ccc(C(=O)Oc2ccc(CC(NC(=O)c3ccc(NC(=O)Cc4cccc5ccccc45)cc3)C(=O)O)cc2OC)cc1] | 126 | 3.15 | 4 |
| 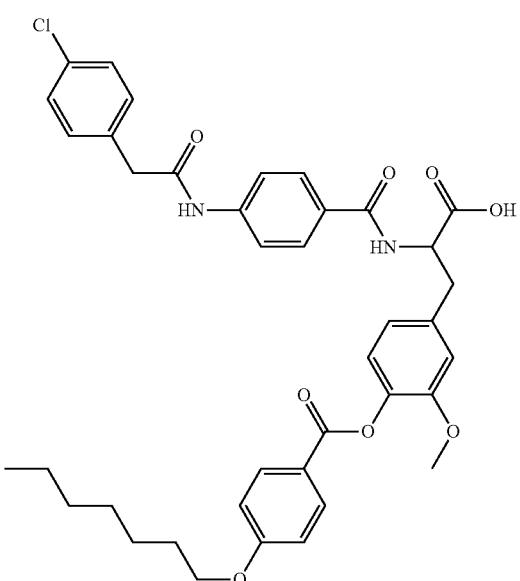 | 127 | 3.13 | 4 |

TABLE 1-continued
| STRUCTURE | COMPOUND NUMBER | LCMS RETENTION TIME (min) | LCMS method |
|---|---|---|---|
| 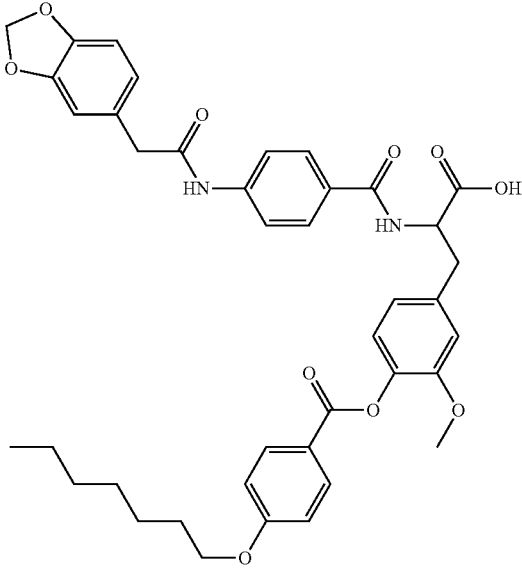 [SMILES: CCCCCCCOc1ccc(C(=O)Oc2ccc(CC(NC(=O)c3ccc(NC(=O)Cc4ccc5c(c4)OCO5)cc3)C(=O)O)cc2OC)cc1] | 128 | 3.03 | 4 |
| 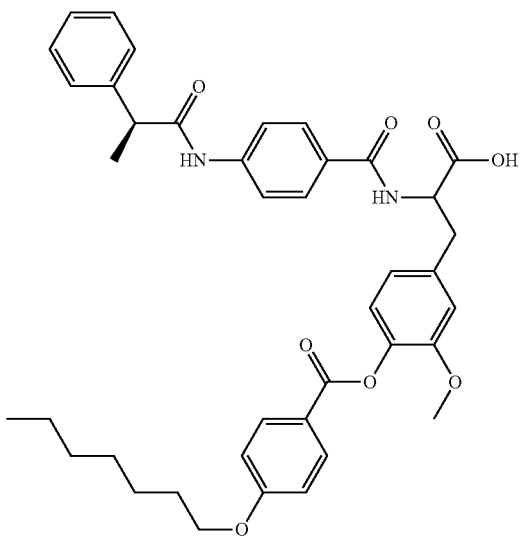 [SMILES: CCCCCCCOc1ccc(C(=O)Oc2ccc(CC(NC(=O)c3ccc(NC(=O)[C@@H](C)c4ccccc4)cc3)C(=O)O)cc2OC)cc1] | 129 | 3.12 | 4 |

TABLE 1-continued
| STRUCTURE | COMPOUND NUMBER | LCMS RETENTION TIME (min) | LCMS method |
|---|---|---|---|
| 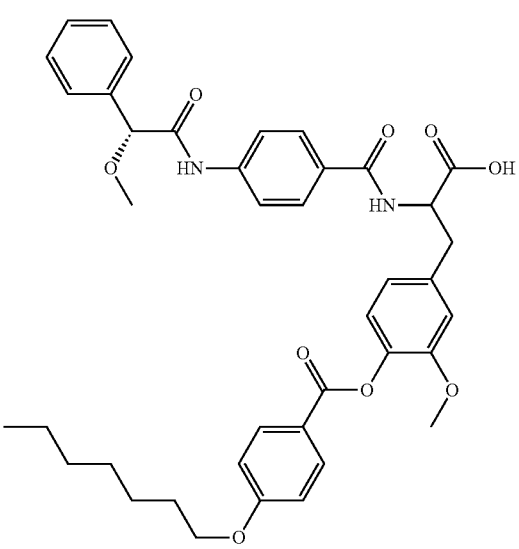 [SMILES: CCCCCCCOc1ccc(C(=O)Oc2ccc(CC(NC(=O)c3ccc(NC(=O)[C@H](OC)c4ccccc4)cc3)C(=O)O)cc2OC)cc1] | 130 | 3.10 | 4 |
| 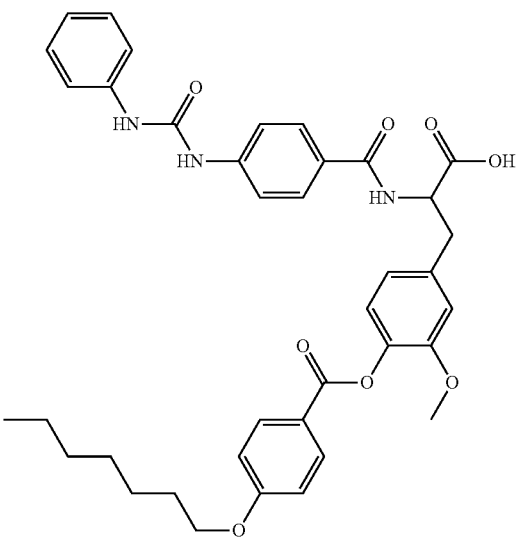 | 131 | 9.42 | 5 |

TABLE 1-continued
| STRUCTURE | COMPOUND NUMBER | LCMS RETENTION TIME (min) | LCMS method |
|---|---|---|---|
| 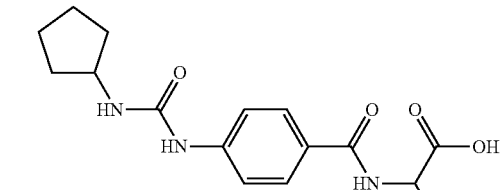 | 132 | 9.35 | 5 |
| 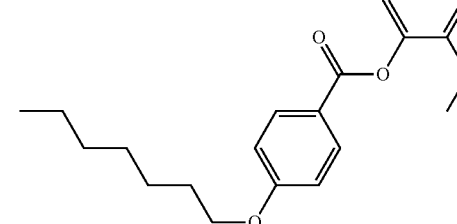 | 133 | 10.56 | 5 |
| 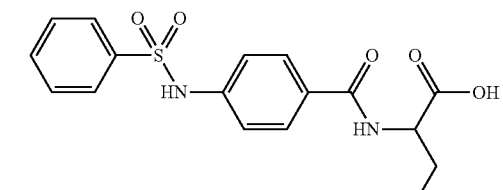 | 134 | 10.66 | 5 |

TABLE 1-continued
| STRUCTURE | COMPOUND NUMBER | LCMS RETENTION TIME (min) | LCMS method |
|---|---|---|---|
| 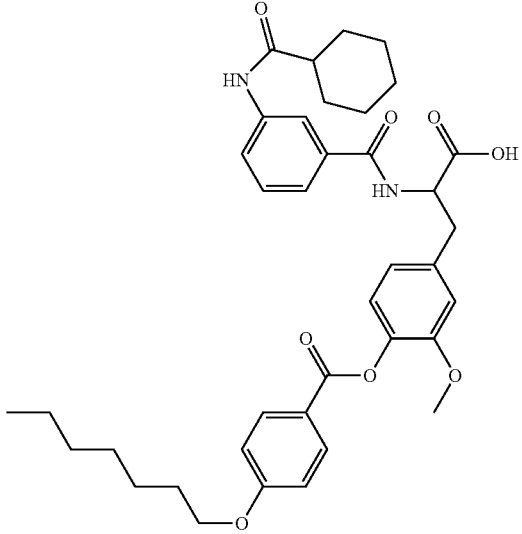 [SMILES: CCCCCCCOc1ccc(C(=O)Oc2ccc(CC(NC(=O)c3cccc(NC(=O)C4CCCCC4)c3)C(=O)O)cc2OC)cc1] | 135 | 3.14 | 4 |
| 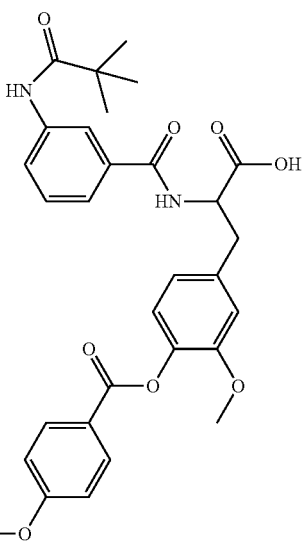 | 136 | 3.08 | 4 |

TABLE 1-continued
| STRUCTURE | COMPOUND NUMBER | LCMS RETENTION TIME (min) | LCMS method |
|---|---|---|---|
| 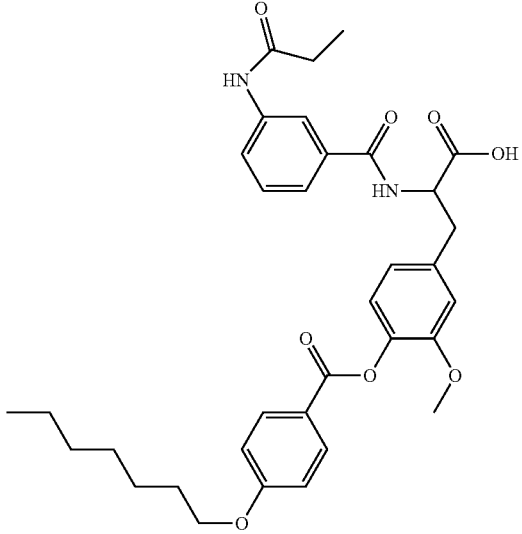 [SMILES: CCCCCCCOc1ccc(C(=O)Oc2ccc(CC(NC(=O)c3cccc(NC(=O)CC)c3)C(=O)O)cc2OC)cc1] | 137 | 2.92 | 4 |
| 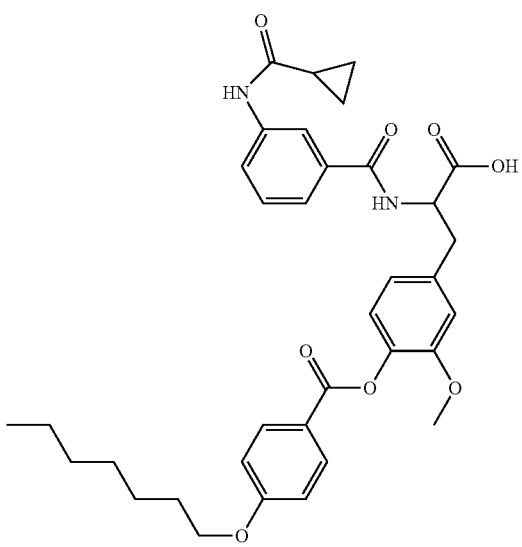 [SMILES: CCCCCCCOc1ccc(C(=O)Oc2ccc(CC(NC(=O)c3cccc(NC(=O)C4CC4)c3)C(=O)O)cc2OC)cc1] | 138 | 2.95 | 4 |

TABLE 1-continued
| STRUCTURE | COMPOUND NUMBER | LCMS RETENTION TIME (min) | LCMS method |
|---|---|---|---|
| 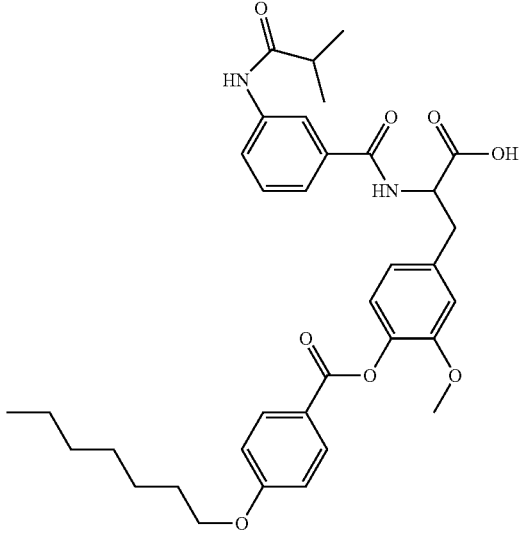 [SMILES: CCCCCCCOc1ccc(C(=O)Oc2ccc(CC(NC(=O)c3cccc(NC(=O)C(C)C)c3)C(=O)O)cc2OC)cc1] | 139 | 3.00 | 4 |
| 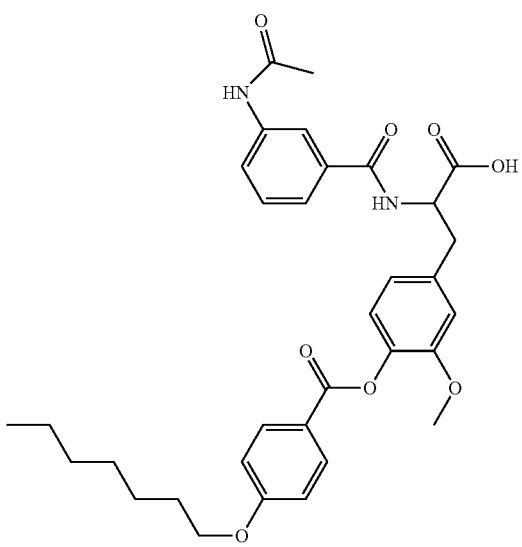 [SMILES: CCCCCCCOc1ccc(C(=O)Oc2ccc(CC(NC(=O)c3cccc(NC(C)=O)c3)C(=O)O)cc2OC)cc1] | 140 | 2.82 | 4 |

TABLE 1-continued

| STRUCTURE | COMPOUND NUMBER | LCMS RETENTION TIME (min) | LCMS method |
|---|---|---|---|
| 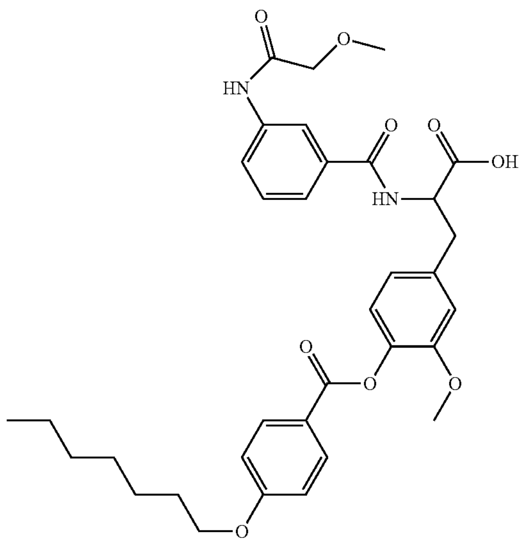 [SMILES: CCCCCCCOc1ccc(C(=O)Oc2ccc(CC(NC(=O)c3cccc(NC(=O)COC)c3)C(=O)O)cc2OC)cc1] | 141 | 2.88 | 4 |
| 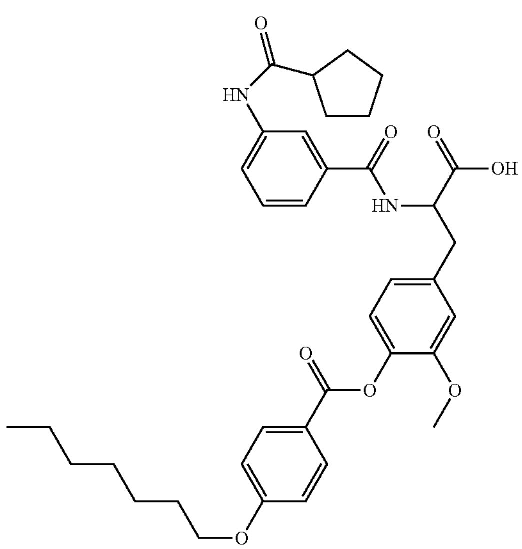 [SMILES: CCCCCCCOc1ccc(C(=O)Oc2ccc(CC(NC(=O)c3cccc(NC(=O)C4CCCC4)c3)C(=O)O)cc2OC)cc1] | 142 | 3.10 | 4 |

TABLE 1-continued

| STRUCTURE | COMPOUND NUMBER | LCMS RETENTION TIME (min) | LCMS method |
|---|---|---|---|
| (structure) | 143 | 3.06 | 4 |
| (structure) | 144 | 3.09 | 4 |

TABLE 1-continued

| STRUCTURE | COMPOUND NUMBER | LCMS RETENTION TIME (min) | LCMS method |
|---|---|---|---|
| (structure) | 145 | 3.13 | 4 |
| (structure) | 146 | 3.11 | 4 |

TABLE 1-continued

| STRUCTURE | COMPOUND NUMBER | LCMS RETENTION TIME (min) | LCMS method |
|---|---|---|---|
| 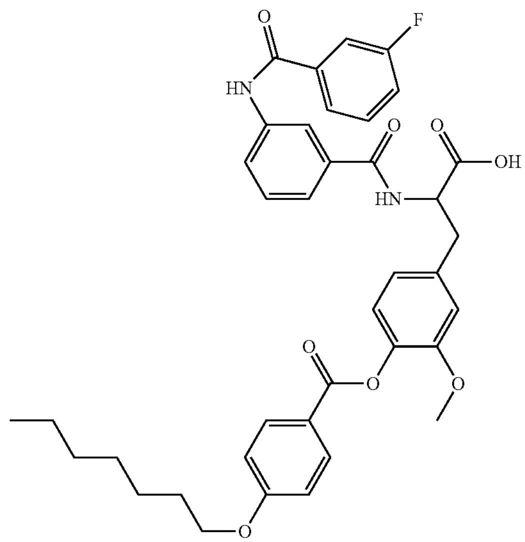 [SMILES: CCCCCCCOc1ccc(C(=O)Oc2ccc(CC(NC(=O)c3cccc(NC(=O)c4cccc(F)c4)c3)C(=O)O)cc2OC)cc1] | 147 | 3.08 | 4 |
| 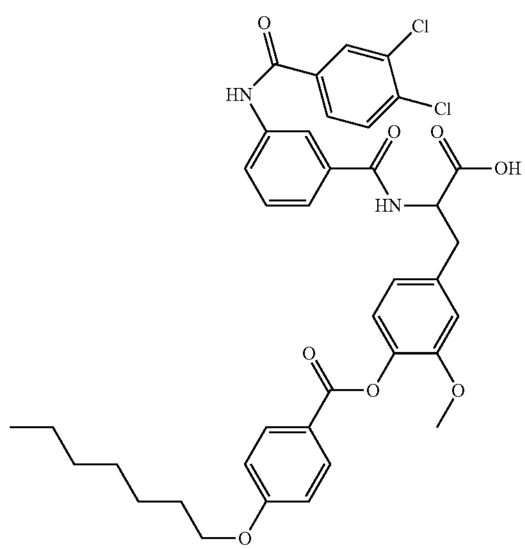 [SMILES: CCCCCCCOc1ccc(C(=O)Oc2ccc(CC(NC(=O)c3cccc(NC(=O)c4ccc(Cl)c(Cl)c4)c3)C(=O)O)cc2OC)cc1] | 148 | 3.21 | 4 |

TABLE 1-continued
| STRUCTURE | COMPOUND NUMBER | LCMS RETENTION TIME (min) | LCMS method |
|---|---|---|---|
| 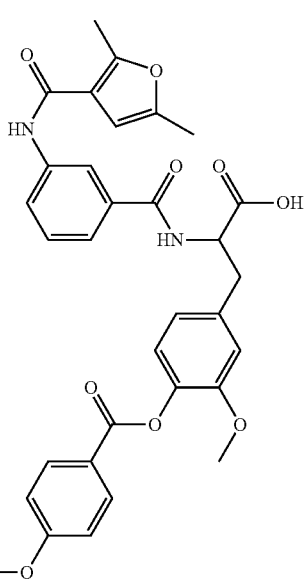 | 149 | 3.11 | 4 |
| 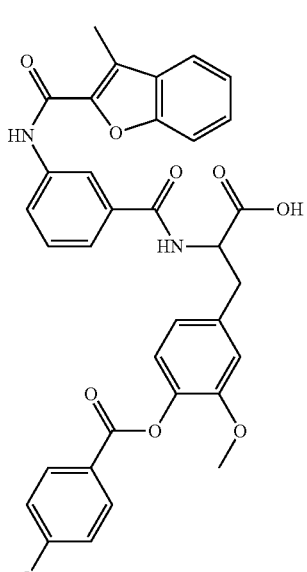 | 150 | 3.20 | 4 |

TABLE 1-continued
| STRUCTURE | COMPOUND NUMBER | LCMS RETENTION TIME (min) | LCMS method |
|---|---|---|---|
| 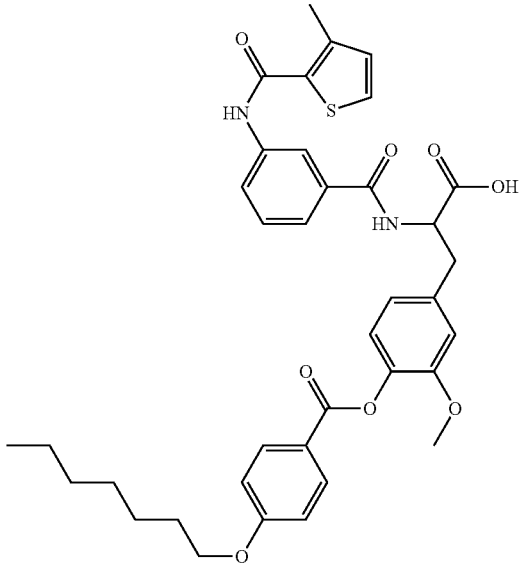 [SMILES: CCCCCCCOc1ccc(C(=O)Oc2ccc(CC(NC(=O)c3cccc(NC(=O)c4sccc4C)c3)C(=O)O)cc2OC)cc1] | 151 | 3.09 | 4 |
| 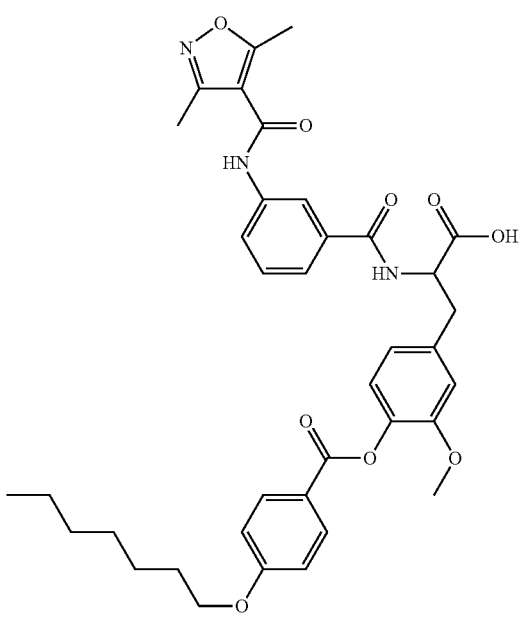 [SMILES: CCCCCCCOc1ccc(C(=O)Oc2ccc(CC(NC(=O)c3cccc(NC(=O)c4c(C)noc4C)c3)C(=O)O)cc2OC)cc1] | 152 | 2.98 | 4 |

TABLE 1-continued
| STRUCTURE | COMPOUND NUMBER | LCMS RETENTION TIME (min) | LCMS method |
|---|---|---|---|
| 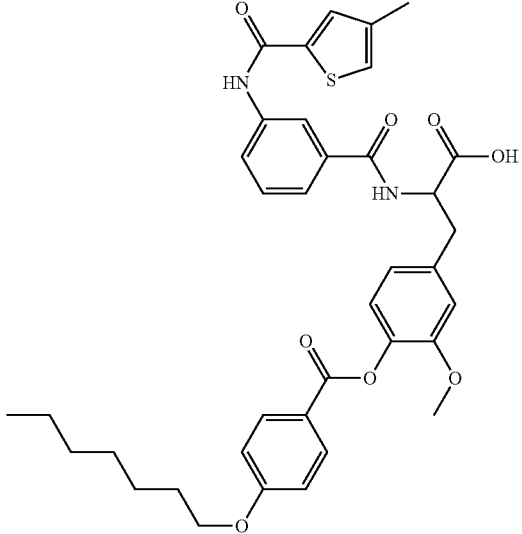 [SMILES: CCCCCCCOc1ccc(C(=O)Oc2ccc(CC(NC(=O)c3cccc(NC(=O)c4cc(C)cs4)c3)C(=O)O)cc2OC)cc1] | 153 | 3.10 | 4 |
| 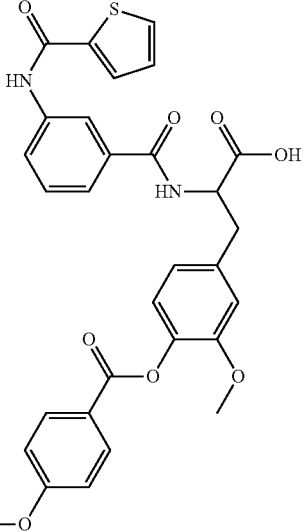 | 154 | 3.05 | 4 |

TABLE 1-continued
| STRUCTURE | COMPOUND NUMBER | LCMS RETENTION TIME (min) | LCMS method |
|---|---|---|---|
| 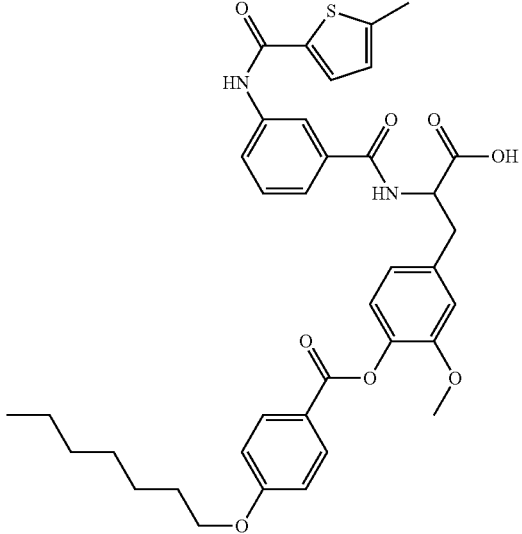 [SMILES: CCCCCCCOc1ccc(C(=O)Oc2ccc(CC(NC(=O)c3cccc(NC(=O)c4ccc(C)s4)c3)C(=O)O)cc2OC)cc1] | 155 | 3.10 | 4 |
| 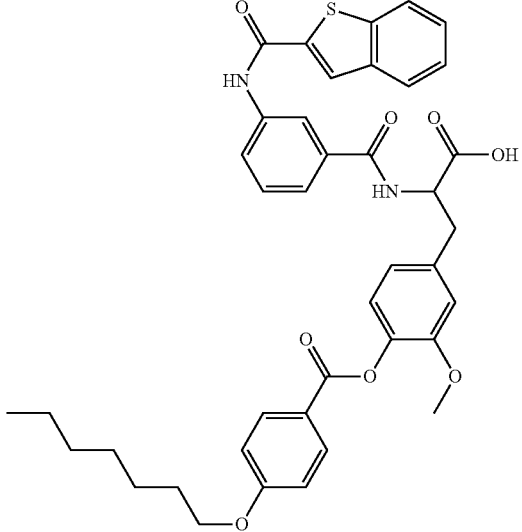 [SMILES: CCCCCCCOc1ccc(C(=O)Oc2ccc(CC(NC(=O)c3cccc(NC(=O)c4cc5ccccc5s4)c3)C(=O)O)cc2OC)cc1] | 156 | 3.17 | 4 |

TABLE 1-continued
| STRUCTURE | COMPOUND NUMBER | LCMS RETENTION TIME (min) | LCMS method |
|---|---|---|---|
| 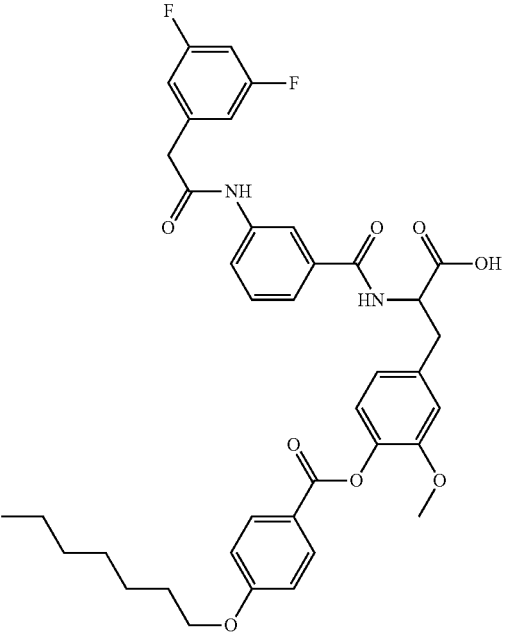 [SMILES: CCCCCCCOc1ccc(C(=O)Oc2ccc(CC(NC(=O)c3cccc(NC(=O)Cc4cc(F)cc(F)c4)c3)C(=O)O)cc2OC)cc1] | 157 | 3.03 | 4 |
| 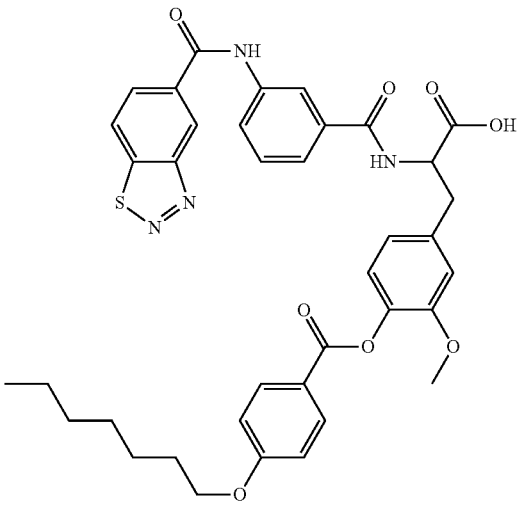 [SMILES: CCCCCCCOc1ccc(C(=O)Oc2ccc(CC(NC(=O)c3cccc(NC(=O)c4ccc5snnc5c4)c3)C(=O)O)cc2OC)cc1] | 158 | 3.07 | 4 |

TABLE 1-continued
| STRUCTURE | COMPOUND NUMBER | LCMS RETENTION TIME (min) | LCMS method |
|---|---|---|---|
| 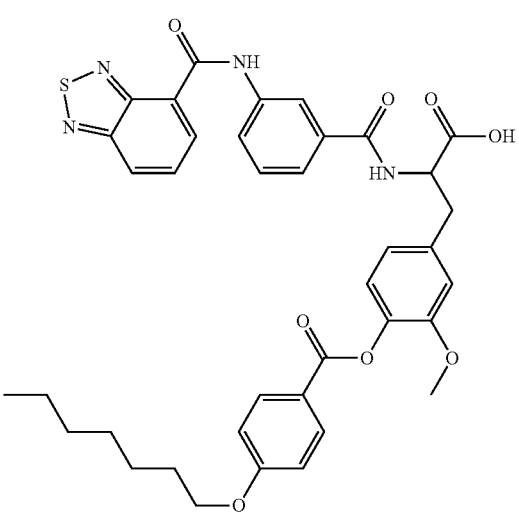 [SMILES: CCCCCCCOc1ccc(C(=O)Oc2ccc(CC(NC(=O)c3cccc(NC(=O)c4cccc5nsnc45)c3)C(=O)O)cc2OC)cc1] | 159 | 3.15 | 4 |
| 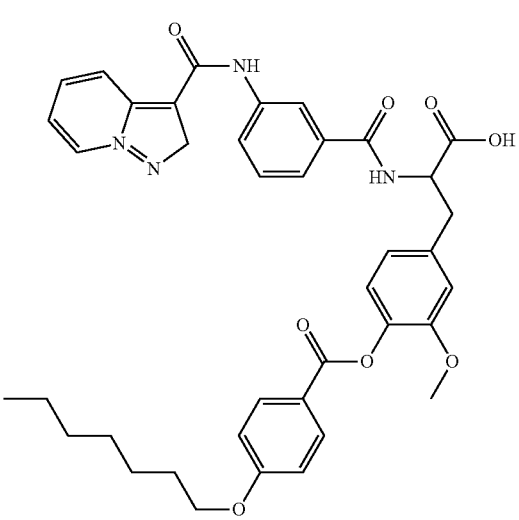 | 160 | 2.97 | 4 |

TABLE 1-continued
| STRUCTURE | COMPOUND NUMBER | LCMS RETENTION TIME (min) | LCMS method |
|---|---|---|---|
| 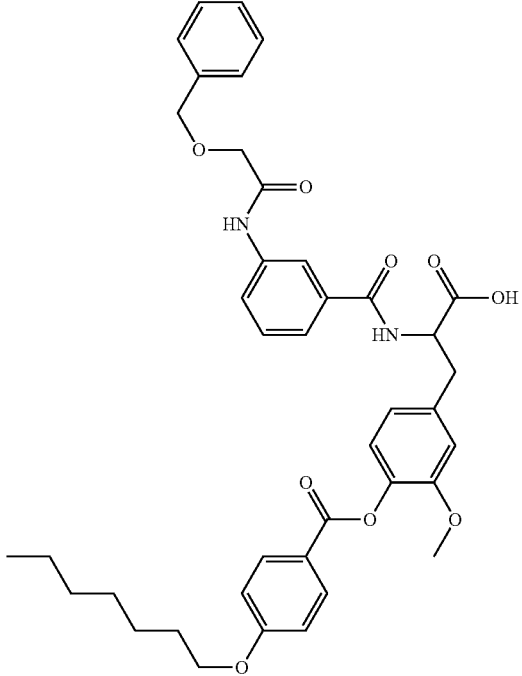 [SMILES: CCCCCCCOc1ccc(C(=O)Oc2ccc(CC(NC(=O)c3cccc(NC(=O)COCc4ccccc4)c3)C(=O)O)cc2OC)cc1] | 161 | 9.99 | 5 |
| 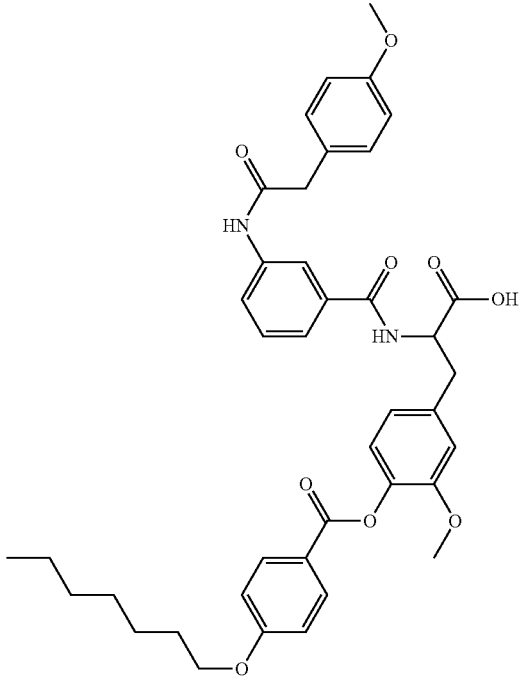 [SMILES: CCCCCCCOc1ccc(C(=O)Oc2ccc(CC(NC(=O)c3cccc(NC(=O)Cc4ccc(OC)cc4)c3)C(=O)O)cc2OC)cc1] | 162 | 3.07 | 4 |

TABLE 1-continued
| STRUCTURE | COMPOUND NUMBER | LCMS RETENTION TIME (min) | LCMS method |
|---|---|---|---|
| 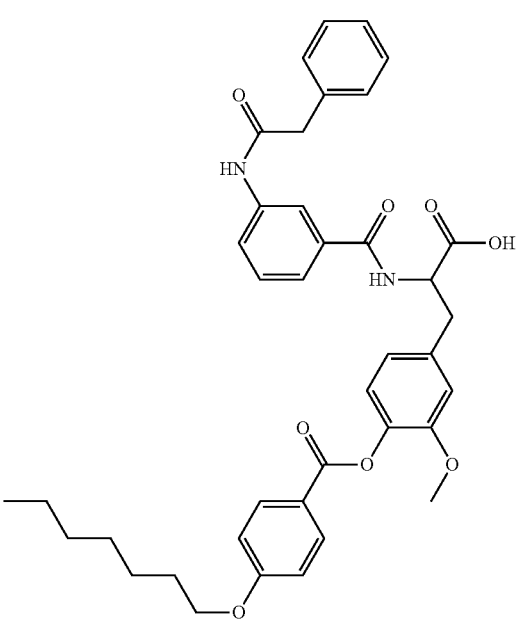 [SMILES: CCCCCCCOc1ccc(C(=O)Oc2ccc(CC(NC(=O)c3cccc(NC(=O)Cc4ccccc4)c3)C(=O)O)cc2OC)cc1] | 163 | 3.09 | 4 |
| 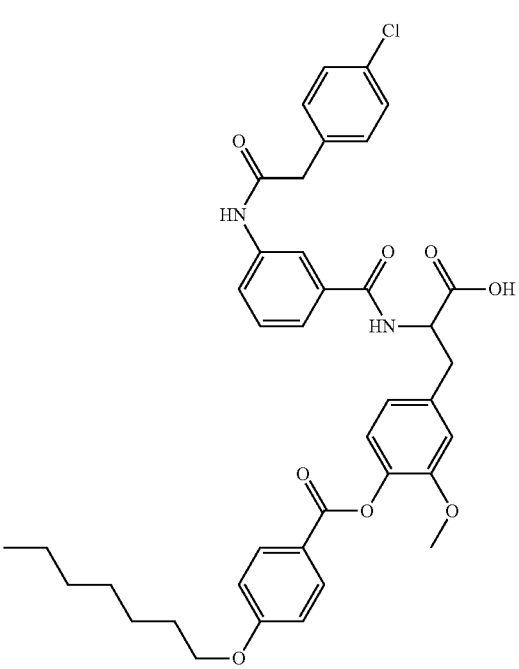 [SMILES: CCCCCCCOc1ccc(C(=O)Oc2ccc(CC(NC(=O)c3cccc(NC(=O)Cc4ccc(Cl)cc4)c3)C(=O)O)cc2OC)cc1] | 164 | 3.14 | 4 |

TABLE 1-continued
| STRUCTURE | COMPOUND NUMBER | LCMS RETENTION TIME (min) | LCMS method |
|---|---|---|---|
| 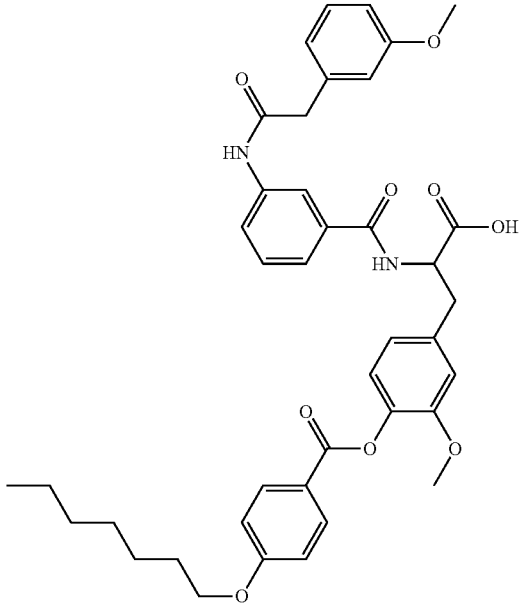 [SMILES: CCCCCCCOc1ccc(C(=O)Oc2ccc(CC(NC(=O)c3cccc(NC(=O)Cc4cccc(OC)c4)c3)C(=O)O)cc2OC)cc1] | 165 | 3.08 | 4 |
| 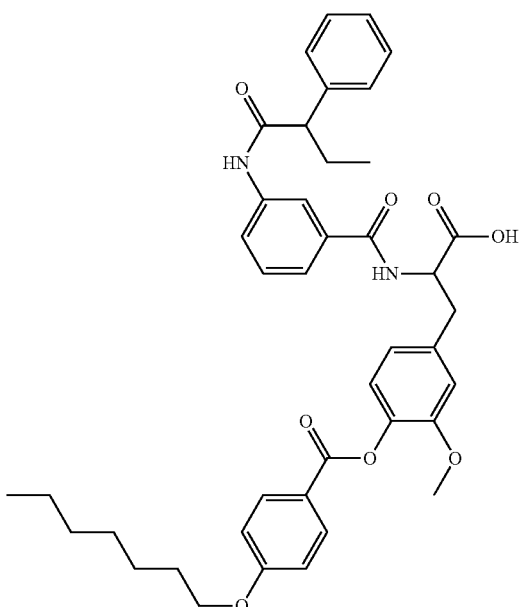 | 166 | 3.18 | 4 |

TABLE 1-continued

| STRUCTURE | COMPOUND NUMBER | LCMS RETENTION TIME (min) | LCMS method |
|---|---|---|---|
| 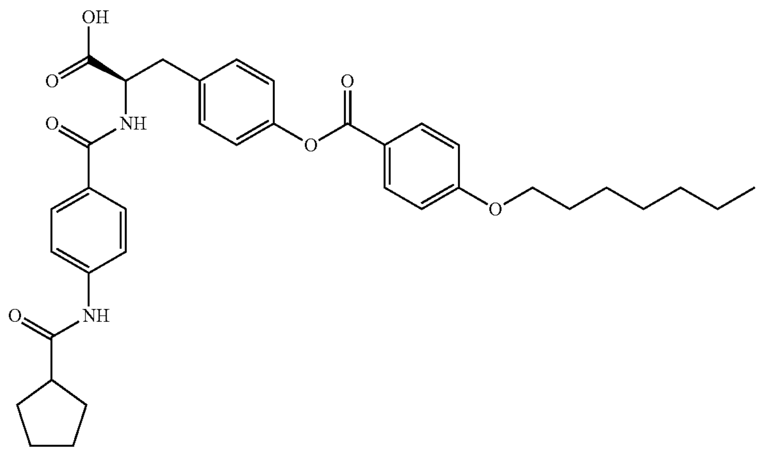 [SMILES: CCCCCCCOc1ccc(C(=O)Oc2ccc(C[C@@H](NC(=O)c3ccc(NC(=O)C4CCCC4)cc3)C(=O)O)cc2)cc1] | 167 | 3.10 | 4 |
| 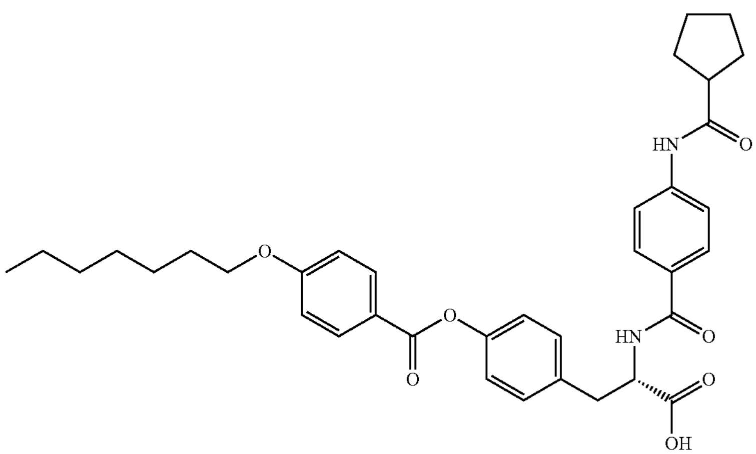 [SMILES: CCCCCCCOc1ccc(C(=O)Oc2ccc(C[C@H](NC(=O)c3ccc(NC(=O)C4CCCC4)cc3)C(=O)O)cc2)cc1] | 168 | 9.70 | 5 |
| 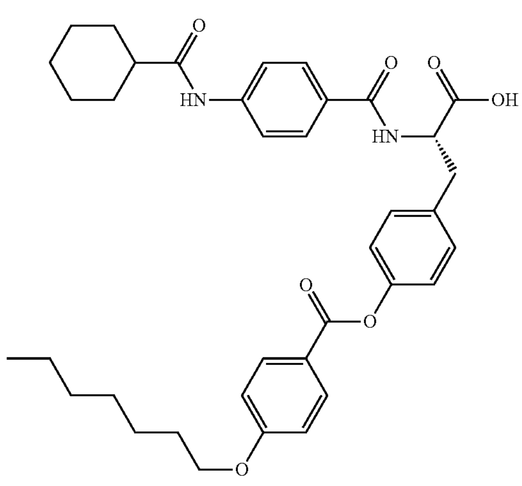 [SMILES: CCCCCCCOc1ccc(C(=O)Oc2ccc(C[C@H](NC(=O)c3ccc(NC(=O)C4CCCCC4)cc3)C(=O)O)cc2)cc1] | 169 | 10.00 | 5 |

TABLE 1-continued
| STRUCTURE | COMPOUND NUMBER | LCMS RETENTION TIME (min) | LCMS method |
| --- | --- | --- | --- |
| 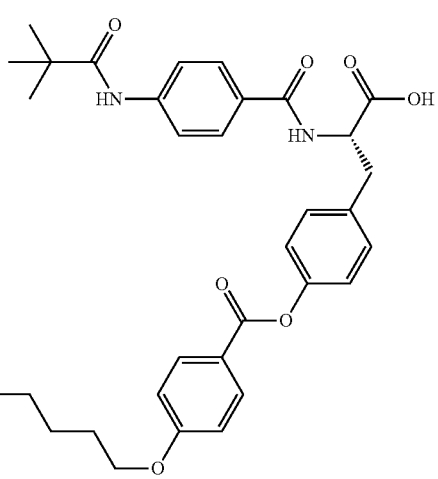 | 170 | 9.62 | 5 |
| 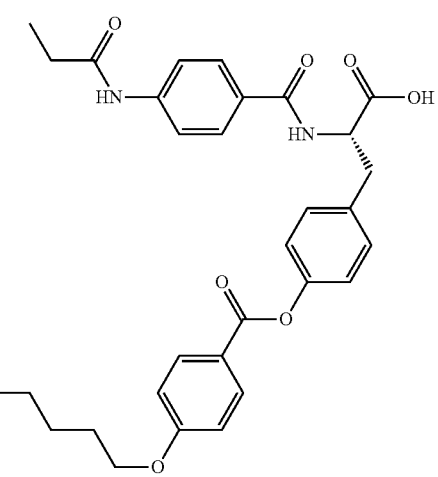 | 171 | 8.80 | 5 |
| 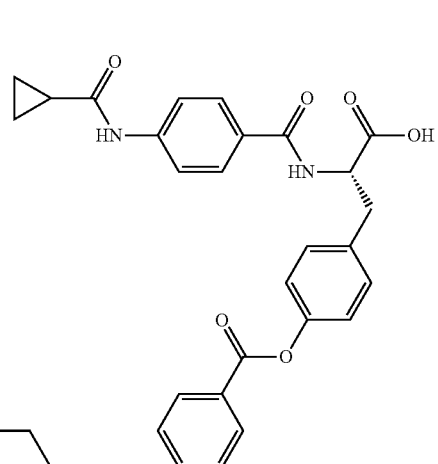 | 172 | 8.97 | 5 |

TABLE 1-continued
| STRUCTURE | COMPOUND NUMBER | LCMS RETENTION TIME (min) | LCMS method |
|---|---|---|---|
| 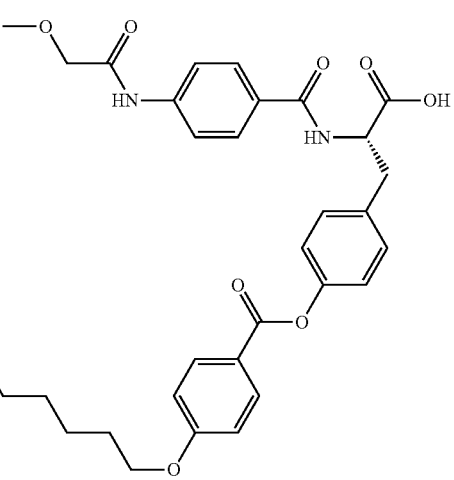 | 173 | 8.65 | 5 |
| 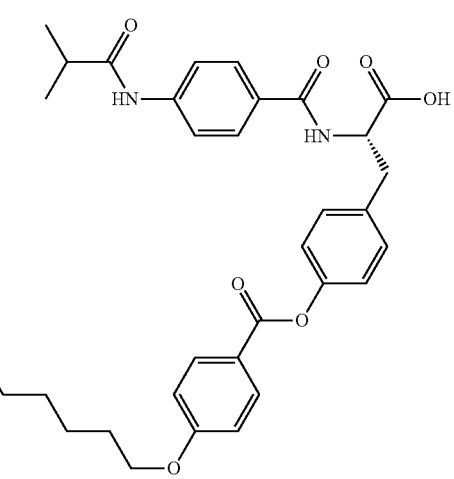 | 174 | 9.17 | 5 |
| 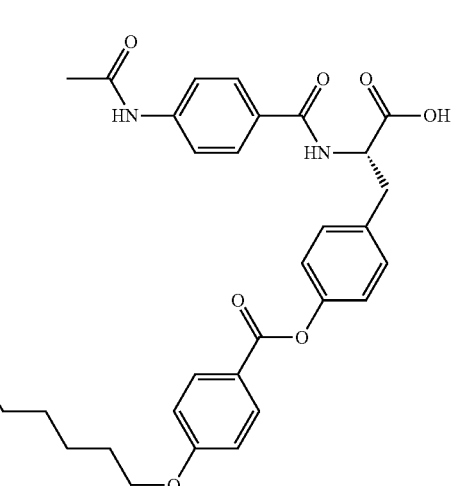 | 175 | 8.37 | 5 |

TABLE 1-continued
| STRUCTURE | COMPOUND NUMBER | LCMS RETENTION TIME (min) | LCMS method |
|---|---|---|---|
| 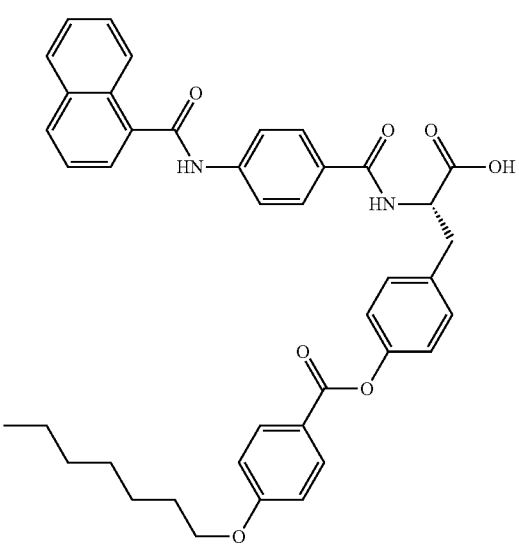 [SMILES: CCCCCCCOc1ccc(C(=O)Oc2ccc(C[C@H](NC(=O)c3ccc(NC(=O)c4cccc5ccccc45)cc3)C(=O)O)cc2)cc1] | 176 | 10.04 | 5 |
| 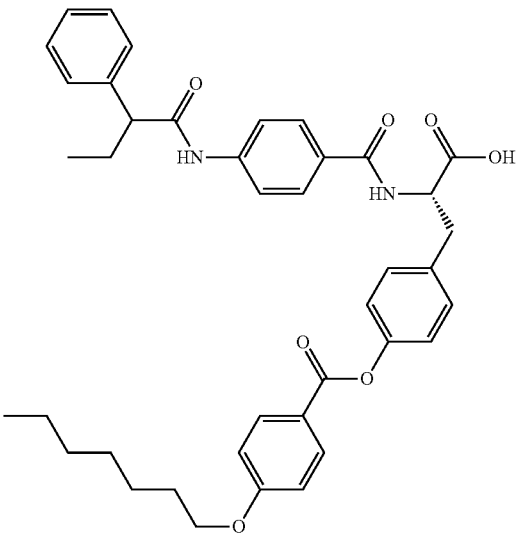 [SMILES: CCCCCCCOc1ccc(C(=O)Oc2ccc(C[C@H](NC(=O)c3ccc(NC(=O)C(CC)c4ccccc4)cc3)C(=O)O)cc2)cc1] | 177 | 10.26 | 5 |

TABLE 1-continued
| STRUCTURE | COMPOUND NUMBER | LCMS RETENTION TIME (min) | LCMS method |
|---|---|---|---|
| 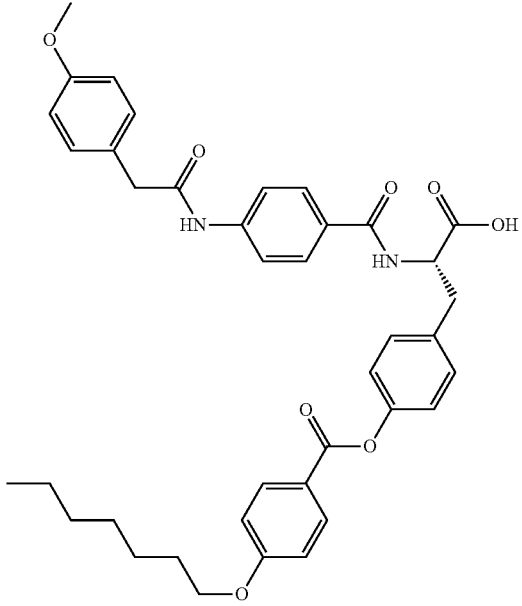 [SMILES: CCCCCCCOc1ccc(C(=O)Oc2ccc(C[C@H](NC(=O)c3ccc(NC(=O)Cc4ccc(OC)cc4)cc3)C(=O)O)cc2)cc1] | 178 | 9.53 | 5 |
| 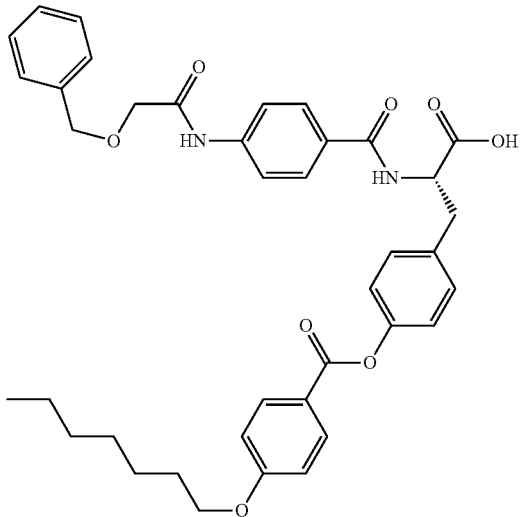 [SMILES: CCCCCCCOc1ccc(C(=O)Oc2ccc(C[C@H](NC(=O)c3ccc(NC(=O)COCc4ccccc4)cc3)C(=O)O)cc2)cc1] | 179 | 9.91 | 5 |

TABLE 1-continued
| STRUCTURE | COMPOUND NUMBER | LCMS RETENTION TIME (min) | LCMS method |
|---|---|---|---|
| 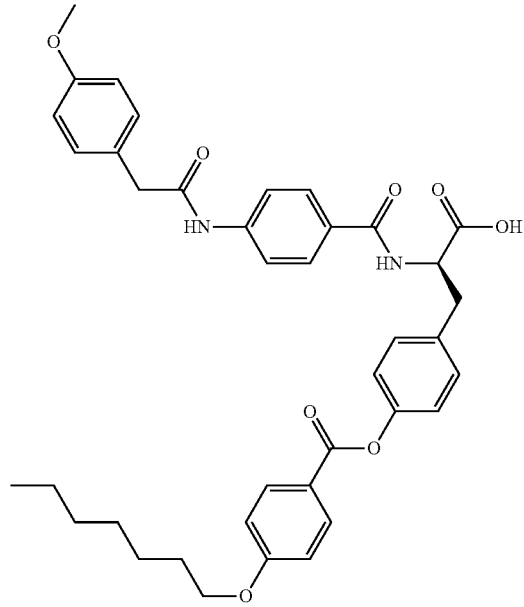 [SMILES: CCCCCCCOc1ccc(C(=O)Oc2ccc(C[C@@H](NC(=O)c3ccc(NC(=O)Cc4ccc(OC)cc4)cc3)C(=O)O)cc2)cc1] | 180 | 3.12 | 4 |
| 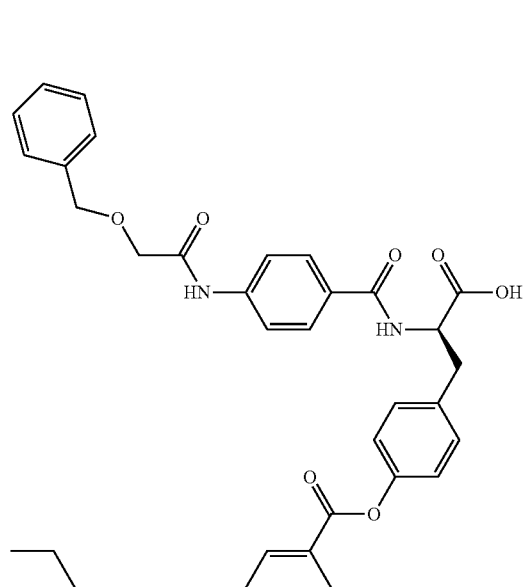 | 181 | 3.06 | 4 |

TABLE 1-continued
| STRUCTURE | COMPOUND NUMBER | LCMS RETENTION TIME (min) | LCMS method |
|---|---|---|---|
| 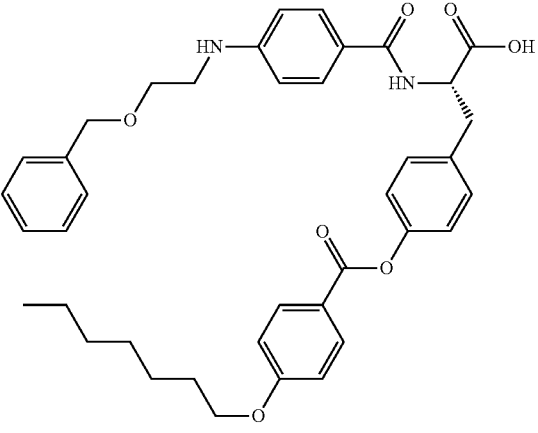 [SMILES: CCCCCCCOc1ccc(C(=O)Oc2ccc(C[C@H](NC(=O)c3ccc(NCCOCc4ccccc4)cc3)C(=O)O)cc2)cc1] | 182 | 3.18 | 4 |
| 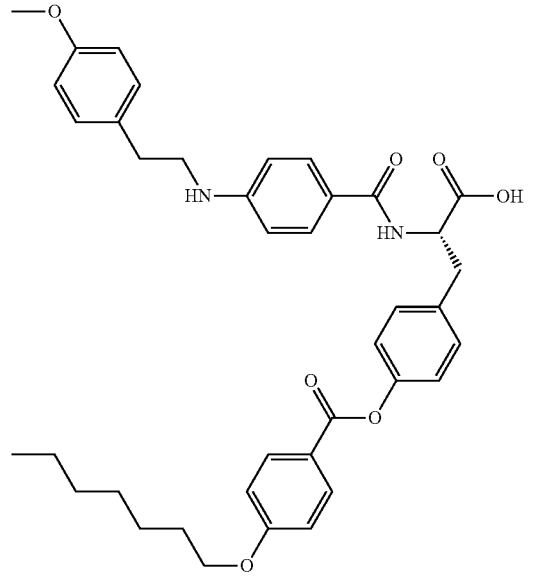 [SMILES: CCCCCCCOc1ccc(C(=O)Oc2ccc(C[C@H](NC(=O)c3ccc(NCCc4ccc(OC)cc4)cc3)C(=O)O)cc2)cc1] | 183 | 10.29 | 5 |
| 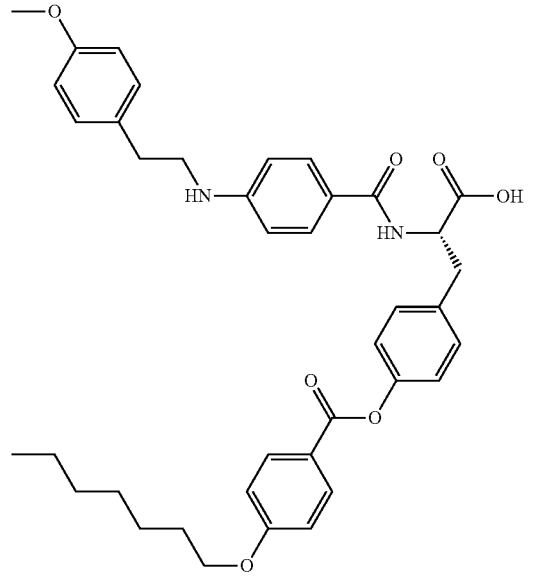 [SMILES: CCCCCCCOc1ccc(C(=O)Oc2ccc(C[C@H](NC(=O)c3ccc(NCCc4ccc(OC)cc4)cc3)C(=O)O)cc2)cc1] | 184 | 9.48 | 5 |

TABLE 1-continued

| STRUCTURE | COMPOUND NUMBER | LCMS RETENTION TIME (min) | LCMS method |
|---|---|---|---|
| 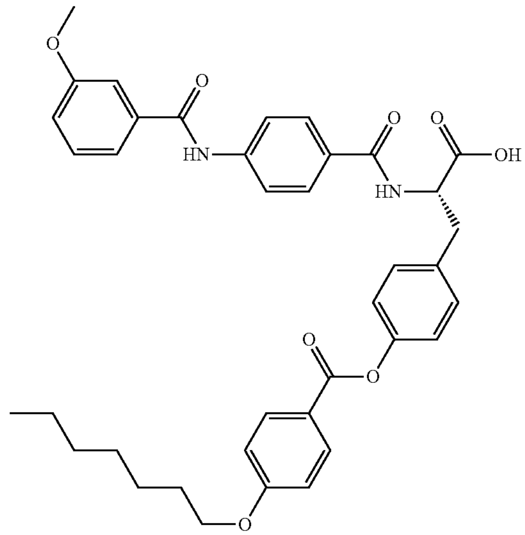 [SMILES: CCCCCCCOc1ccc(C(=O)Oc2ccc(C[C@H](NC(=O)c3ccc(NC(=O)c4cccc(OC)c4)cc3)C(=O)O)cc2)cc1] | 185 | 9.59 | 5 |
| 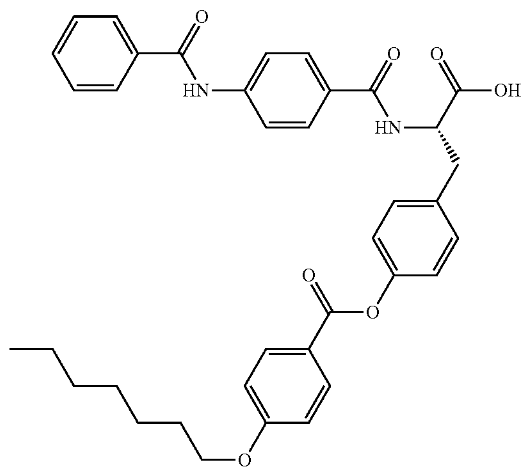 [SMILES: CCCCCCCOc1ccc(C(=O)Oc2ccc(C[C@H](NC(=O)c3ccc(NC(=O)c4ccccc4)cc3)C(=O)O)cc2)cc1] | 186 | 9.50 | 5 |
| 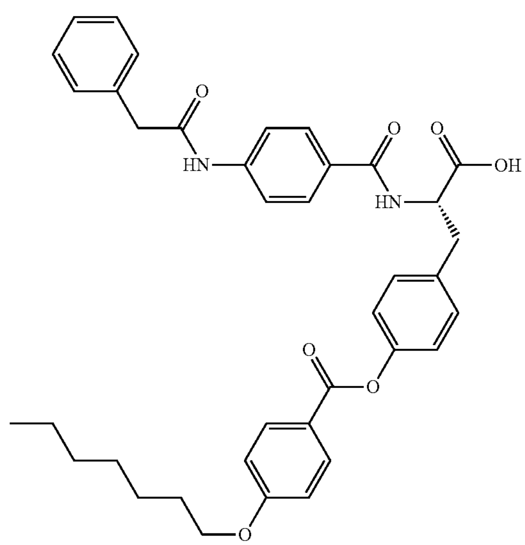 [SMILES: CCCCCCCOc1ccc(C(=O)Oc2ccc(C[C@H](NC(=O)c3ccc(NC(=O)Cc4ccccc4)cc3)C(=O)O)cc2)cc1] | 187 | 9.54 | 5 |

TABLE 1-continued
| STRUCTURE | COMPOUND NUMBER | LCMS RETENTION TIME (min) | LCMS method |
|---|---|---|---|
| 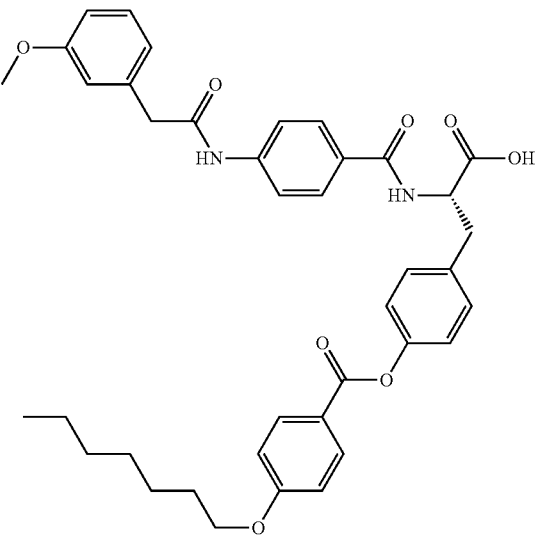 [SMILES: CCCCCCCOc1ccc(C(=O)Oc2ccc(C[C@H](NC(=O)c3ccc(NC(=O)Cc4cccc(OC)c4)cc3)C(=O)O)cc2)cc1] | 188 | 9.59 | 5 |
| 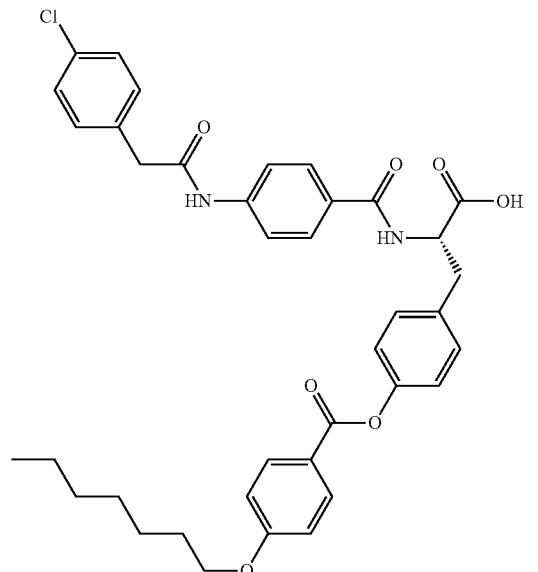 | 189 | 9.98 | 5 |

TABLE 1-continued
| STRUCTURE | COMPOUND NUMBER | LCMS RETENTION TIME (min) | LCMS method |
|---|---|---|---|
| 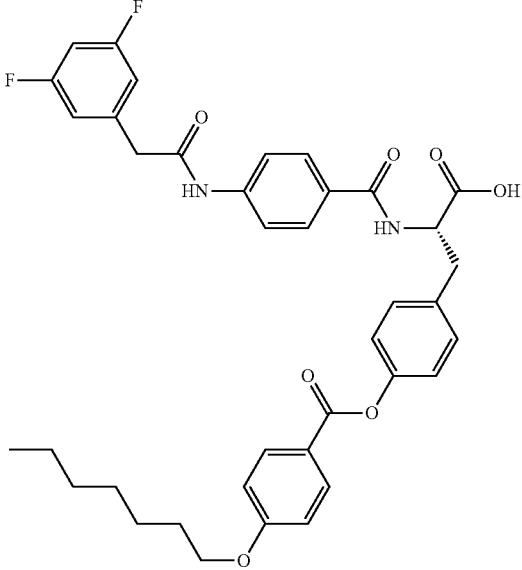 [SMILES: CCCCCCCOc1ccc(C(=O)Oc2ccc(C[C@H](NC(=O)c3ccc(NC(=O)Cc4cc(F)cc(F)c4)cc3)C(=O)O)cc2)cc1] | 190 | 9.79 | 5 |
| 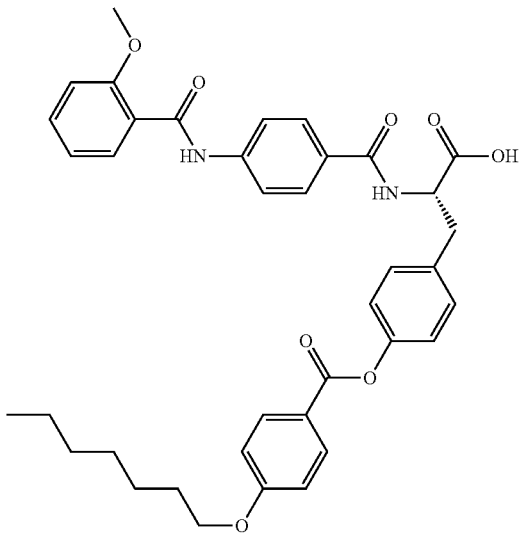 [SMILES: CCCCCCCOc1ccc(C(=O)Oc2ccc(C[C@H](NC(=O)c3ccc(NC(=O)c4ccccc4OC)cc3)C(=O)O)cc2)cc1] | 191 | 9.82 | 5 |
| 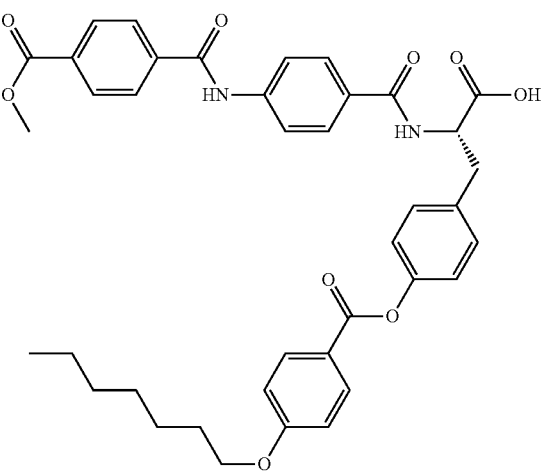 [SMILES: CCCCCCCOc1ccc(C(=O)Oc2ccc(C[C@H](NC(=O)c3ccc(NC(=O)c4ccc(C(=O)OC)cc4)cc3)C(=O)O)cc2)cc1] | 192 | 9.55 | 5 |

TABLE 1-continued
| STRUCTURE | COMPOUND NUMBER | LCMS RETENTION TIME (min) | LCMS method |
|---|---|---|---|
| 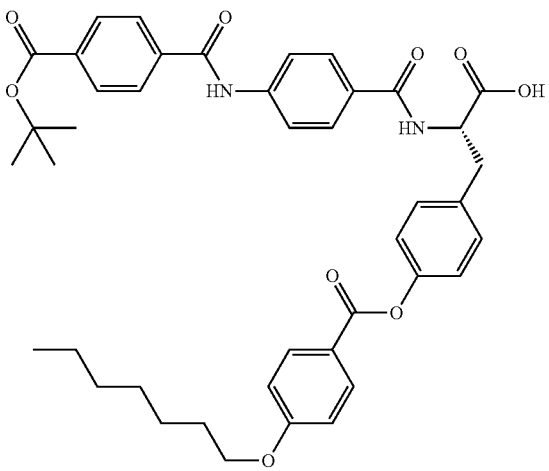 [SMILES: CCCCCCCOc1ccc(C(=O)Oc2ccc(C[C@H](NC(=O)c3ccc(NC(=O)c4ccc(C(=O)OC(C)(C)C)cc4)cc3)C(=O)O)cc2)cc1] | 193 | 8.52 | 5 |
| 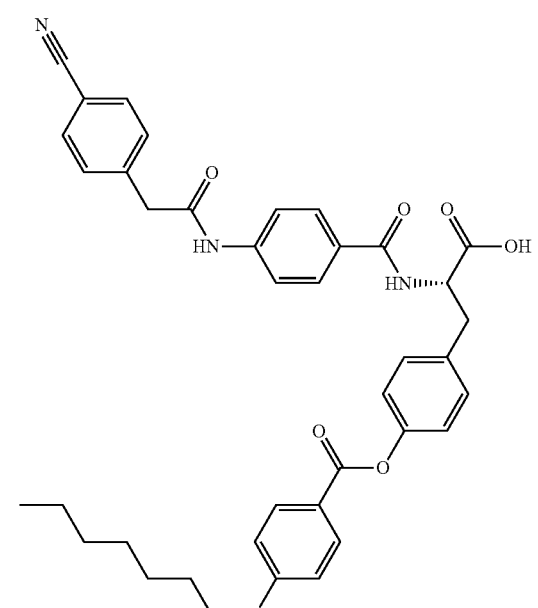 | 194 | 9.20 | 5 |

TABLE 1-continued
| STRUCTURE | COMPOUND NUMBER | LCMS RETENTION TIME (min) | LCMS method |
|---|---|---|---|
| 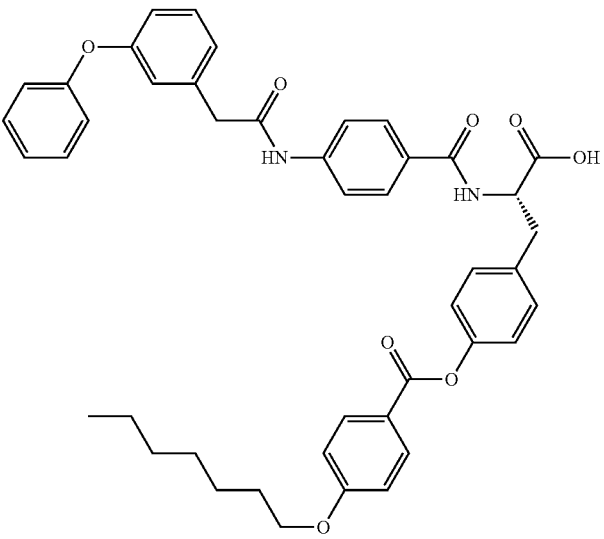 [SMILES: CCCCCCCOc1ccc(C(=O)Oc2ccc(C[C@H](NC(=O)c3ccc(NC(=O)Cc4cccc(Oc5ccccc5)c4)cc3)C(=O)O)cc2)cc1] | 195 | 10.51 | 5 |
| 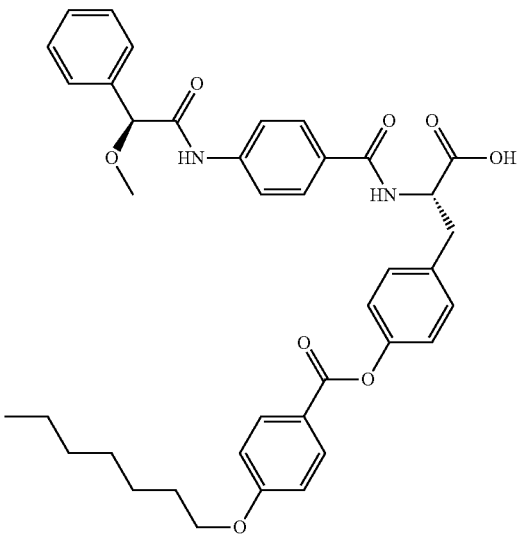 [SMILES: CCCCCCCOc1ccc(C(=O)Oc2ccc(C[C@H](NC(=O)c3ccc(NC(=O)[C@@H](OC)c4ccccc4)cc3)C(=O)O)cc2)cc1] | 196 | 9.92 | 5 |

TABLE 1-continued
| STRUCTURE | COMPOUND NUMBER | LCMS RETENTION TIME (min) | LCMS method |
|---|---|---|---|
| 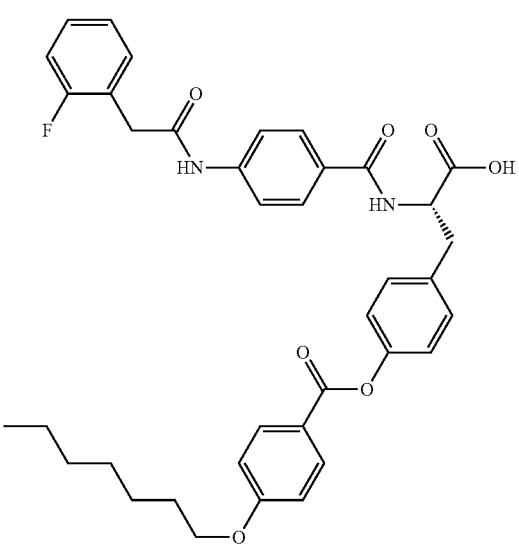 [SMILES: CCCCCCCOc1ccc(C(=O)Oc2ccc(C[C@H](NC(=O)c3ccc(NC(=O)Cc4ccccc4F)cc3)C(=O)O)cc2)cc1] | 197 | 9.57 | 5 |
| 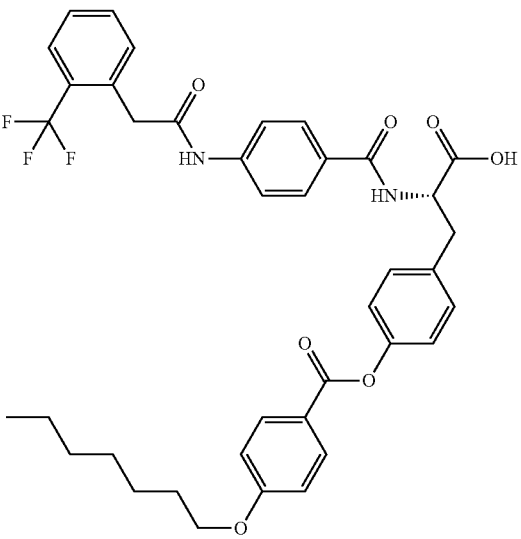 [SMILES: CCCCCCCOc1ccc(C(=O)Oc2ccc(C[C@H](NC(=O)c3ccc(NC(=O)Cc4ccccc4C(F)(F)F)cc3)C(=O)O)cc2)cc1] | 198 | 10.00 | 5 |

TABLE 1-continued
| STRUCTURE | COMPOUND NUMBER | LCMS RETENTION TIME (min) | LCMS method |
|---|---|---|---|
| 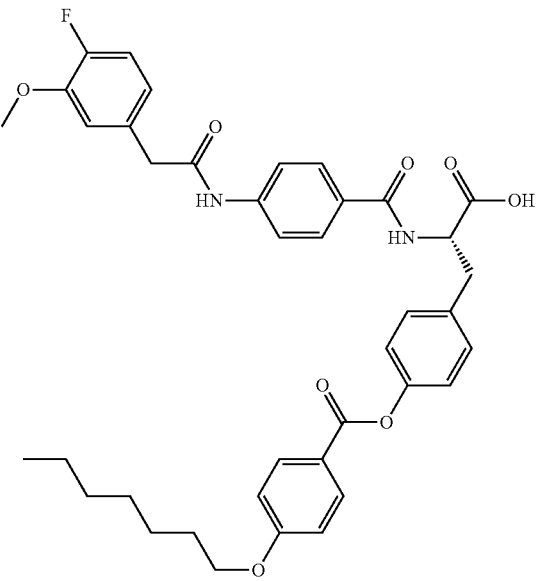 [SMILES: CCCCCCCOc1ccc(C(=O)Oc2ccc(C[C@H](NC(=O)c3ccc(NC(=O)Cc4ccc(F)c(OC)c4)cc3)C(=O)O)cc2)cc1] | 199 | 9.52 | 5 |
| 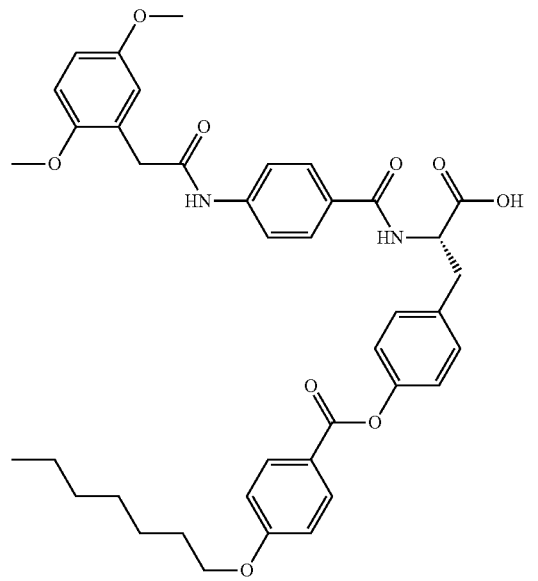 [SMILES: CCCCCCCOc1ccc(C(=O)Oc2ccc(C[C@H](NC(=O)c3ccc(NC(=O)Cc4cc(OC)ccc4OC)cc3)C(=O)O)cc2)cc1] | 200 | 9.56 | 5 |

TABLE 1-continued
| STRUCTURE | COMPOUND NUMBER | LCMS RETENTION TIME (min) | LCMS method |
|---|---|---|---|
| 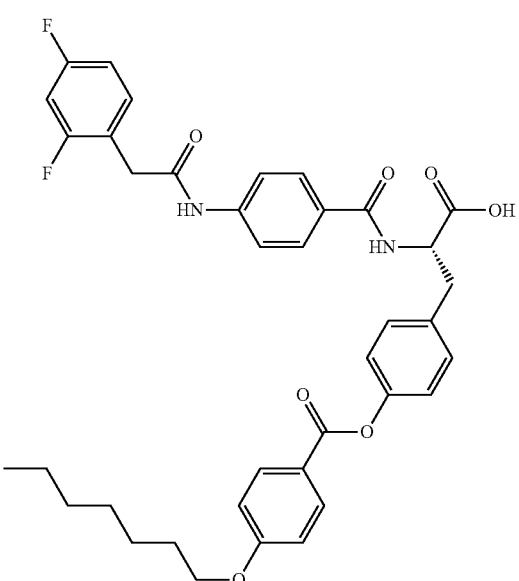 | 201 | 9.69 | 5 |
| 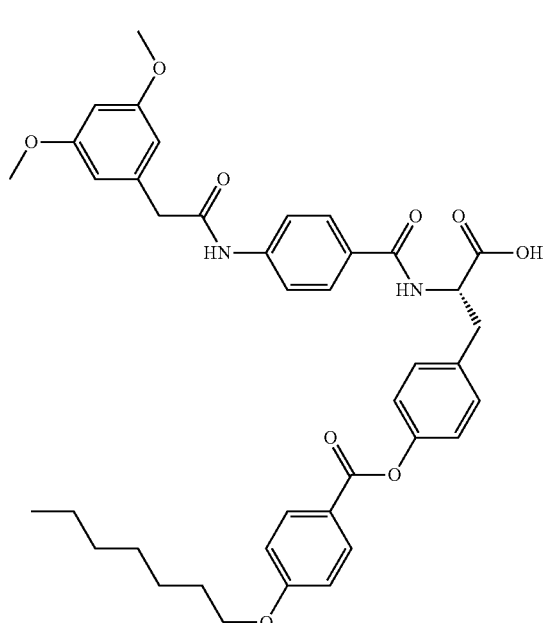 | 202 | 9.52 | 5 |

TABLE 1-continued
| STRUCTURE | COMPOUND NUMBER | LCMS RETENTION TIME (min) | LCMS method |
|---|---|---|---|
| 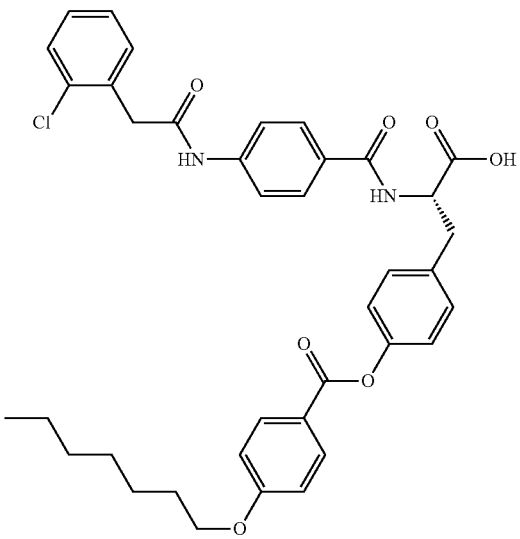 [SMILES: CCCCCCCOc1ccc(C(=O)Oc2ccc(C[C@H](NC(=O)c3ccc(NC(=O)Cc4ccccc4Cl)cc3)C(=O)O)cc2)cc1] | 203 | 9.81 | 5 |
| 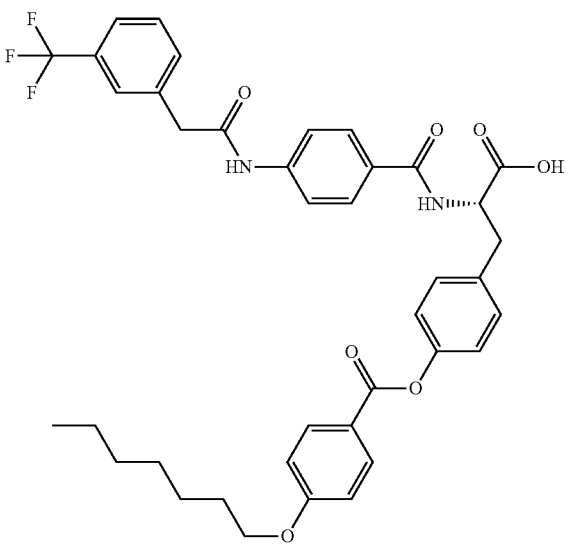 [SMILES: CCCCCCCOc1ccc(C(=O)Oc2ccc(C[C@H](NC(=O)c3ccc(NC(=O)Cc4cccc(C(F)(F)F)c4)cc3)C(=O)O)cc2)cc1] | 204 | 10.13 | 5 |

TABLE 1-continued
| STRUCTURE | COMPOUND NUMBER | LCMS RETENTION TIME (min) | LCMS method |
|---|---|---|---|
| 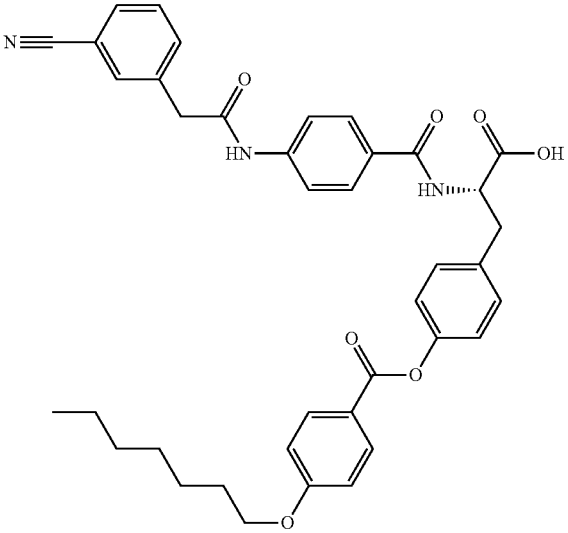 [SMILES: CCCCCCCOc1ccc(C(=O)Oc2ccc(C[C@H](NC(=O)c3ccc(NC(=O)Cc4cccc(C#N)c4)cc3)C(=O)O)cc2)cc1] | 205 | 9.25 | 5 |
| 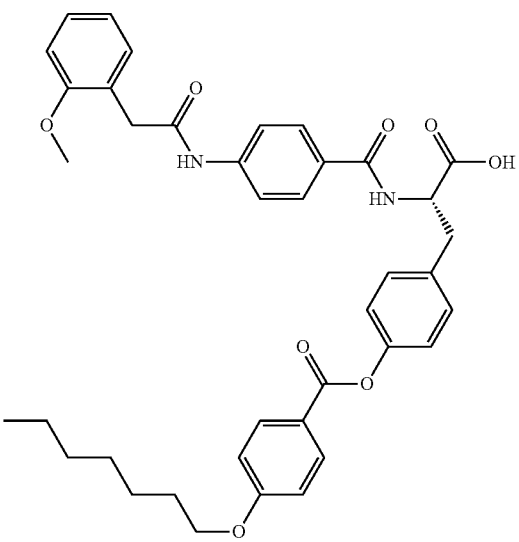 [SMILES: CCCCCCCOc1ccc(C(=O)Oc2ccc(C[C@H](NC(=O)c3ccc(NC(=O)Cc4ccccc4OC)cc3)C(=O)O)cc2)cc1] | 206 | 9.63 | 5 |

TABLE 1-continued

| STRUCTURE | COMPOUND NUMBER | LCMS RETENTION TIME (min) | LCMS method |
| --- | --- | --- | --- |
| 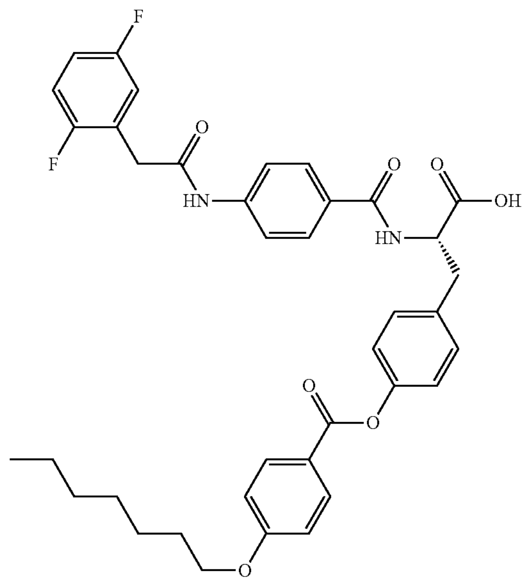 [SMILES: CCCCCCCOc1ccc(C(=O)Oc2ccc(C[C@H](NC(=O)c3ccc(NC(=O)Cc4cc(F)ccc4F)cc3)C(=O)O)cc2)cc1] | 207 | 9.65 | 5 |
| 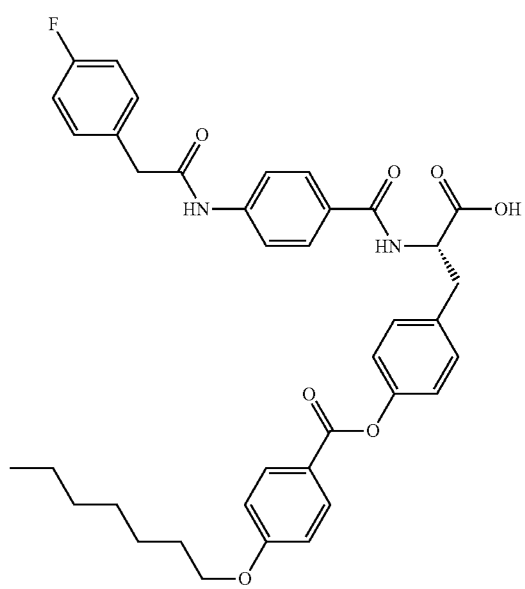 [SMILES: CCCCCCCOc1ccc(C(=O)Oc2ccc(C[C@H](NC(=O)c3ccc(NC(=O)Cc4ccc(F)cc4)cc3)C(=O)O)cc2)cc1] | 208 | 9.60 | 5 |

TABLE 1-continued

| STRUCTURE | COMPOUND NUMBER | LCMS RETENTION TIME (min) | LCMS method |
|---|---|---|---|
| 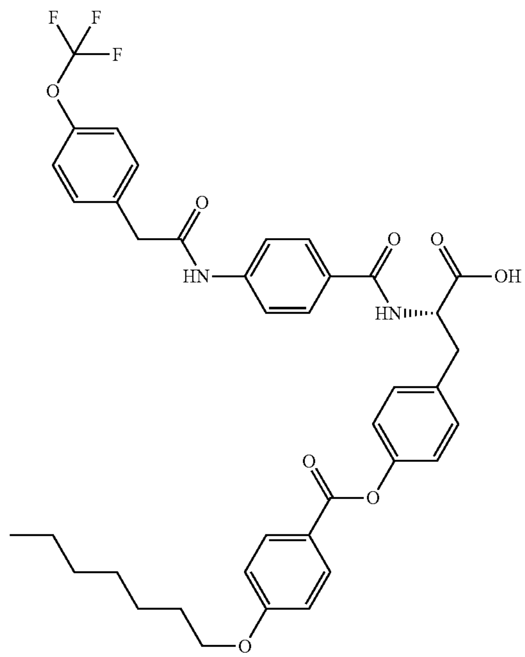 [SMILES: CCCCCCCOc1ccc(C(=O)Oc2ccc(C[C@H](NC(=O)c3ccc(NC(=O)Cc4ccc(OC(F)(F)F)cc4)cc3)C(=O)O)cc2)cc1] | 209 | 10.27 | 5 |
| 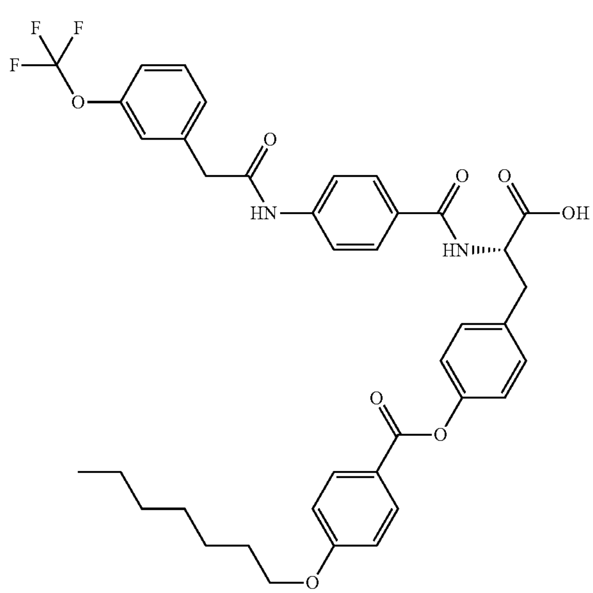 [SMILES: CCCCCCCOc1ccc(C(=O)Oc2ccc(C[C@H](NC(=O)c3ccc(NC(=O)Cc4cccc(OC(F)(F)F)c4)cc3)C(=O)O)cc2)cc1] | 210 | 10.27 | 5 |

TABLE 1-continued
| STRUCTURE | COMPOUND NUMBER | LCMS RETENTION TIME (min) | LCMS method |
|---|---|---|---|
| 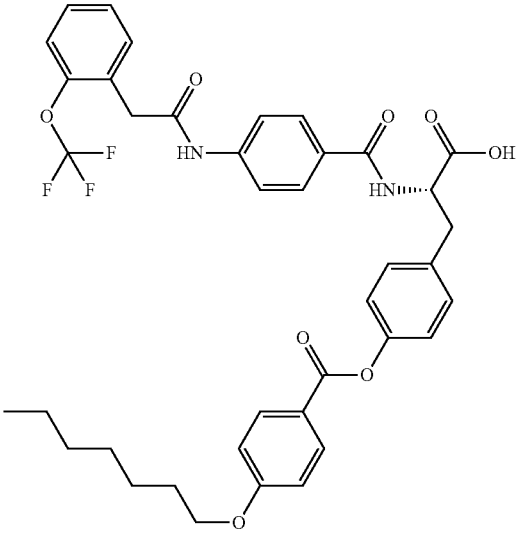 [SMILES: CCCCCCCOc1ccc(C(=O)Oc2ccc(C[C@H](NC(=O)c3ccc(NC(=O)Cc4ccccc4OC(F)(F)F)cc3)C(=O)O)cc2)cc1] | 211 | 10.13 | 5 |
| 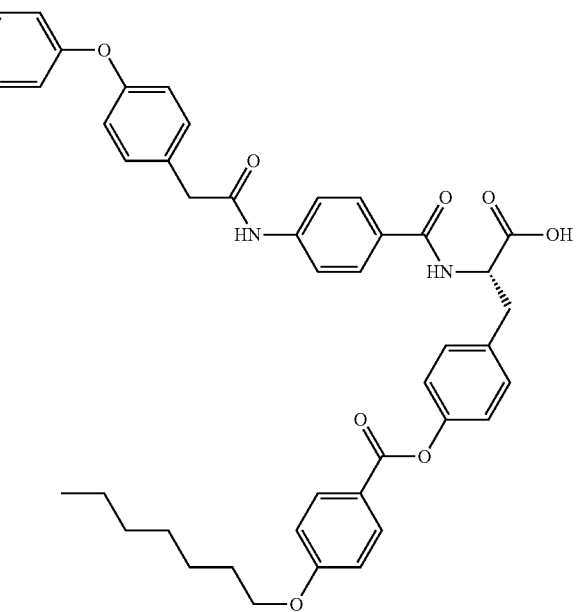 | 212 | 10.49 | 5 |

TABLE 1-continued
| STRUCTURE | COMPOUND NUMBER | LCMS RETENTION TIME (min) | LCMS method |
|---|---|---|---|
| 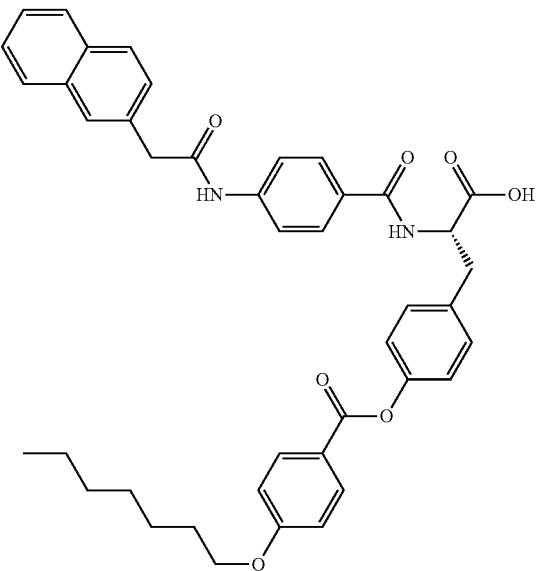 [SMILES: CCCCCCCOc1ccc(C(=O)Oc2ccc(C[C@H](NC(=O)c3ccc(NC(=O)Cc4ccc5ccccc5c4)cc3)C(=O)O)cc2)cc1] | 213 | 10.17 | 5 |
| 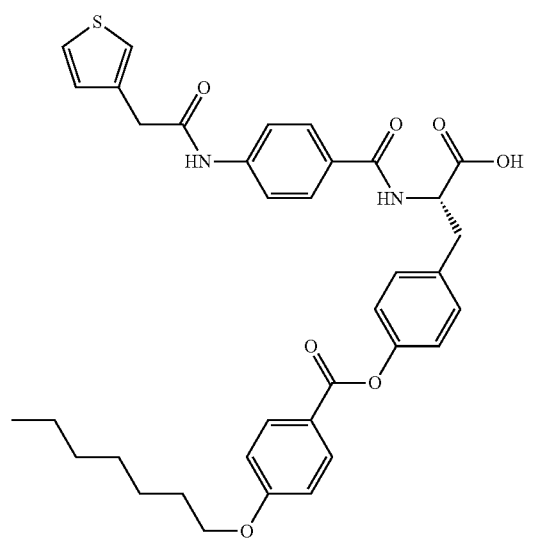 [SMILES: CCCCCCCOc1ccc(C(=O)Oc2ccc(C[C@H](NC(=O)c3ccc(NC(=O)Cc4ccsc4)cc3)C(=O)O)cc2)cc1] | 214 | 9.41 | 5 |

TABLE 1-continued
| STRUCTURE | COMPOUND NUMBER | LCMS RETENTION TIME (min) | LCMS method |
|---|---|---|---|
| 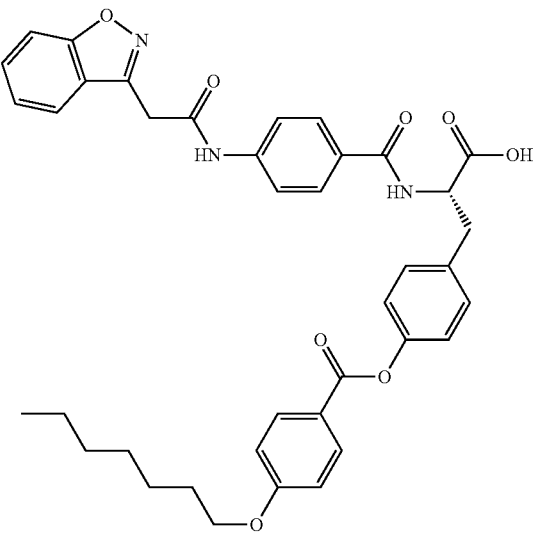 [SMILES: CCCCCCCOc1ccc(C(=O)Oc2ccc(C[C@H](NC(=O)c3ccc(NC(=O)Cc4noc5ccccc45)cc3)C(=O)O)cc2)cc1] | 215 | 9.47 | 5 |
| 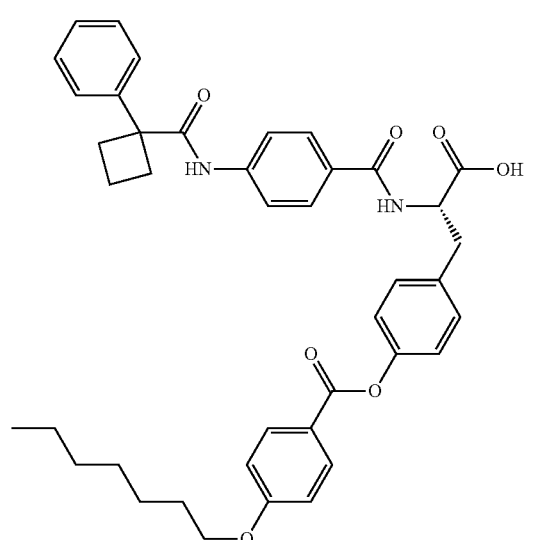 | 216 | 10.45 | 5 |

TABLE 1-continued

| STRUCTURE | COMPOUND NUMBER | LCMS RETENTION TIME (min) | LCMS method |
|---|---|---|---|
| 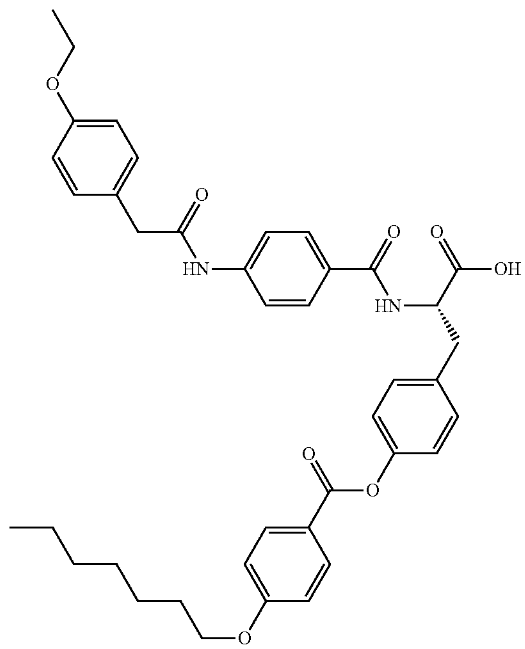 [SMILES: CCCCCCCOc1ccc(C(=O)Oc2ccc(C[C@H](NC(=O)c3ccc(NC(=O)Cc4ccc(OCC)cc4)cc3)C(=O)O)cc2)cc1] | 217 | 9.81 | 5 |
| 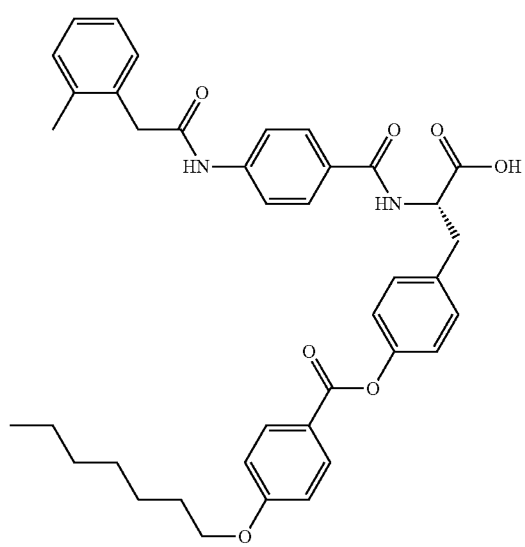 [SMILES: CCCCCCCOc1ccc(C(=O)Oc2ccc(C[C@H](NC(=O)c3ccc(NC(=O)Cc4ccccc4C)cc3)C(=O)O)cc2)cc1] | 218 | 9.84 | 5 |

TABLE 1-continued
| STRUCTURE | COMPOUND NUMBER | LCMS RETENTION TIME (min) | LCMS method |
|---|---|---|---|
| 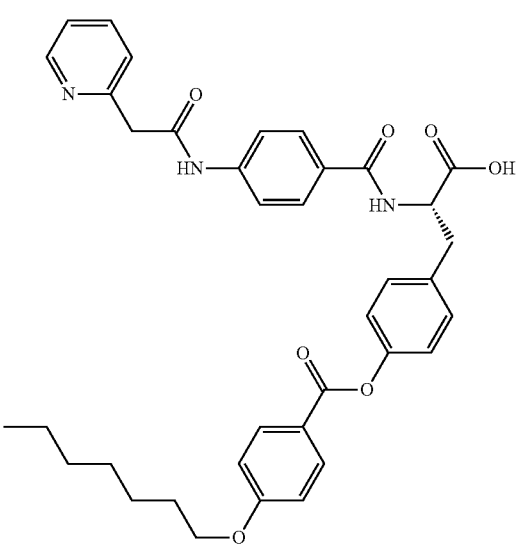 [SMILES: CCCCCCCOc1ccc(C(=O)Oc2ccc(C[C@H](NC(=O)c3ccc(NC(=O)Cc4ccccn4)cc3)C(=O)O)cc2)cc1] | 219 | 7.50 | 5 |
| 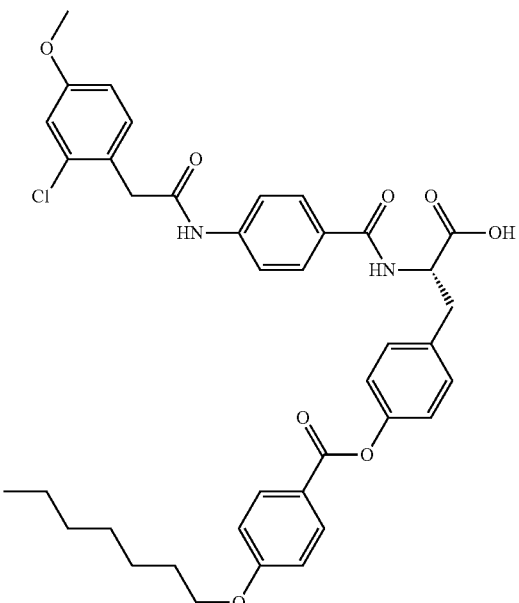 | 220 | 9.83 | 5 |

TABLE 1-continued
| STRUCTURE | COMPOUND NUMBER | LCMS RETENTION TIME (min) | LCMS method |
|---|---|---|---|
| 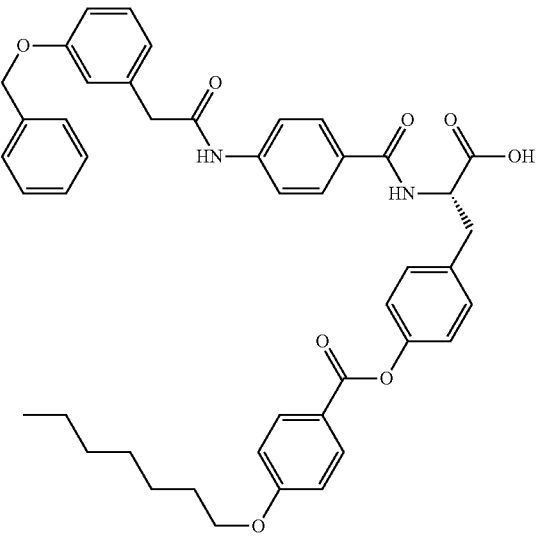 [SMILES: CCCCCCCOc1ccc(C(=O)Oc2ccc(C[C@H](NC(=O)c3ccc(NC(=O)Cc4cccc(OCc5ccccc5)c4)cc3)C(=O)O)cc2)cc1] | 221 | 10.45 | 5 |
| 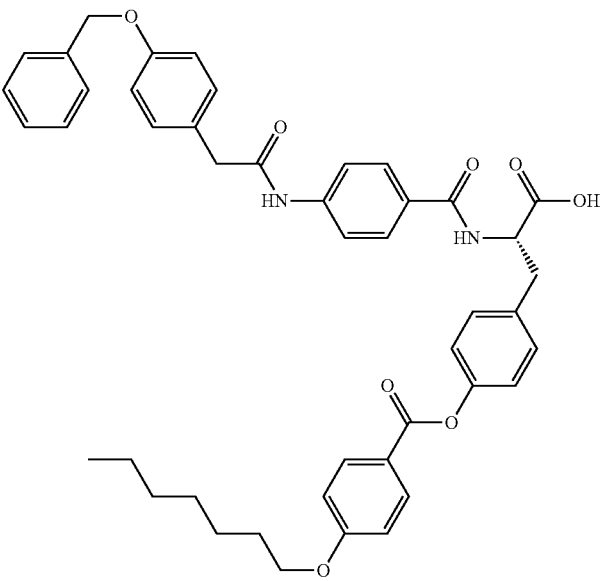 [SMILES: CCCCCCCOc1ccc(C(=O)Oc2ccc(C[C@H](NC(=O)c3ccc(NC(=O)Cc4ccc(OCc5ccccc5)cc4)cc3)C(=O)O)cc2)cc1] | 222 | 10.44 | 5 |

TABLE 1-continued
| STRUCTURE | COMPOUND NUMBER | LCMS RETENTION TIME (min) | LCMS method |
|---|---|---|---|
| 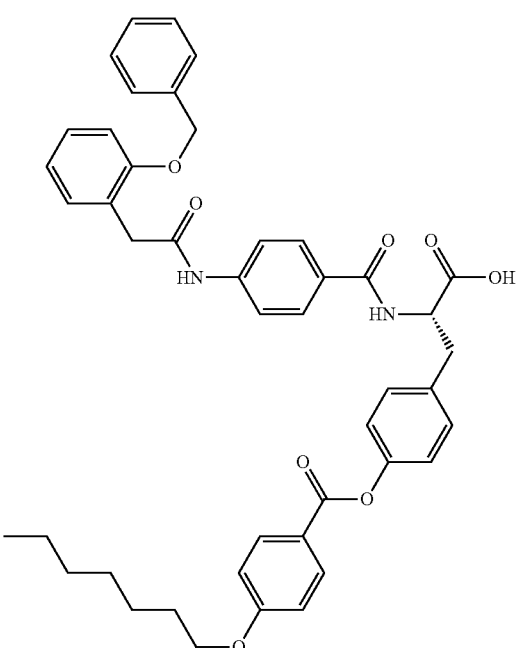 [SMILES: CCCCCCCOc1ccc(C(=O)Oc2ccc(C[C@H](NC(=O)c3ccc(NC(=O)Cc4ccccc4OCc4ccccc4)cc3)C(=O)O)cc2)cc1] | 223 | 10.42 | 5 |
| 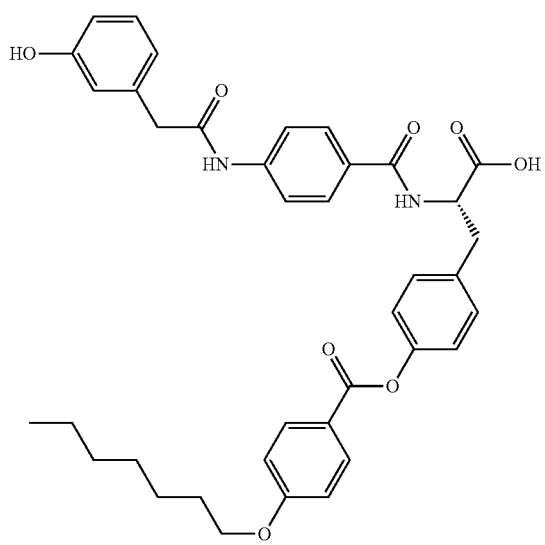 [SMILES: CCCCCCCOc1ccc(C(=O)Oc2ccc(C[C@H](NC(=O)c3ccc(NC(=O)Cc4cccc(O)c4)cc3)C(=O)O)cc2)cc1] | 224 | 8.67 | 5 |

TABLE 1-continued
| STRUCTURE | COMPOUND NUMBER | LCMS RETENTION TIME (min) | LCMS method |
|---|---|---|---|
| 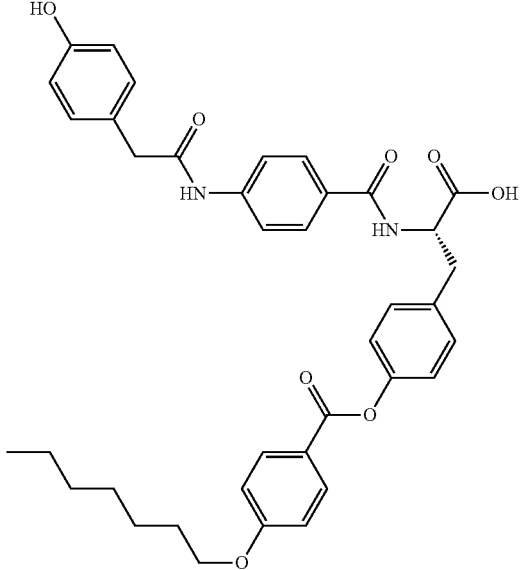 | 225 | 8.55 | 5 |
| 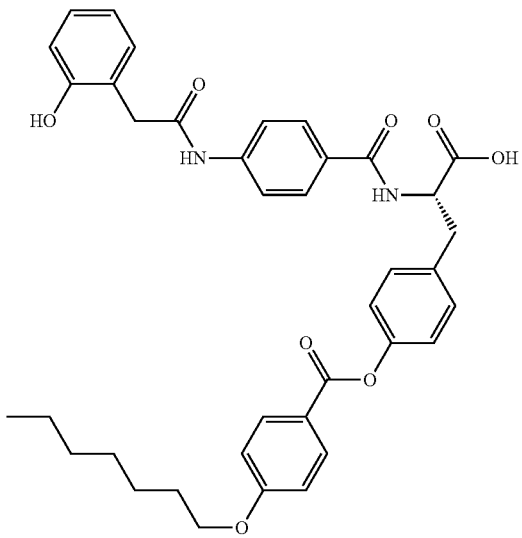 | 226 | 9.11 | 5 |

TABLE 1-continued
| STRUCTURE | COMPOUND NUMBER | LCMS RETENTION TIME (min) | LCMS method |
|---|---|---|---|
| 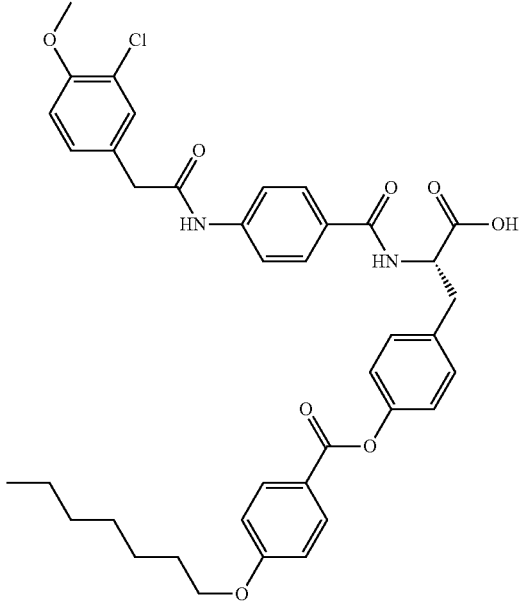 [SMILES: CCCCCCCOc1ccc(C(=O)Oc2ccc(C[C@H](NC(=O)c3ccc(NC(=O)Cc4ccc(OC)c(Cl)c4)cc3)C(=O)O)cc2)cc1] | 227 | 9.74 | 5 |
| 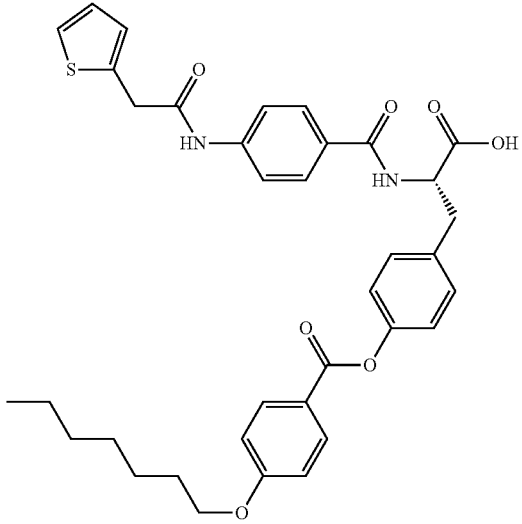 [SMILES: CCCCCCCOc1ccc(C(=O)Oc2ccc(C[C@H](NC(=O)c3ccc(NC(=O)Cc4cccs4)cc3)C(=O)O)cc2)cc1] | 228 | 9.41 | 5 |

TABLE 1-continued
| STRUCTURE | COMPOUND NUMBER | LCMS RETENTION TIME (min) | LCMS method |
|---|---|---|---|
| 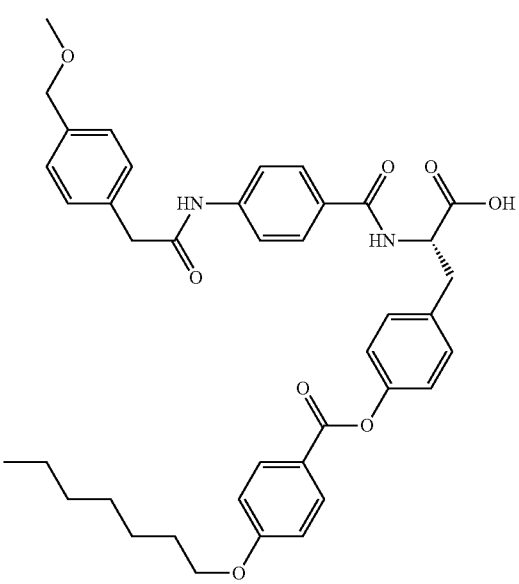 [SMILES: CCCCCCCOc1ccc(C(=O)Oc2ccc(C[C@H](NC(=O)c3ccc(NC(=O)Cc4ccc(COC)cc4)cc3)C(=O)O)cc2)cc1] | 229 | 9.37 | 5 |
| 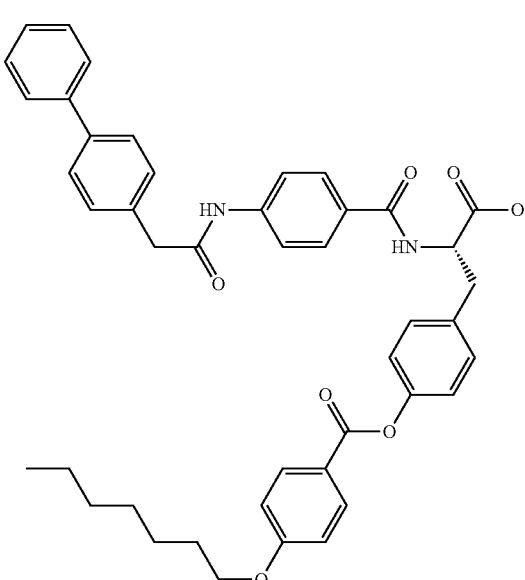 | 230 | 10.49 | 5 |

TABLE 1-continued
| STRUCTURE | COMPOUND NUMBER | LCMS RETENTION TIME (min) | LCMS method |
|---|---|---|---|
| 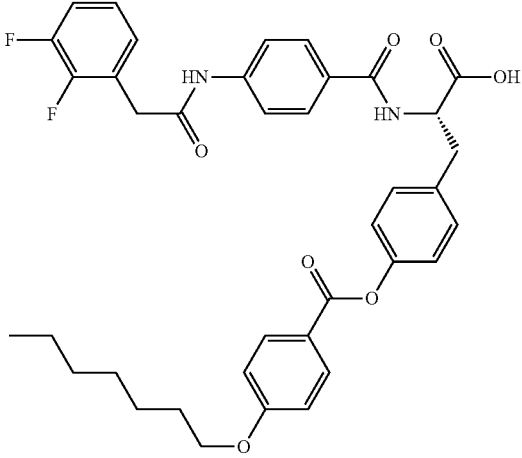 | 231 | 9.66 | 5 |
| 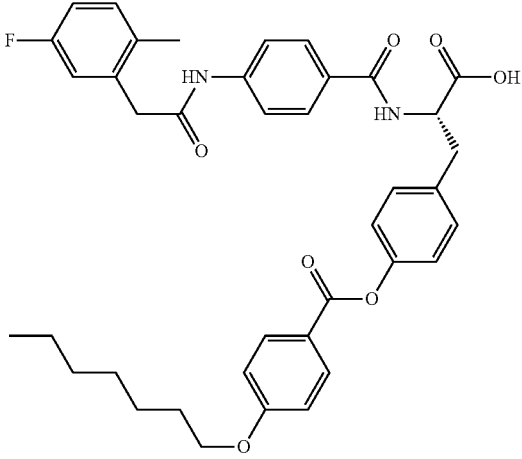 [SMILES: CCCCCCCOc1ccc(C(=O)Oc2ccc(C[C@H](NC(=O)c3ccc(NC(=O)Cc4cc(F)ccc4C)cc3)C(=O)O)cc2)cc1] | 232 | 9.90 | 5 |
| 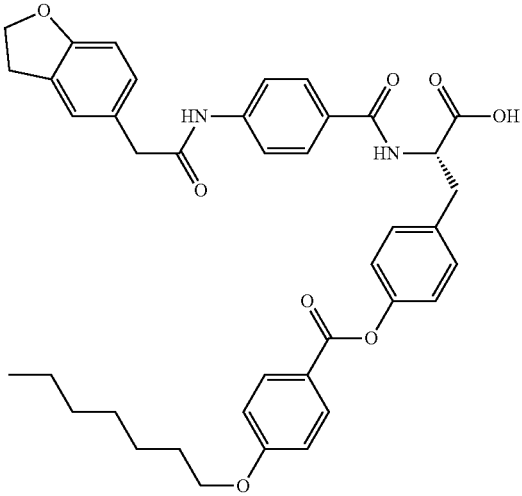 [SMILES: CCCCCCCOc1ccc(C(=O)Oc2ccc(C[C@H](NC(=O)c3ccc(NC(=O)Cc4ccc5c(c4)CCO5)cc3)C(=O)O)cc2)cc1] | 233 | 9.43 | 5 |

TABLE 1-continued
| STRUCTURE | COMPOUND NUMBER | LCMS RETENTION TIME (min) | LCMS method |
|---|---|---|---|
| 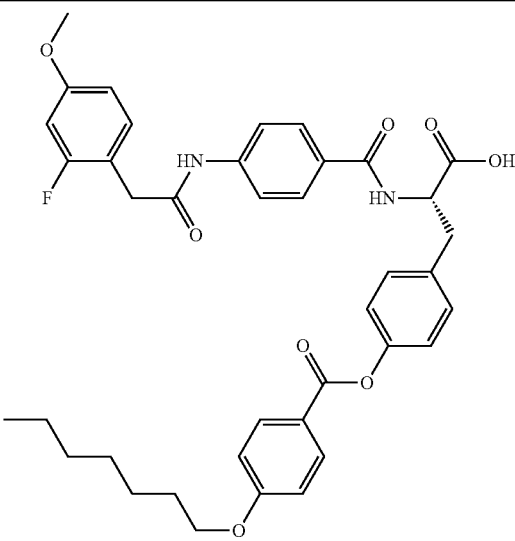 | 234 | 9.60 | 5 |
| 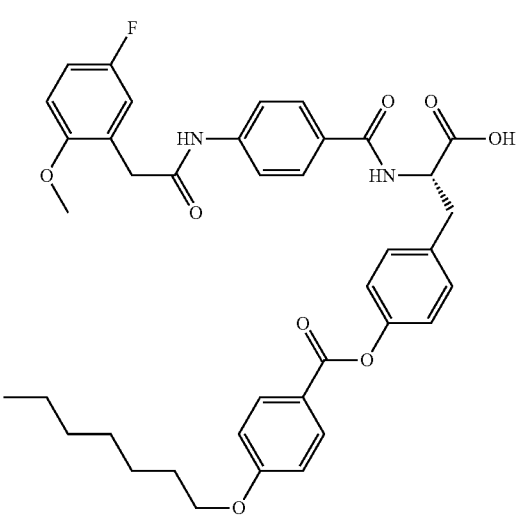 [SMILES: CCCCCCCOc1ccc(C(=O)Oc2ccc(C[C@H](NC(=O)c3ccc(NC(=O)Cc4cc(F)ccc4OC)cc3)C(=O)O)cc2)cc1] | 235 | 9.67 | 5 |
| 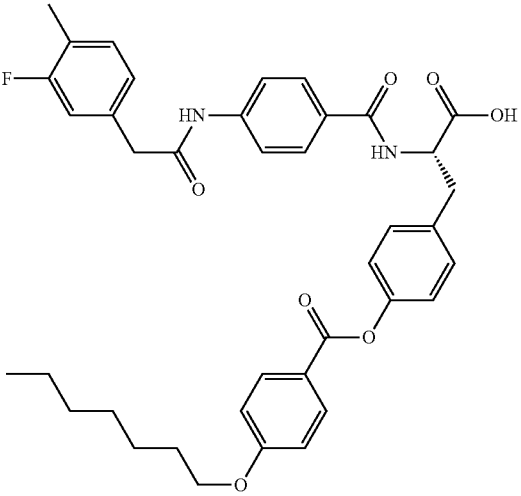 [SMILES: CCCCCCCOc1ccc(C(=O)Oc2ccc(C[C@H](NC(=O)c3ccc(NC(=O)Cc4ccc(C)c(F)c4)cc3)C(=O)O)cc2)cc1] | 236 | 9.96 | 5 |

TABLE 1-continued

| STRUCTURE | COMPOUND NUMBER | LCMS RETENTION TIME (min) | LCMS method |
|---|---|---|---|
| (4-chloro-3-fluorophenyl acetamide-phenyl-benzamide-tyrosine-4-(heptyloxy)benzoate structure) | 237 | 10.06 | 5 |
| (3-fluoro-4-methoxyphenyl acetamide-phenyl-benzamide-tyrosine-4-(heptyloxy)benzoate structure) | 238 | 9.46 | 5 |
| (4-methoxy-3-methylphenyl acetamide-phenyl-benzamide-tyrosine-4-(heptyloxy)benzoate structure) | 239 | 9.87 | 5 |

TABLE 1-continued

| STRUCTURE | COMPOUND NUMBER | LCMS RETENTION TIME (min) | LCMS method |
|---|---|---|---|
| (structure) | 240 | 9.54 | 5 |
| (structure) | 241 | 9.88 | 5 |
| (structure) | 242 | 9.98 | 5 |

TABLE 1-continued
| STRUCTURE | COMPOUND NUMBER | LCMS RETENTION TIME (min) | LCMS method |
|---|---|---|---|
| 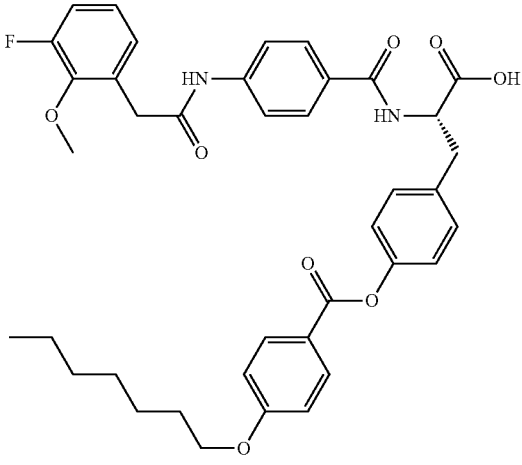 [SMILES: CCCCCCCOc1ccc(C(=O)Oc2ccc(C[C@H](NC(=O)c3ccc(NC(=O)Cc4cccc(F)c4OC)cc3)C(=O)O)cc2)cc1] | 243 | 9.72 | 5 |
| 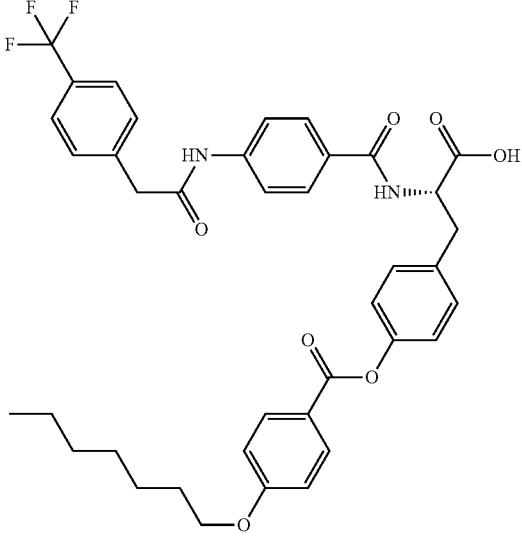 [SMILES: CCCCCCCOc1ccc(C(=O)Oc2ccc(C[C@H](NC(=O)c3ccc(NC(=O)Cc4ccc(C(F)(F)F)cc4)cc3)C(=O)O)cc2)cc1] | 244 | 10.13 | 5 |
| 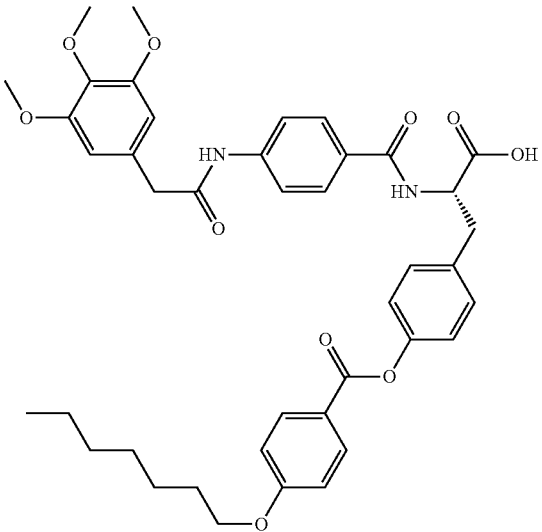 [SMILES: CCCCCCCOc1ccc(C(=O)Oc2ccc(C[C@H](NC(=O)c3ccc(NC(=O)Cc4cc(OC)c(OC)c(OC)c4)cc3)C(=O)O)cc2)cc1] | 245 | 9.15 | 5 |

TABLE 1-continued

| STRUCTURE | COMPOUND NUMBER | LCMS RETENTION TIME (min) | LCMS method |
|---|---|---|---|
| 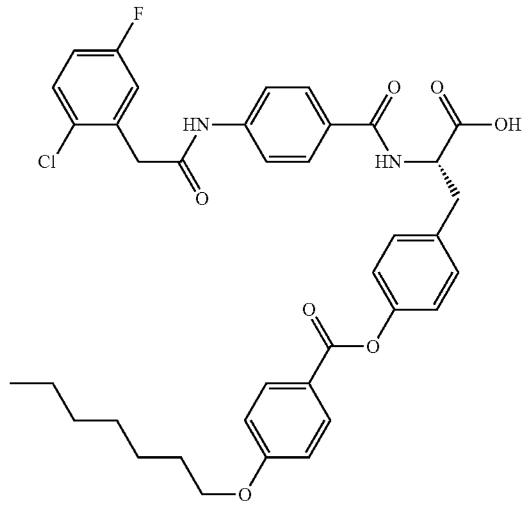 [SMILES: CCCCCCCOc1ccc(C(=O)Oc2ccc(C[C@H](NC(=O)c3ccc(NC(=O)Cc4cc(F)ccc4Cl)cc3)C(=O)O)cc2)cc1] | 246 | 9.88 | 5 |
| 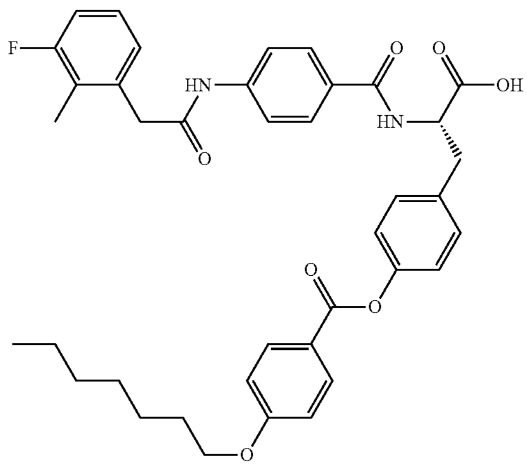 | 247 | 9.90 | 5 |
| 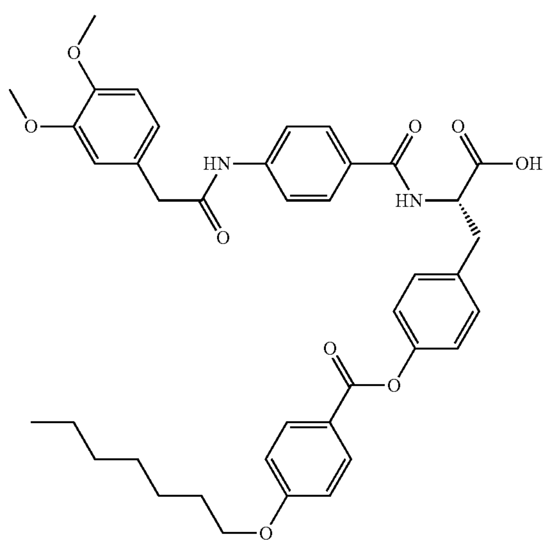 | 248 | 9.09 | 5 |

TABLE 1-continued
| STRUCTURE | COMPOUND NUMBER | LCMS RETENTION TIME (min) | LCMS method |
|---|---|---|---|
| 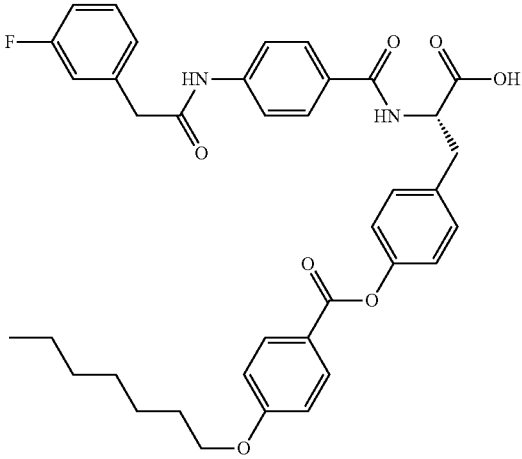 [SMILES: CCCCCCCOc1ccc(C(=O)Oc2ccc(C[C@H](NC(=O)c3ccc(NC(=O)Cc4cccc(F)c4C)cc3)C(=O)O)cc2)cc1] | 249 | 9.61 | 5 |
| 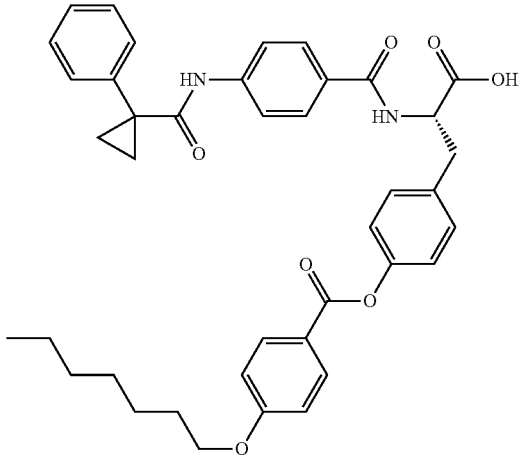 [SMILES: CCCCCCCOc1ccc(C(=O)Oc2ccc(C[C@H](NC(=O)c3ccc(NC(=O)C4(c5ccccc5)CC4)cc3)C(=O)O)cc2)cc1] | 250 | 10.32 | 5 |
| 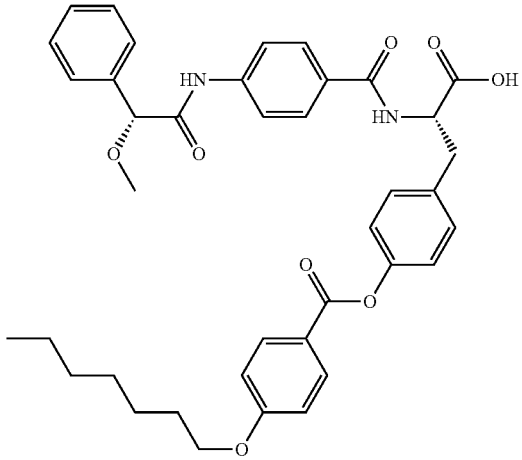 [SMILES: CCCCCCCOc1ccc(C(=O)Oc2ccc(C[C@H](NC(=O)c3ccc(NC(=O)[C@H](OC)c4ccccc4)cc3)C(=O)O)cc2)cc1] | 251 | 9.78 | 5 |

TABLE 1-continued

| STRUCTURE | COMPOUND NUMBER | LCMS RETENTION TIME (min) | LCMS method |
|---|---|---|---|
| 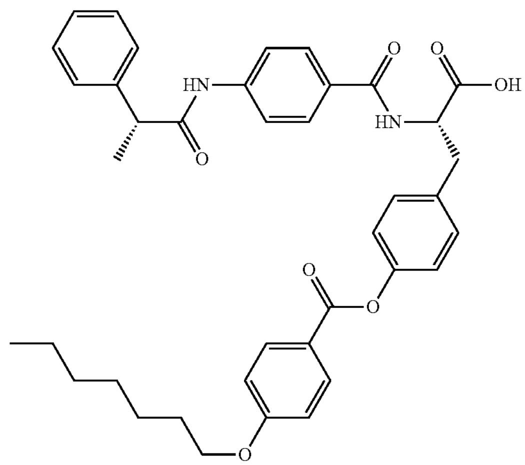 [SMILES: CCCCCCCOc1ccc(C(=O)Oc2ccc(C[C@H](NC(=O)c3ccc(NC(=O)[C@H](C)c4ccccc4)cc3)C(=O)O)cc2)cc1] | 252 | 9.92 | 5 |
| 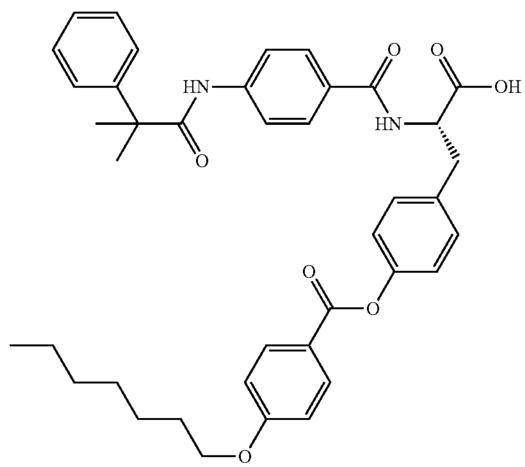 [SMILES: CCCCCCCOc1ccc(C(=O)Oc2ccc(C[C@H](NC(=O)c3ccc(NC(=O)C(C)(C)c4ccccc4)cc3)C(=O)O)cc2)cc1] | 253 | 10.29 | 5 |
| 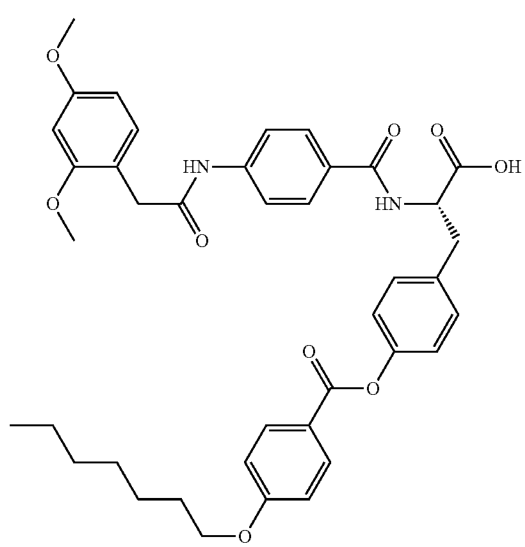 [SMILES: CCCCCCCOc1ccc(C(=O)Oc2ccc(C[C@H](NC(=O)c3ccc(NC(=O)Cc4ccc(OC)cc4OC)cc3)C(=O)O)cc2)cc1] | 254 | 9.57 | 5 |

TABLE 1-continued
| STRUCTURE | COMPOUND NUMBER | LCMS RETENTION TIME (min) | LCMS method |
|---|---|---|---|
| 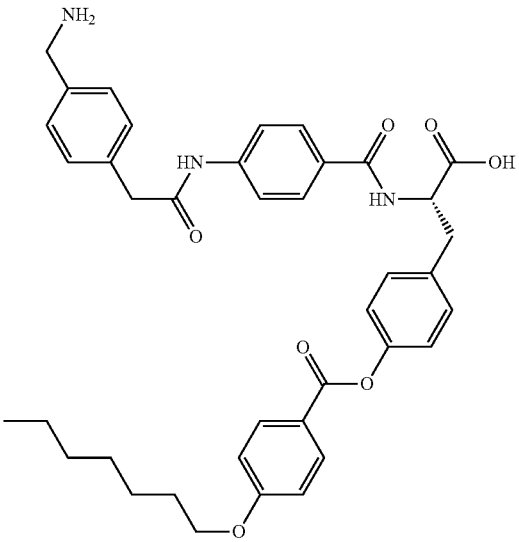 [SMILES: CCCCCCCOc1ccc(C(=O)Oc2ccc(C[C@H](NC(=O)c3ccc(NC(=O)Cc4ccc(CN)cc4)cc3)C(=O)O)cc2)cc1] | 255 | 6.04 | 5 |
| 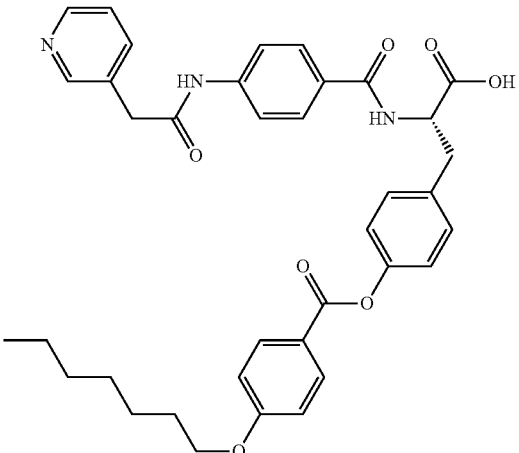 | 256 | 6.74 | 5 |
| 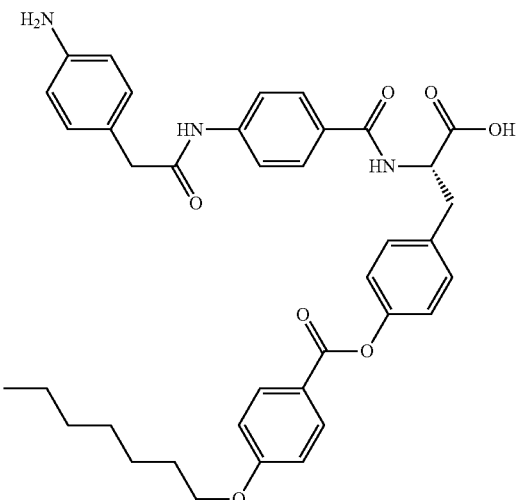 | 257 | 7.40 | 5 |

TABLE 1-continued
| STRUCTURE | COMPOUND NUMBER | LCMS RETENTION TIME (min) | LCMS method |
|---|---|---|---|
| 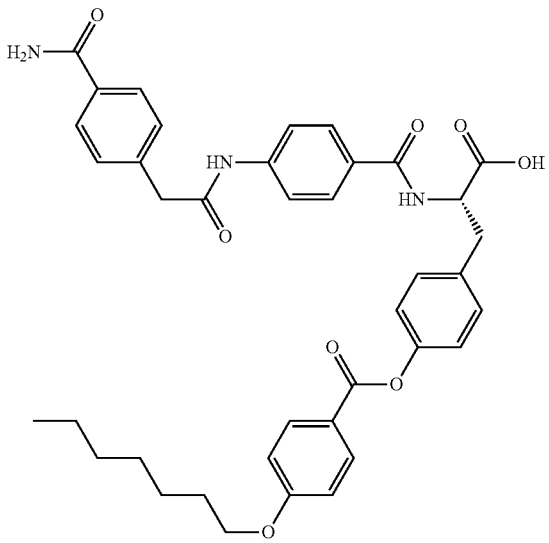 [SMILES: CCCCCCCOc1ccc(C(=O)Oc2ccc(C[C@H](NC(=O)c3ccc(NC(=O)Cc4ccc(C(N)=O)cc4)cc3)C(=O)O)cc2)cc1] | 258 | 8.04 | 5 |
| 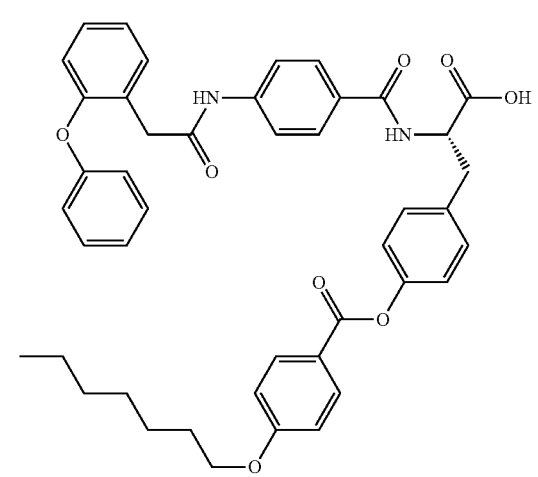 [SMILES: CCCCCCCOc1ccc(C(=O)Oc2ccc(C[C@H](NC(=O)c3ccc(NC(=O)Cc4ccccc4Oc4ccccc4)cc3)C(=O)O)cc2)cc1] | 259 | 10.44 | 5 |
| 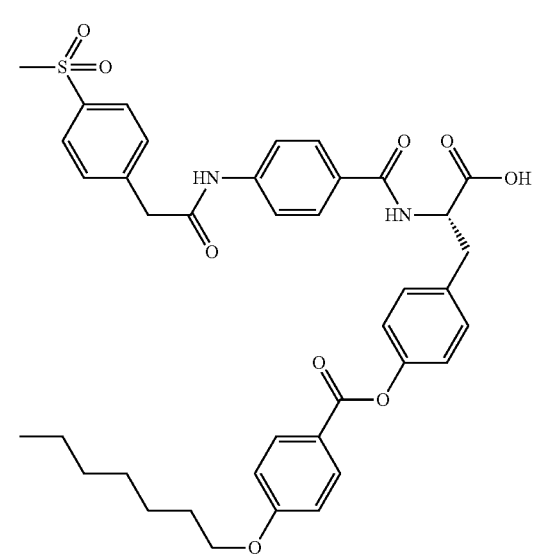 [SMILES: CCCCCCCOc1ccc(C(=O)Oc2ccc(C[C@H](NC(=O)c3ccc(NC(=O)Cc4ccc(S(C)(=O)=O)cc4)cc3)C(=O)O)cc2)cc1] | 260 | 8.66 | 5 |

TABLE 1-continued

| STRUCTURE | COMPOUND NUMBER | LCMS RETENTION TIME (min) | LCMS method |
|---|---|---|---|
| 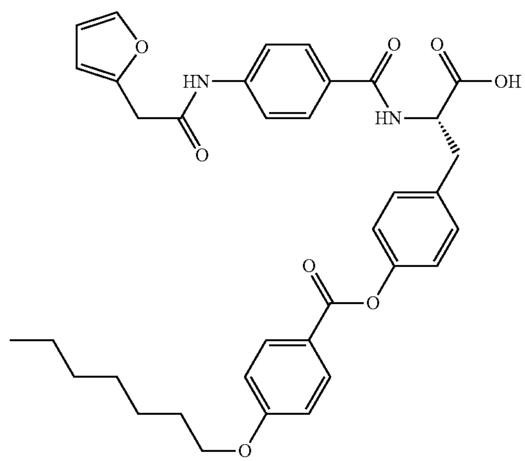 [SMILES: CCCCCCCOc1ccc(C(=O)Oc2ccc(C[C@H](NC(=O)c3ccc(NC(=O)Cc4ccco4)cc3)C(=O)O)cc2)cc1] | 261 | 9.12 | 5 |
| 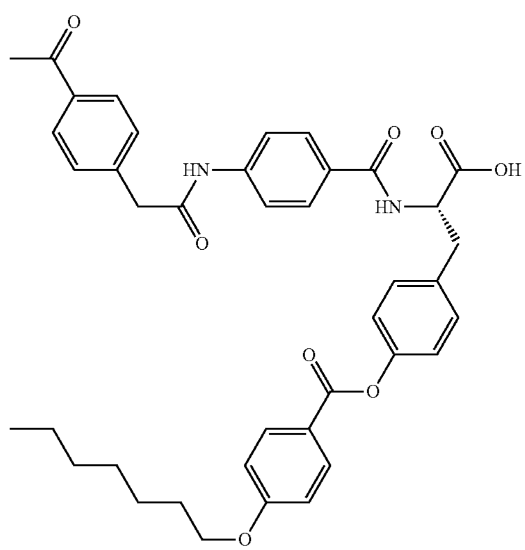 [SMILES: CCCCCCCOc1ccc(C(=O)Oc2ccc(C[C@H](NC(=O)c3ccc(NC(=O)Cc4ccc(C(C)=O)cc4)cc3)C(=O)O)cc2)cc1] | 262 | 9.21 | 5 |
| 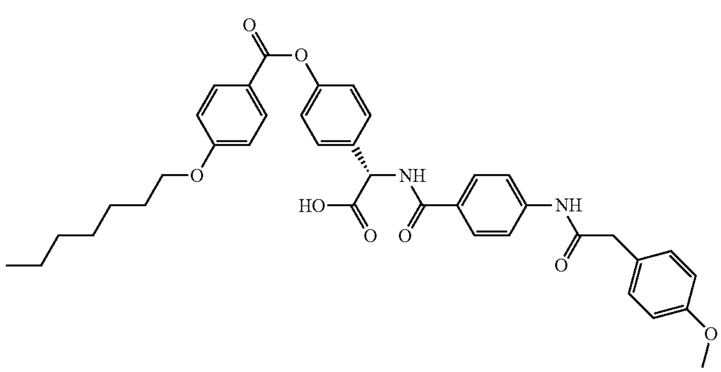 [SMILES: CCCCCCCOc1ccc(C(=O)Oc2ccc([C@H](NC(=O)c3ccc(NC(=O)Cc4ccc(OC)cc4)cc3)C(=O)O)cc2)cc1] | 263 | 9.50 | 5 |

TABLE 1-continued

| STRUCTURE | COMPOUND NUMBER | LCMS RETENTION TIME (min) | LCMS method |
|---|---|---|---|
| 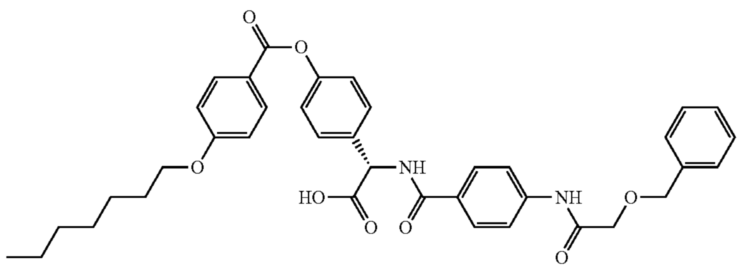 [SMILES: CCCCCCCOc1ccc(C(=O)Oc2ccc([C@H](NC(=O)c3ccc(NC(=O)COCc4ccccc4)cc3)C(=O)O)cc2)cc1] | 264 | 9.86 | 5 |
| 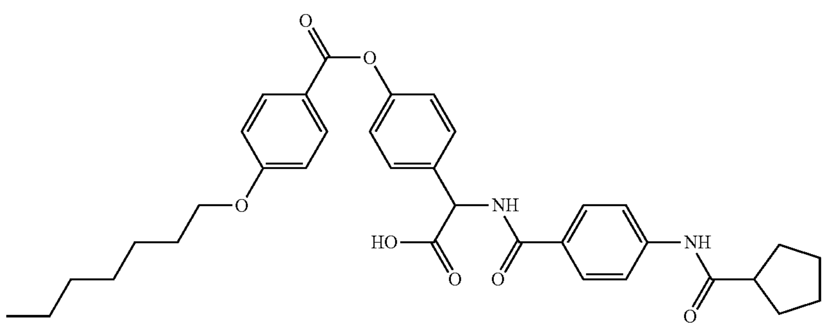 [SMILES: CCCCCCCOc1ccc(C(=O)Oc2ccc(C(NC(=O)c3ccc(NC(=O)C4CCCC4)cc3)C(=O)O)cc2)cc1] | 265 | 9.58 | 5 |
| 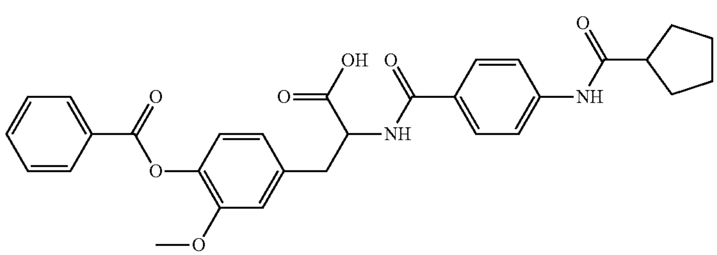 [SMILES: COc1cc(CC(NC(=O)c2ccc(NC(=O)C3CCCC3)cc2)C(=O)O)ccc1OC(=O)c1ccccc1] | 266 | 3.30 | 1 |
| 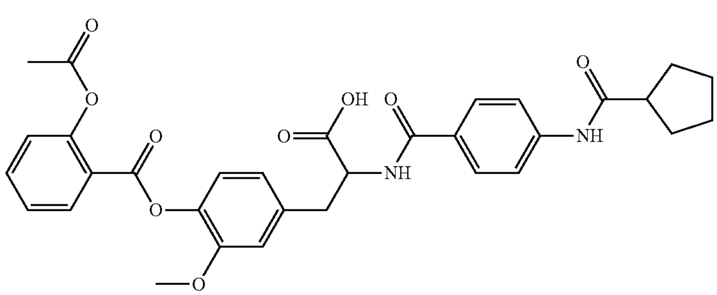 [SMILES: COc1cc(CC(NC(=O)c2ccc(NC(=O)C3CCCC3)cc2)C(=O)O)ccc1OC(=O)c1ccccc1OC(C)=O] | 267 | 8.14 | 2 |
| 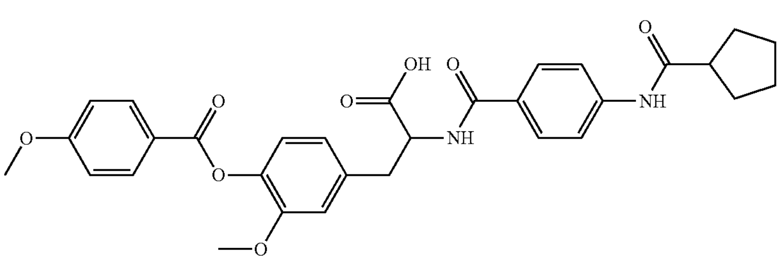 [SMILES: COc1ccc(C(=O)Oc2ccc(CC(NC(=O)c3ccc(NC(=O)C4CCCC4)cc3)C(=O)O)cc2OC)cc1] | 268 | 8.38 | 2 |

TABLE 1-continued
| STRUCTURE | COMPOUND NUMBER | LCMS RETENTION TIME (min) | LCMS method |
|---|---|---|---|
| 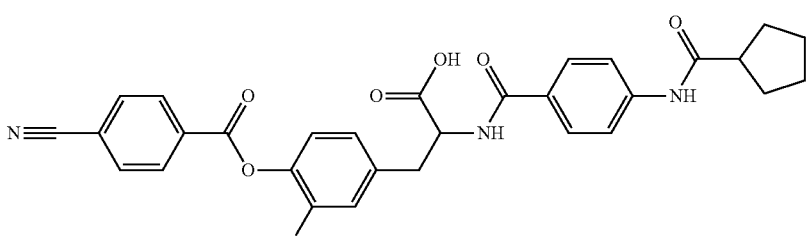 | 269 | 8.17 | 2 |
| 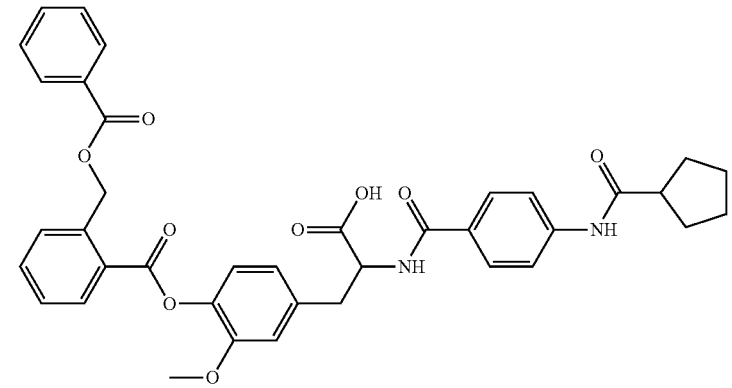 [SMILES: COc1cc(CC(NC(=O)c2ccc(NC(=O)C3CCCC3)cc2)C(=O)O)ccc1OC(=O)c1ccccc1COC(=O)c1ccccc1] | 270 | 9.46 | 2 |
| 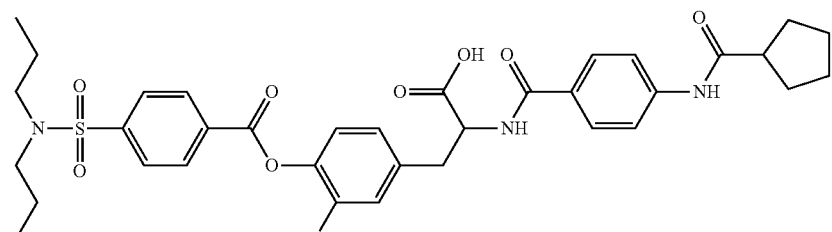 | 271 | 9.41 | 2 |
| 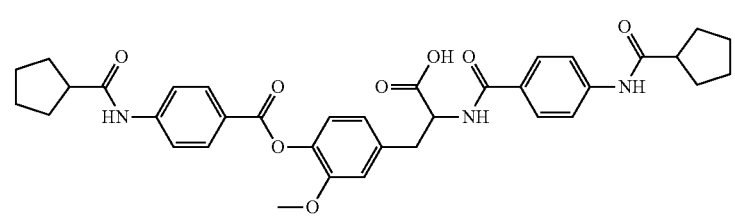 [SMILES: COc1cc(CC(NC(=O)c2ccc(NC(=O)C3CCCC3)cc2)C(=O)O)ccc1OC(=O)c1ccc(NC(=O)C2CCCC2)cc1] | 272 | 8.56 | 2 |
| 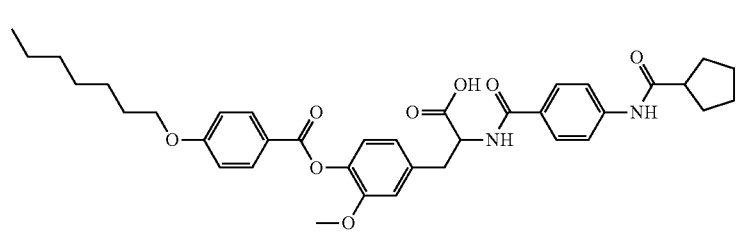 [SMILES: CCCCCCCOc1ccc(C(=O)Oc2ccc(CC(NC(=O)c3ccc(NC(=O)C4CCCC4)cc3)C(=O)O)cc2OC)cc1] | 273 | 11.17 | 2 |

TABLE 1-continued
| STRUCTURE | COMPOUND NUMBER | LCMS RETENTION TIME (min) | LCMS method |
|---|---|---|---|
| 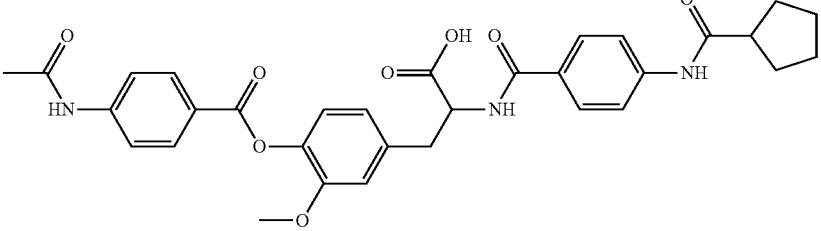 | 274 | 7.19 | 2 |
| 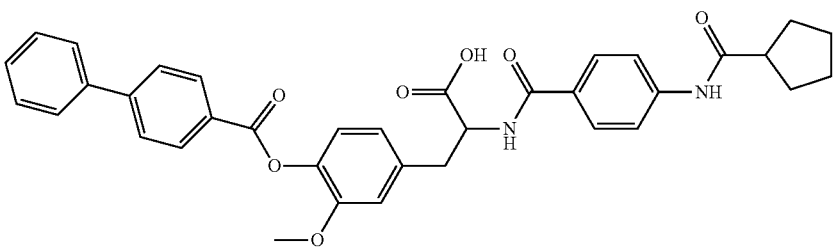 [SMILES: COc1cc(CC(NC(=O)c2ccc(NC(=O)C3CCCC3)cc2)C(=O)O)ccc1OC(=O)c1ccc(-c2ccccc2)cc1] | 275 | 9.60 | 2 |
| 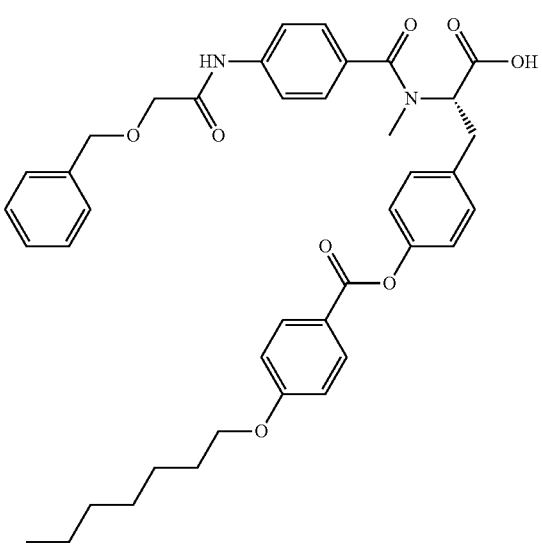 [SMILES: CCCCCCCOc1ccc(C(=O)Oc2ccc(C[C@@H](C(=O)O)N(C)C(=O)c3ccc(NC(=O)COCc4ccccc4)cc3)cc2)cc1] | 276 | 10.01 | 5 |
| 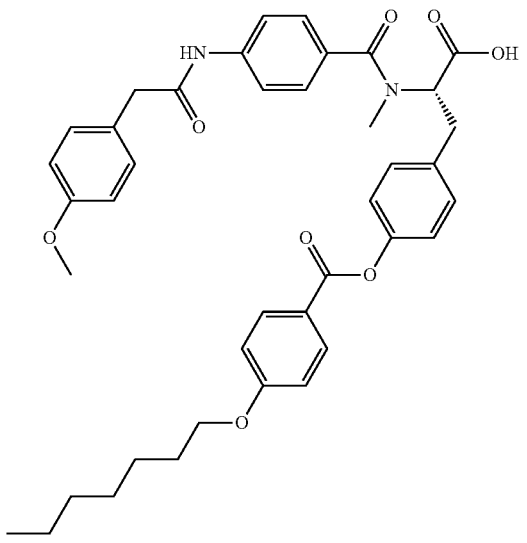 [SMILES: CCCCCCCOc1ccc(C(=O)Oc2ccc(C[C@@H](C(=O)O)N(C)C(=O)c3ccc(NC(=O)Cc4ccc(OC)cc4)cc3)cc2)cc1] | 277 | 9.62 | 5 |

TABLE 1-continued

| STRUCTURE | COMPOUND NUMBER | LCMS RETENTION TIME (min) | LCMS method |
| --- | --- | --- | --- |
| 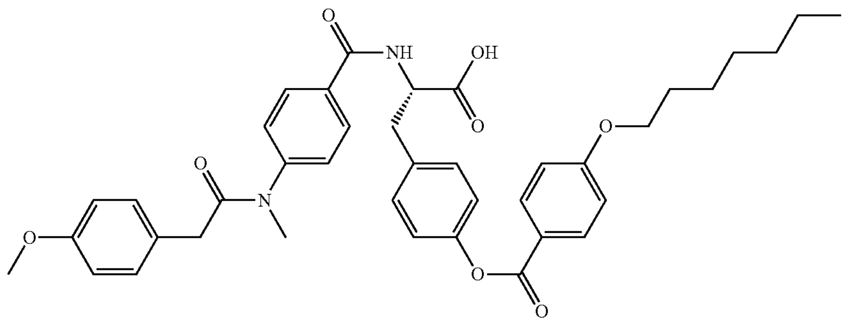 [SMILES: CCCCCCCOc1ccc(C(=O)Oc2ccc(C[C@H](NC(=O)c3ccc(N(C)C(=O)Cc4ccc(OC)cc4)cc3)C(=O)O)cc2)cc1] | 278 | 9.53 | 5 |
| 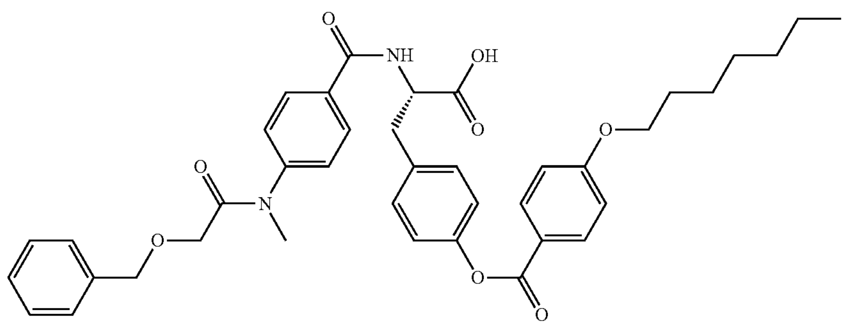 [SMILES: CCCCCCCOc1ccc(C(=O)Oc2ccc(C[C@H](NC(=O)c3ccc(N(C)C(=O)COCc4ccccc4)cc3)C(=O)O)cc2)cc1] | 279 | 9.56 | 5 |
| 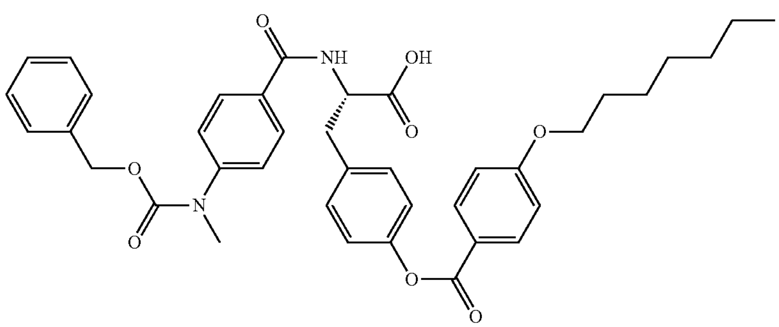 [SMILES: CCCCCCCOc1ccc(C(=O)Oc2ccc(C[C@H](NC(=O)c3ccc(N(C)C(=O)OCc4ccccc4)cc3)C(=O)O)cc2)cc1] | 280 | 10.24 | 5 |
| 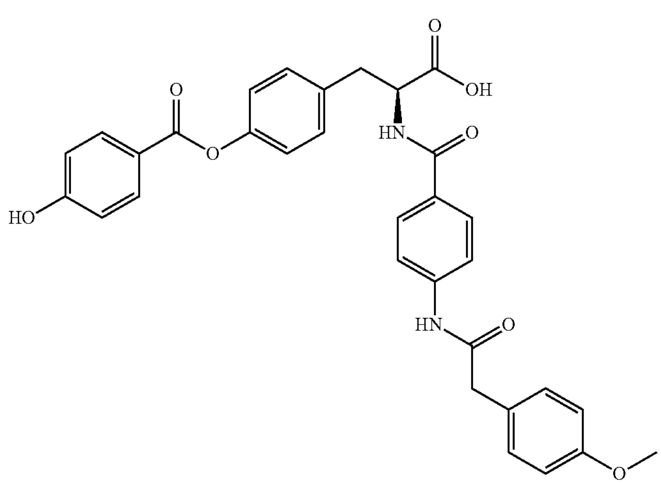 [SMILES: COc1ccc(CC(=O)Nc2ccc(C(=O)N[C@@H](Cc3ccc(OC(=O)c4ccc(O)cc4)cc3)C(=O)O)cc2)cc1] | 281 | 5.15 | 5 |

TABLE 1-continued

| STRUCTURE | COMPOUND NUMBER | LCMS RETENTION TIME (min) | LCMS method |
|---|---|---|---|
| 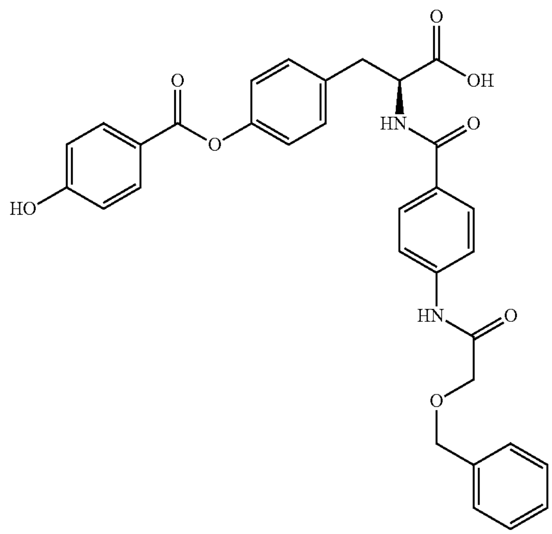 [SMILES: O=C(COCc1ccccc1)Nc1ccc(C(=O)N[C@@H](Cc2ccc(OC(=O)c3ccc(O)cc3)cc2)C(=O)O)cc1] | 282 | 5.51 | 5 |
| 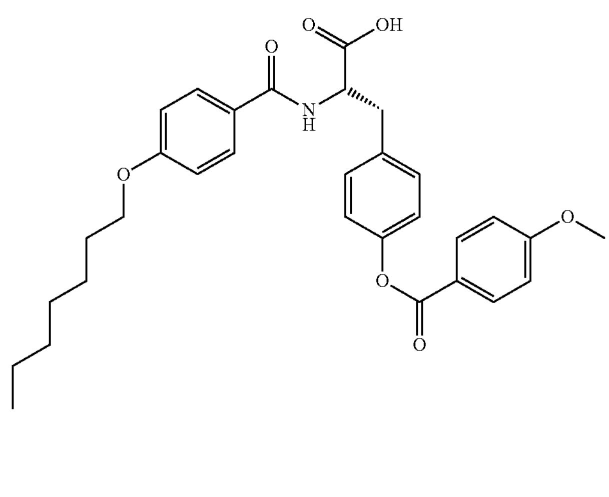 | 283 | 9.10 | 5 |

TABLE 1-continued

| STRUCTURE | COMPOUND NUMBER | LCMS RETENTION TIME (min) | LCMS method |
|---|---|---|---|
| 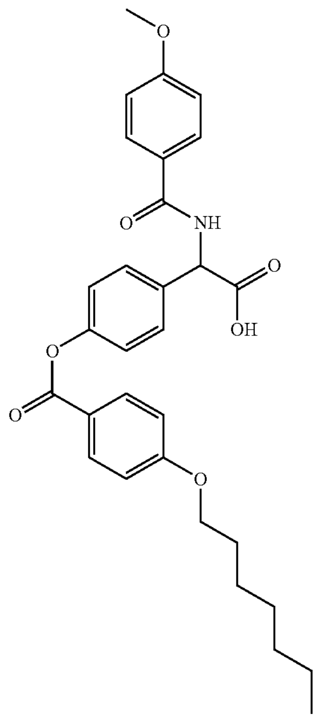 [SMILES: CCCCCCCOc1ccc(C(=O)Oc2ccc(C(NC(=O)c3ccc(OC)cc3)C(=O)O)cc2)cc1] | 284 | 9.32 | 5 |
| 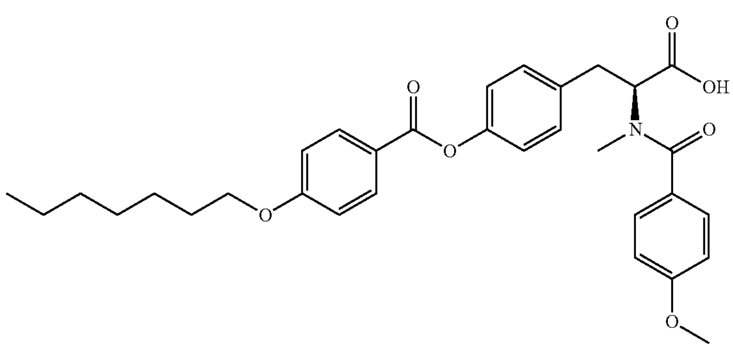 [SMILES: CCCCCCCOc1ccc(C(=O)Oc2ccc(C[C@@H](C(=O)O)N(C)C(=O)c3ccc(OC)cc3)cc2)cc1] | 285 | 9.88 | 5 |
| 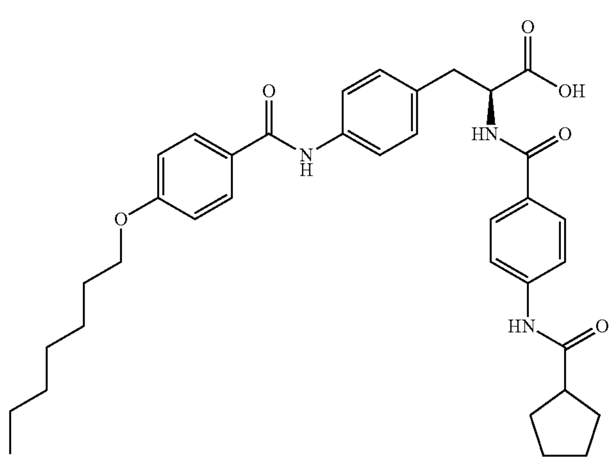 [SMILES: CCCCCCCOc1ccc(C(=O)Nc2ccc(C[C@H](NC(=O)c3ccc(NC(=O)C4CCCC4)cc3)C(=O)O)cc2)cc1] | 286 | 9.56 | 5 |

TABLE 1-continued

| STRUCTURE | COMPOUND NUMBER | LCMS RETENTION TIME (min) | LCMS method |
| --- | --- | --- | --- |
| 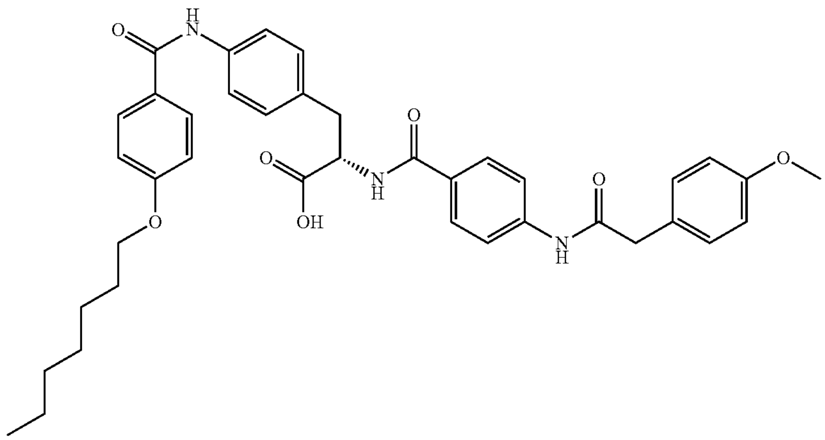 [SMILES: CCCCCCCOc1ccc(C(=O)Nc2ccc(C[C@H](NC(=O)c3ccc(NC(=O)Cc4ccc(OC)cc4)cc3)C(=O)O)cc2)cc1] | 287 | 8.42 | 5 |
| 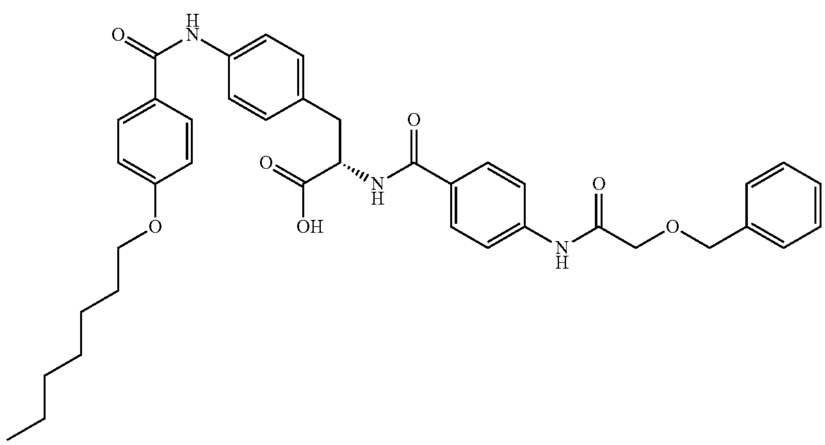 [SMILES: CCCCCCCOc1ccc(C(=O)Nc2ccc(C[C@H](NC(=O)c3ccc(NC(=O)COCc4ccccc4)cc3)C(=O)O)cc2)cc1] | 288 | 8.75 | 5 |
| 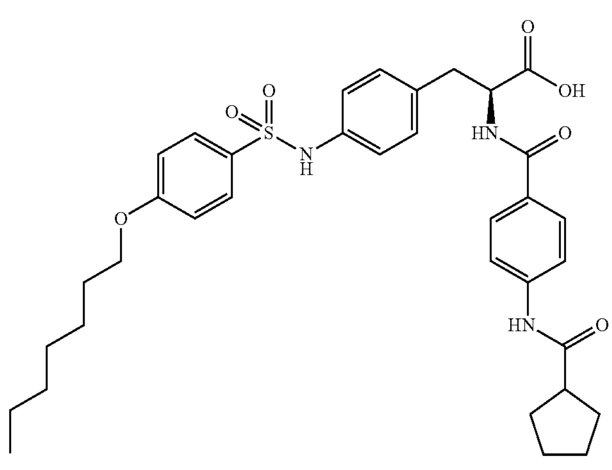 [SMILES: CCCCCCCOc1ccc(S(=O)(=O)Nc2ccc(C[C@H](NC(=O)c3ccc(NC(=O)C4CCCC4)cc3)C(=O)O)cc2)cc1] | 289 | 8.18 | 5 |

TABLE 1-continued
| STRUCTURE | COMPOUND NUMBER | LCMS RETENTION TIME (min) | LCMS method |
|---|---|---|---|
| 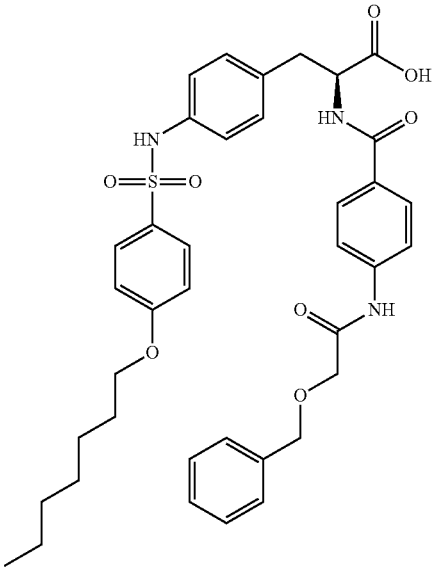 [SMILES: CCCCCCCOc1ccc(S(=O)(=O)Nc2ccc(C[C@H](NC(=O)c3ccc(NC(=O)COCc4ccccc4)cc3)C(=O)O)cc2)cc1] | 290 | 8.27 | 5 |
| 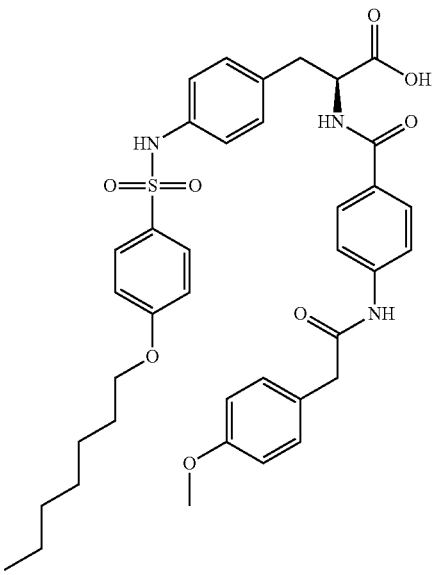 [SMILES: CCCCCCCOc1ccc(S(=O)(=O)Nc2ccc(C[C@H](NC(=O)c3ccc(NC(=O)Cc4ccc(OC)cc4)cc3)C(=O)O)cc2)cc1] | 291 | 7.92 | 5 |

TABLE 1-continued

| STRUCTURE | COMPOUND NUMBER | LCMS RETENTION TIME (min) | LCMS method |
|---|---|---|---|
| 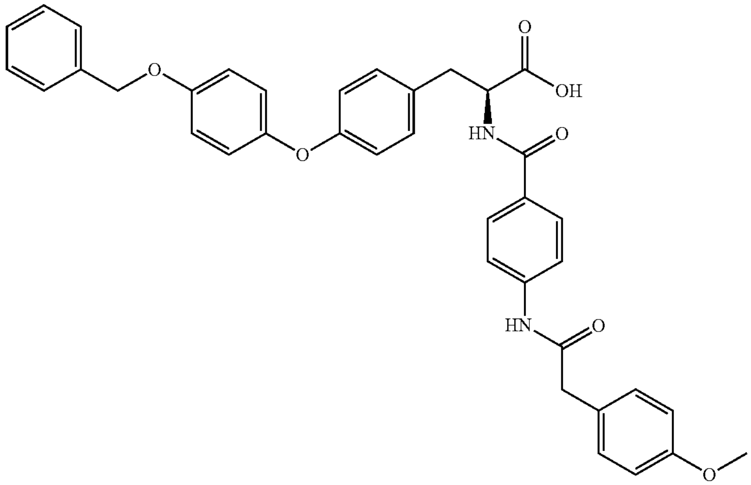 [SMILES: COc1ccc(CC(=O)Nc2ccc(C(=O)N[C@@H](Cc3ccc(Oc4ccc(OCc5ccccc5)cc4)cc3)C(=O)O)cc2)cc1] | 292 | 7.66 | 5 |
| 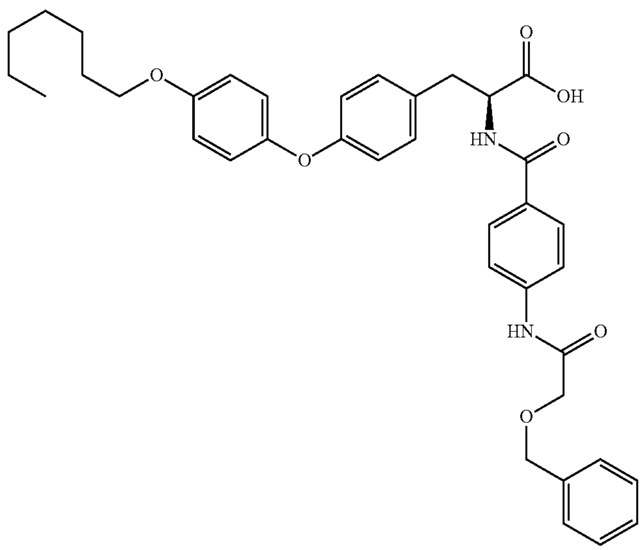 [SMILES: CCCCCCCOc1ccc(Oc2ccc(C[C@H](NC(=O)c3ccc(NC(=O)COCc4ccccc4)cc3)C(=O)O)cc2)cc1] | 293 | 9.75 | 5 |
| 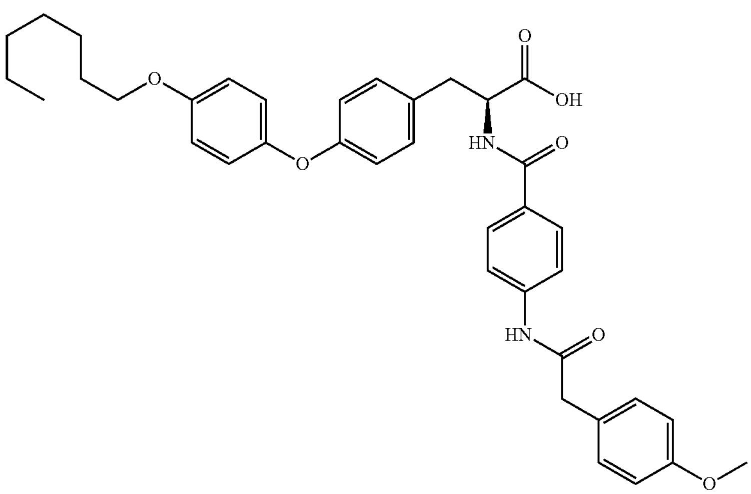 [SMILES: CCCCCCCOc1ccc(Oc2ccc(C[C@H](NC(=O)c3ccc(NC(=O)Cc4ccc(OC)cc4)cc3)C(=O)O)cc2)cc1] | 294 | 9.34 | 5 |

| STRUCTURE | COMPOUND NUMBER | LCMS RETENTION TIME (min) | LCMS method |
|---|---|---|---|
| 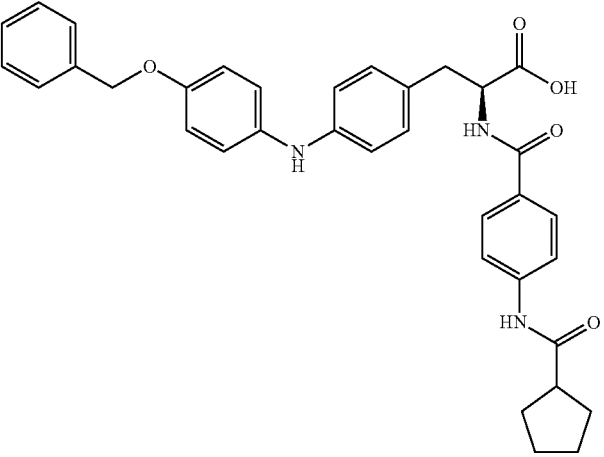 [SMILES: O=C(N[C@@H](Cc1ccc(Nc2ccc(OCc3ccccc3)cc2)cc1)C(=O)O)c1ccc(NC(=O)C2CCCC2)cc1] | 295 | 7.38 | 5 |
| 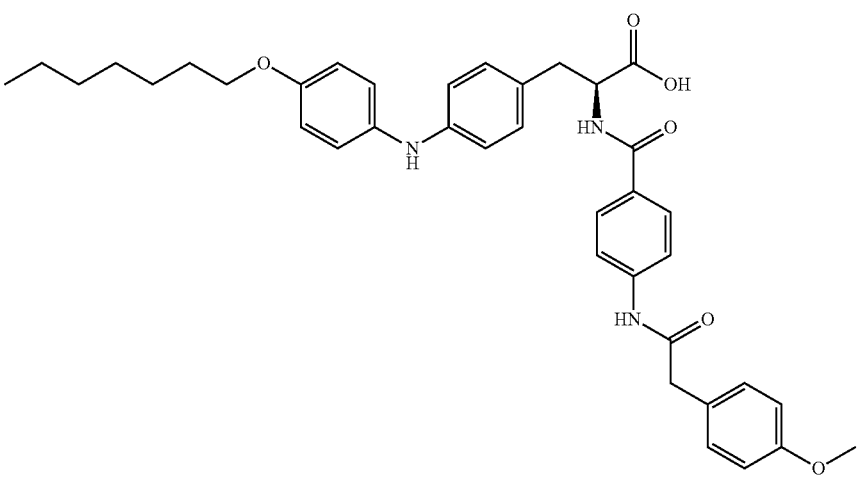 [SMILES: CCCCCCCOc1ccc(Nc2ccc(C[C@H](NC(=O)c3ccc(NC(=O)Cc4ccc(OC)cc4)cc3)C(=O)O)cc2)cc1] | 296 | 8.86 | 5 |
| 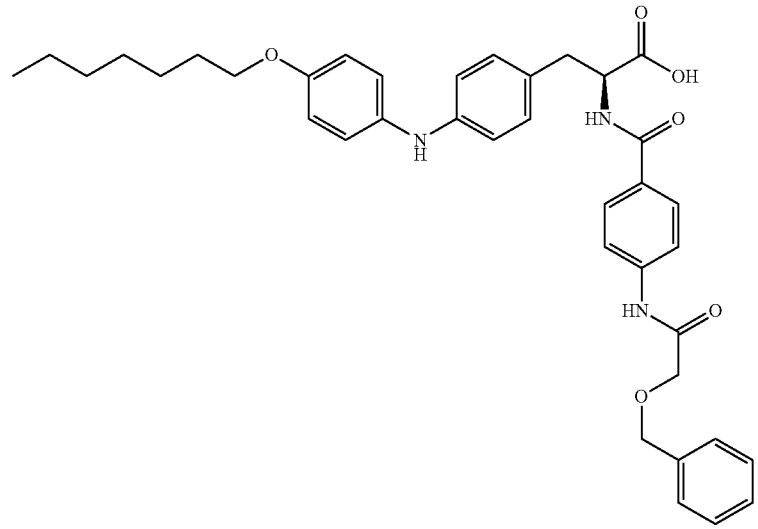 [SMILES: CCCCCCCOc1ccc(Nc2ccc(C[C@H](NC(=O)c3ccc(NC(=O)COCc4ccccc4)cc3)C(=O)O)cc2)cc1] | 297 | 9.24 | 5 |

TABLE 1-continued
| STRUCTURE | COMPOUND NUMBER | LCMS RETENTION TIME (min) | LCMS method |
|---|---|---|---|
| 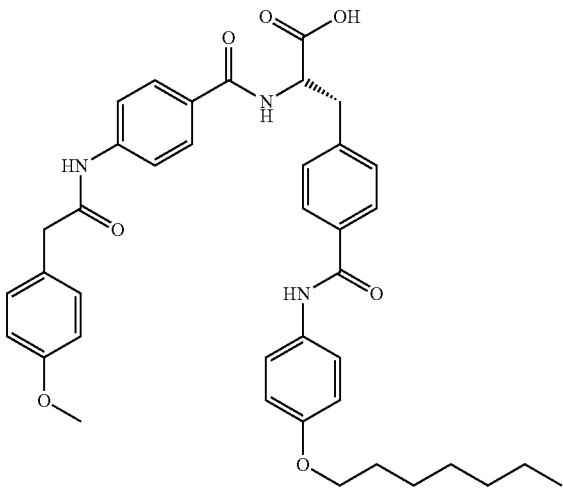 | 298 | 8.38 | 5 |
| 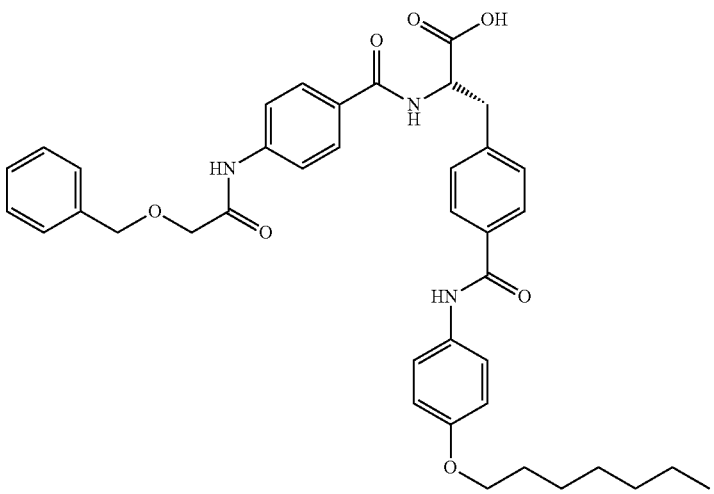 | 299 | 8.71 | 5 |
| 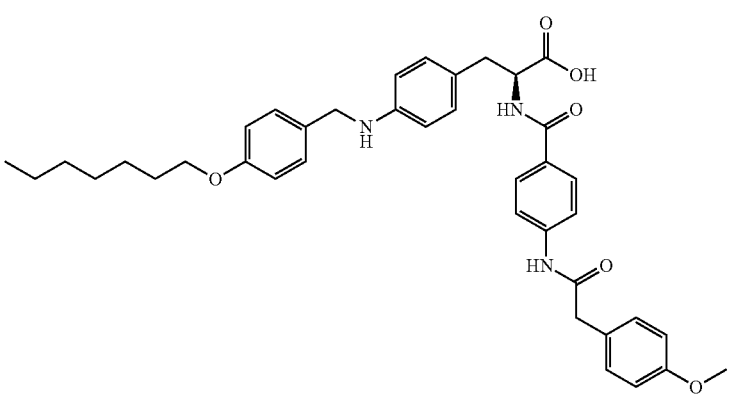 [SMILES: CCCCCCCOc1ccc(CNc2ccc(C[C@H](NC(=O)c3ccc(NC(=O)Cc4ccc(OC)cc4)cc3)C(=O)O)cc2)cc1] | 300 | 8.38 | 5 |

TABLE 1-continued

| STRUCTURE | COMPOUND NUMBER | LCMS RETENTION TIME (min) | LCMS method |
|---|---|---|---|
| 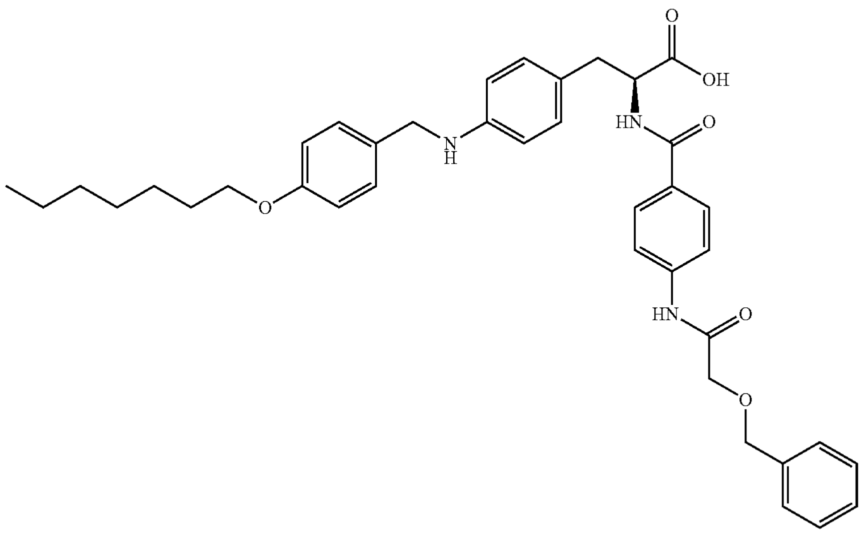 [SMILES: CCCCCCCOc1ccc(CNc2ccc(C[C@H](NC(=O)c3ccc(NC(=O)COCc4ccccc4)cc3)C(=O)O)cc2)cc1] | 301 | 8.82 | 5 |
| 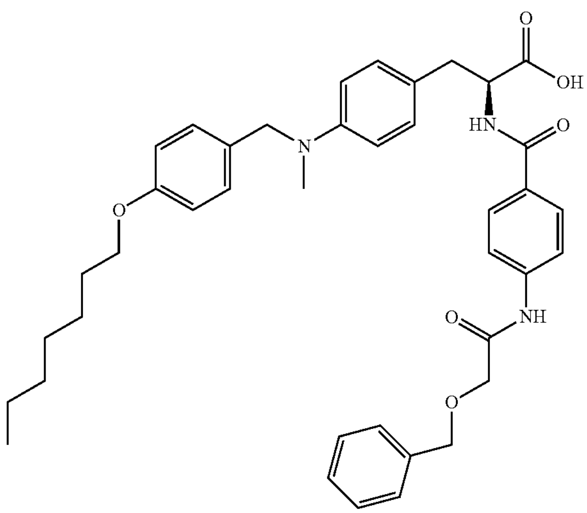 [SMILES: CCCCCCCOc1ccc(CN(C)c2ccc(C[C@H](NC(=O)c3ccc(NC(=O)COCc4ccccc4)cc3)C(=O)O)cc2)cc1] | 302 | 9.04 | 5 |
| 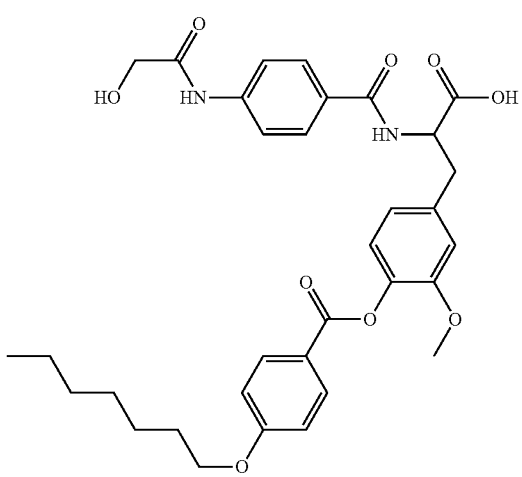 [SMILES: CCCCCCCOc1ccc(C(=O)Oc2ccc(CC(NC(=O)c3ccc(NC(=O)CO)cc3)C(=O)O)cc2OC)cc1] | 303 | 8.00 | 5 |

TABLE 1-continued
| STRUCTURE | COMPOUND NUMBER | LCMS RETENTION TIME (min) | LCMS method |
|---|---|---|---|
| 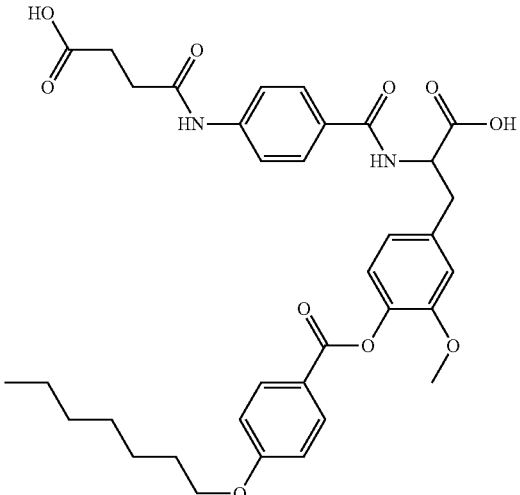 | 304 | 8.01 | 5 |
| 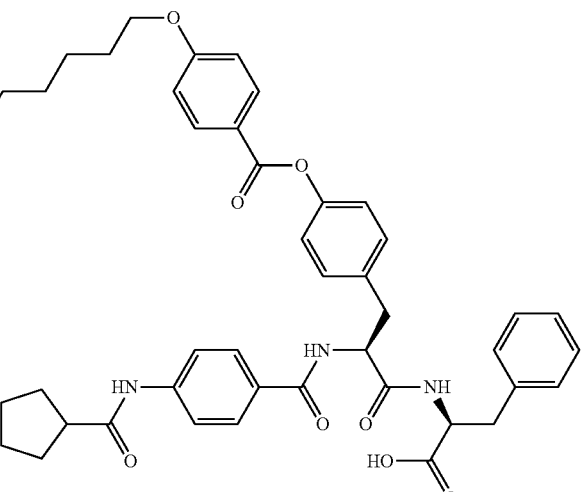 | 305 | 10.13 | 5 |
| 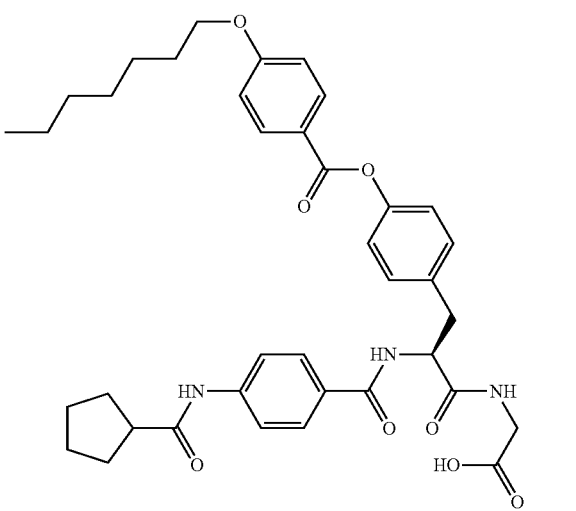 [SMILES: CCCCCCCOc1ccc(C(=O)Oc2ccc(C[C@H](NC(=O)c3ccc(NC(=O)C4CCCC4)cc3)C(=O)NCC(=O)O)cc2)cc1] | 306 | 9.26 | 5 |

TABLE 1-continued
| STRUCTURE | COMPOUND NUMBER | LCMS RETENTION TIME (min) | LCMS method |
|---|---|---|---|
| 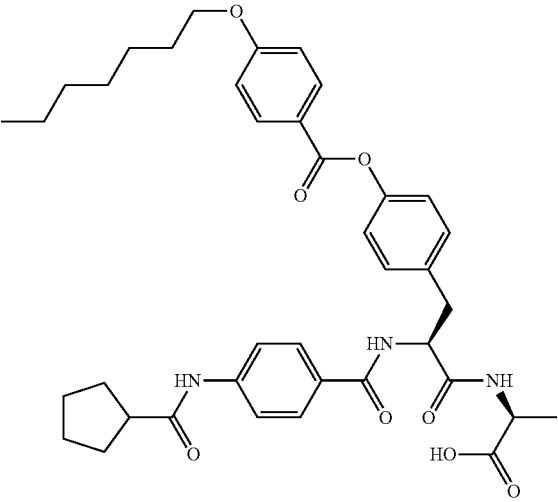 [SMILES: CCCCCCCOc1ccc(C(=O)Oc2ccc(C[C@H](NC(=O)c3ccc(NC(=O)C4CCCC4)cc3)C(=O)N[C@@H](C)C(=O)O)cc2)cc1] | 307 | 9.38 | 5 |
| 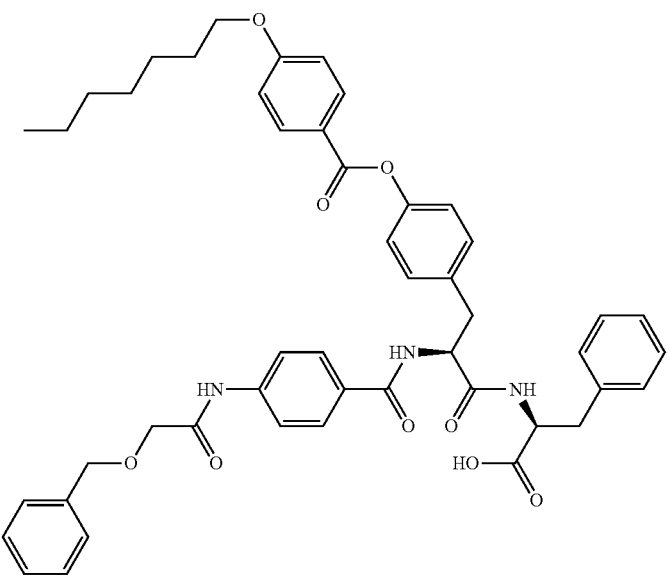 [SMILES: CCCCCCCOc1ccc(C(=O)Oc2ccc(C[C@H](NC(=O)c3ccc(NC(=O)COCc4ccccc4)cc3)C(=O)N[C@@H](Cc3ccccc3)C(=O)O)cc2)cc1] | 308 | 10.23 | 5 |

TABLE 1-continued
| STRUCTURE | COMPOUND NUMBER | LCMS RETENTION TIME (min) | LCMS method |
|---|---|---|---|
| 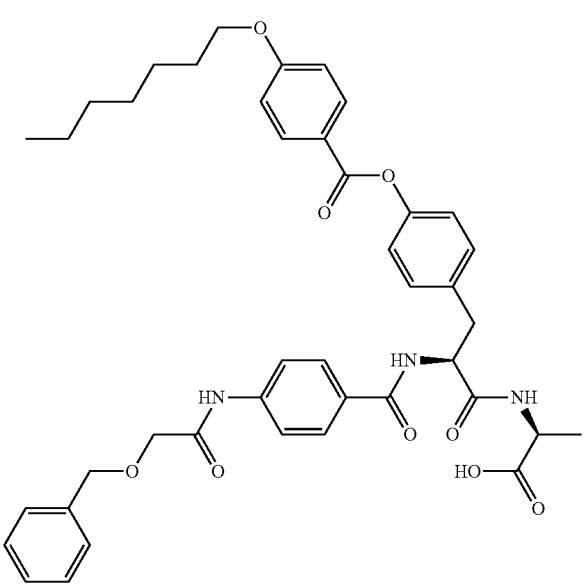 [SMILES: CCCCCCCOc1ccc(C(=O)Oc2ccc(C[C@H](NC(=O)c3ccc(NC(=O)COCc4ccccc4)cc3)C(=O)N[C@@H](C)C(=O)O)cc2)cc1] | 309 | 9.56 | 5 |
| 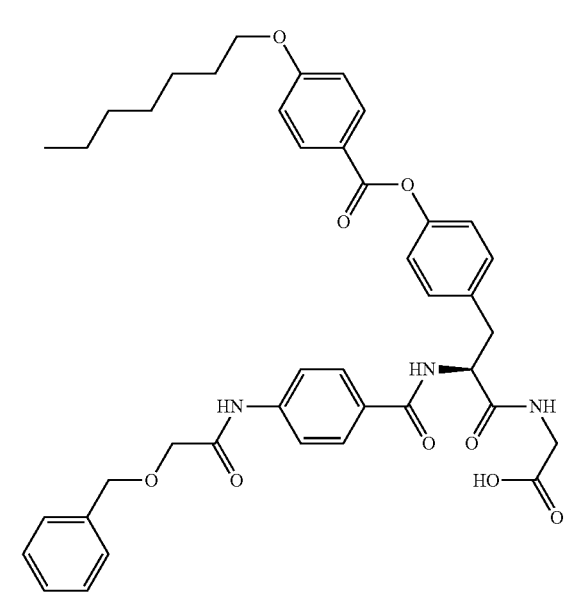 [SMILES: CCCCCCCOc1ccc(C(=O)Oc2ccc(C[C@H](NC(=O)c3ccc(NC(=O)COCc4ccccc4)cc3)C(=O)NCC(=O)O)cc2)cc1] | 310 | 9.14 | 5 |

TABLE 1-continued
| STRUCTURE | COMPOUND NUMBER | LCMS RETENTION TIME (min) | LCMS method |
|---|---|---|---|
| 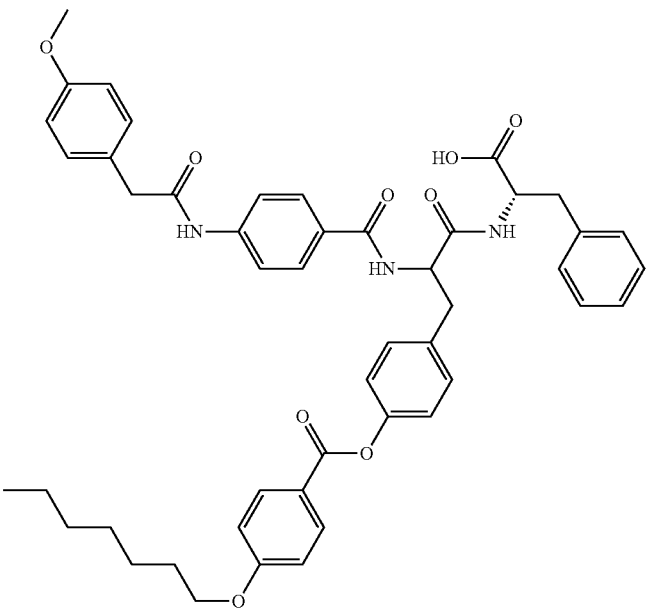 [SMILES: CCCCCCCOc1ccc(C(=O)Oc2ccc(CC(NC(=O)c3ccc(NC(=O)Cc4ccc(OC)cc4)cc3)C(=O)N[C@@H](Cc3ccccc3)C(=O)O)cc2)cc1] | 311 | 9.86 | 5 |
| 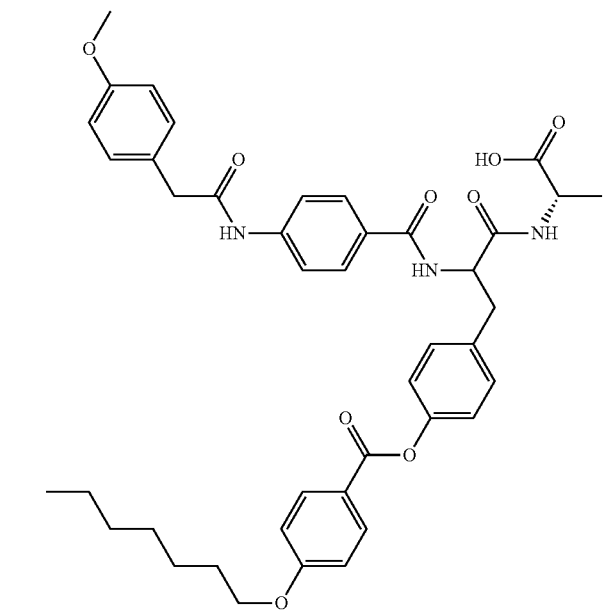 [SMILES: CCCCCCCOc1ccc(C(=O)Oc2ccc(CC(NC(=O)c3ccc(NC(=O)Cc4ccc(OC)cc4)cc3)C(=O)N[C@@H](C)C(=O)O)cc2)cc1] | 312 | 9.16 | 5 |

TABLE 1-continued

| STRUCTURE | COMPOUND NUMBER | LCMS RETENTION TIME (min) | LCMS method |
|---|---|---|---|
| 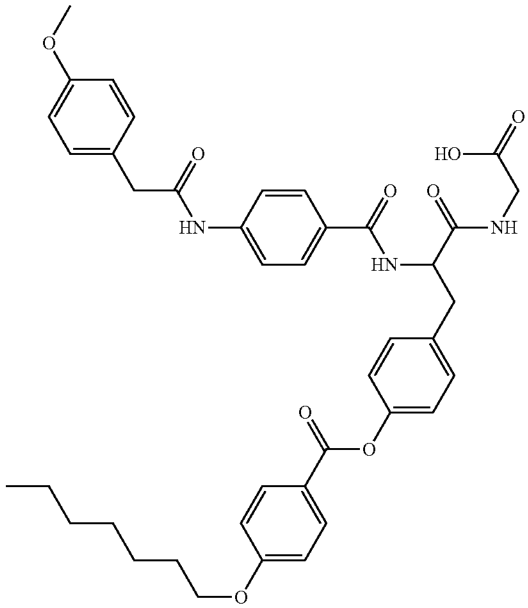 [SMILES: CCCCCCCOc1ccc(C(=O)Oc2ccc(CC(NC(=O)c3ccc(NC(=O)Cc4ccc(OC)cc4)cc3)C(=O)NCC(=O)O)cc2)cc1] | 313 | 9.05 | 5 |
| 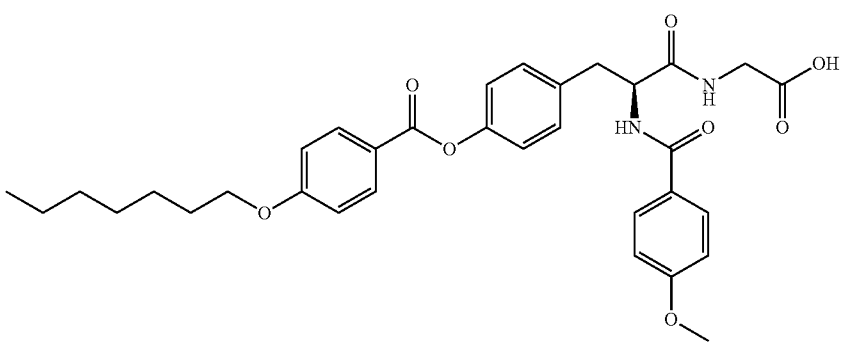 [SMILES: CCCCCCCOc1ccc(C(=O)Oc2ccc(C[C@H](NC(=O)c3ccc(OC)cc3)C(=O)NCC(=O)O)cc2)cc1] | 314 | 8.86 | 5 |
| 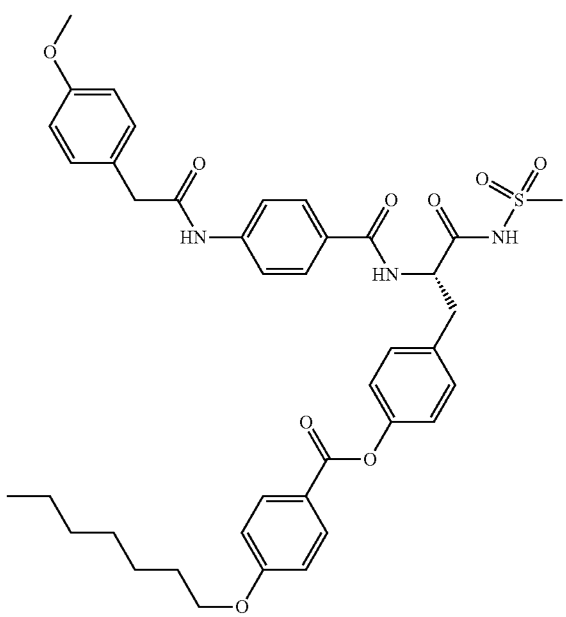 [SMILES: CCCCCCCOc1ccc(C(=O)Oc2ccc(C[C@H](NC(=O)c3ccc(NC(=O)Cc4ccc(OC)cc4)cc3)C(=O)NS(C)(=O)=O)cc2)cc1] | 315 | 9.74 | 5 |

TABLE 1-continued
| STRUCTURE | COMPOUND NUMBER | LCMS RETENTION TIME (min) | LCMS method |
|---|---|---|---|
| 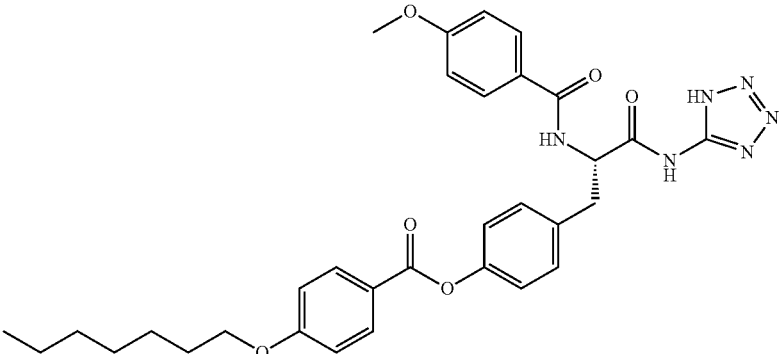 | 316 | 9.10 | 7 |
| 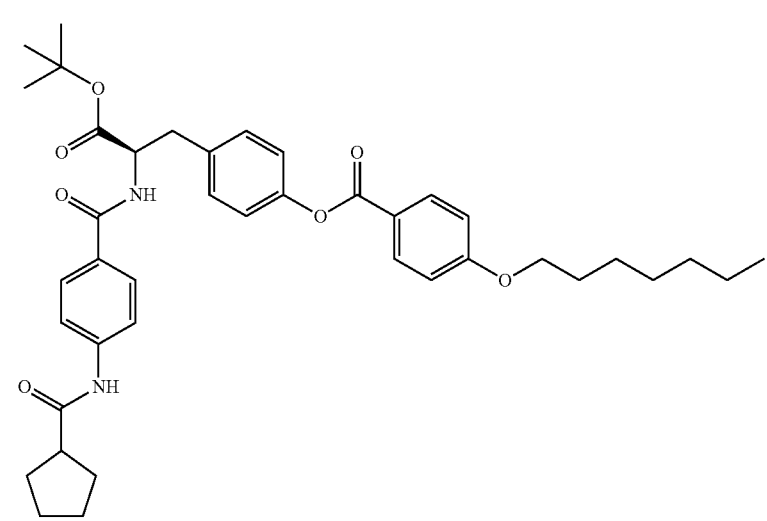 [SMILES: CCCCCCCOc1ccc(C(=O)Oc2ccc(C[C@@H](NC(=O)c3ccc(NC(=O)C4CCCC4)cc3)C(=O)OC(C)(C)C)cc2)cc1] | 317 | 3.31 | 5 |
| 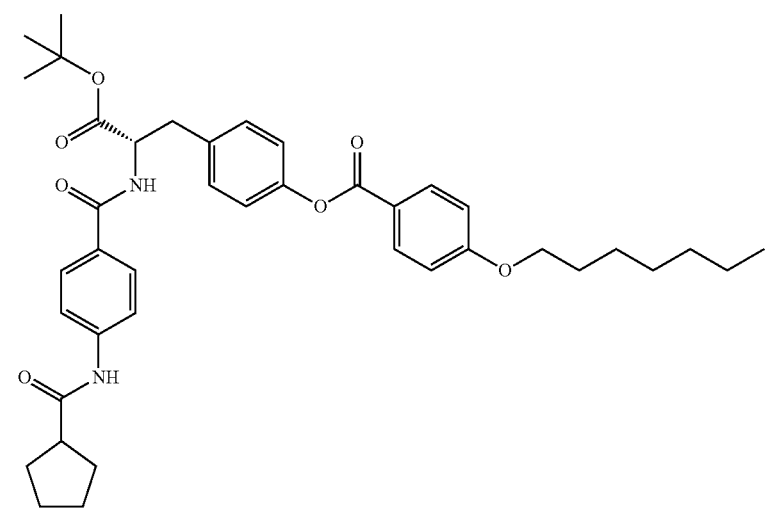 [SMILES: CCCCCCCOc1ccc(C(=O)Oc2ccc(C[C@H](NC(=O)c3ccc(NC(=O)C4CCCC4)cc3)C(=O)OC(C)(C)C)cc2)cc1] | 318 | 3.32 | 5 |

TABLE 1-continued

| STRUCTURE | COMPOUND NUMBER | LCMS RETENTION TIME (min) | LCMS method |
|---|---|---|---|
| 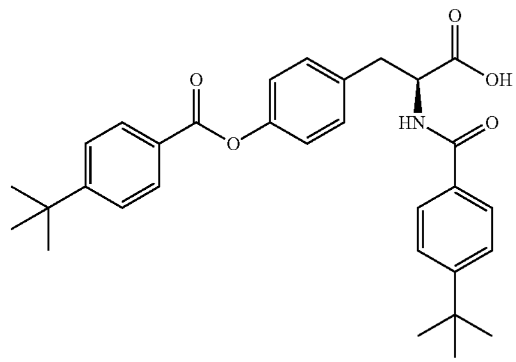 [SMILES: CC(C)(C)c1ccc(C(=O)N[C@@H](Cc2ccc(OC(=O)c3ccc(C(C)(C)C)cc3)cc2)C(=O)O)cc1] | 319 | 10.93 | 2 |
| 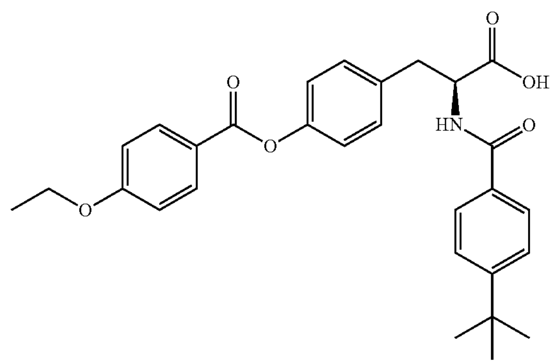 [SMILES: CCOc1ccc(C(=O)Oc2ccc(C[C@H](NC(=O)c3ccc(C(C)(C)C)cc3)C(=O)O)cc2)cc1] | 320 | 9.88 | 2 |
| 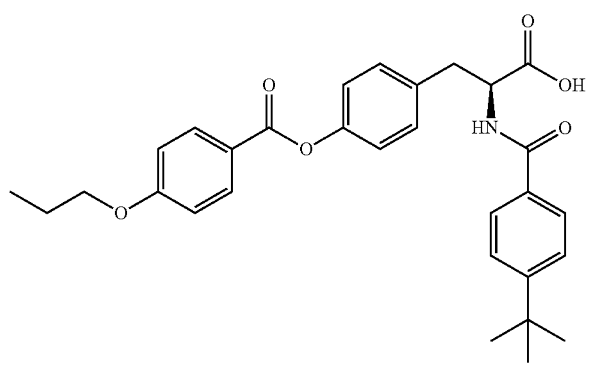 [SMILES: CCCOc1ccc(C(=O)Oc2ccc(C[C@H](NC(=O)c3ccc(C(C)(C)C)cc3)C(=O)O)cc2)cc1] | 321 | 10.42 | 2 |
| 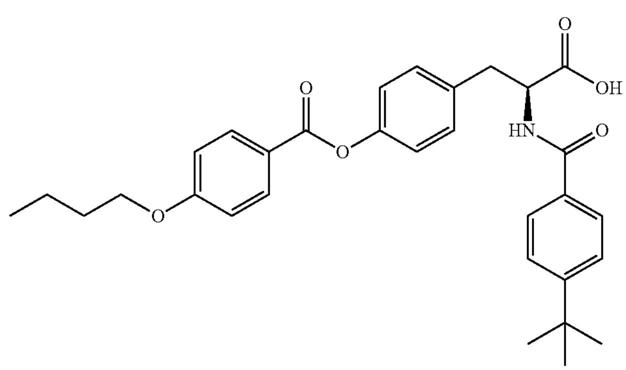 [SMILES: CCCCOc1ccc(C(=O)Oc2ccc(C[C@H](NC(=O)c3ccc(C(C)(C)C)cc3)C(=O)O)cc2)cc1] | 322 | 10.72 | 2 |

TABLE 1-continued

| STRUCTURE | COMPOUND NUMBER | LCMS RETENTION TIME (min) | LCMS method |
|---|---|---|---|
| 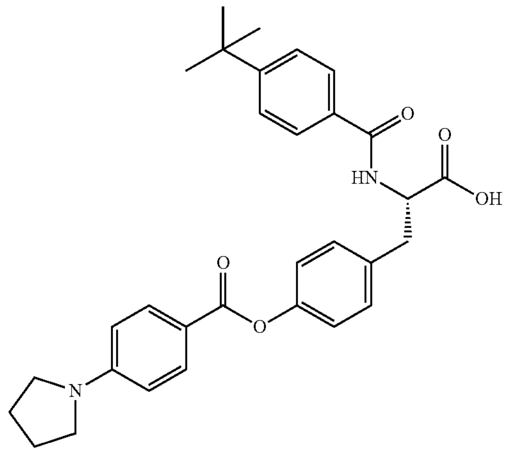 [SMILES: CC(C)(C)c1ccc(C(=O)N[C@@H](Cc2ccc(OC(=O)c3ccc(N4CCCC4)cc3)cc2)C(=O)O)cc1] | 323 | 8.45 | |
| 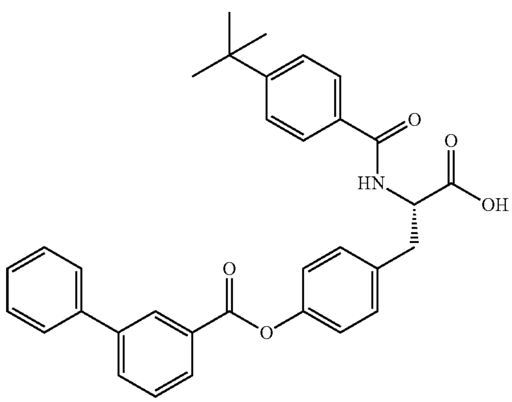 [SMILES: CC(C)(C)c1ccc(C(=O)N[C@@H](Cc2ccc(OC(=O)c3cccc(-c4ccccc4)c3)cc2)C(=O)O)cc1] | 324 | 8.83 | |
| 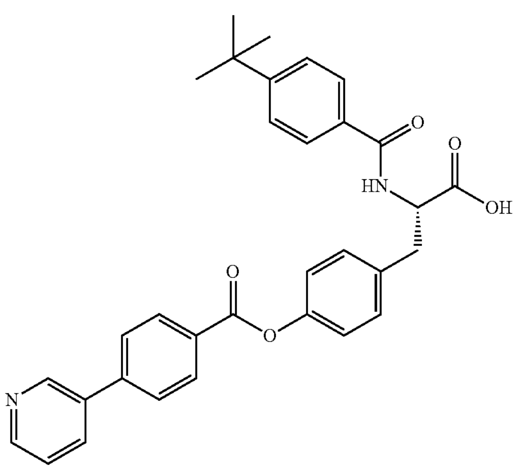 [SMILES: CC(C)(C)c1ccc(C(=O)N[C@@H](Cc2ccc(OC(=O)c3ccc(-c4cccnc4)cc3)cc2)C(=O)O)cc1] | 325 | 6.01 | |

TABLE 1-continued

| STRUCTURE | COMPOUND NUMBER | LCMS RETENTION TIME (min) | LCMS method |
|---|---|---|---|
| 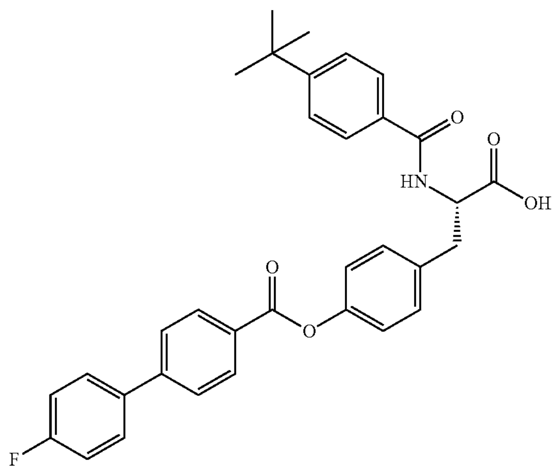 [SMILES: CC(C)(C)c1ccc(C(=O)N[C@@H](Cc2ccc(OC(=O)c3ccc(-c4ccc(F)cc4)cc3)cc2)C(=O)O)cc1] | 326 | 8.87 | |
| 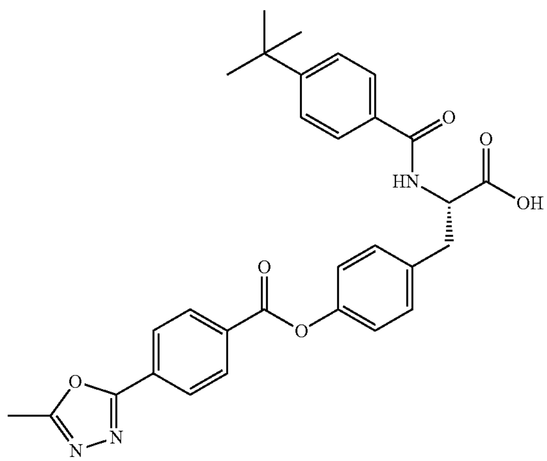 [SMILES: Cc1nnc(-c2ccc(C(=O)Oc3ccc(C[C@H](NC(=O)c4ccc(C(C)(C)C)cc4)C(=O)O)cc3)cc2)o1] | 327 | 6.44 | |
| 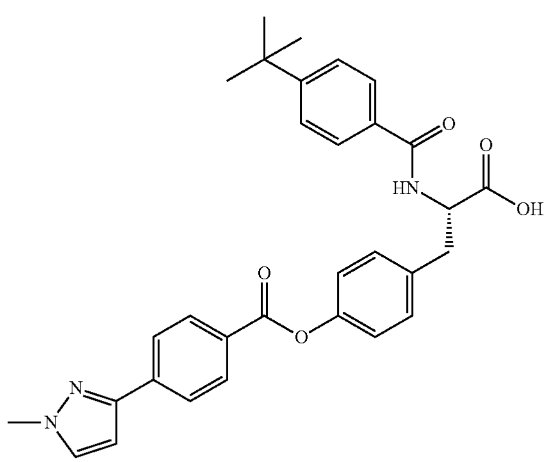 [SMILES: Cn1ccc(-c2ccc(C(=O)Oc3ccc(C[C@H](NC(=O)c4ccc(C(C)(C)C)cc4)C(=O)O)cc3)cc2)n1] | 328 | 7 | |

TABLE 1-continued

| STRUCTURE | COMPOUND NUMBER | LCMS RETENTION TIME (min) | LCMS method |
|---|---|---|---|
| 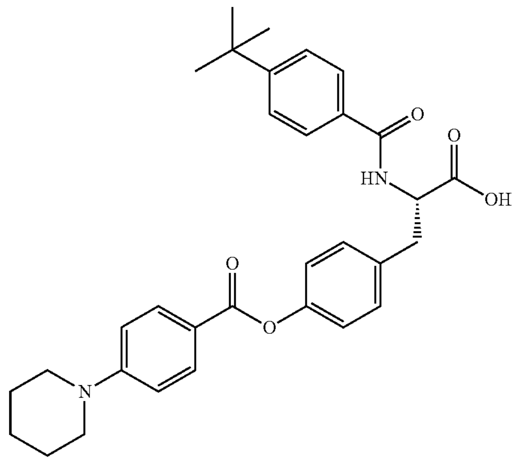 [SMILES: CC(C)(C)c1ccc(C(=O)N[C@@H](Cc2ccc(OC(=O)c3ccc(N4CCCCC4)cc3)cc2)C(=O)O)cc1] | 329 | 8.75 | |
| 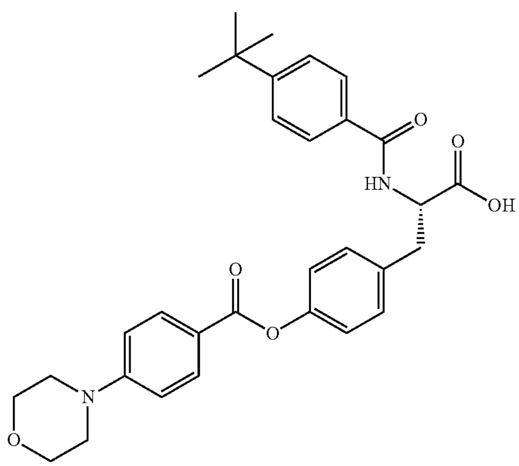 [SMILES: CC(C)(C)c1ccc(C(=O)N[C@@H](Cc2ccc(OC(=O)c3ccc(N4CCOCC4)cc3)cc2)C(=O)O)cc1] | 330 | 7.02 | |
| 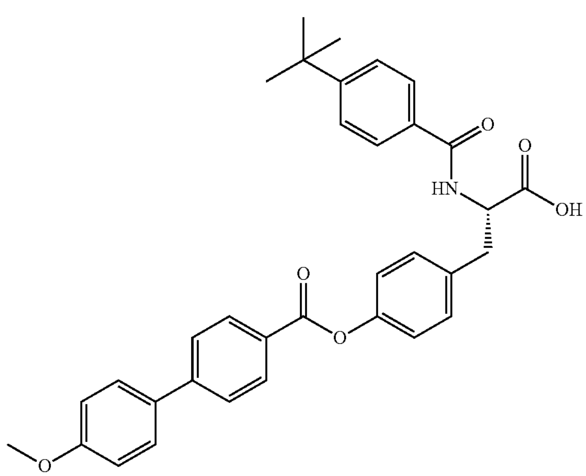 [SMILES: COc1ccc(-c2ccc(C(=O)Oc3ccc(C[C@H](NC(=O)c4ccc(C(C)(C)C)cc4)C(=O)O)cc3)cc2)cc1] | 331 | 8.88 | |

TABLE 1-continued

| STRUCTURE | COMPOUND NUMBER | LCMS RETENTION TIME (min) | LCMS method |
|---|---|---|---|
| 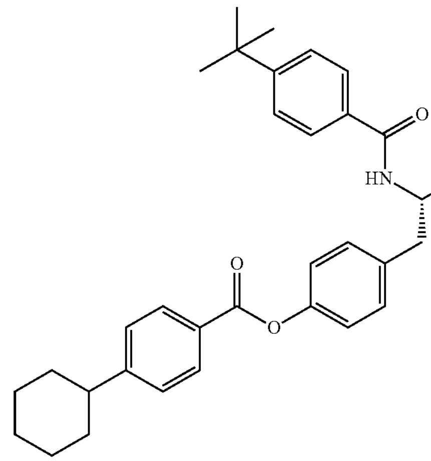 | 332 | 10.16 | |
| 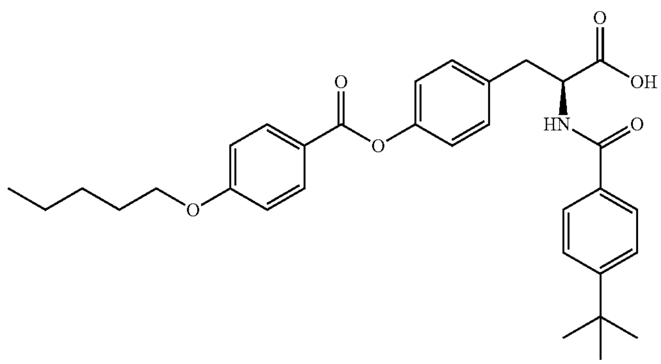 [SMILES: CCCCCOc1ccc(C(=O)Oc2ccc(C[C@H](NC(=O)c3ccc(C(C)(C)C)cc3)C(=O)O)cc2)cc1] | 333 | 11.25 | 2 |
| 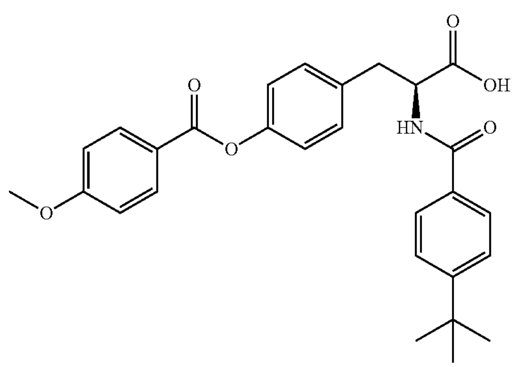 [SMILES: COc1ccc(C(=O)Oc2ccc(C[C@H](NC(=O)c3ccc(C(C)(C)C)cc3)C(=O)O)cc2)cc1] | 334 | 9.37 | 2 |

Biological Assays

Assay Procedures

GLP-1 PAM shift assays: dosing peptides RP-101868 and GLP-1 (9-36) in presence of fixed compound concentration—direct cAMP response A GLP-1R expressing CRE-bla CHO-K1 cell line was purchased from Invitrogen. Cells were seeded into 384-well white flat bottom plates at 5000 cells/well/20 μL culture media (DMEM-High glucose, 10% dialyzed FBS, 0.1 mM NEAA, 25 mM Hepes, 100 U/mL penicillin/100 μg/mL streptomycin, 5 μg/mL Blasticidin, 600 μg/mL Hygromycin) and incubated for 18 h at 37° C. in 5% $CO_2$. Peptide dose response curves (12-point) were generated in assay buffer (Hanks Balanced Salt solution, 10 mM Hepes, 0.1% BSA, pH7.4) in the presence of 1.5 mM IBMX, 12.5% DMSO, and 50 μM compound. Cells were washed 1× with assay buffer prior to adding 3 μL of PAM dose response curve to 12 μL assay buffer and incubated for 30 min at 37° C. Direct detection of cAMP was carried out using DiscoveRx HitHunter cAMP kit according to manufacturer's instructions and luminescence was read using a SpectraMax M5 plate reader. The luminescence signal was analyzed by non-linear regression to determine the $EC_{50}$ values for cAMP dose response curves and values were compared to peptide curves without compound.

GLP-1 PAM $EC_{20}$ Assay: Dosing Compound in the Presence of Fixed GLP-1 (9-36)-Direct cAMP Response GLP-1R CRE-bla CHO-K1 cells were seeded into 384-well white flat bottom plates at 10,000 cells/well/20 µL culture media (same culture media used for PAM shift assay) and incubated for 18 h at 37° C. in 5% $CO_2$. Compound dose response curves (12-point) and a separate 30×$EC_{20}$ GLP-1 (9-36) stock solution were generated in assay buffer (same assay buffer used for PAM shift assay) in presence of 1.5 mM IBMX and 12.5% DMSO. Cells were washed 1× with assay buffer prior to adding 3 µL of compound dose response curve and 0.5 µL $EC_{20}$ GLP-1 (9-36) to 12 µL assay buffer and incubated for 30 min at 37° C. Direct detection of cAMP was carried out using DiscoveRx HitHunter cAMP kit according to manufacturer's instructions (substituting 5 µL Antibody portion with 2 µL) and luminescence was read using a SpectraMax M5 plate reader. Luminescence signal was converted to total cAMP using a cAMP standard curve and data was analyzed by non-linear regression to determine the $EC_{50}$ values for cAMP dose response curves.

Peptide Sequences

```
                                            (SEQ ID NO: 1)
GLP-1 (7-36): HAEGTFTSDVSSYLEGQAAKEFIAWLVKGR-NH2

(SEQ ID NO: 2)
GLP-1 (9-36): EGTFTSDVSSYLEGQAAKEFIAWLVKGR-NH2

(SEQ ID NO: 3)
RP-101868: GEGTFTS-Nle-LSKQMEEEAVRLFIEWLKNGR-NH2
```

GLP-1 (7-36) was purchased from GenScript.

GLP-1 (9-36) and RP-101868 (Ex_RPG-14) were purchased from Biopeptide Co., Inc.

Reported GLP-1 Activity

Activity data for selected GLP-1 modulators is displayed in Table 2. The GLP-1 (9-36) PAM activity range is denoted as follows: + denotes activity <10 nM. ++ denotes activity between 10 to 100 nM, and +++ denotes activity between 100-1000 nM, and ++++ denotes activity >1000 nM. The GLP-1 (RP-101868) PAM activity range is denoted as follows: + denotes activity <0.1 nM. ++ denotes activity between 0.1 to 1 nM, and +++ denotes activity between 1-10 nM, and ++++ denotes activity >10 nM. N/A denotes not available.

TABLE 2

| COMPOUND NUMBER | GLP-1 (9-36) PAM ACTIVITY | GLP-1 (RP-101868) PAM ACTIVITY |
|---|---|---|
| 1 | N/A | +++ |
| 2 | +++ | ++ |
| 3 | +++ | ++ |
| 4 | ++++ | ++ |
| 5 | N/A | +++ |
| 6 | N/A | +++ |
| 7 | N/A | +++ |
| 8 | N/A | +++ |
| 9 | N/A | +++ |
| 10 | N/A | +++ |
| 11 | ++++ | N/A |
| 12 | ++++ | N/A |
| 13 | ++++ | N/A |
| 14 | +++ | N/A |
| 15 | +++ | N/A |
| 16 | ++++ | N/A |
| 17 | ++++ | N/A |
| 18 | +++ | N/A |
| 19 | ++++ | N/A |
| 20 | +++ | N/A |
| 21 | ++++ | N/A |
| 22 | +++ | N/A |
| 23 | ++++ | N/A |
| 24 | +++ | N/A |
| 25 | ++++ | N/A |
| 26 | +++ | N/A |
| 27 | ++++ | N/A |
| 28 | ++ | N/A |
| 29 | ++++ | N/A |
| 30 | ++++ | N/A |
| 31 | ++++ | N/A |
| 32 | +++ | N/A |
| 33 | ++++ | N/A |
| 34 | ++++ | N/A |
| 35 | ++++ | N/A |
| 36 | +++ | N/A |
| 37 | ++++ | N/A |
| 38 | +++ | N/A |
| 39 | ++++ | N/A |
| 40 | ++++ | N/A |
| 41 | ++++ | N/A |
| 42 | +++ | N/A |
| 43 | ++++ | N/A |
| 44 | +++ | N/A |
| 45 | +++ | N/A |
| 46 | ++++ | N/A |
| 47 | +++ | N/A |
| 48 | +++ | N/A |
| 49 | ++++ | N/A |
| 50 | ++++ | N/A |
| 51 | ++++ | N/A |
| 52 | ++++ | N/A |
| 53 | +++ | N/A |
| 54 | +++ | N/A |
| 55 | ++++ | N/A |
| 56 | +++ | N/A |
| 57 | + | N/A |
| 58 | +++ | N/A |
| 59 | +++ | N/A |
| 60 | ++++ | N/A |
| 61 | +++ | N/A |
| 62 | +++ | +++ |
| 63 | +++ | +++ |
| 64 | +++ | +++ |
| 65 | N/A | +++ |
| 66 | N/A | +++ |
| 67 | +++ | +++ |
| 68 | ++++ | +++ |
| 69 | N/A | +++ |
| 70 | ++++ | +++ |
| 71 | ++++ | +++ |
| 72 | N/A | +++ |
| 73 | +++ | +++ |
| 74 | N/A | +++ |
| 75 | N/A | +++ |
| 76 | N/A | +++ |
| 77 | N/A | +++ |
| 78 | ++++ | +++ |
| 79 | N/A | +++ |
| 80 | +++ | +++ |
| 81 | N/A | +++ |
| 82 | ++++ | +++ |
| 83 | N/A | +++ |
| 84 | N/A | +++ |
| 85 | ++++ | +++ |
| 86 | N/A | +++ |
| 87 | +++ | +++ |
| 88 | N/A | +++ |
| 89 | N/A | +++ |
| 90 | N/A | +++ |
| 91 | N/A | +++ |
| 92 | N/A | +++ |
| 93 | N/A | +++ |
| 94 | ++++ | +++ |
| 95 | N/A | +++ |
| 96 | N/A | +++ |
| 97 | +++ | +++ |

TABLE 2-continued

| COMPOUND NUMBER | GLP-1 (9-36) PAM ACTIVITY | GLP-1 (RP-101868) PAM ACTIVITY |
|---|---|---|
| 98 | +++ | +++ |
| 99 | N/A | +++ |
| 100 | N/A | +++ |
| 101 | N/A | +++ |
| 102 | N/A | +++ |
| 103 | ++ | ++ |
| 104 | ++++ | +++ |
| 105 | N/A | +++ |
| 106 | N/A | +++ |
| 107 | N/A | +++ |
| 108 | N/A | +++ |
| 109 | N/A | +++ |
| 110 | +++ | ++ |
| 111 | N/A | +++ |
| 112 | N/A | ++++ |
| 113 | N/A | +++ |
| 114 | N/A | +++ |
| 115 | ++++ | +++ |
| 116 | N/A | +++ |
| 117 | ++++ | +++ |
| 118 | N/A | +++ |
| 119 | N/A | +++ |
| 120 | +++ | ++ |
| 121 | N/A | +++ |
| 122 | ++ | ++ |
| 123 | +++ | ++ |
| 124 | +++ | ++ |
| 125 | N/A | +++ |
| 126 | ++ | ++ |
| 127 | N/A | +++ |
| 128 | +++ | +++ |
| 129 | ++++ | +++ |
| 130 | +++ | ++ |
| 131 | ++++ | +++ |
| 132 | N/A | +++ |
| 133 | N/A | +++ |
| 134 | N/A | +++ |
| 135 | +++ | ++ |
| 136 | ++++ | ++ |
| 137 | N/A | +++ |
| 138 | N/A | +++ |
| 139 | N/A | +++ |
| 140 | N/A | +++ |
| 141 | N/A | +++ |
| 142 | N/A | +++ |
| 143 | ++++ | ++ |
| 144 | ++++ | +++ |
| 145 | N/A | +++ |
| 146 | ++++ | ++ |
| 147 | ++++ | ++ |
| 148 | ++++ | +++ |
| 149 | N/A | +++ |
| 150 | ++++ | ++ |
| 151 | N/A | +++ |
| 152 | N/A | +++ |
| 153 | ++++ | +++ |
| 154 | ++++ | +++ |
| 155 | ++++ | +++ |
| 156 | ++++ | +++ |
| 157 | N/A | +++ |
| 158 | N/A | +++ |
| 159 | N/A | +++ |
| 160 | N/A | +++ |
| 161 | N/A | +++ |
| 162 | N/A | +++ |
| 163 | N/A | +++ |
| 164 | N/A | +++ |
| 165 | ++++ | +++ |
| 166 | ++++ | +++ |
| 167 | +++ | +++ |
| 168 | +++ | +++ |
| 169 | N/A | +++ |
| 170 | N/A | +++ |
| 171 | N/A | +++ |
| 172 | ++++ | +++ |
| 173 | N/A | +++ |
| 174 | N/A | +++ |
| 175 | N/A | +++ |
| 176 | ++++ | ++ |
| 177 | ++++ | +++ |
| 178 | +++ | ++ |
| 179 | ++ | ++ |
| 180 | +++ | +++ |
| 181 | +++ | +++ |
| 182 | +++ | +++ |
| 183 | +++ | +++ |
| 184 | ++++ | N/A |
| 185 | +++ | N/A |
| 186 | ++++ | N/A |
| 187 | +++ | N/A |
| 188 | +++ | N/A |
| 189 | +++ | N/A |
| 190 | +++ | N/A |
| 191 | ++++ | N/A |
| 192 | ++++ | N/A |
| 193 | ++++ | N/A |
| 194 | ++++ | N/A |
| 195 | ++++ | N/A |
| 196 | ++++ | N/A |
| 197 | +++ | N/A |
| 198 | +++ | N/A |
| 199 | +++ | N/A |
| 200 | +++ | N/A |
| 201 | +++ | N/A |
| 202 | +++ | N/A |
| 203 | +++ | N/A |
| 204 | +++ | N/A |
| 205 | +++ | N/A |
| 206 | +++ | N/A |
| 207 | +++ | N/A |
| 208 | ++++ | N/A |
| 209 | +++ | N/A |
| 210 | +++ | N/A |
| 211 | +++ | N/A |
| 212 | ++++ | N/A |
| 213 | +++ | N/A |
| 214 | ++++ | N/A |
| 215 | +++ | N/A |
| 216 | +++ | N/A |
| 217 | +++ | N/A |
| 218 | +++ | N/A |
| 219 | +++ | N/A |
| 220 | +++ | N/A |
| 221 | ++++ | N/A |
| 222 | +++ | N/A |
| 223 | +++ | N/A |
| 224 | +++ | N/A |
| 225 | +++ | N/A |
| 226 | +++ | N/A |
| 227 | +++ | N/A |
| 228 | +++ | N/A |
| 229 | +++ | N/A |
| 230 | +++ | N/A |
| 231 | ++++ | N/A |
| 232 | ++++ | N/A |
| 233 | +++ | N/A |
| 234 | +++ | N/A |
| 235 | +++ | N/A |
| 236 | +++ | N/A |
| 237 | ++++ | N/A |
| 238 | +++ | N/A |
| 239 | +++ | N/A |
| 240 | +++ | N/A |
| 241 | +++ | N/A |
| 242 | +++ | N/A |
| 243 | +++ | N/A |
| 244 | ++++ | N/A |
| 245 | ++++ | N/A |
| 246 | +++ | N/A |
| 247 | +++ | N/A |
| 248 | ++++ | N/A |
| 249 | ++++ | N/A |

TABLE 2-continued

| COMPOUND NUMBER | GLP-1 (9-36) PAM ACTIVITY | GLP-1 (RP-101868) PAM ACTIVITY |
|---|---|---|
| 250 | +++ | N/A |
| 251 | +++ | N/A |
| 252 | +++ | N/A |
| 253 | +++ | N/A |
| 254 | +++ | N/A |
| 255 | ++++ | N/A |
| 256 | +++ | N/A |
| 257 | ++++ | N/A |
| 258 | ++++ | N/A |
| 259 | ++++ | N/A |
| 260 | ++++ | N/A |
| 261 | ++++ | N/A |
| 262 | ++++ | N/A |
| 263 | ++ | +++ |
| 264 | +++ | +++ |
| 265 | N/A | +++ |
| 266 | ++++ | N/A |
| 267 | ++++ | N/A |
| 268 | ++++ | N/A |
| 269 | ++++ | N/A |
| 270 | ++++ | N/A |
| 271 | ++++ | N/A |
| 272 | ++++ | N/A |
| 273 | +++ | +++ |
| 274 | ++++ | N/A |
| 275 | ++++ | N/A |
| 276 | +++ | ++ |
| 277 | +++ | ++ |
| 278 | +++ | +++ |
| 279 | +++ | +++ |
| 280 | ++++ | +++ |
| 281 | ++++ | +++ |
| 282 | ++++ | N/A |
| 283 | ++++ | N/A |
| 284 | +++ | N/A |
| 285 | +++ | N/A |
| 286 | N/A | +++ |
| 287 | ++++ | +++ |
| 288 | ++++ | +++ |
| 289 | N/A | +++ |
| 290 | ++++ | +++ |
| 291 | ++++ | N/A |
| 292 | ++++ | +++ |
| 293 | ++++ | +++ |
| 294 | +++ | +++ |
| 295 | ++++ | ++++ |
| 296 | ++++ | N/A |
| 297 | ++++ | N/A |
| 298 | ++++ | +++ |
| 299 | +++ | +++ |
| 300 | +++ | N/A |
| 301 | ++++ | N/A |
| 302 | ++++ | N/A |
| 303 | N/A | +++ |
| 304 | N/A | +++ |
| 305 | N/A | +++ |
| 306 | +++ | +++ |
| 307 | +++ | +++ |
| 308 | +++ | ++ |
| 309 | +++ | ++ |
| 310 | ++ | ++ |
| 311 | N/A | ++++ |
| 312 | +++ | +++ |
| 313 | +++ | +++ |
| 314 | +++ | N/A |
| 315 | +++ | +++ |
| 316 | +++ | N/A |
| 317 | N/A | +++ |
| 318 | N/A | +++ |
| 319 | +++ | N/A |
| 320 | +++ | N/A |
| 321 | +++ | N/A |
| 322 | ++ | N/A |
| 323 | ++ | N/A |
| 324 | +++ | N/A |
| 325 | +++ | N/A |
| 326 | ++ | N/A |
| 327 | +++ | N/A |
| 328 | +++ | N/A |
| 329 | ++ | N/A |
| 330 | +++ | N/A |
| 331 | ++ | N/A |
| 332 | ++ | N/A |
| 333 | ++ | N/A |
| 334 | +++ | N/A |

Stabilization Assays

Assay Procedures

Generation of GLP-1R Protein Used in the Stability Induction Assay

A synthetic gene for a modified GLP-1R enhanced for expression in insect cells was created using overlap extension PCR to encode the amino acid sequence containing a signal peptide, N-terminal Flag (Sigma) epitope tag, mGLP-1R, GFP and a 10× histidine tag.

This gene product was cloned into the insect cell transfer vector, pFastBac1 (Invitrogen) for transposition into the baculovirus DNA hosted in the DH10Bac strain $E.$ $coli.$ The transposition event resulted in recombination of the GLP-1R gene into the baculovirus genome, the resulting virus was then isolated from the $E.$ $coli$ cells and used to infect a culture of Sf9 cells for viral amplification. High titer viral stock of the recombinant GLP-1R baculovirus was recovered and used to infect a healthy population of SF9 insect cells for expression under the control of the $^{ie1}$GP64 baculovirus promoter (EMD biosciences).

Recombinant protein was isolated from the membranes of the insect cells by extraction using 1% β-dodecylmaltopyranoside followed by purification using immobilized metal affinity chromatography resin and standard protocols After elution the protein was analyzed by analytical size exclusion chromatography to determine its retention time relative to an unliganded receptor.

Size Exclusion Chromatography Peak Shift Assay—Characterization of Stability Induction for Compounds The protein's hydrodynamic radius was analyzed on an analytical size exclusion chromatography column (Sepax Zenix SEC-300 250 mm×4.6 mm column) equilibrated with 20 mM Hepes pH 7.5, 500 mM NaCl, 2% v/v glycerol, 0.05% w/v DDM and 0.01% w/v CHS and attached to a Dionex Ultimate HPLC which continuously pumped running buffer at a flow rate of 0.5 mL/min. The HPLC was equipped with an ultraviolet absorption and a fluorescence detector which enabled detection of total protein absorbance and GFP fluorescent emission respectively. The peak profiles of the GLP-1R in the presence of multiple compounds could be determined from impure mixtures using fluorescence detection.

Each tested compound was assayed for its ability to alter the hydrodynamic radius. This change can manifest as either a positive or negative shift in retention time in the peak shift assay. A positive shift represents a decrease in apparent molecular weight of the complex, while a negative shift represents an increase in size. Compounds that result in a negative shift in retention time (i.e. increased size) may do so by destabilizing the receptor or by causing non-specific aggregation. Compounds that result in a positive shift in retention time (i.e. decreased size) may do so either by stabilizing the receptor in a more compact conformation or by disrupting the oligomeric state (e.g. Dimer->monomer transition).

For this assay we reported the relative shift in retention time of each compound with respect to the apo protein (without ligand) and a positive control. The results were normalized on a scale from 0 to 5 if they displayed a positive shift or −5 to 0 if they displayed a negative shift.

Reported Stability Induction of Compounds on the GLP-1R

Stability induction data for selected GLP-1R compounds are displayed in Table 3. The values all correspond to an effect on dimer stability and range from −1.1 to 1. This data can be used to select compounds that retain binding to the receptor with either a positive or negative effect on the hydrodynamic radius.

TABLE 3

| COMPOUND NUMBER | PEAK SHIFT ASSAY |
| --- | --- |
| 266 | 0.88 |
| 267 | 0.25 |
| 268 | 0.46 |
| 269 | 0.34 |
| 270 | 0 |
| 271 | 0.52 |
| 272 | −1.15 |

TABLE 3-continued

| COMPOUND NUMBER | PEAK SHIFT ASSAY |
| --- | --- |
| 273 | 0.69 |
| 274 | 0.83 |
| 275 | 0 |

Activity data for selected GLP-1 modulators is displayed in Table 4.

TABLE 4

| COMPOUND NUMBER | GLP-1 (9-36) PAM $EC_{50}$ (nM) | GLP-1 (9-36) PAM % Efficacy | $EC_{20}$ GLP-1 (9-36) PAM $EC_{50}$ (μM) | $EC_{20}$ GLP-1 (9-36) PAM max cAMP (nM) |
| --- | --- | --- | --- | --- |
| 2 | 196 | 48 | >20 | 189 |
| 57 | 9.9 | 98 | 3.67 | 237 |
| 63 | 165 | 56 | >10 | 72 |
| 103 | 43.1 | 70 | 5.49 | 204 |
| 120 | 123 | 67 | 4.05 | 174 |
| 178 | 208 | 77 | 6.31 | 98 |
| 179 | 75 | 76 | 4.84 | 160 |
| 263 | 65.4 | 80 | 2.78 | 216 |
| 273 | 493 | 16 | >10 | 27 |

We claim:

1. A method of activation or agonism of a glucagon-like peptide 1 (GLP-1) receptor comprising contacting the receptor with an effective amount of a compound having the structure of Formula I-R or I-S or a pharmaceutically acceptable isomer, enantiomer, racemate, or salt thereof:

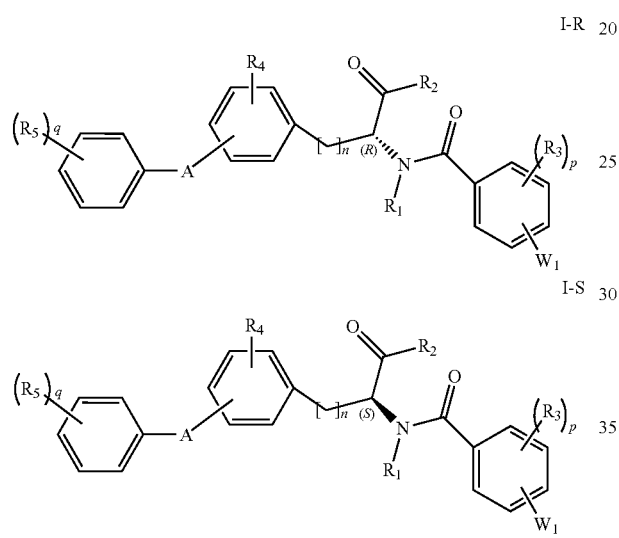

wherein
- each $R_1$ is independently H or $C_{1-4}$ alkyl;
- $R_2$ is $-N(R_1)-SO_2-R_8$, $-N(R_1)-(CR_aR_b)_m-COOH$, or $-N(R_1)$-tetrazolyl;
- each $R_3$ and $R_4$ is independently H, alkyl, alkoxy, halo, $-NO_2$, $-CN$, perhaloalkyl, perhaloalkoxy, haloalkyl, alkyl substituted with $R_{31}$, $-OR_{40}$, $-NR_{41}R_{42}$;
- each $R_{40}$ is independently H or alkyl;
- each $R_{41}$ and $R_{42}$ is independently H or alkyl, $-(CH_2)-COO-R_{40}$, $-C(O)-R_{40}$, aryl, heteroaryl, or two taken together with the N atom to which they are attached can form a 3- to 7-membered heterocyclic ring;
- each $R_{31}$ is independently H, halo, hydroxyl, $-NR_{41}R_{42}$, or alkoxy;
- each A is independently, from the proximal to distal end of the structure of Formula I-R or I-S, $-(O)-$, $-OC(O)-$, $-NR_1-$, $-NR_1-CH_2-$, $-C(O)NR_1-$, $-N(R_1)-C(O)-$, or $-N(R_1)-S(O_2)-$,
- $W_1$ is null or $-L_1-(CR_aR_b)_m-L_1-R_6$;
- each $L_1$ is independently, from the proximal to distal end of the structure of Formula I-R or I-S, null, A, $-C(O)O-$, $-S(O_2)-$, $-S-$, $-N(R_1)-C(O)-N(R_1)-$, $-N(R_1)-C(O)-O-$, $-C(O)-$ or $-S(O_2)-NR_1-$;
- each $R_a$ and $R_b$ is independently H, alkyl, alkoxy, aralkyl, or two taken together with the carbon to which they are attached form a cycloalkyl;
- $R_6$ is H, alkyl, cycloalkyl, aryl, heteroaryl, heterocyclyl, heterocycloalkyl, any of which may be optionally singly or multiply substituted with $R_7$ or $-(CH_2)_m-L_2-(CH_2)_m-R_7$;
- $R_7$ is H, halo, alkyl, alkoxy, $-OH$, $-CN$, $-S(O)-R_8$, $-S(O)_2-R_8$, $-S(O)_2-NR_1R_8$, $-NR_1-S(O)_2-R_8$, or a ring moiety selected from cycloalkyl, phenyl, aryl, heteroaryl, heterocyclyl, or heterocycloalkyl, where such ring moiety may be optionally singly or multiply substitutued with halo, alkyl, alkoxy, perhaloalkyl, perhaloalkoxy, haloalkyl, hydroxy, cyano, $-S(O)-R_8$, $-S(O)_2-R_8$, $-S(O)_2-NR_1R_8$, or $-NR_1-S(O)_2-R_8$;
- $L_2$ is independently, from the proximal to distal end of the structure of Formula I-R or I-S, null, $-(O)-$, $-OC(O)-$, $-NR_1-$, $-C(O)NR_1-$, $-N(R_1)-C(O)-$, $-S(O_2)-$, $-C(O)-$ or $-S(O_2)-N(R_1)-$;
- $R_5$ is $R_7$, $-(CH_2)_m-L_2-(CH_2)_m-R_7$, or $-(-L_3-(CR_aR_b)_r-)_s-L_3-R_7$.
- each $L_3$ is independently null, $-O-$, or $-N(R_1)-$
- each $R_8$ is independently H, $C_{1-7}$ alkyl, cycloalkyl or aryl;
- each m is independently 0, 1, 2, 3, 4, 5, or 6;
- each n is independently 0 or 1;
- p is 0, 1, 2, or 3;
- q is 0, 1, 2, or 3;
- each r is independently 2, 3, or 4; and
- each s is independently 1, 2, 3, or 4.

2. A method of activation or agonism of a glucagon-like peptide 1 (GLP-1) receptor in a subject in need thereof, said method comprising administering to the subject a compound having the structure of Formula I-R or I-S or a pharmaceutically acceptable isomer, enantiomer, racemate, or salt thereof:

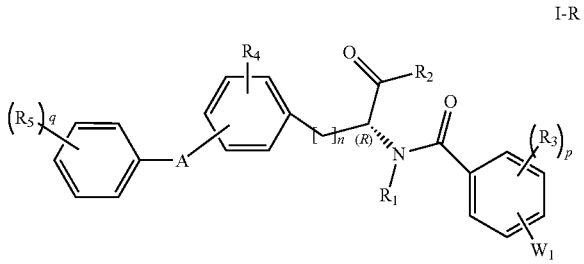

-continued

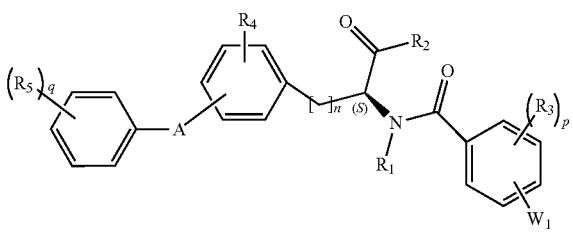

I-S wherein
each $R_1$ is independently H or $C_{1-4}$ alkyl;
$R_2$ is —N($R_1$)—$SO_2$—$R_8$, —N($R_1$)—$(CR_aR_b)_m$—COOH, or —N($R_1$)-tetrazolyl;
each $R_3$ and $R_4$ is independently H, alkyl, alkoxy, halo, —$NO_2$, —CN, perhaloalkyl, perhaloalkoxy, haloalkyl, alkyl substituted with $R_{31}$, —$OR_{40}$, —$NR_{41}R_{42}$;
each $R_{40}$ is independently H or alkyl;
each $R_{41}$ and $R_{42}$ is independently H or alkyl, —$(CH_2)_n$—COO—$R_{40}$, —C(O)—$R_{40}$, aryl, heteroaryl, or two taken together with the N atom to which they are attached can form a 3- to 7-membered heterocyclic ring;
each $R_{31}$ is independently H, halo, hydroxyl, —$NR_{41}R_{42}$, or alkoxy;
each A is independently, from the proximal to distal end of the structure of Formula I-R or I-S, —(O)—, —OC(O)—, —$NR_1$—, —$NR_1$—$CH_2$—, —C(O)$NR_1$—, —N($R_1$)—C(O)—, or —N($R_1$)—S($O_2$)—;
$W_1$ is null or -$L_1$-$(CR_aR_b)_m$-$L_1$-$R_6$;
each $L_1$ is independently, from the proximal to distal end of the structure of Formula I-R or I-S, null, A, —C(O)O—, —S($O_2$)—, —S—, —N($R_1$)—C(O)—N($R_1$)—, —N($R_1$)—C(O)—O—, —C(O)— or —S($O_2$)—$NR_1$—;
each $R_a$ and $R_b$ is independently H, alkyl, alkoxy, aralkyl, or two taken together with the carbon to which they are attached form a cycloalkyl;
$R_6$ is H, alkyl, cycloalkyl, aryl, heteroaryl, heterocyclyl, heterocycloalkyl, any of which may be optionally singly or multiply substituted with $R_7$ or —$(CH_2)_m$-$L_2$-$(CH_2)_m$—$R_7$;
$R_7$ is H, halo, alkyl, alkoxy, —OH, —CN, —S(O)—$R_8$, —S(O)$_2$—$R_8$, —S(O)$_2$—$NR_1R_8$, —$NR_1$—S(O)$_2$—$R_8$, or a ring moiety selected from cycloalkyl, phenyl, aryl, heteroaryl, heterocyclyl, or heterocycloalkyl, where such ring moiety may be optionally singly or multiply substitutued with halo, alkyl, alkoxy, perhaloalkyl, perhaloalkoxy, haloalkyl, hydroxy, cyano, —S(O)—$R_8$, —S(O)$_2$—$R_8$, —S(O)$_2$—$NR_1R_8$, or —$NR_1$—S(O)$_2$—$R_8$;
$L_2$ is independently, from the proximal to distal end of the structure of Formula I-R or I-S, null, —(O)—, —OC(O)—, —$NR_1$—, —C(O)$NR_1$—, —N($R_1$)—C(O)—, —S($O_2$)—, —C(O)— or —S($O_2$)—N($R_1$)—;
$R_5$ is $R_7$, —$(CH_2)_m$-$L_2$-$(CH_2)_m$—$R_7$, or -(-$L_3$-$(CR_aR_b)_r$—$)_s$-$L_3$-$R_7$;
each $L_3$ is independently null, —O—, or —N($R_1$)—
each $R_8$ is independently H, $C_{1-7}$ alkyl, cycloalkyl or aryl;
each m is independently 0, 1, 2, 3, 4, 5, or 6;
each n is independently 0 or 1;
p is 0, 1, 2, or 3;
q is 0, 1, 2, or 3;
each r is independently 2, 3, or 4; and
each s is independently 1, 2, 3, or 4.

3. The method of claim 2 wherein subject is a human being.

4. A method of treatment of a malcondition, selected from the group consisting of type I diabetes, type II diabetes, gestational diabetes, obesity, excessive appetite, insufficient satiety, and metabolic disorder, in a subject for which activation or agonism of a glucagon-like peptide 1 (GLP-1) receptor is medically indicated, comprising administering an effective amount of a compound having the structure of Formula I-R or I-S or a pharmaceutically acceptable isomer, enantiomer, racemate, or salt thereof to the subject at a frequency and for a duration of time sufficient to provide a beneficial effect to the subject:

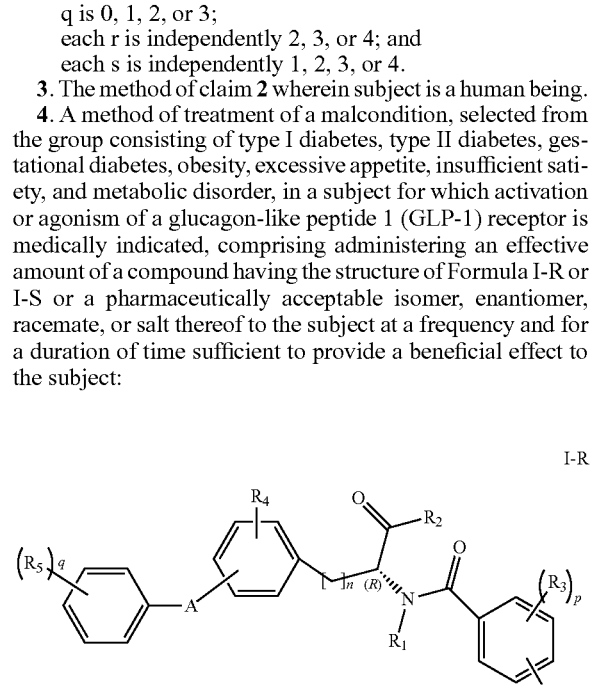

wherein
each $R_1$ is independently H or $C_{1-4}$ alkyl;
$R_2$ is —N($R_1$)—$SO_2$—$R_8$, —N($R_1$)—$(CR_aR_b)_m$—COOH, or —N($R_1$)-tetrazolyl;
each $R_3$ and $R_4$ is independently H, alkyl, alkoxy, halo, —$NO_2$, —CN, perhaloalkyl, perhaloalkoxy, haloalkyl, alkyl substituted with $R_{31}$, —$OR_{40}$, —$NR_{41}R_{42}$;.
each $R_{40}$ is independently H or alkyl;
each $R_{41}$ and $R_{42}$ is independently H or alkyl, —$(CH_2)$—COO—$R_{40}$, —C(O)—$R_{40}$, aryl, heteroaryl, or two taken together with the N atom to which they are attached can form a 3- to 7-membered heterocyclic ring;
each $R_{31}$ is independently H, halo, hydroxyl, —$NR_{41}R_{42}$, or alkoxy;
each A is independently, from the proximal to distal end of the structure of Formula I-R or I-S, —(O)—, —OC(O)—, —$NR_1$—, —$NR_1$—$CH_2$—, —C(O)$NR_1$—, —N($R_1$)—C(O)—, or —N($R_1$)—S($O_2$)—,
$W_1$ is null or -$L_1$-$(CR_aR_b)_m$-$L_1$-$R_6$;
each $L_1$ is independently, from the proximal to distal end of the structure of Formula I-R or I-S, null, A, —C(O)O—, —S($O_2$)—, —S—, —N($R_1$)—C(O)—N($R_1$)—, —N($R_1$)—C(O)—O—, —C(O)— or —S($O_2$)—$NR_1$—;
each $R_a$ and $R_b$ is independently H, alkyl, alkoxy, aralkyl, or two taken together with the carbon to which they are attached form a cycloalkyl;

$R_6$ is H, alkyl, cycloalkyl, aryl, heteroaryl, heterocyclyl, heterocycloalkyl, any of which may be optionally singly or multiply substituted with $R_7$ or —$(CH_2)_m$-$L_2$-$(CH^2)_m$—$R_7$;

$R_7$ is H, halo, alkyl, alkoxy, —OH, —CN, —S(O)—$R_8$, —S(O)$_2$—$R_8$, —S(O)$_2$—NR$_1$R$_8$, —NR$_1$—S(O)$_2$—$R_8$, or a ring moiety selected from cycloalkyl, phenyl, aryl, heteroaryl, heterocyclyl, or heterocycloalkyl, where such ring moiety may be optionally singly or multiply substitutued with halo, alkyl, alkoxy, perhaloalkyl, perhaloalkoxy, haloalkyl, hydroxy, cyano, —S(O)—$R_8$, —S(O)$_2$—$R_8$, —S(O)$_2$—NR$_1$R$_8$, or —NR$_1$—S(O)$_2$—$R_8$;

$L_2$ is independently, from the proximal to distal end of the structure of Formula I-R or I-S, null, —(O)—, —OC(O)—, —NR$_1$—, —C(O)NR$_1$—, —N(R$_1$)—C(O)—, —S(O$_2$)—, —C(O)— or —S(O$_2$)—N(R$_1$)—;

$R_5$ is $R_7$, —(CH$_2$)$_m$-L$_2$-(CH$_2$)$_m$—$R_7$, or -(-L$_3$-(CR$_aR_b$)$_r$—)$_s$-L$_3$-R$_7$;

each $L_3$ is independently null, —O—, or —N(R$_1$)— each $R_8$ is independently H, $C_{1-7}$ alkyl, cycloalkyl or aryl;

each m is independently 0, 1, 2, 3, 4, 5, or 6;

each n is independently 0 or 1;

p is 0, 1, 2, or 3;

q is 0, 1, 2, or 3;

each r is independently 2, 3, or 4; and each s is independently 1, 2, 3, or 4.

5. The method of claim 4, wherein the malcondition is selected from type II diabetes, obesity and metabolic disorder.

6. The method of claim 4 any of claims 4 wherein the method additionally comprises administering to the subject a second medicament selected from the group of peptidic GLP-1 agonists and DPP-4 inhibitors.

7. The method of claim 6 wherein the second medicament is exenatide or sitagliptin.

8. The method of claim 4 wherein the compound has the structure of Formula I-R or a pharmaceutically acceptable isomer, enantiomer, racemate, or salt thereof 9. The method of claim 4 wherein the compound has the structure of Formula I-S or a pharmaceutically acceptable isomer, enantiomer, racemate, or salt thereof.

10. The method of claim 4 wherein the compound is substantially enantiomerically pure.

11. The method of claim 10 wherein $W_i$ is -L$_1$-(CR$_aR_{b;)m}$-L$_1$-R$_6$.

12. The method of claim 10 wherein $W_1$ is -L$_1$-(CR$_aR_b$)$_m$—R$_6$.

13. The method of claim 10 wherein one of $L_1$ is —O—.

14. The method of claim 10 wherein one of $L_1$ is —C(O)O—.

15. The method of claim 10 wherein one of $L_1$ is —S(O$_2$)—.

16. The method of claim 10 wherein one of $L_1$ is —S—.

17. The method of claim 10 wherein one of $L_1$ is —N(R$_1$).

18. The method of claim 10 wherein one of $L_1$ is —N(R$_1$)—C(O)—N(R$_1$)—.

19. The method of claim 10 wherein one of $L_1$ is —N(R$_1$)—C(O)—.

20. The method of claim 10 wherein one of $L_1$ is —S(O$_2$)—N(R$_1$)—.

21. The method of claim 10 wherein $R_1$ is H.

22. The method of claim 10 wherein one of $L_1$ is —O—.

23. The method of claim 10 wherein both $R_a$ and $R_b$ are H.

24. The method of claim 10 wherein one of $R_a$ and $R_b$ is methyl.

25. The method of claim 10 wherein one of $R_a$ and $R_b$ is methoxy.

26. The method of claim 10 wherein at least one instance $R_a$ and $R_b$ taken together with the carbon to which they are attached form a cycloalkyl.

27. The method of claim 10 wherein $R_6$ is alkyl substituted with $R_7$ and $R_7$ is phenyl.

28. The method of claim 10 wherein $W_1$ is —NHC(O)—(CH$_2$)$_m$-L$_1$-R$_6$.

29. The method of claim 28 wherein $R_6$ is H or alkyl.

30. The method of claim 28 wherein $R_6$ is cycloalkyl, aryl, heteroaryl, or heterocycloalkyl, and any of which may be optionally singly or multiply substituted with alkyl, alkoxy or halo.

31. The method of claim 30 wherein $R_6$ is cyclopentyl, cyclohexyl, phenyl, pyridinyl, naphthyl, furyl, thiophenyl, benzo[b]furanyl, oxazolyl, isoxazolyl, benzothiazolyl, tetrahydro-2H-pyranyl, pyrazolyl, benzo[b]thiophenyl, quinoxalinyl, quinolinyl, thiazolyl, pyrolidinyl, pyrrolyl, pyrazolo[1,5-α]pyridinyl, imidazolyl, benzo[d]isoxazolyl, and $R_6$ may be optionally singly or mulitply substituted with methyl, methoxy, chloro or fluoro.

32. The method of claim 10 wherein m is 0, 1 or 2.

33. The method of claim 10 wherein $W_1$ is attached in the para position.

34. The method of claim 10 wherein $W_1$ is null.

35. The method of claim 34 wherein each $R_3$ is independently H, methyl, ethyl, t-butyl, methoxy, isopropoxy, ethoxy, chloro, fluoro, —CF$_3$, —OCF$_3$, —OCF$_2$H, —CN, or —NO$_2$.

36. The method of claim 35 wherein each $R_3$ is independently H, t-butyl, or methoxy.

37. The method of claim 34 wherein p is 1.

38. The method of claim 10 wherein $R_1$ is H.

39. The method of claim 10 wherein $R_4$ is H.

40. The method of claim 10 wherein $R_4$ is alkoxy.

41. The method of claim 40 wherein $R_4$ is methoxy.

42. The method of claim 10 wherein A is —OC(O)—, —N(R$_1$)—S(O$_2$)—, —O—, or —N(R$_1$)—C(O)—.

43. The method of claim 42 wherein A is —OC(O)—.

44. The method of claim 43 wherein A is in the para position.

45. The method of claim 10 wherein p is 1.

46. The method of claim 10 wherein $R_5$ is alkoxy.

47. The method of claim 46 wherein $R_5$ is heptoxy.

48. The method of claim 10 wherein n is 1.

* * * * *

UNITED STATES PATENT AND TRADEMARK OFFICE
CERTIFICATE OF CORRECTION

PATENT NO. : 8,501,982 B2  
APPLICATION NO. : 13/157264  
DATED : August 6, 2013  
INVENTOR(S) : Marcus F. Boehm et al.

Page 1 of 1

It is certified that error appears in the above-identified patent and that said Letters Patent is hereby corrected as shown below:

In the Claims

Claim 1, Column 313, Line 52:
"-($CH_2$)-COO-$R_{40}$, -C(O)-$R_{40}$, aryl," should read, -- -($CH_2$)$_n$-COO-$R_{40}$, -C(O)-$R_{40}$, aryl,--.

Claim 1, Column 313, Line 61:
"-N($R_1$)-C(O)-, or –N($R_1$)-S($O_2$)-," should read, -- -N($R_1$)-C(O)-, or –N($R_1$)-S($O_2$)-;--.

Claim 1, Column 314, Lines 34-35:
"$R_5$ is $R_7$, -($CH_2$)$_m$-$L_2$-($CH_2$)$_m$-$R_7$, or –(-$L_3$-(CR$_a$R$_b$)$_r$-)$_s$-$L_3$-$R_7$." should read,
--$R_5$ is $R_7$, -($CH_2$)$_m$-$L_2$-($CH_2$)$_m$-$R_7$, or –(-$L_3$-(CR$_a$R$_b$)$_r$-)$_s$-$L_3$-$R_7$;--.

Claim 4, Column 316, Line 46:
"-N$R_{41}R_{42}$;." should read, -- -N$R_{41}R_{42}$;--.

Claim 4, Column 316, Line 48:
"each $R_{41}$ and $R_{42}$ is independently H or alkyl, -($CH_2$-" should read,
--each $R_{41}$ and $R_{42}$ is independently H or alkyl, -($CH_2$)$_n$--.

Claim 6, Column 317, Line 32:
"6. The method of claim 4 any of claims 4 wherein the" should read,
--6. The method of claim 4 wherein the--.

Claim 11, Column 317, Lines 46-47:
"11. The method of claim 10 wherein $W_i$ is –$L_1$-(CR$_a$R$_b$;)$_m$-$L_1$-$R_6$." should read,
--11. The method of claim 10 wherein $W_1$ is –$L_1$-(CR$_a$R$_b$)$_m$-$L_1$-$R_6$.--.

Signed and Sealed this  
Thirtieth Day of September, 2014

Michelle K. Lee  
*Deputy Director of the United States Patent and Trademark Office*